United States Patent
Cho et al.

(10) Patent No.: US 7,816,019 B2
(45) Date of Patent: *Oct. 19, 2010

(54) COMPOUND AND ORGANIC LIGHT EMITTING DEVICE USING THE SAME

(75) Inventors: Wook Dong Cho, Daejeon Metropolitan (KR); Ji Eun Kim, Daejeon Metropolitan (KR); Byung Sun Jeon, Seoul (KR); Sang Young Jeon, Seoul (KR); Seok Hee Yoon, Daejeon Metropolitan (KR); Jae Min Moon, Daejeon Metropolitan (KR)

(73) Assignee: LG Chem, Ltd., Seoul (KR)

( * ) Notice: Subject to any disclaimer, the term of this patent is extended or adjusted under 35 U.S.C. 154(b) by 822 days.

This patent is subject to a terminal disclaimer.

(21) Appl. No.: 11/658,993

(22) PCT Filed: Sep. 23, 2005

(86) PCT No.: PCT/KR2005/003178

§ 371 (c)(1),
(2), (4) Date: Jan. 31, 2007

(87) PCT Pub. No.: WO2006/080645

PCT Pub. Date: Aug. 3, 2006

(65) Prior Publication Data

US 2009/0045721 A1    Feb. 19, 2009

(30) Foreign Application Priority Data

Sep. 24, 2004    (KR) .................... 10-2004-0077214

(51) Int. Cl.
*H01L 51/54* (2006.01)
(52) U.S. Cl. ............... 428/690; 428/917; 313/504; 313/506; 252/301.16; 257/40; 257/E51.032; 556/408; 546/15; 546/16; 546/18
(58) Field of Classification Search .............. 556/408
See application file for complete search history.

(56) References Cited

U.S. PATENT DOCUMENTS

| 6,605,373 B2 | 8/2003 | Woo et al. |
| 6,613,454 B2 | 9/2003 | Ara et al. |
| 6,630,254 B2 | 10/2003 | Leclerc et al. |
| 2004/0219386 A1 | 11/2004 | Thoms |

FOREIGN PATENT DOCUMENTS

| EP | 1 310 539 B1 | 3/2005 |
| JP | 2008-510801 | 4/2008 |
| JP | 2008-511155 | 4/2008 |
| JP | 2008-511156 | 4/2008 |
| JP | 2008-511162 | 4/2008 |
| WO | WO 93/09074 | 5/1993 |
| WO | WO 2004/020371 A1 | 3/2004 |
| WO | WO 2006/003564 | 3/2006 |
| WO | WO 2006/080637 | 8/2006 |
| WO | WO 2006/080638 | 8/2006 |
| WO | WO 2006/080645 | 8/2006 |
| WO | WO 2006/080646 | 8/2006 |

OTHER PUBLICATIONS

W. Tritschler, *Synthese un Konformation von Spiroacridanen*, Chem. Ber. 117, pp. 2703-2713; 1984.

*Primary Examiner*—D. Lawrence Tarazano
*Assistant Examiner*—Michael Wilson
(74) *Attorney, Agent, or Firm*—McKenna Long & Aldridge LLP

(57) ABSTRACT

Disclosed is an organic light emitting device. The organic light emitting device comprises a first electrode, organic material layer(s) comprising a light emitting layer, and a second electrode. The first electrode, the organic material layer(s), and the second electrode form layered structure and at least one layer of the organic material layer(s) include the compound of Formula 1 or the compound of Formula 1 into which a thermosetting or photo-crosslinkable functional group is introduced.

8 Claims, 1 Drawing Sheet

COMPOUND AND ORGANIC LIGHT EMITTING DEVICE USING THE SAME

This application claims priority to International Application No. PCT/KR2005/003178, filed on Sep. 23, 2005, and Korean Patent Application No. 10-2004-0077214, filed on Sep. 24, 2004, which are hereby incorporated by reference in their entirety.

TECHNICAL FIELD

The present invention relates to an organic light emitting device in which a novel compound capable of significantly improving a lifespan, efficiency, and electrochemical and thermal stabilities of the organic light emitting device is contained in an organic compound layer.

BACKGROUND ART

An organic light emission phenomenon is an example of a conversion of current into visible rays through an internal process of a specific organic molecule. The organic light emission phenomenon is based on the following mechanism. When organic material layers are interposed between an anode and a cathode, if voltage is applied between the two electrodes, electrons and holes are injected from the cathode and the anode into the organic material layer. The electrons and the holes which are injected into the organic material layer are recombined to form an exciton, and the exciton is reduced to a bottom state to emit light. An organic light emitting device which is based on the above mechanism typically comprises a cathode, an anode, and organic material layer(s), for example, organic material layers including a hole injection layer, a hole transport layer, a light emitting layer, and an electron transport layer, interposed therebetween.

The materials used in the organic light emitting device are mostly pure organic materials or complexes of organic material and metal. The material used in the organic light emitting device may be classified as a hole injection material, a hole transport material, a light emitting material, an electron transport material, or an electron injection material, according to its use. In connection with this, an organic material having a p-type property, which is easily oxidized and is electrochemically stable when it is oxidized, is mostly used as the hole injection material or the hole transport material. Meanwhile, an organic material having an n-type property, which is easily reduced and is electrochemically stable when it is reduced, is used as the electron injection material or the electron transport material. As the light emitting layer material, an organic material having both p-type and n-type properties is preferable, which is stable when it is oxidized and when it is reduced. Also a material having high light emission efficiency for conversion of the exciton into light when the exciton is formed is preferable.

In addition, it is preferable that the material used in the organic light emitting device further have the following properties.

First, it is preferable that the material used in the organic light emitting device have excellent thermal stability. The reason is that joule heat is generated by movement of electric charges in the organic light emitting device. NPB, which has recently been used as the hole transport layer material, has a glass transition temperature of 100° C. or lower, thus it is difficult to apply to an organic light emitting device requiring a high current.

Second, in order to produce an organic light emitting device that is capable of being actuated at low voltage and has high efficiency, holes and electrons which are injected into the organic light emitting device must be smoothly transported to a light emitting layer, and must not be released out of the light emitting layer. To achieve this, a material used in the organic light emitting device must have a proper band gap and a proper HOMO or LUMO energy levels. A LUMO energy level of PEDOT:PSS, which is currently used as a hole transport material of an organic light emitting device produced using a solution coating method, is lower than that of an organic material used as a light emitting layer material, thus it is difficult to produce an organic light emitting device having high efficiency and a long lifespan.

Moreover, the material used in the organic light emitting device must have excellent chemical stability, electric charge mobility, and interfacial characteristic with an electrode or an adjacent layer. That is to say, the material used in the organic light emitting device must be little deformed by moisture or oxygen. Furthermore, proper hole or electron mobility must be assured so as to balance densities of the holes and of the electrons in the light emitting layer of the organic light emitting device to maximize the formation of excitons. Additionally, it has to be able to have a good interface with an electrode including metal or metal oxides so as to assure stability of the device.

Accordingly, there is a need to develop an organic light emitting device including an organic material having the above-mentioned requirements in the art.

DISCLOSURE OF INVENTION

Technical Problem

Therefore, the object of the present inventions is to provide an organic light emitting device which is capable of satisfying conditions required of a material usable for an organic light emitting device, for example, a proper energy level, electrochemical stability, and thermal stability, and which includes a fluorene derivative having a chemical structure capable of playing various roles required in the organic light emitting device, depending on a substituent group.

Technical Solution

The present invention provides an organic light emitting device which comprises a first electrode, organic material layer(s) comprising a light emitting layer, and a second electrode, wherein the first electrode, the organic material layer(s), and the second electrode form a layered structure and at least one layer of the organic material layer(s) includes a compound of the following Formula 1 or a compound of Formula 1 into which a thermosetting or photo-crosslinkable functional group is introduced:

[Formula 1]

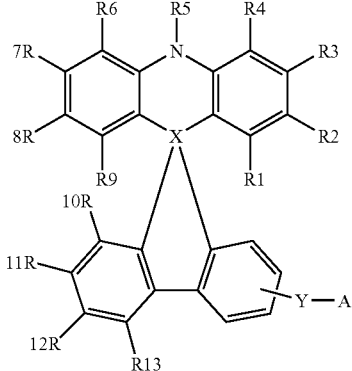

In Formula 1, X is C or Si;
A is

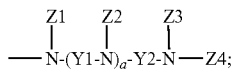

and
a is zero or positive integer;
Y is a bond; bivalent aromatic hydrocarbons; bivalent aromatic hydrocarbons which are substituted with at least one substituent group selected from the group consisting of nitro, nitrile, halogen, alkyl, alkoxy, and amino groups; a bivalent heterocyclic group; or a bivalent heterocyclic group which is substituted with at least one substituent group selected from the group consisting of nitro, nitrile, halogen, alkyl, alkoxy, and amino groups.

Y1 and Y2 are each independently bivalent aromatic hydrocarbons; bivalent aromatic hydrocarbons which are substituted with at least one substituent group selected from the group consisting of nitro, nitrile, halogen, alkyl, alkoxy, and amino groups; a bivalent heterocyclic group; or a bivalent heterocyclic group which is substituted with at least one substituent group selected from the group consisting of nitro, nitrile, halogen, alkyl, alkoxy, and amino groups.

Z1 to Z4 are each independently hydrogen; aliphatic hydrocarbons having a carbon number of 1-20; aromatic hydrocarbons; aromatic hydrocarbons which are substituted with at least one substituent group selected from the group consisting of the nitro, nitrile, halogen, alkyl, alkoxy, amino, aromatic hydrocarbon, and heterocyclic groups; a silicon group substituted with aromatic hydrocarbons; a heterocyclic group; a heterocyclic group which is substituted with at least one substituent group selected from the group consisting of the nitro, nitrile, halogen, alkyl, alkoxy, amino, aromatic hydrocarbon, and heterocyclic groups; a thiophene group which is substituted with hydrocarbons having a carbon number of 1-20 or aromatic hydrocarbons having a carbon number of 6-20; or a boron group which is substituted with aromatic hydrocarbons.

R1 to R4 and R6 to R13 are each independently selected from the group consisting of hydrogen, a substituted or unsubstituted alkyl group, a substituted or unsubstituted alkoxy group, a substituted or unsubstituted alkenyl group, a substituted or un-substituted aryl group, a substituted or unsubstituted arylamine group, a substituted or unsubstituted heterocyclic group, an amino group, a nitrile group, a nitro group, a halogen group, an amide group, and an ester group. They may form aliphatic or hetero condensation rings along with adjacent groups.

R5 is selected from the group consisting of hydrogen, a substituted or unsubstituted alkyl group, a substituted or unsubstituted cycloalkyl group, a substituted or un-substituted alkenyl group, a substituted or unsubstituted aryl group, and a substituted or unsubstituted heterocyclic group.

Carbon at an ortho-position of the aryl or heterocyclic group and R4 or R6 may form a condensation ring along with a group selected from the group consisting of O, S, NR, PR, C=O, CRR', and SiRR', with the proviso that R5 is the aryl group or the heterocyclic group. R and R' are each independently selected from the group consisting of hydrogen, a substituted or unsubstituted alkyl group, a substituted or unsubstituted alkoxy group, a substituted or unsubstituted alkenyl group, a substituted or un-substituted aryl group, a substituted or unsubstituted arylamine group, a substituted or unsubstituted heterocyclic group, a nitrile group, an amide group, and an ester group, and R and R' may form a condensation ring to form a spiro compound.

A detailed description will be given of the substituent groups of Formula 1.

In Z1 to Z2 as the substituent groups of Formula 1, the aromatic compounds are exemplified by monocyclic aromatic rings, such as phenyl, biphenyl, and terphenyl, and multicyclic aromatic rings, such as naphthyl, anthracenyl, pyrenyl, and perylenyl. The hetero aromatic compounds are exemplified by thiophene, furan, pyrrole, imidazole, thiazole, oxazole, oxadiazole, thiadiazole, triazole, pyridyl, pyridazyl, pyrazine, quinoline, and isoquinoline.

Examples of aliphatic hydrocarbons having a carbon number of 1-20 include straight chain aliphatic hydrocarbons, branched chain aliphatic hydrocarbons, saturated aliphatic hydrocarbons, and unsaturated aliphatic hydrocarbons. They are exemplified by an alkyl group, such as a methyl group, an ethyl group, an n-propyl group, an iso-propyl group, an n-butyl group, a sec-butyl group, an iso-butyl group, a ter-butyl group, a pentyl group, and a hexyl group; an alkenyl group having a double bond, such as styryl; and an alkynyl group having a triple bond, such as an acetylene group.

The carbon number of the alkyl, alkoxy, and alkenyl groups of R1 to R13 of Formula 1 is not limited, but is preferably 1-20.

The length of the alkyl group contained in the compound does not affect the conjugate length of the compound, but may affect the method of applying the compound to the organic light emitting device, for example, a vacuum deposition method or a solution coating method.

Illustrative, but non-limiting, examples of the aryl group of R1 to R13 of Formula 1 include monocyclic aromatic rings, such as a phenyl group, a biphenyl group, a terphenyl group, and a stilbene group, and multicyclic aromatic rings, such as a naphthyl group, an anthracenyl group, a phenanthrene group, a pyrenyl group, and a perylenyl group.

Illustrative, but non-limiting, examples of the arylamine group of R1 to R13 of Formula 1 include a diphenylamine group, a dinaphthylamine group, a dibiphenylamine group, a phenylnaphthylamine group, a phenyldiphetylamine group, a ditolylamine group, a phenyltolylamine group, a carbazole group, and a triphenylamine group.

Illustrative, but non-limiting, examples of the heterocyclic group of R1 to R13 of Formula 1 include a thiophene group, a furan group, a pyrrole group, an imidazole group, a thiazole group, an oxazole group, an oxadiazole group, a triazole group, a pyridyl group, a pyradazine group, a quinolinyl group, an isoquinoline group, and an acridyl group.

R1 to R13 of Formula 1 is exemplified by a halogen group, a cyano group, and a nitro group.

In addition, illustrative, but non-limiting, examples of the alkenyl, aryl, arylamine, and heterocyclic groups of R1 to R13 of Formula 1 include compounds shown in the following Formulae.

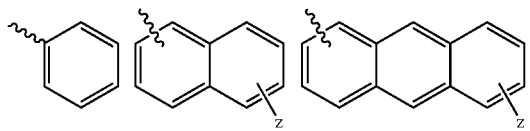

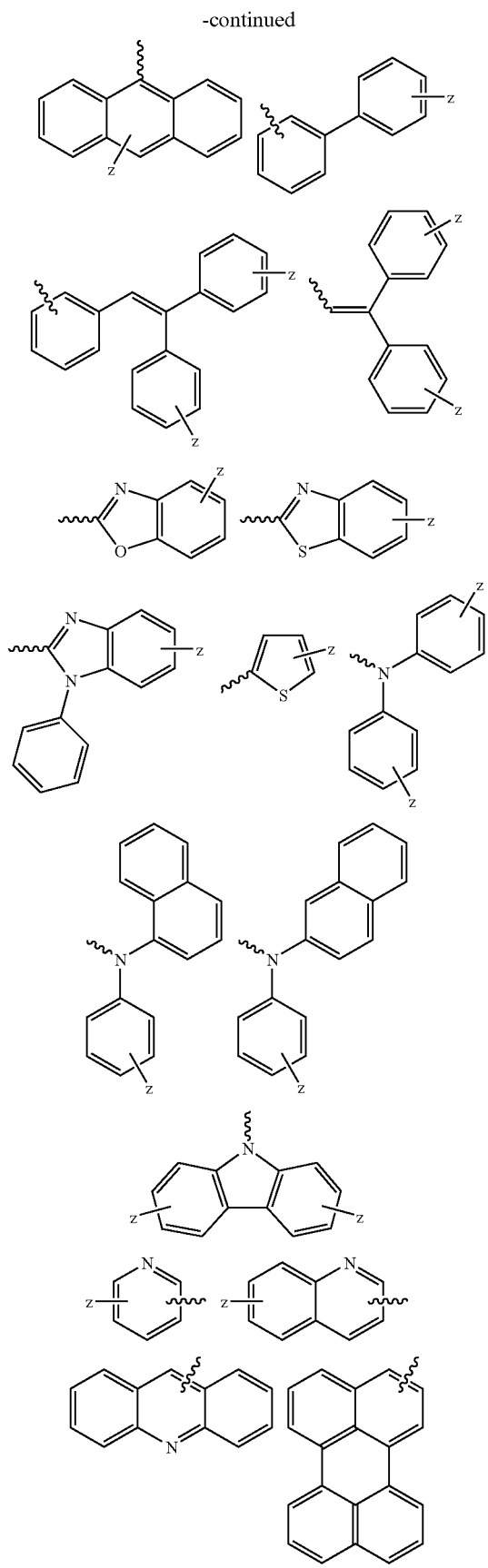
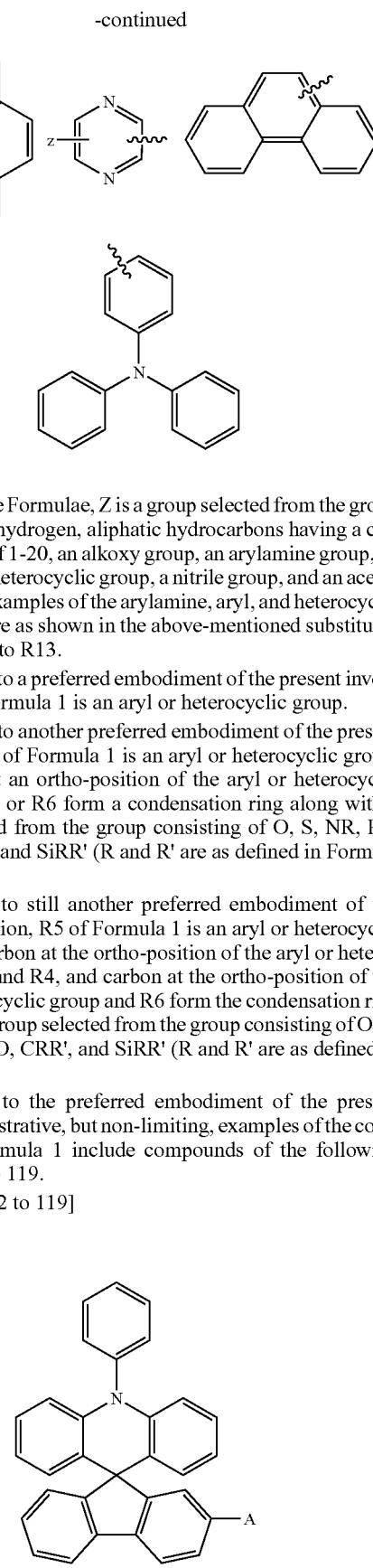

In the above Formulae, Z is a group selected from the group consisting of hydrogen, aliphatic hydrocarbons having a carbon number of 1-20, an alkoxy group, an arylamine group, an aryl group, a heterocyclic group, a nitrile group, and an acetylene group. Examples of the arylamine, aryl, and heterocyclic groups of Z are as shown in the above-mentioned substituent groups of R1 to R13.

According to a preferred embodiment of the present invention, R5 of Formula 1 is an aryl or heterocyclic group.

According to another preferred embodiment of the present invention, R5 of Formula 1 is an aryl or heterocyclic group, and carbon at an ortho-position of the aryl or heterocyclic group and R4 or R6 form a condensation ring along with a group selected from the group consisting of O, S, NR, PR, C=O, CRR', and SiRR' (R and R' are as defined in Formula 1).

According to still another preferred embodiment of the present invention, R5 of Formula 1 is an aryl or heterocyclic group, and carbon at the ortho-position of the aryl or heterocyclic group and R4, and carbon at the ortho-position of the aryl or heterocyclic group and R6 form the condensation ring along with a group selected from the group consisting of O, S, NR, PR, C=O, CRR', and SiRR' (R and R' are as defined in Formula 1).

According to the preferred embodiment of the present invention, illustrative, but non-limiting, examples of the compound of Formula 1 include compounds of the following Formulae 2 to 119.

[Formulae 2 to 119]

3
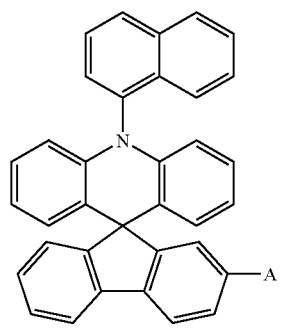
4
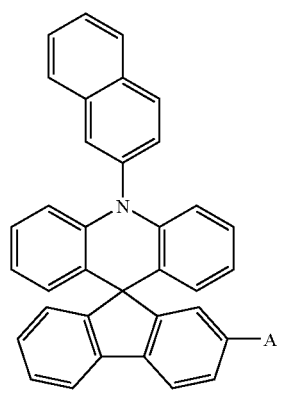
5
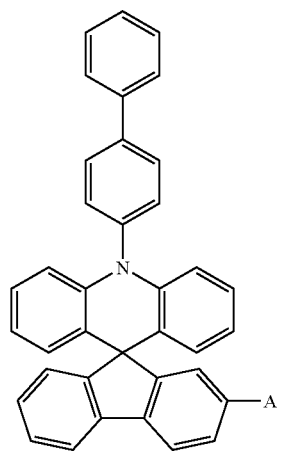
6
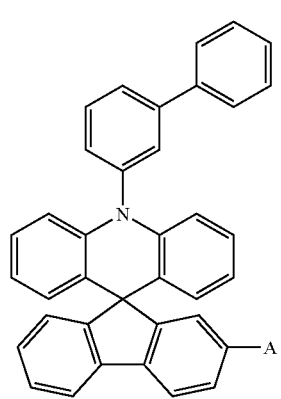
7
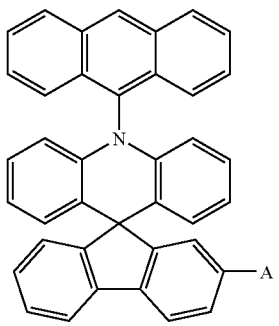
8
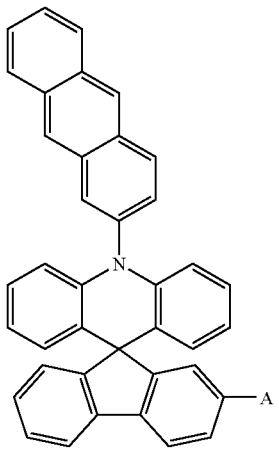
9
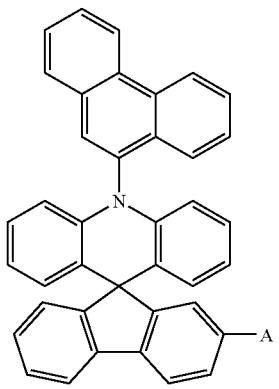
6
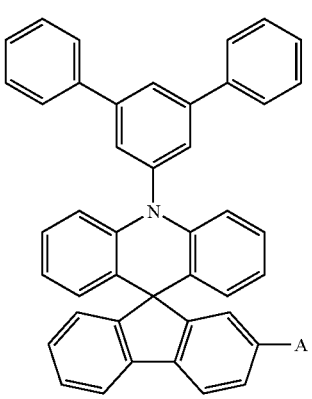

7
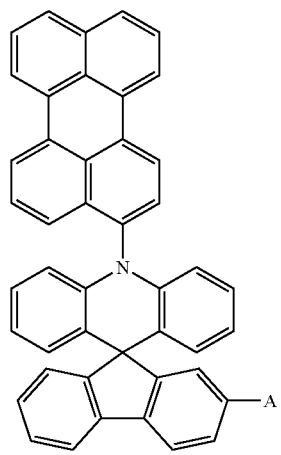
8
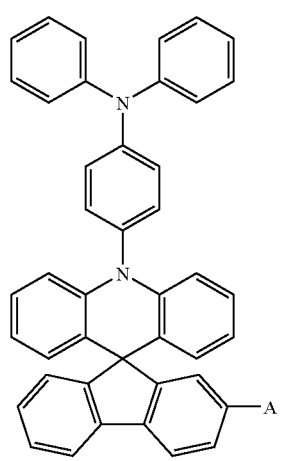
9
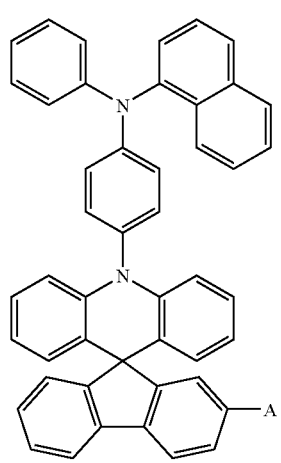
10
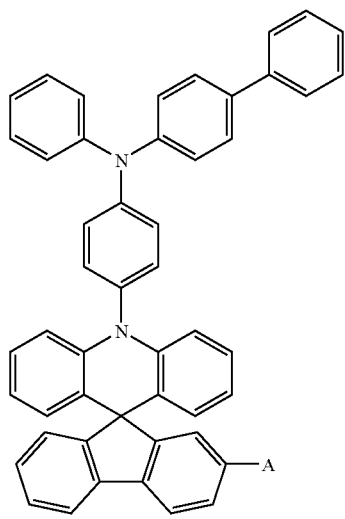
11
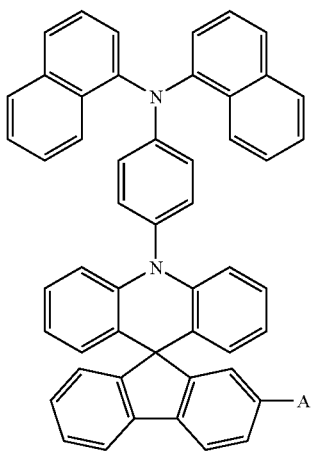
12
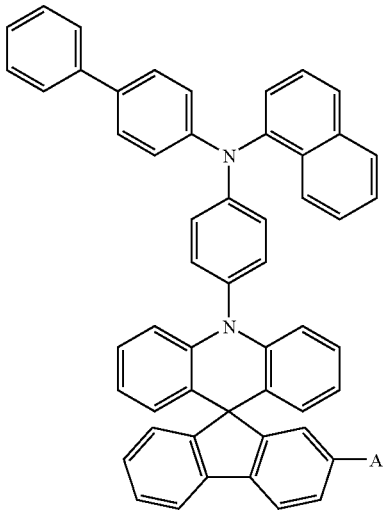

-continued
13
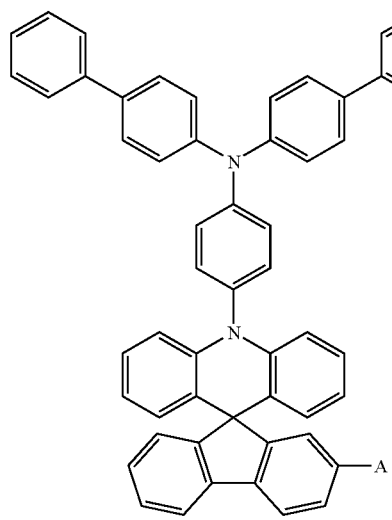
14
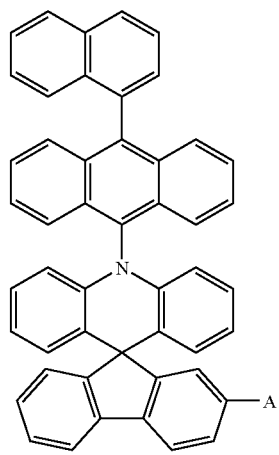
15
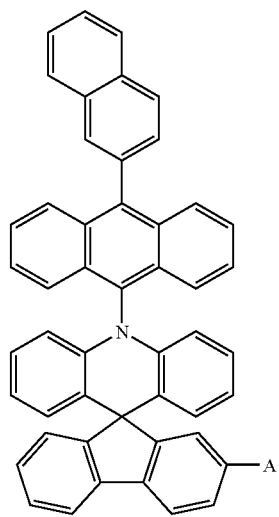
-continued
16
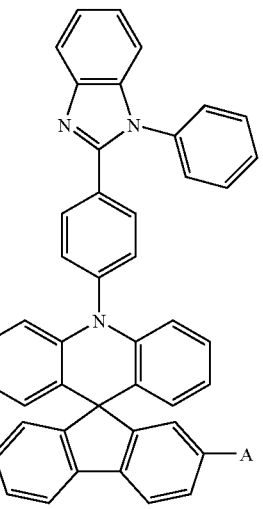
17
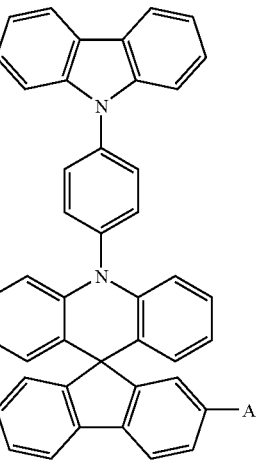
18
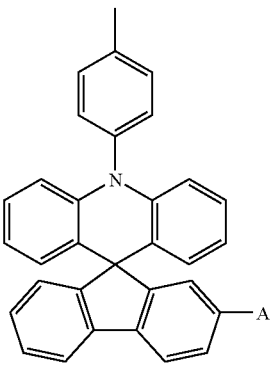

-continued
19
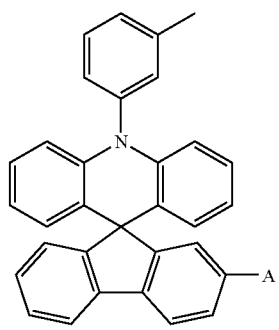
20
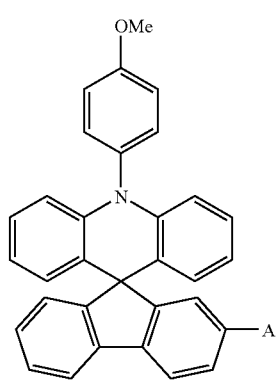
21
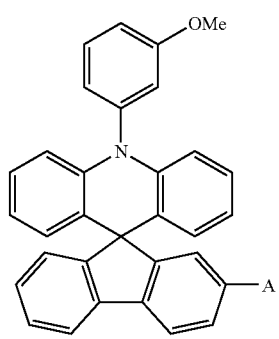
22
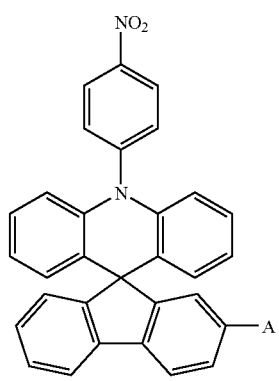
-continued
23
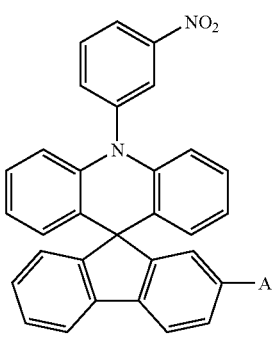
24
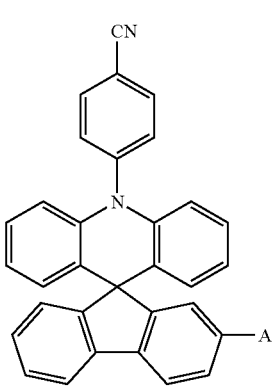
25
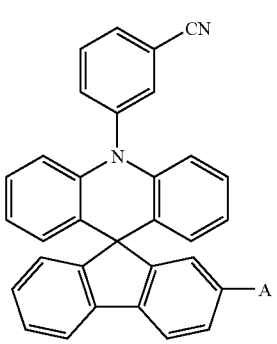
26
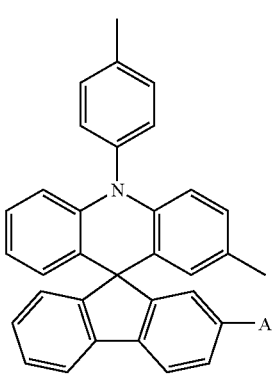

-continued
27
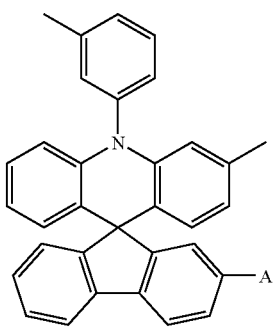
28
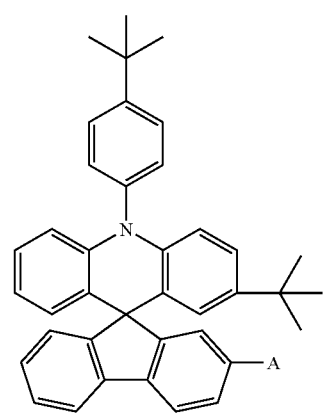
29
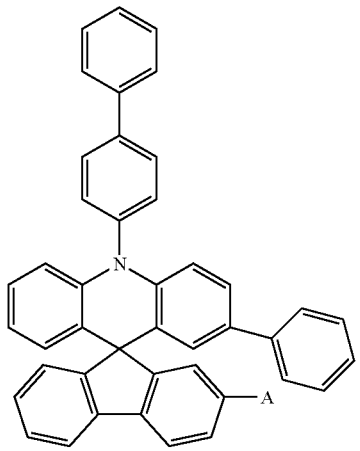
30
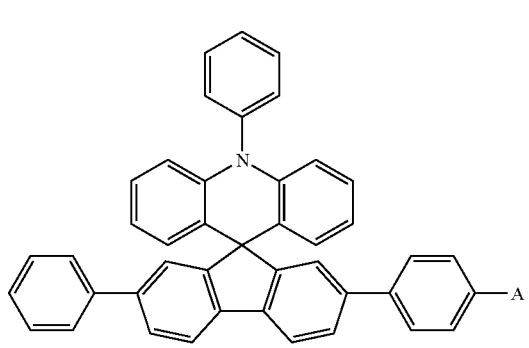
-continued
31
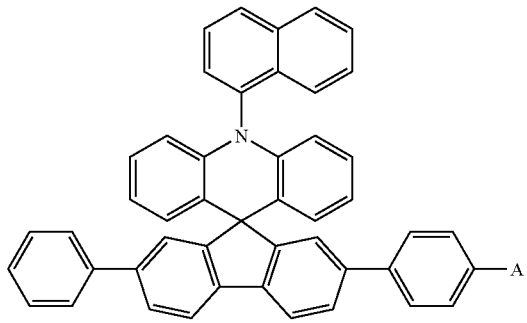
32
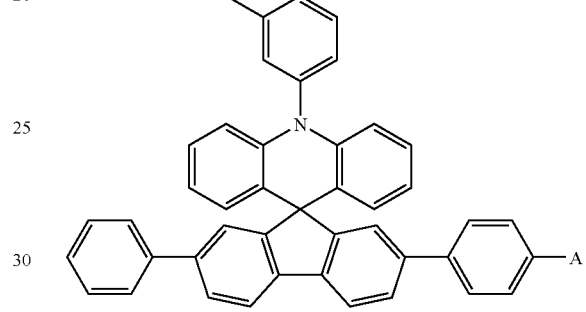
33
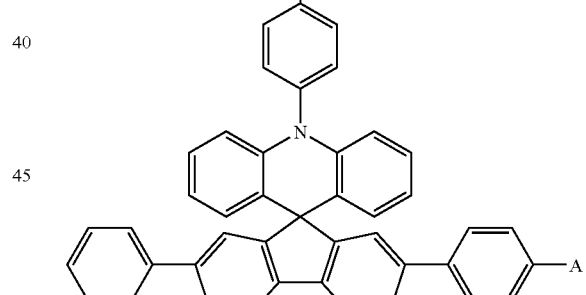
34
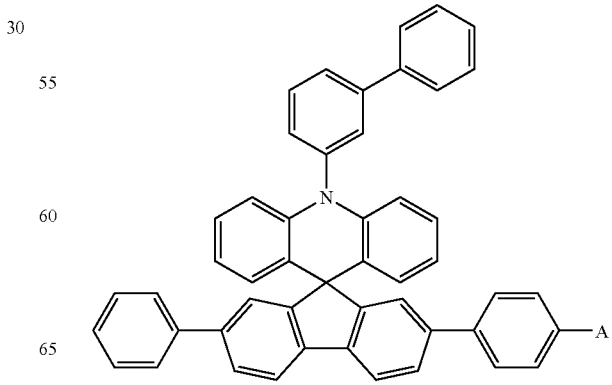

35
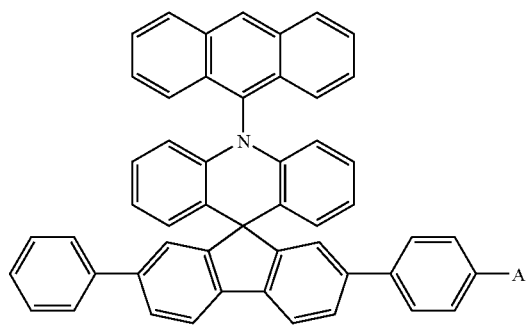
36
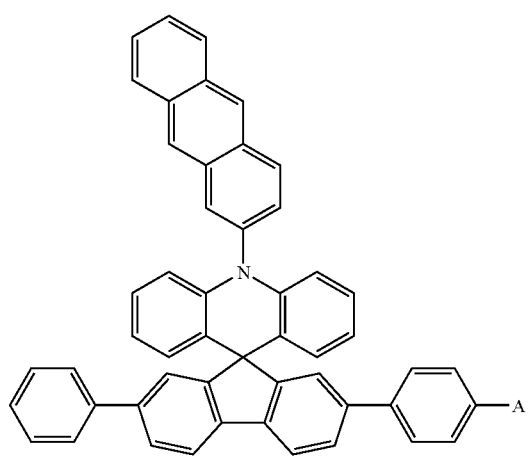
37
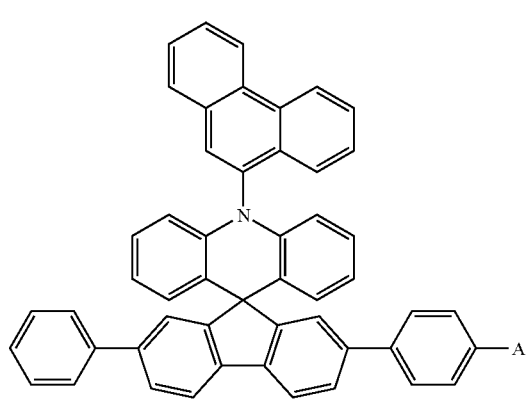
38
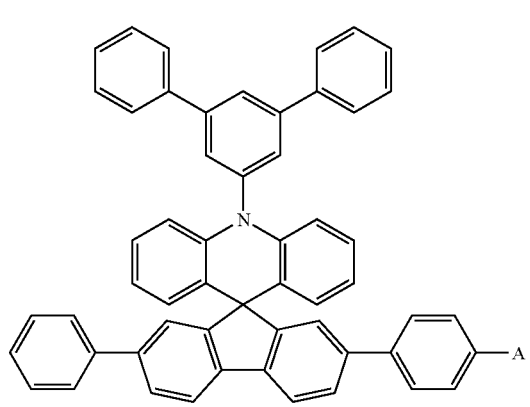
39
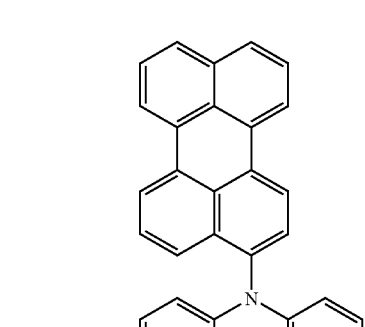
40
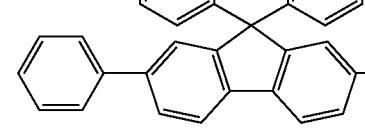
41
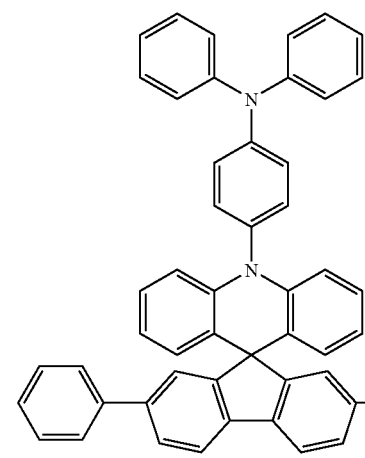

-continued
42
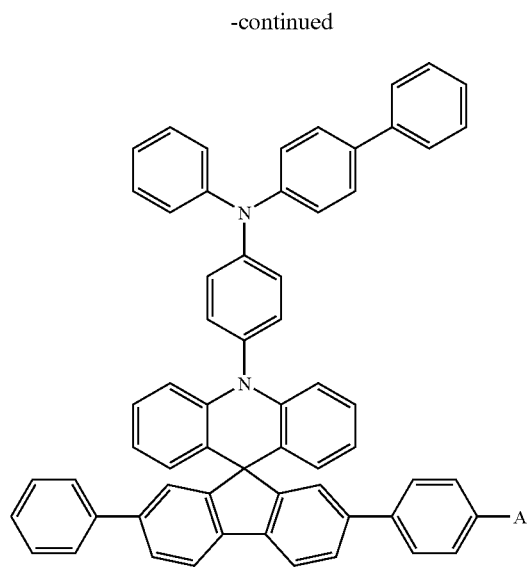
43
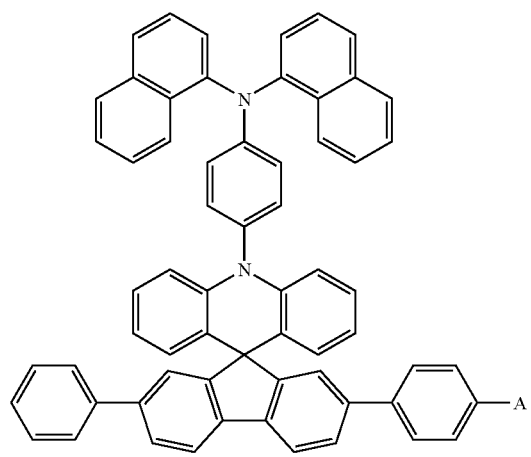
44
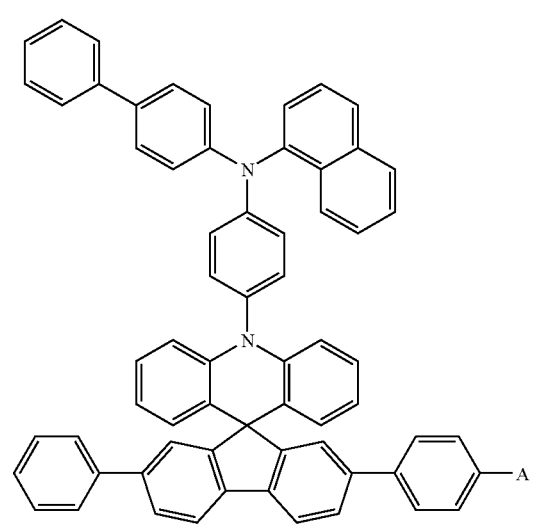
-continued
45
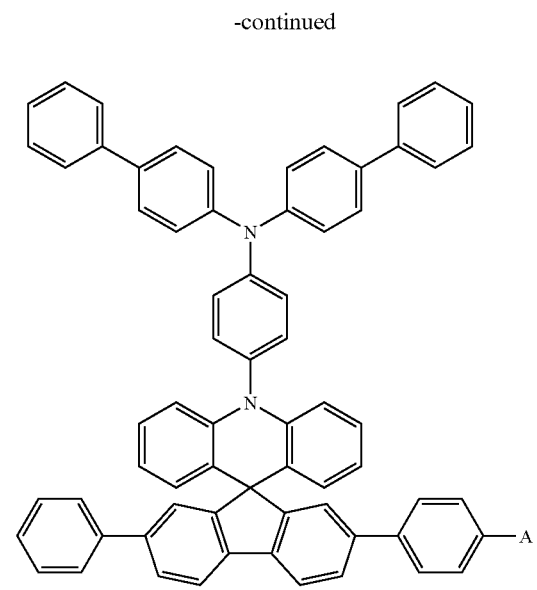
46
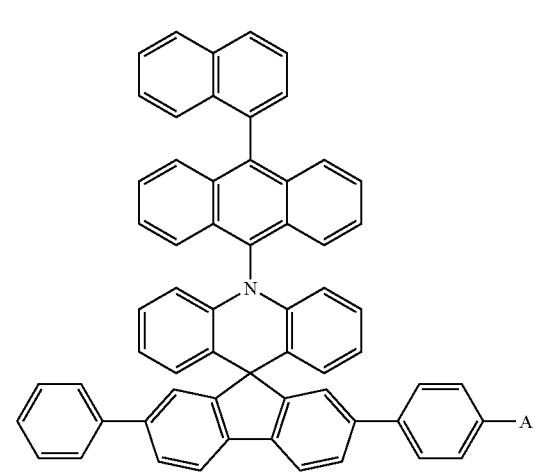
47
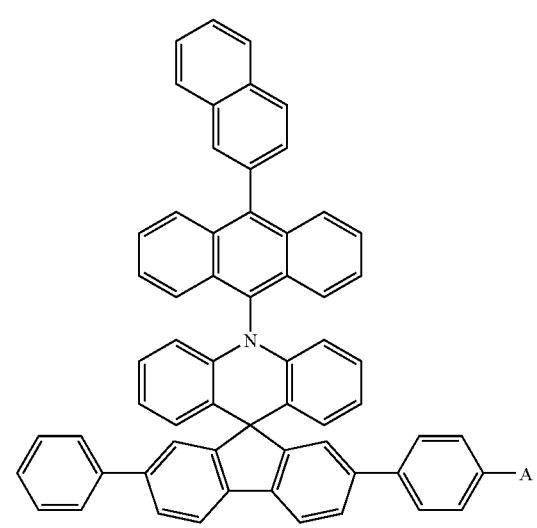

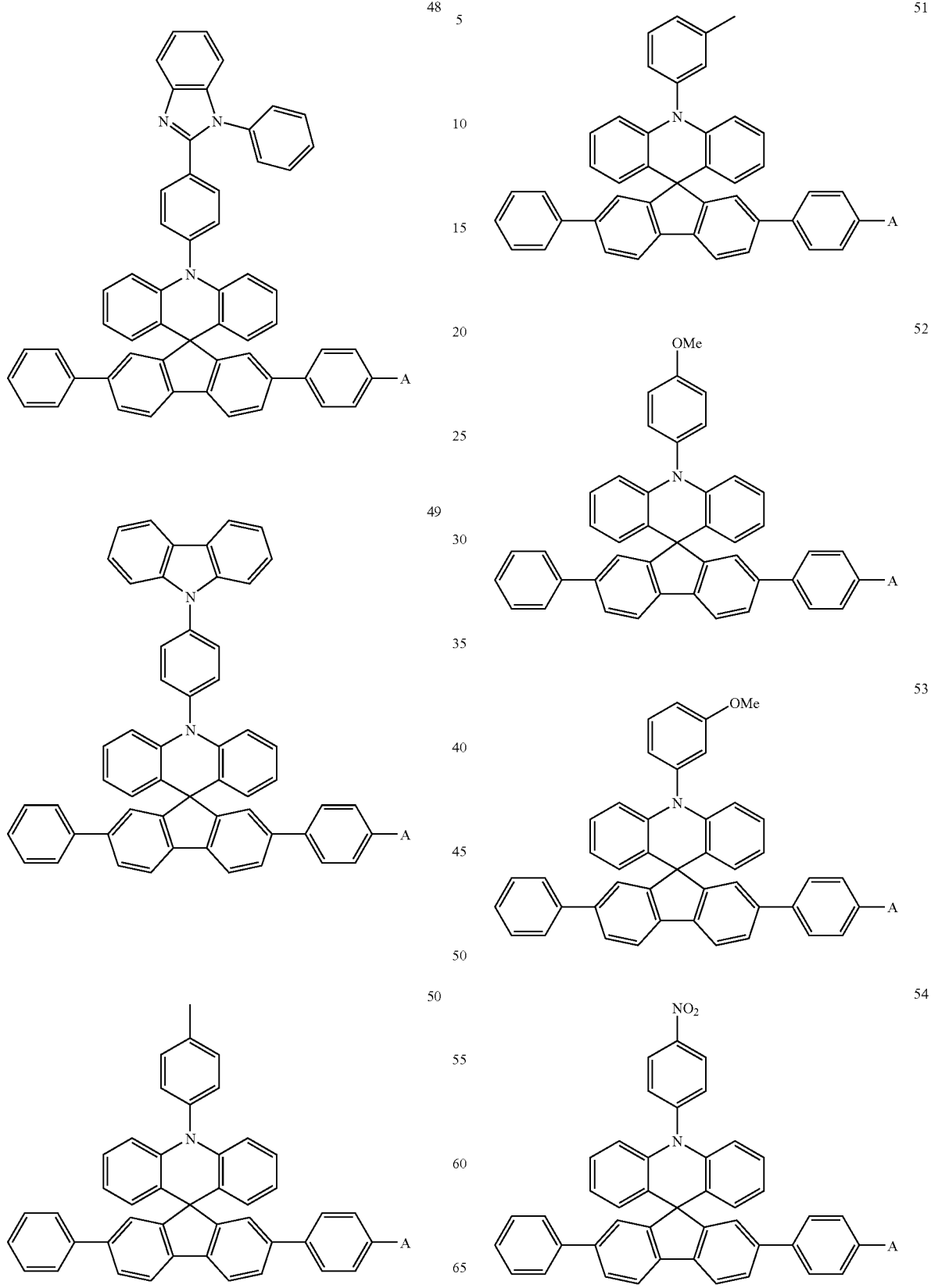

-continued
55
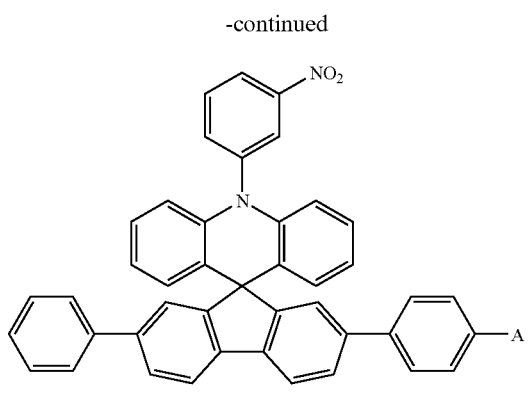
56
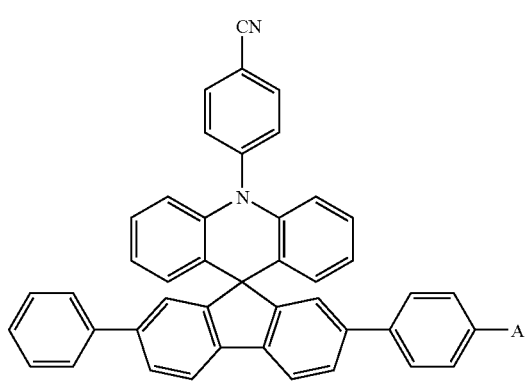
57
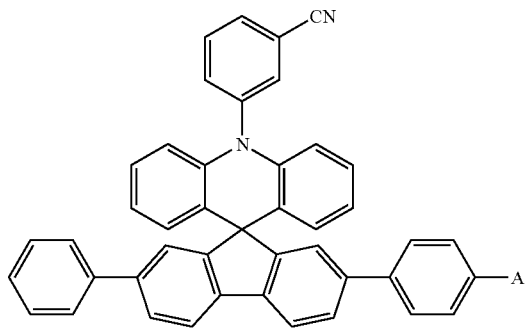
58
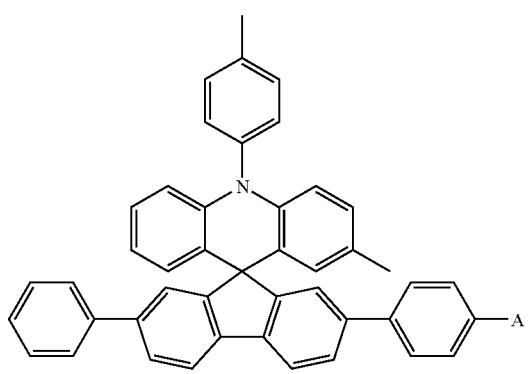
-continued
59
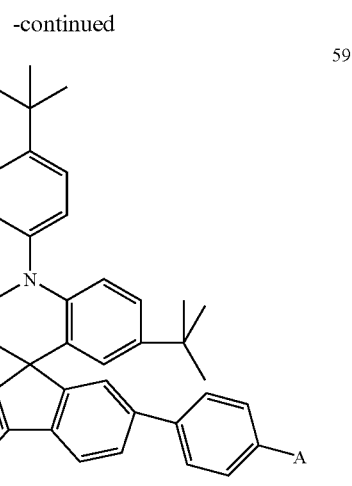
60
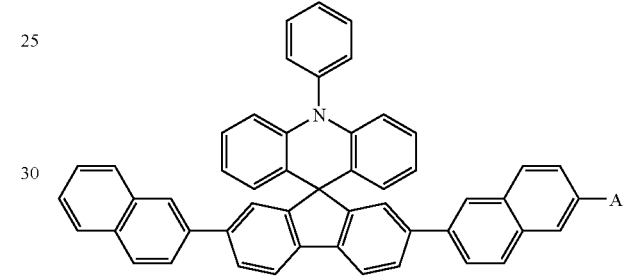
61
62
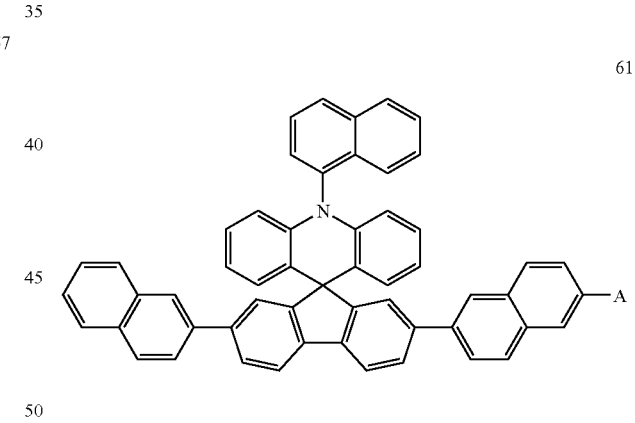

63
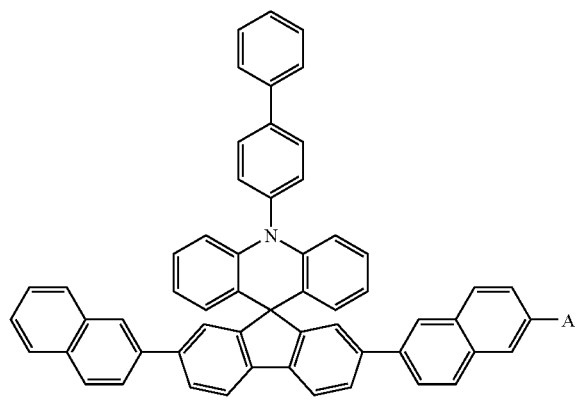
64
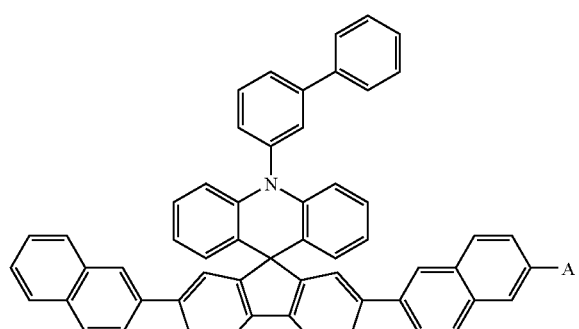
65
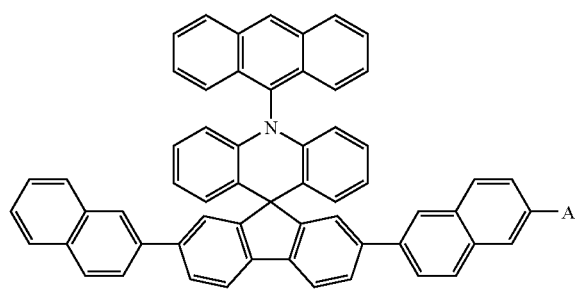
66
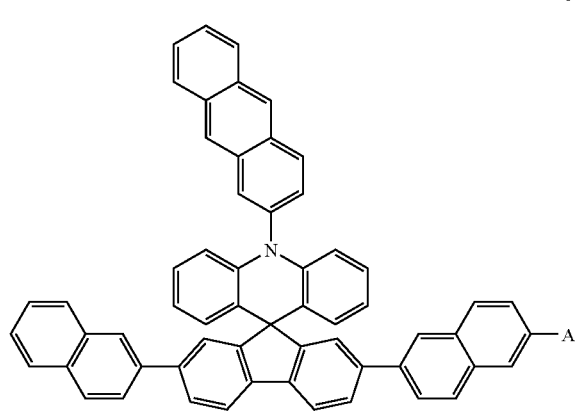
67
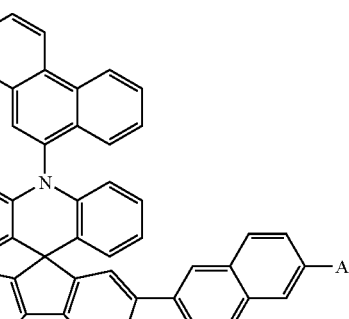
68
69
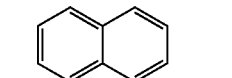
70
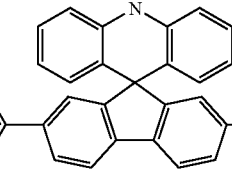

-continued
71
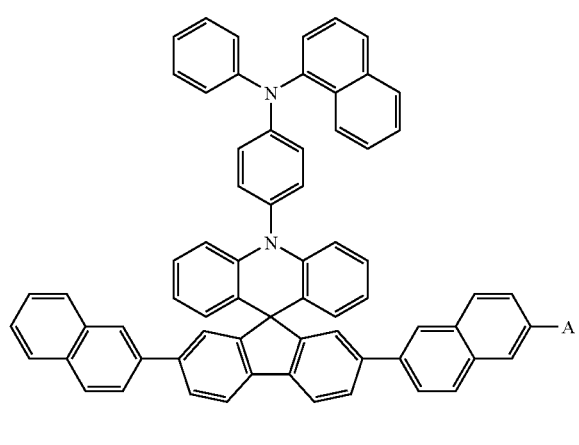
72
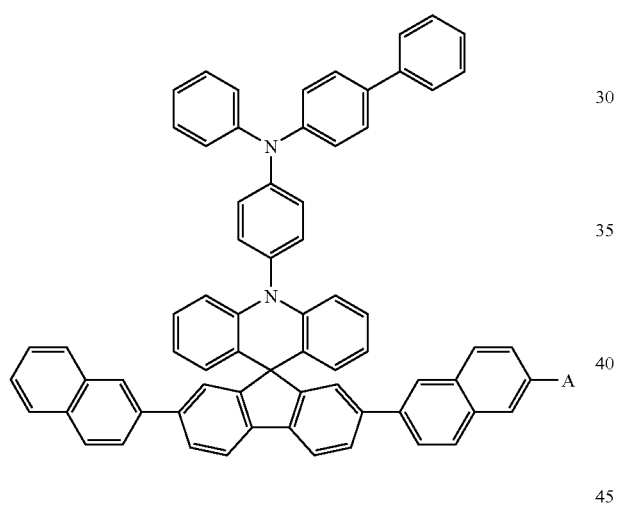
73
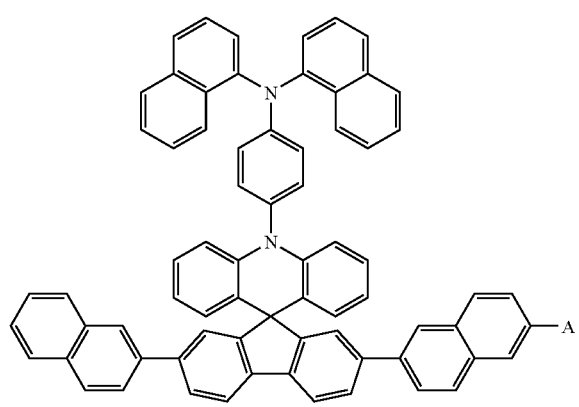
-continued
74
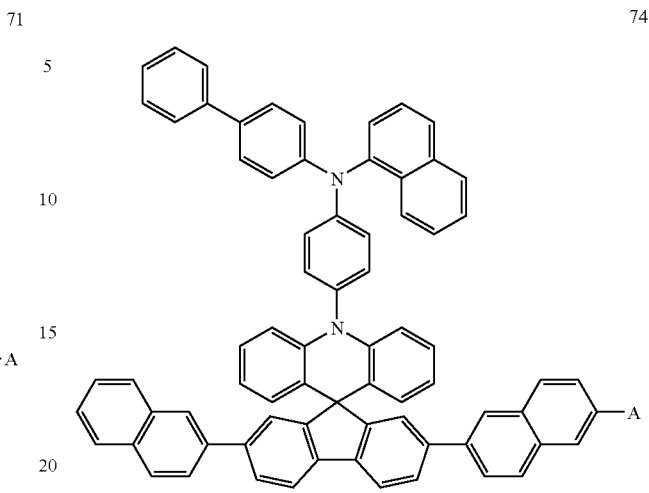
75
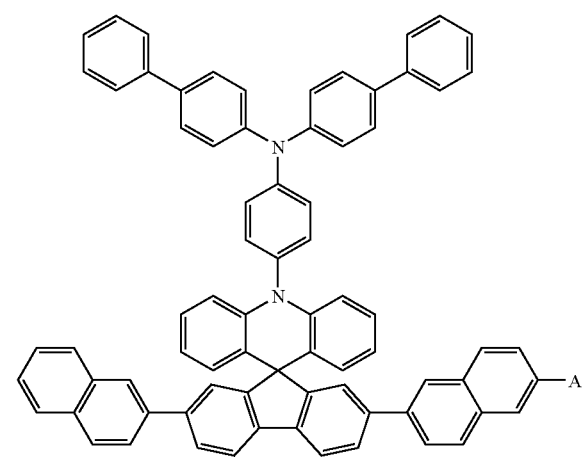
76
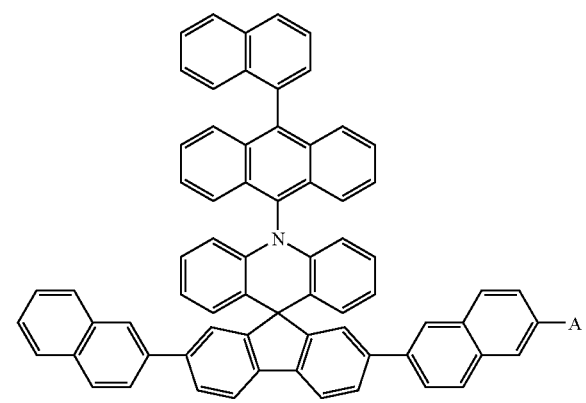

77
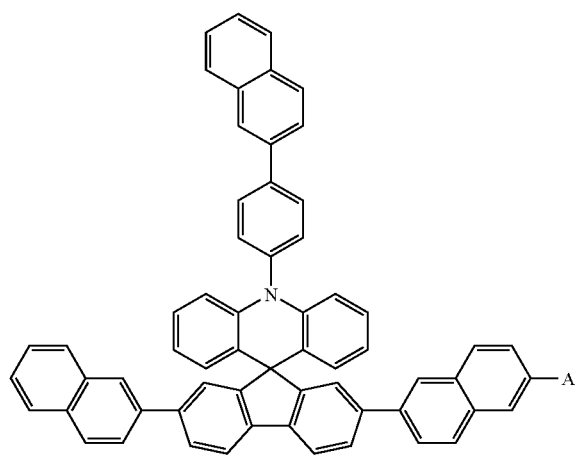
78
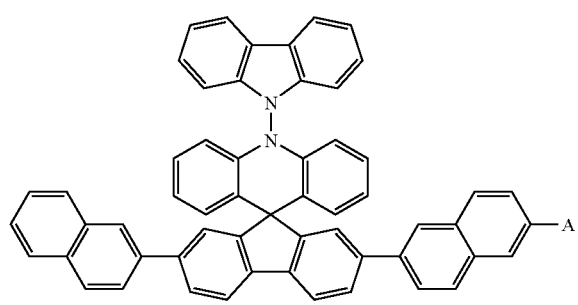
79
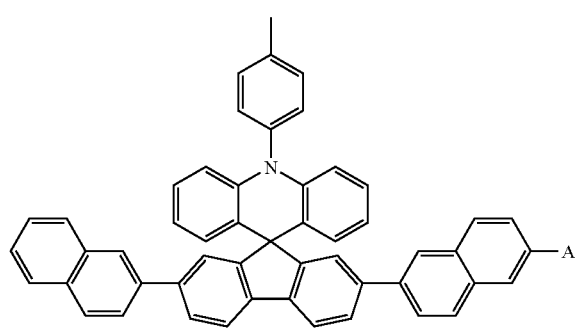
81
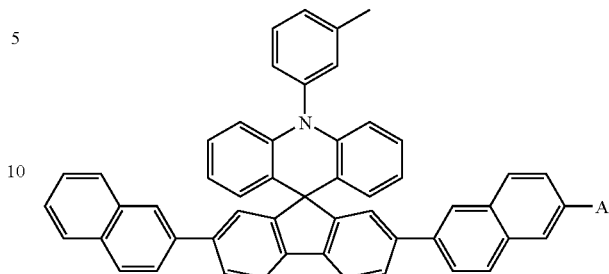
82
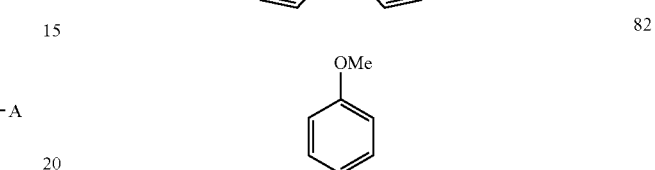
83
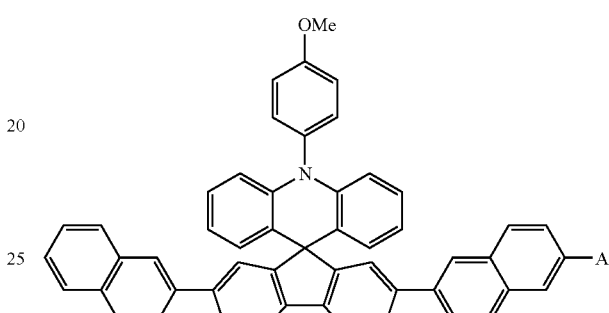
84
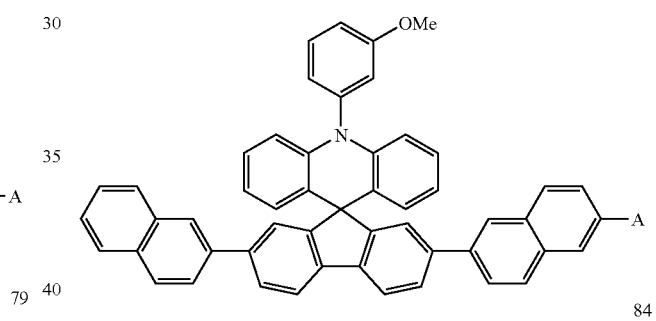
85
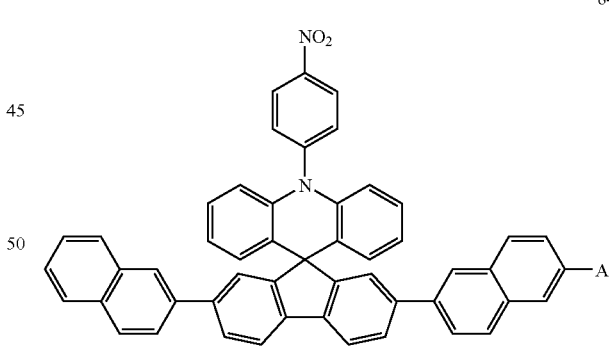
80
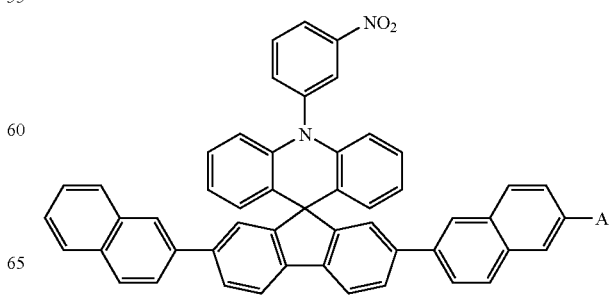

-continued
86
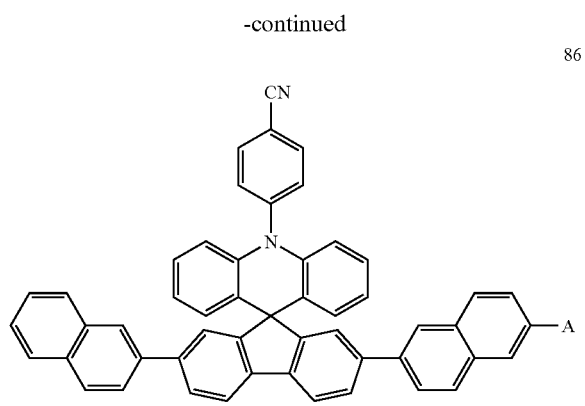
87
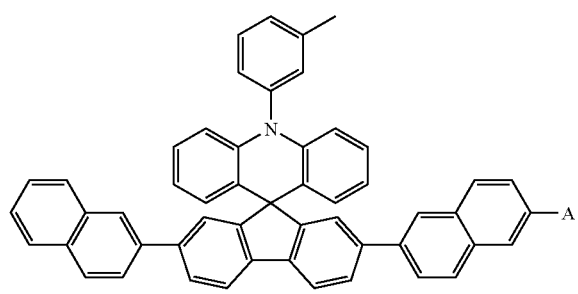
88
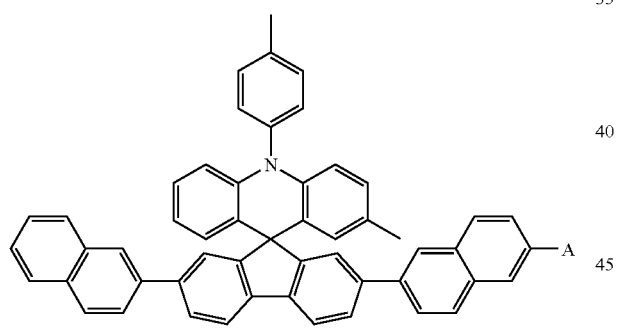
89
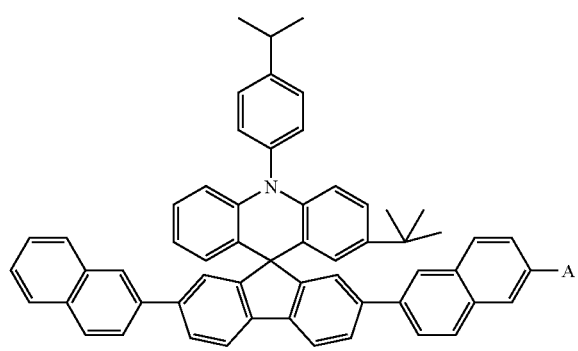
-continued
90
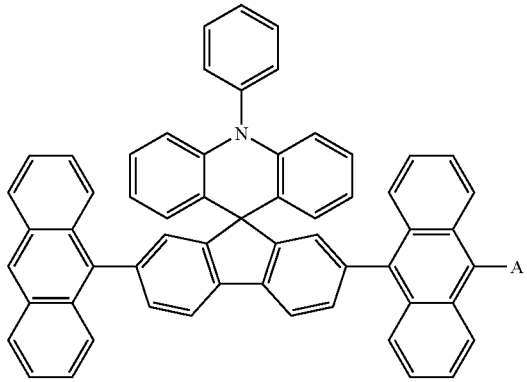
91
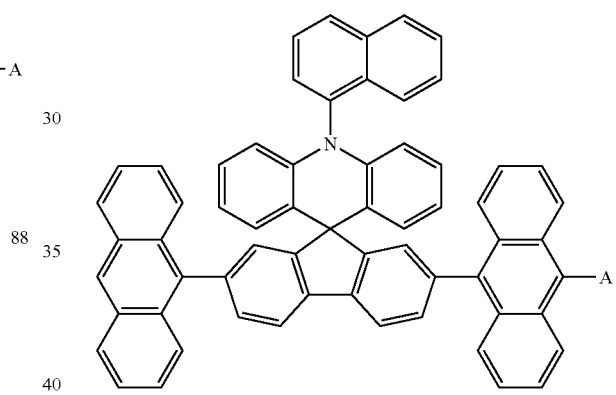
92
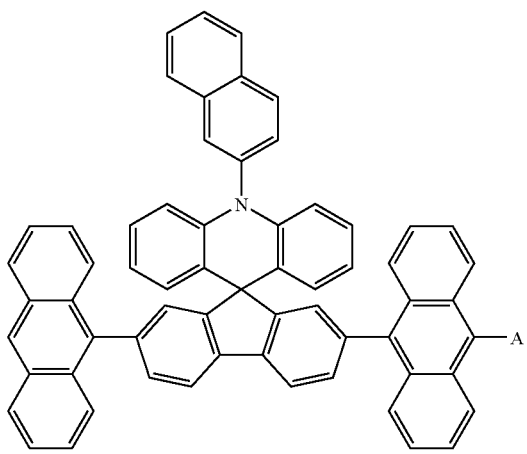

-continued
93
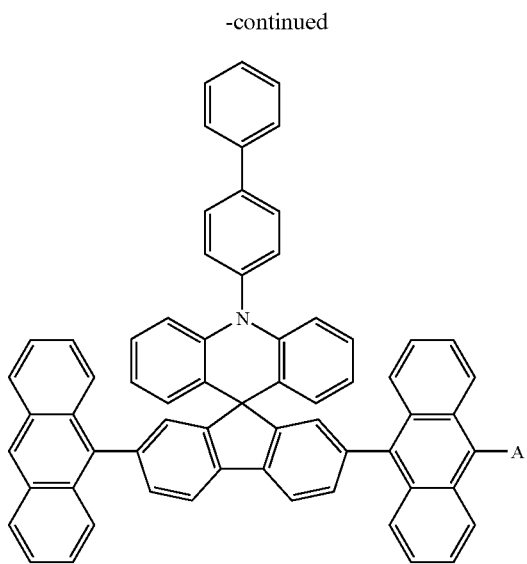
94
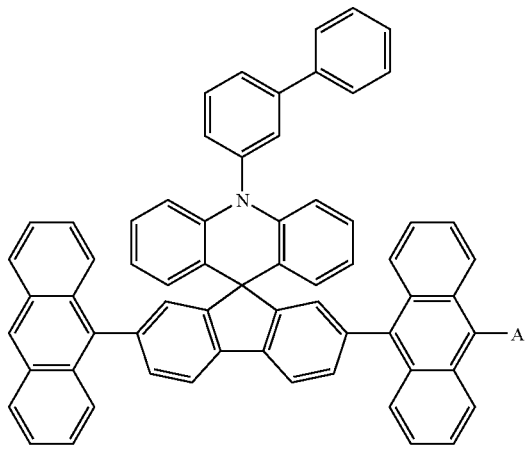
95
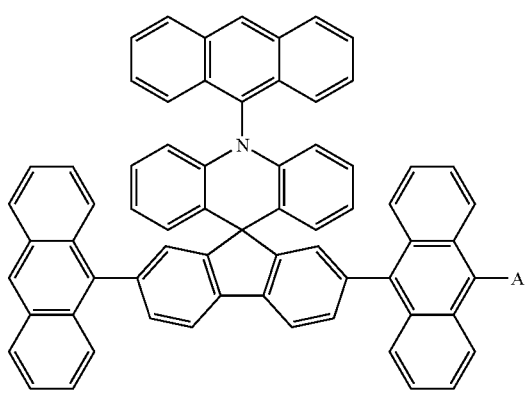
-continued
96
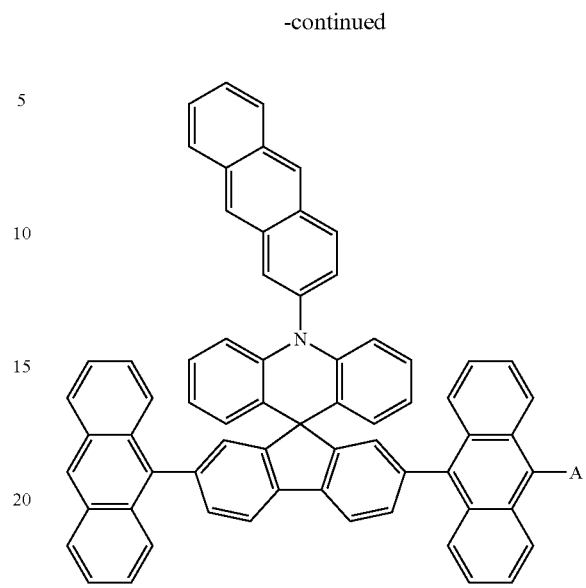
97
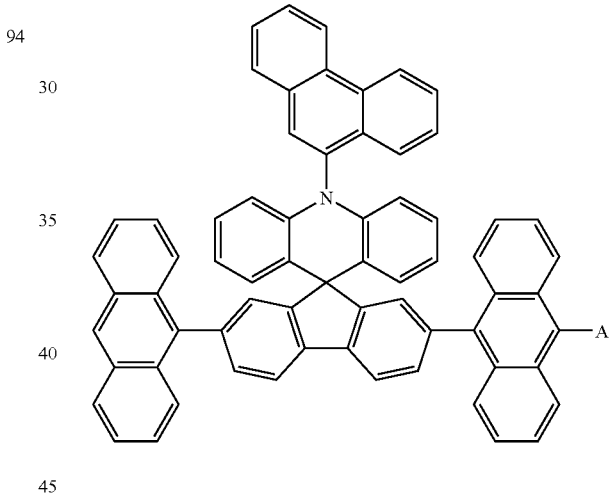
98
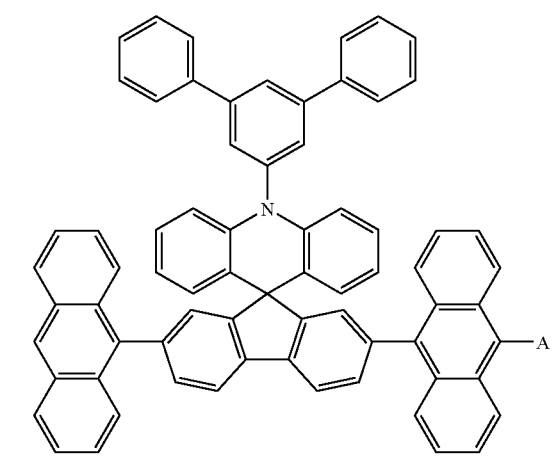

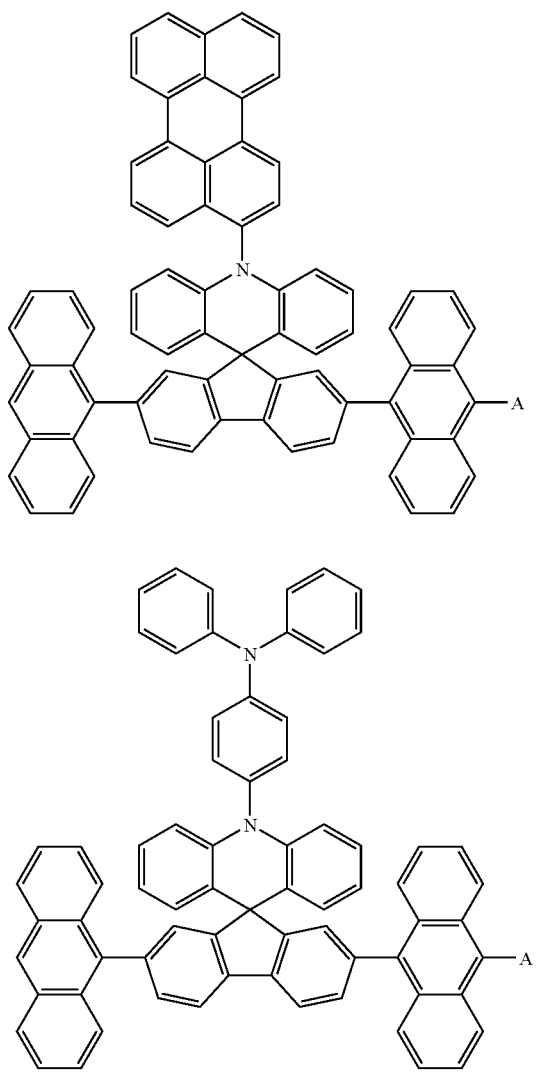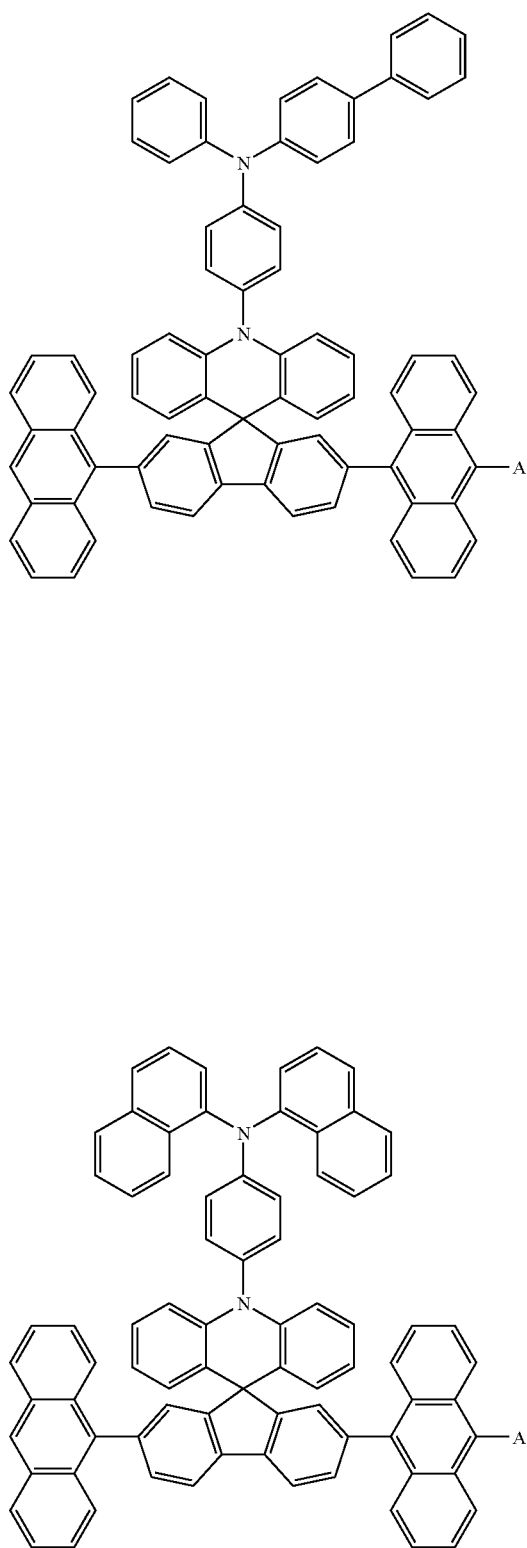

104
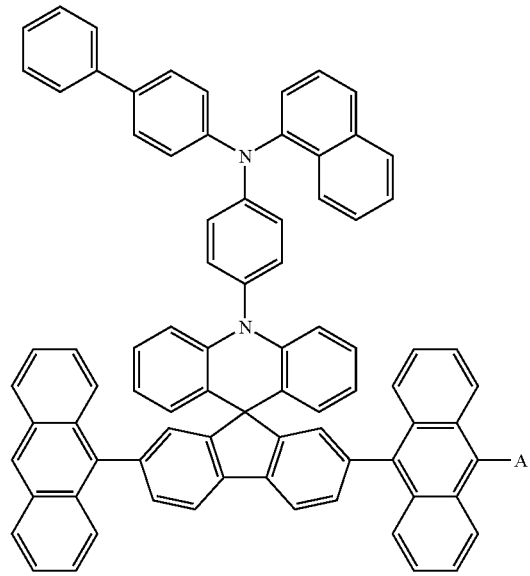
105
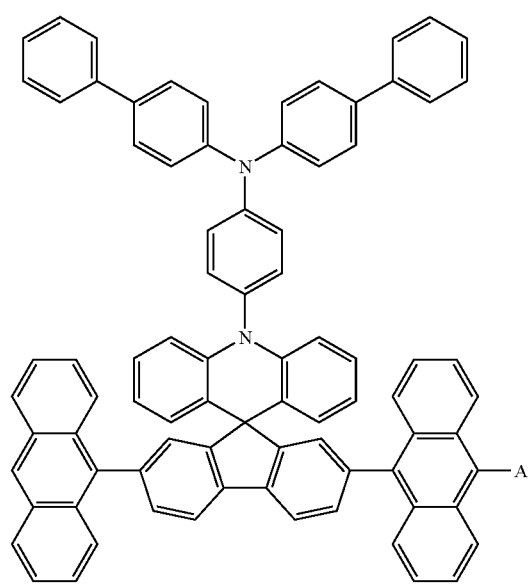
106
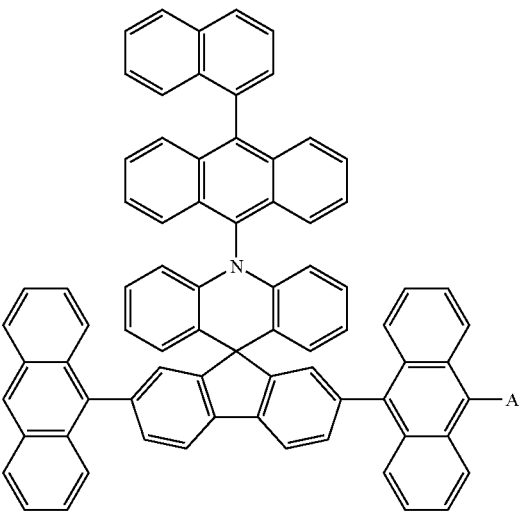
107
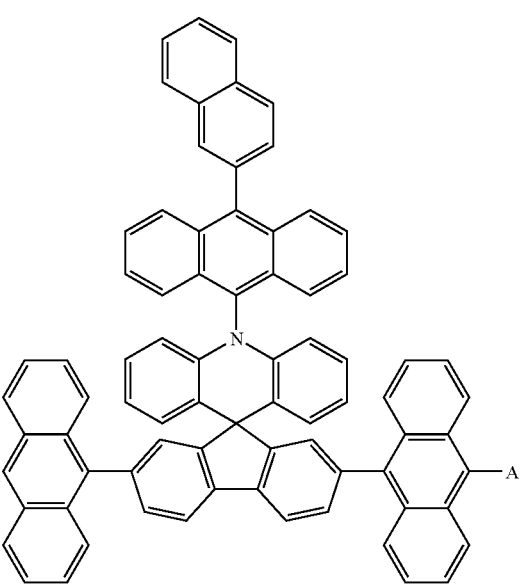

-continued
108
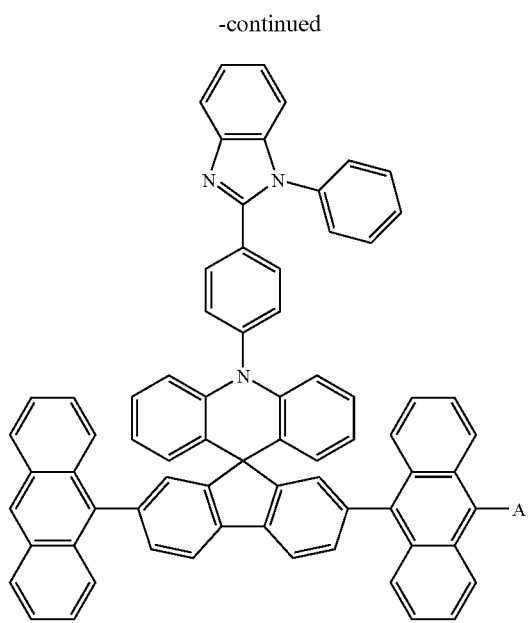
109
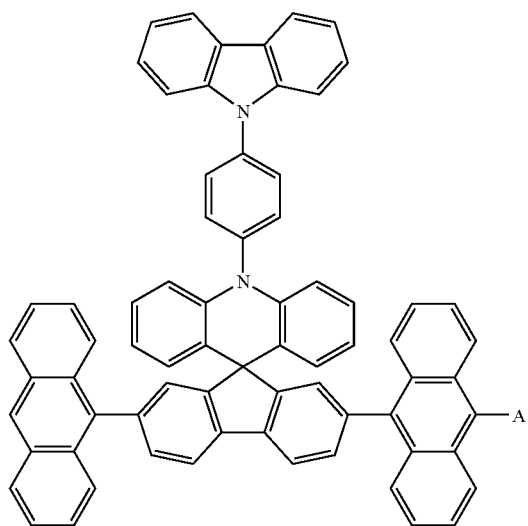
110
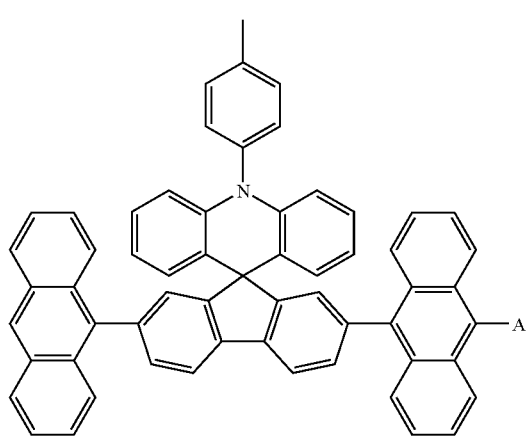
-continued
111
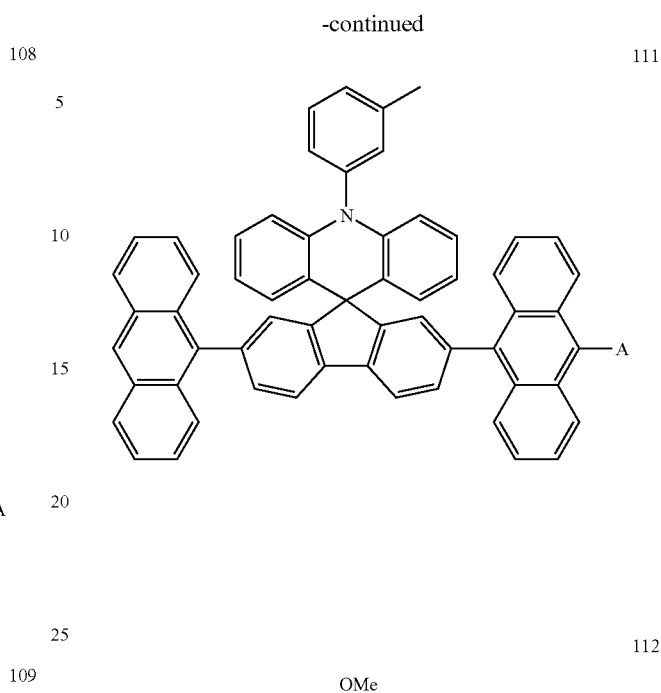
112
113
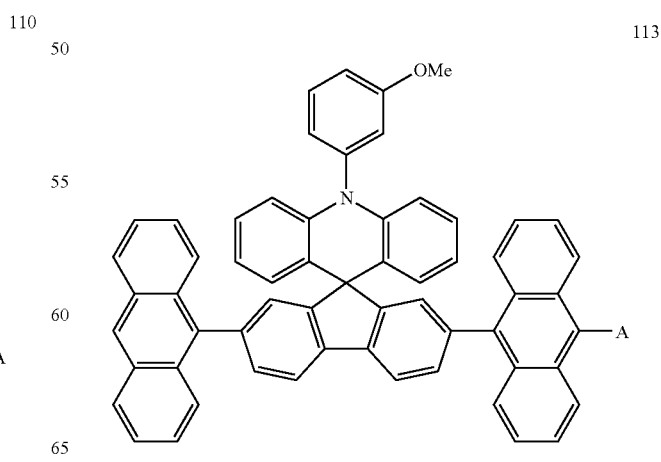

114
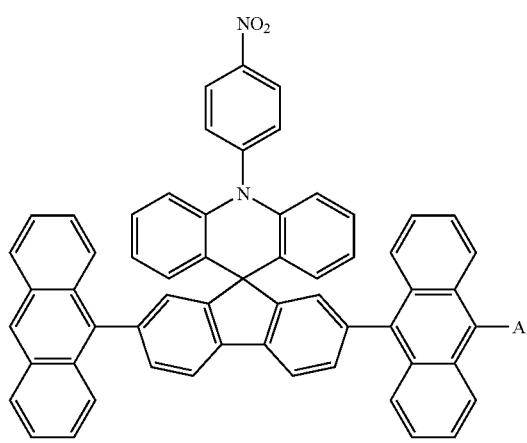

115
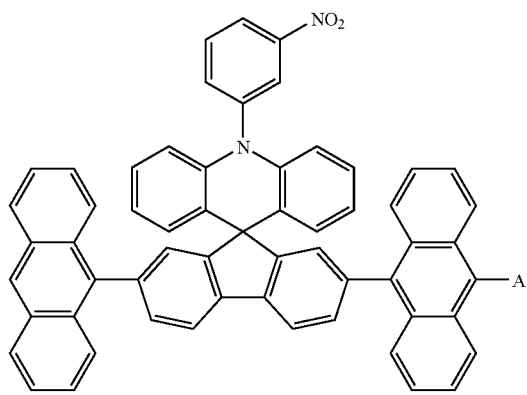

116
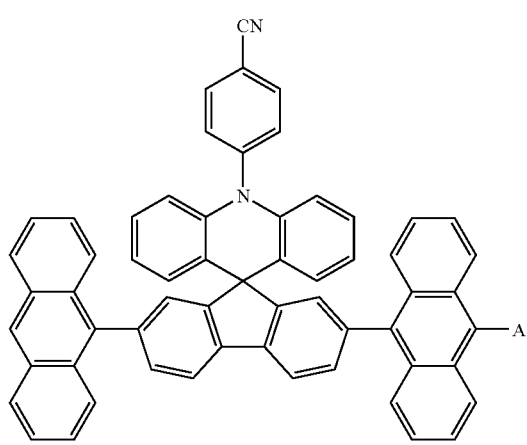

117
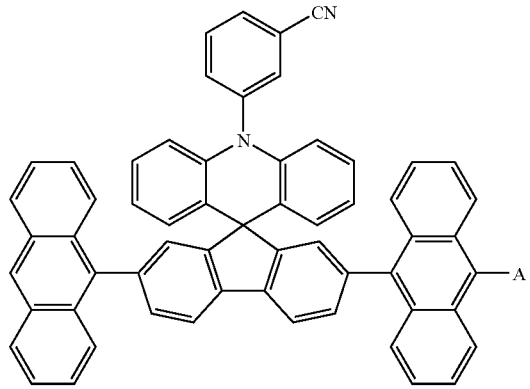

118
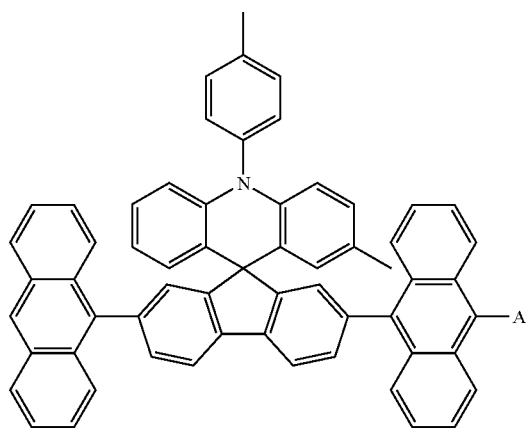

119
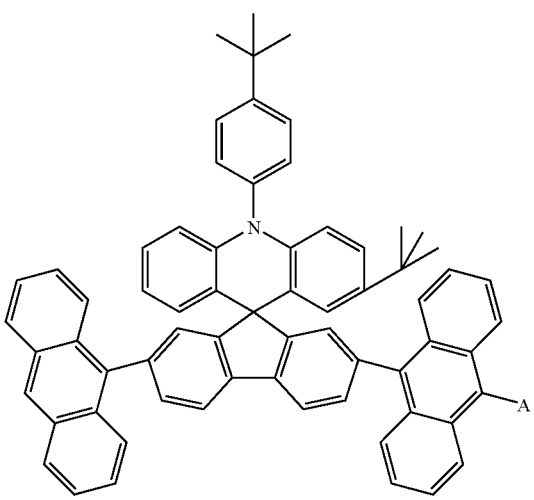

In the above Formulae, A is as defined in Formula 1.

Illustrative, but non-limiting, examples of A are as follows. Combination of the compounds of Formulae 2 to 119 and the following substituent group A can form various derivative compounds. For example, if the compound of Formula 2 is combined with the substituent group 1, the resulting product will be designated by the compound of Formula 2-1.

[A Group]
1
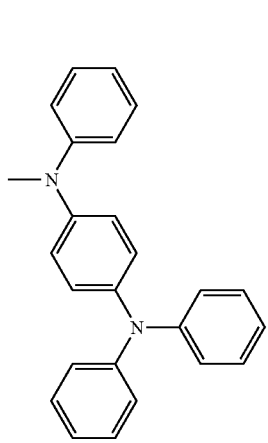
2
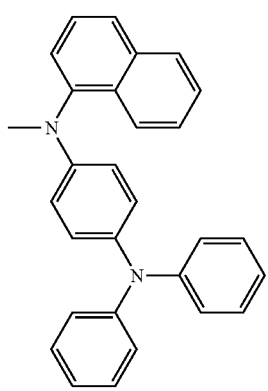
3
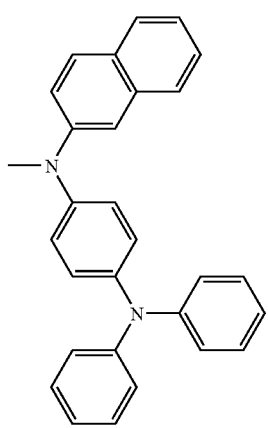
-continued
4
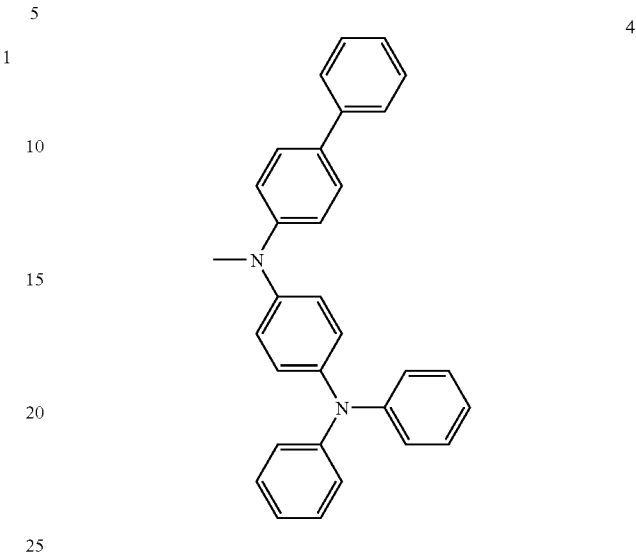
5
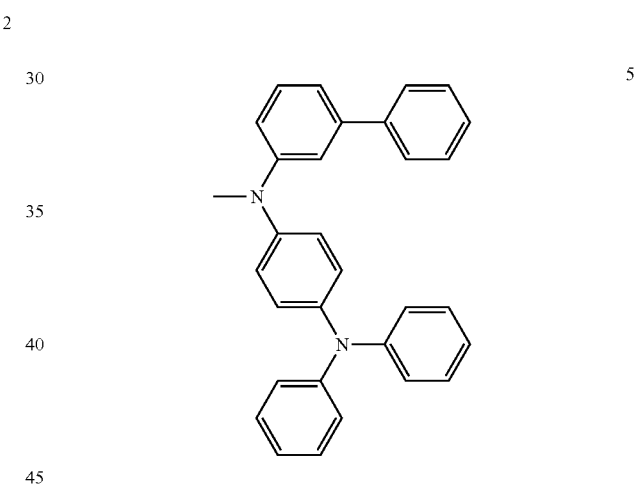
6
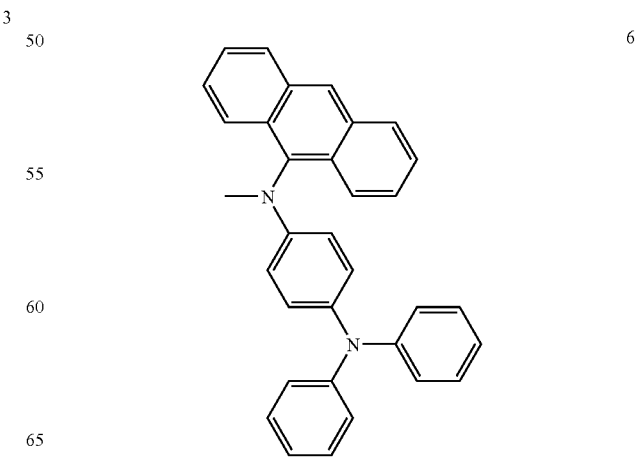

-continued
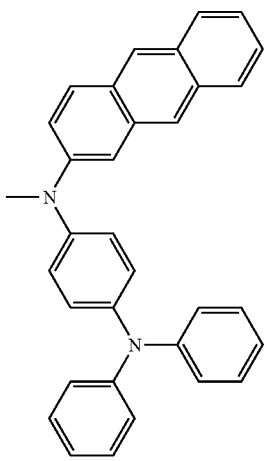
7
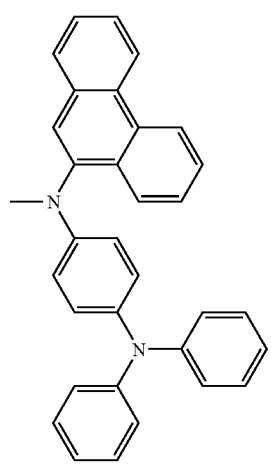
8
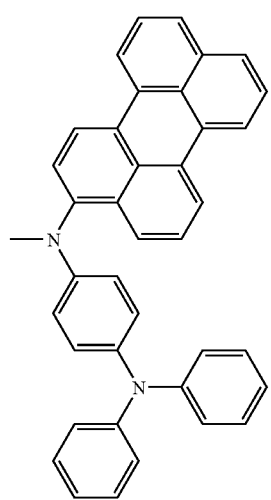
9
-continued
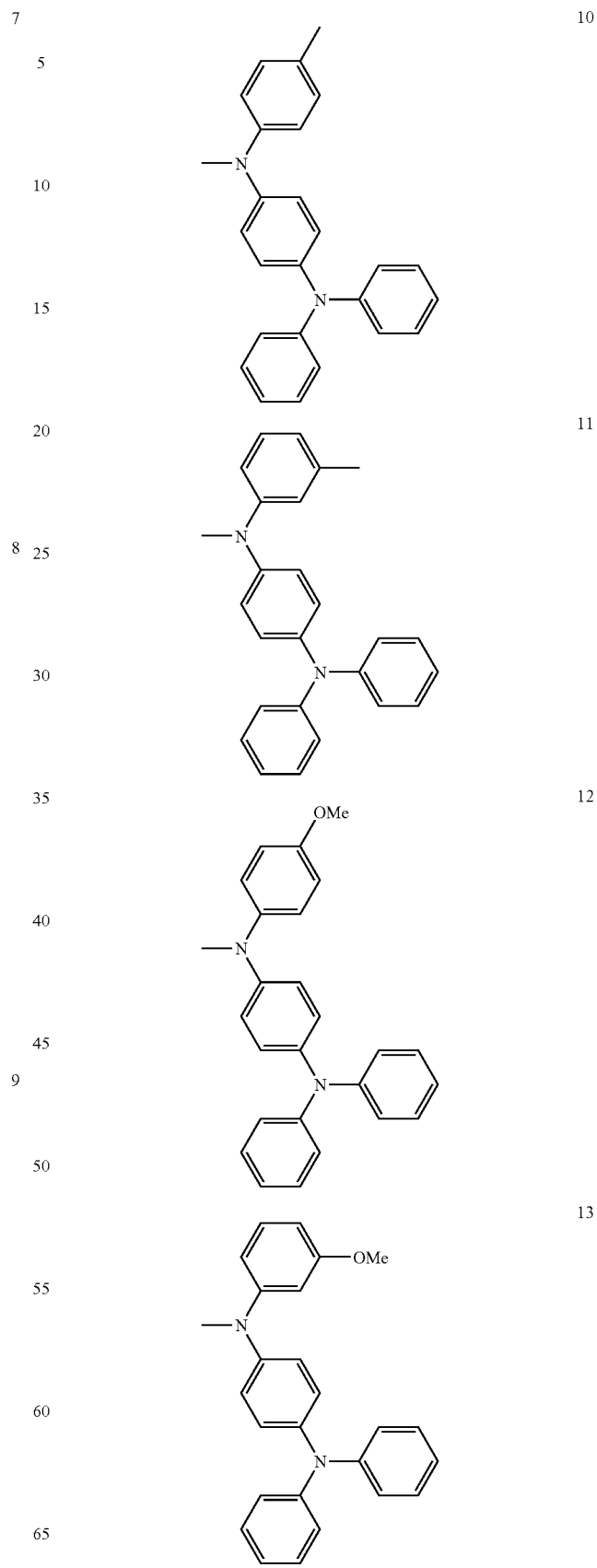

-continued
14
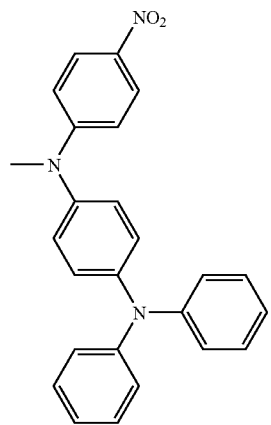
15
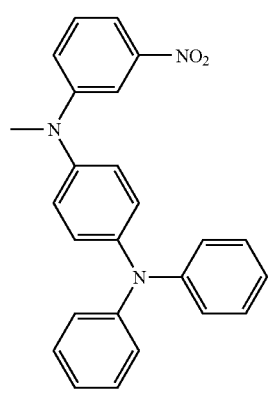
16
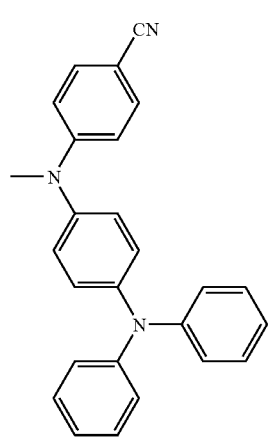
17
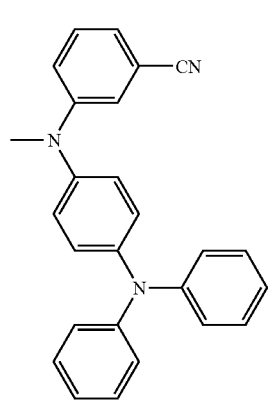
-continued
18
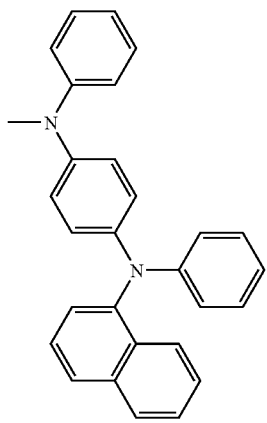
19
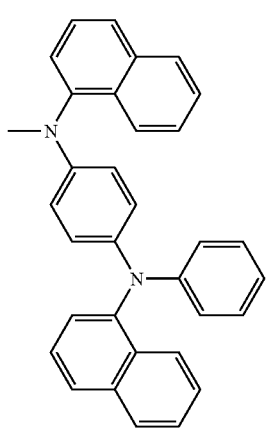
20
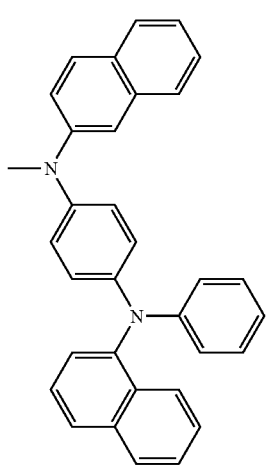

-continued
21
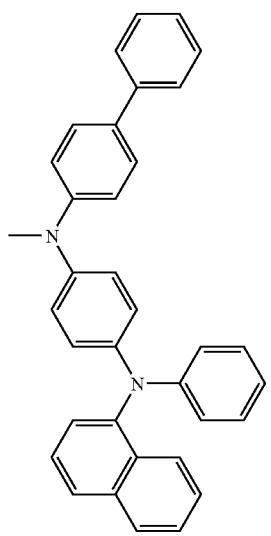
22
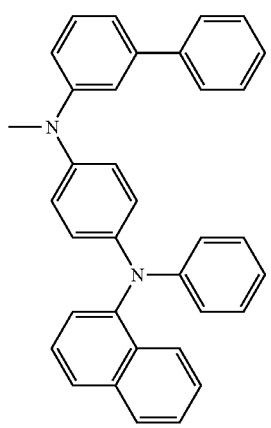
23
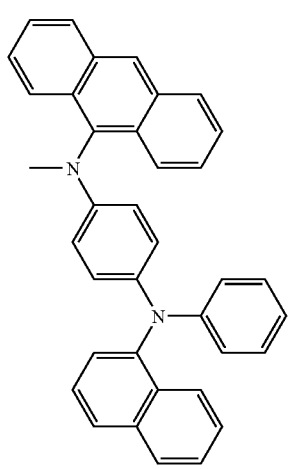
-continued
24
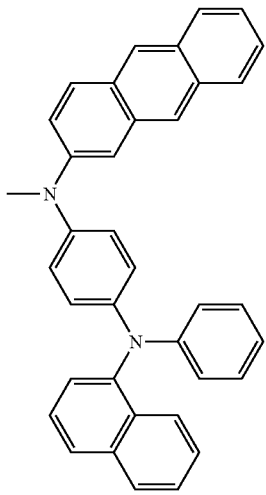
25
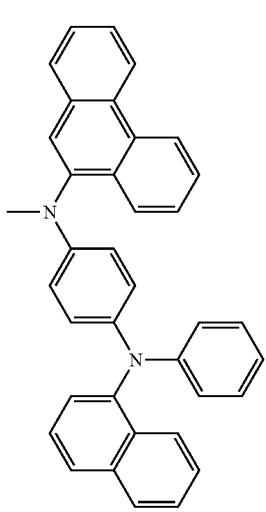
26
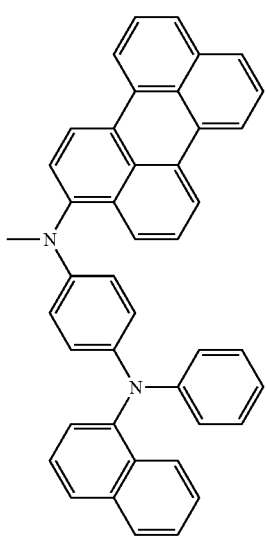

27
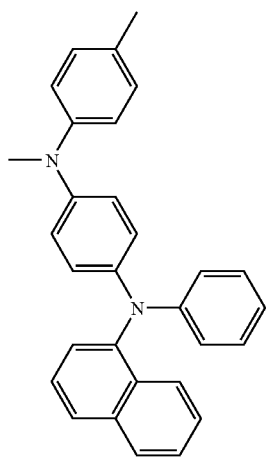
28
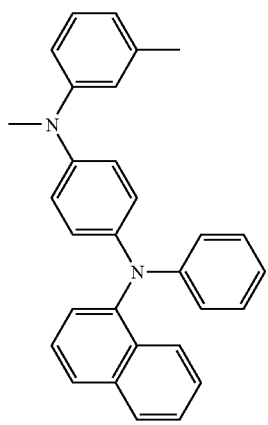
29
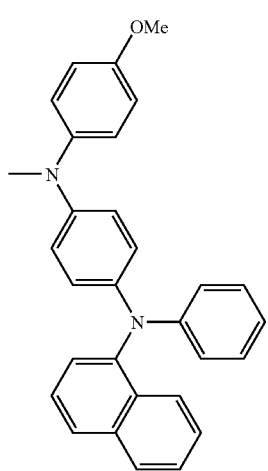
30
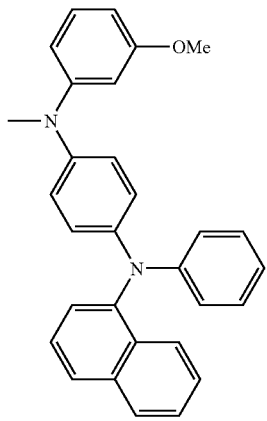
31
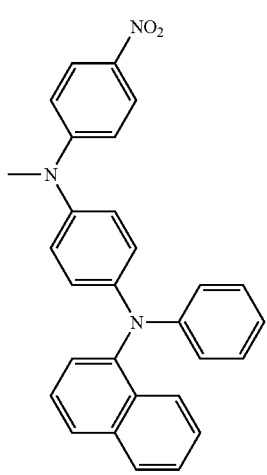
32
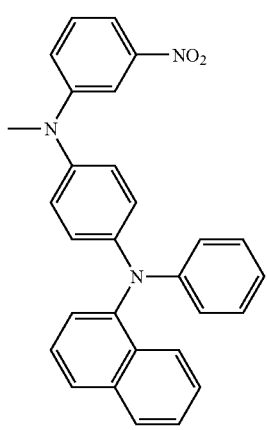

-continued
33
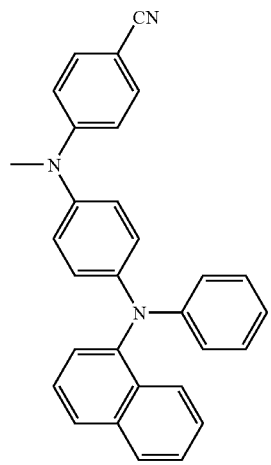
34
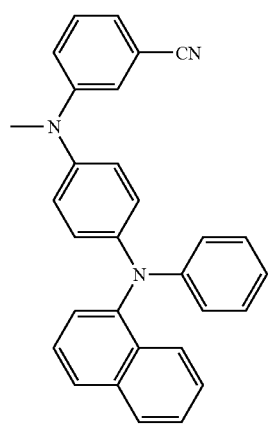
35
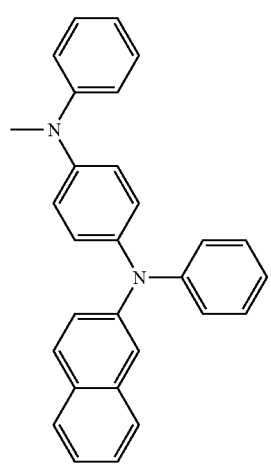
-continued
36
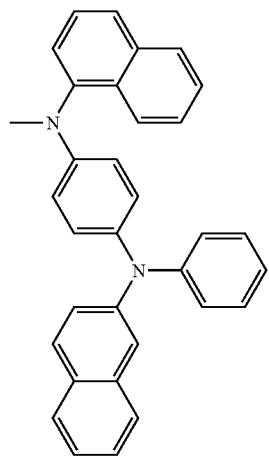
37
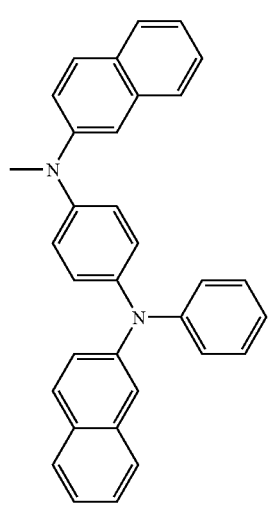
38
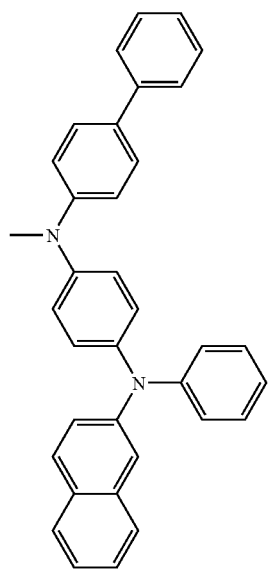

39
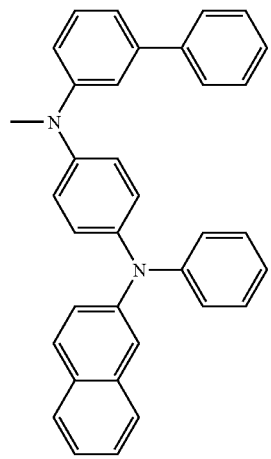
40
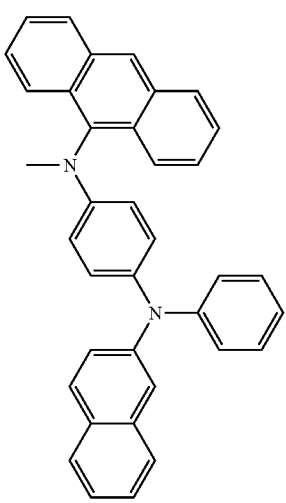
41
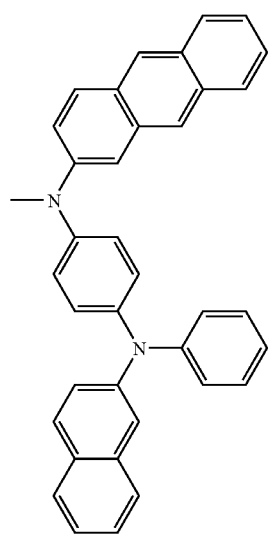
42
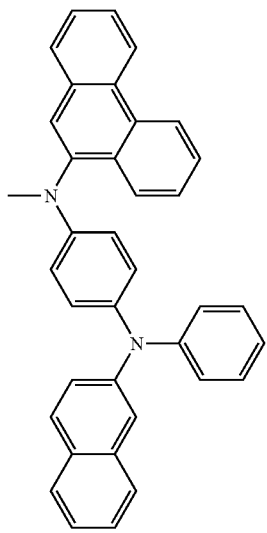
43
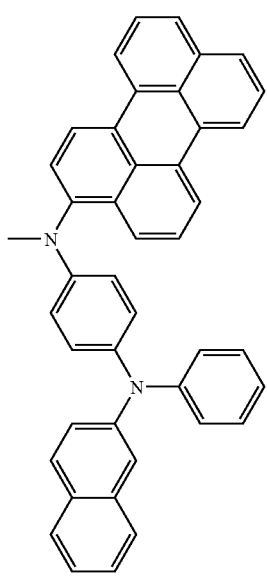
44

-continued
45
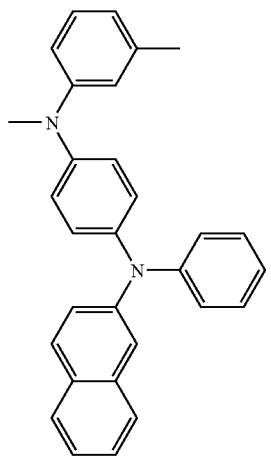
46
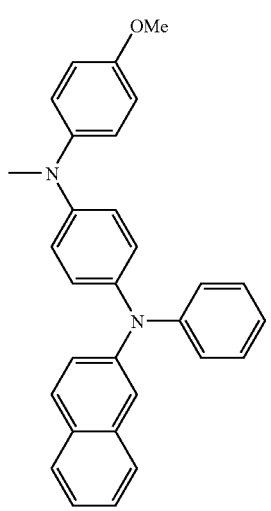
47
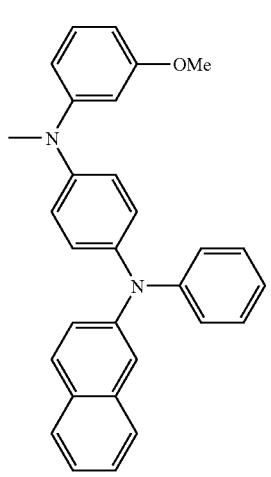
-continued
48
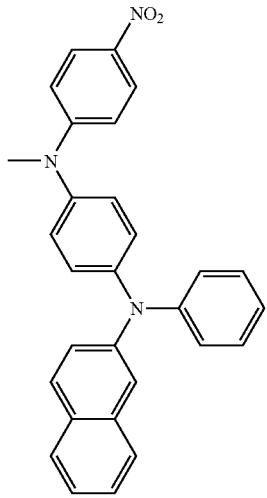
49
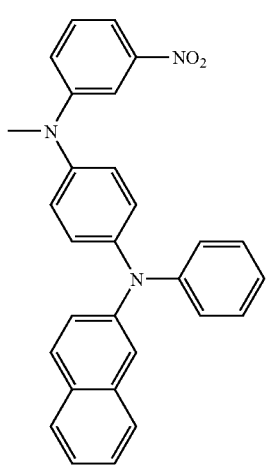
50
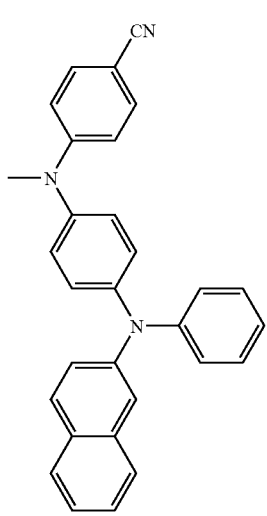

-continued
51 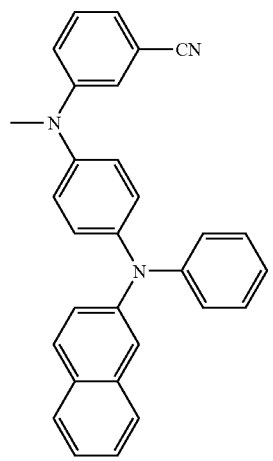
52 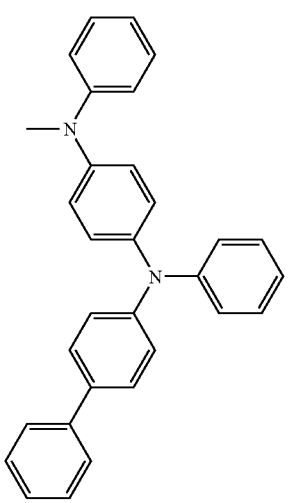
53 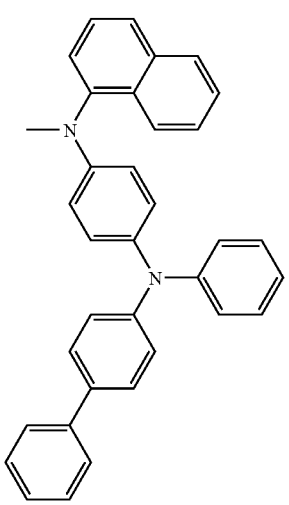
54 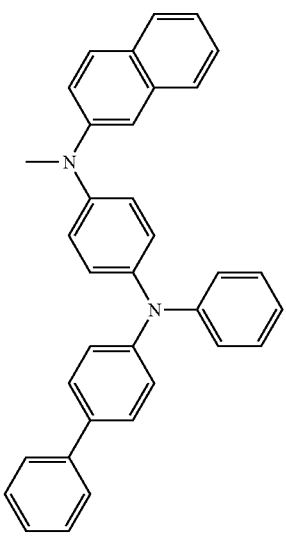
55 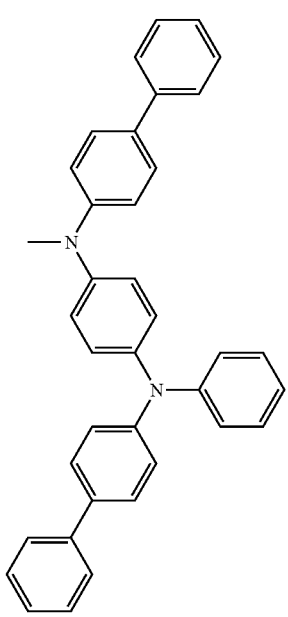
56 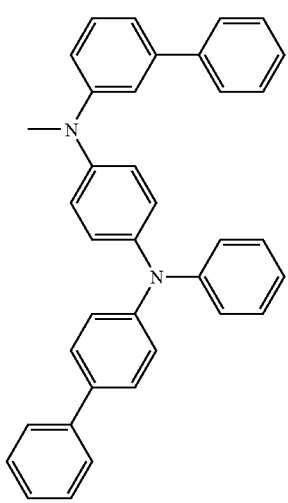

-continued
57
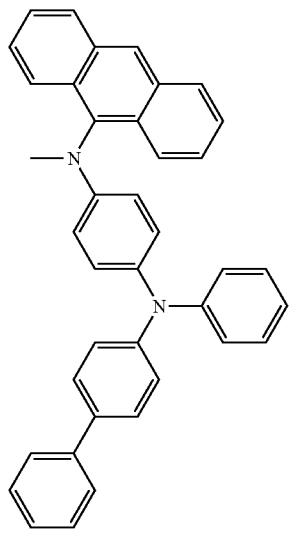
58
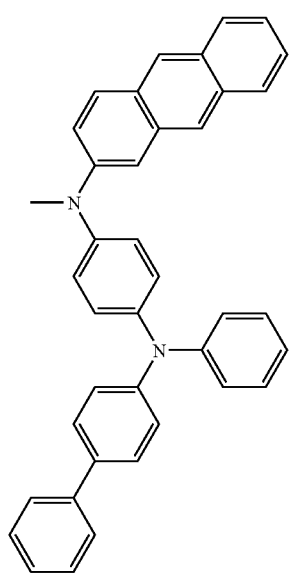
-continued
59
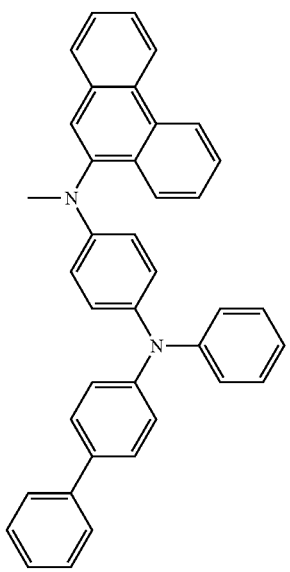
60
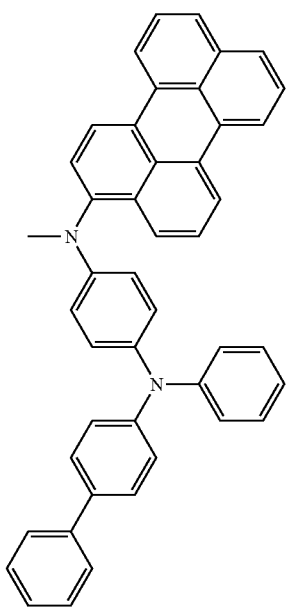

-continued
61
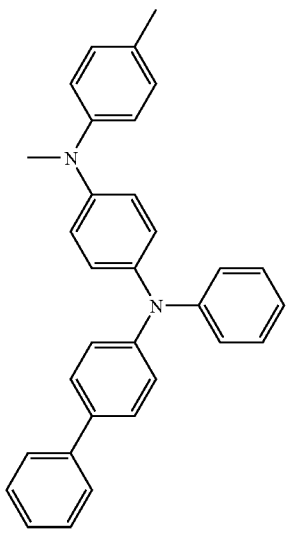
62
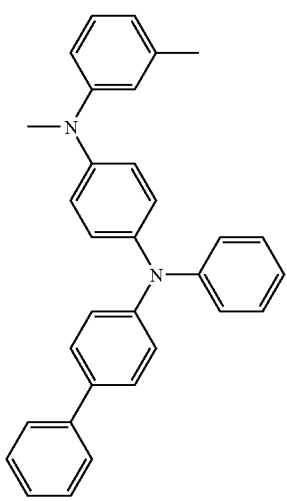
63
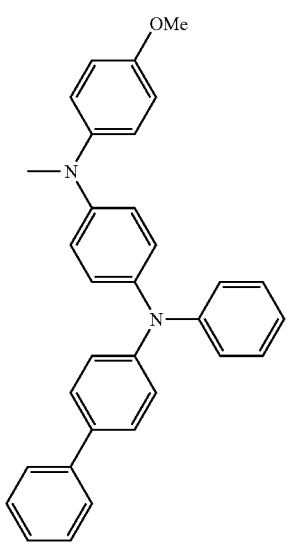
-continued
64
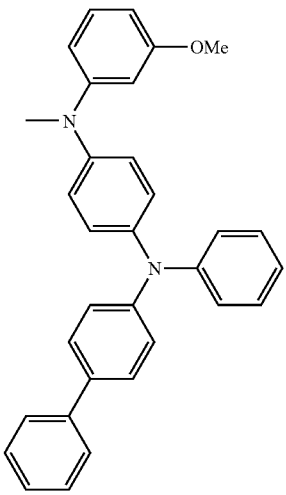
65
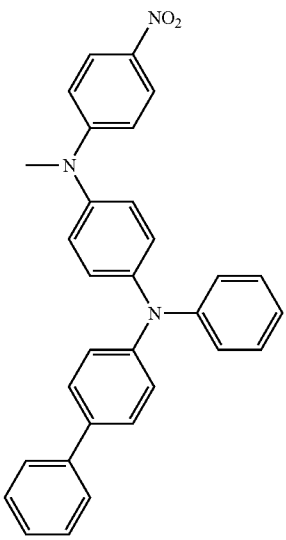
66
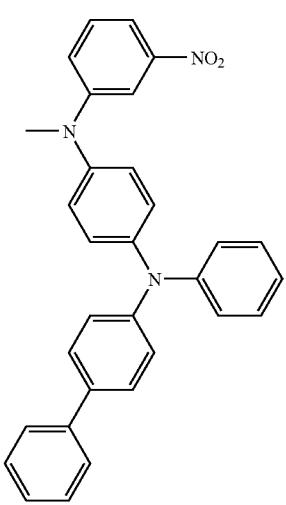

-continued
67
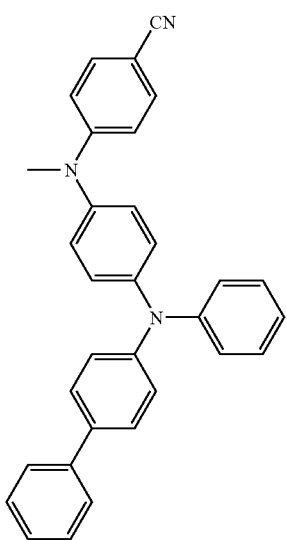
68
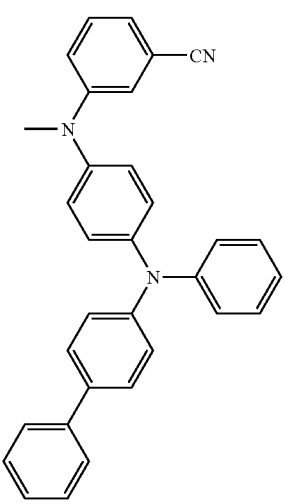
69
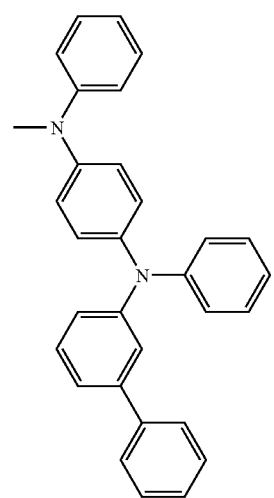
-continued
70
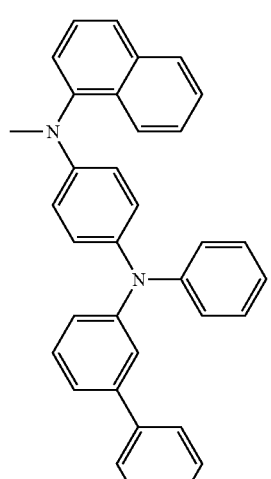
71
72

-continued
73
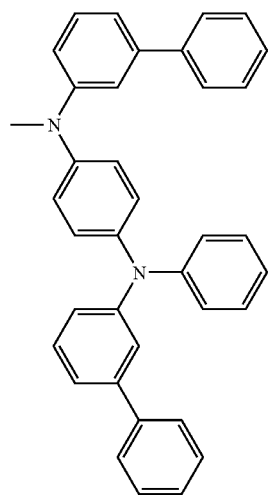
74
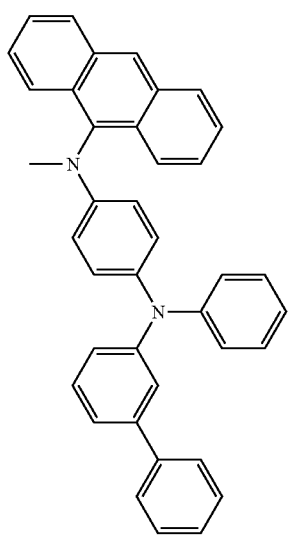
75
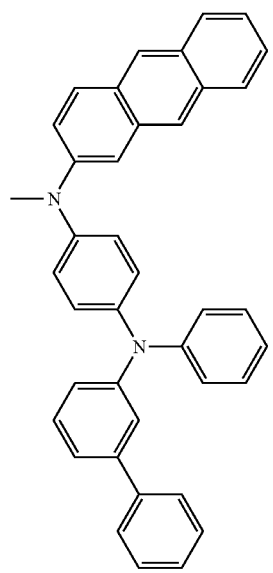
-continued
76
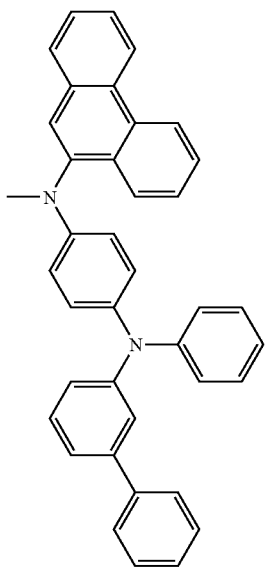
77
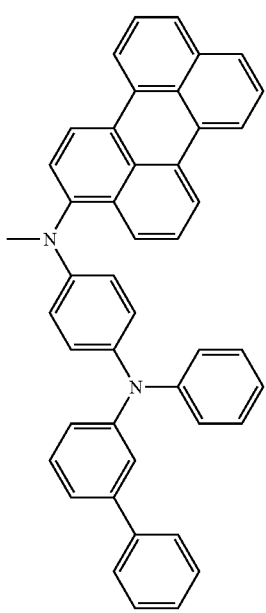

78
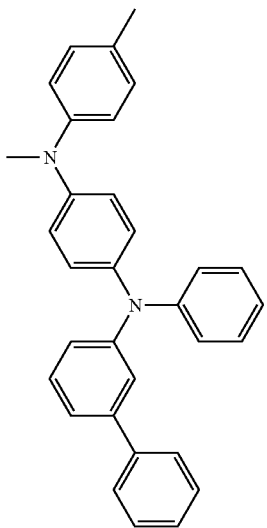
79
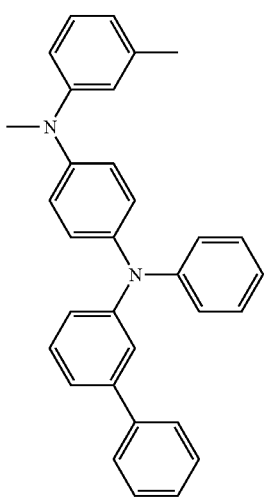
80
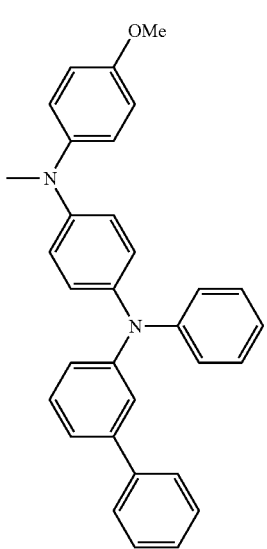
81
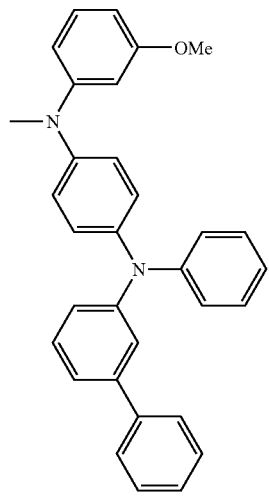
82
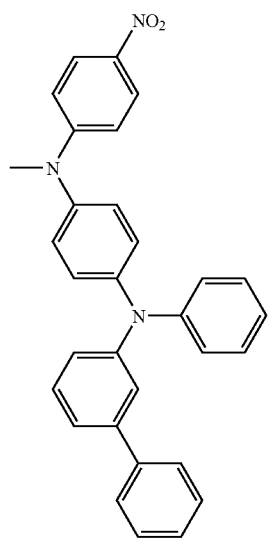
83
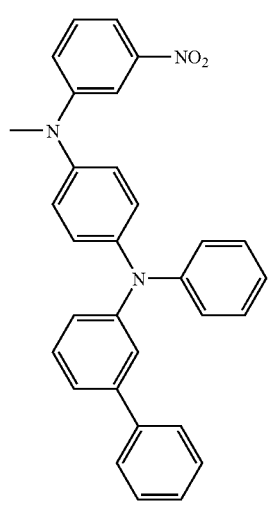

84
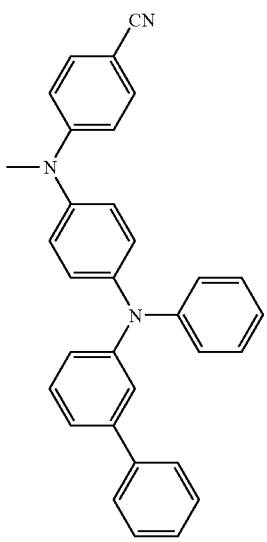
85
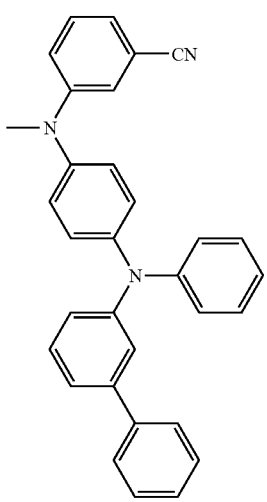
86
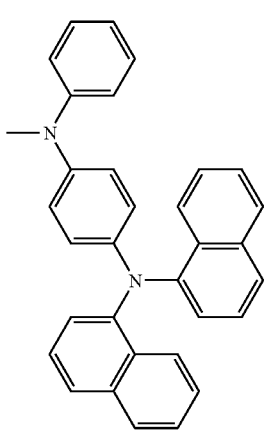
87
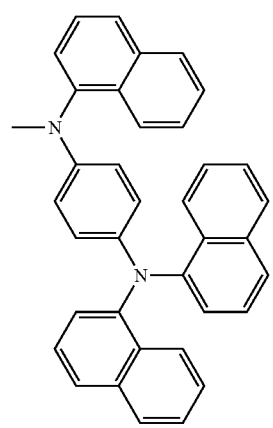
88
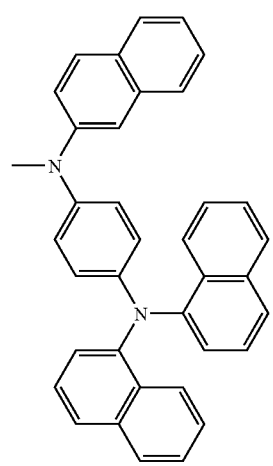
89
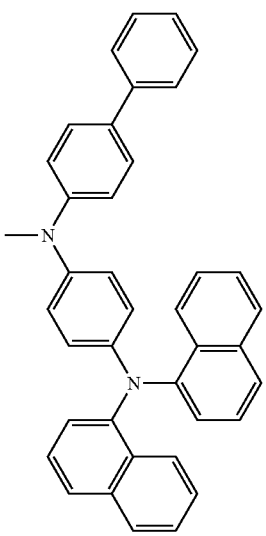

90
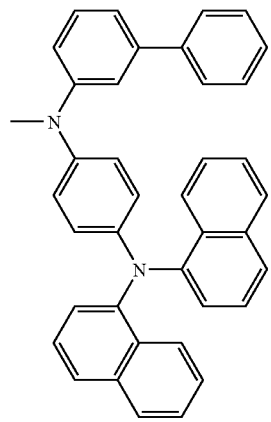
91
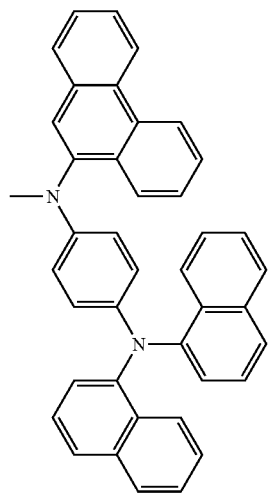
93
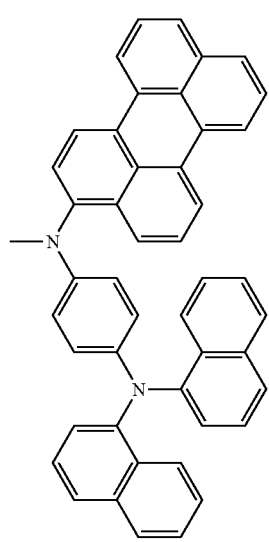
94
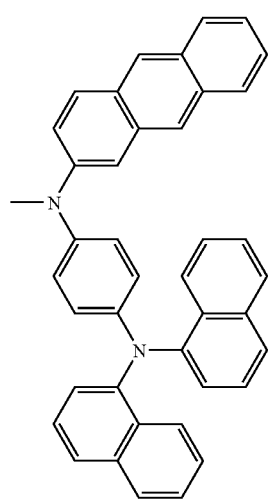
92
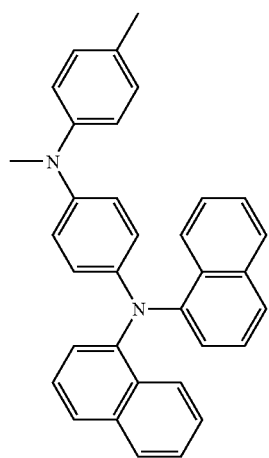
95

96 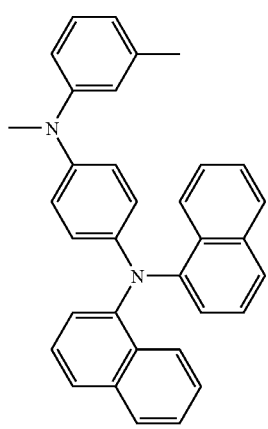
97 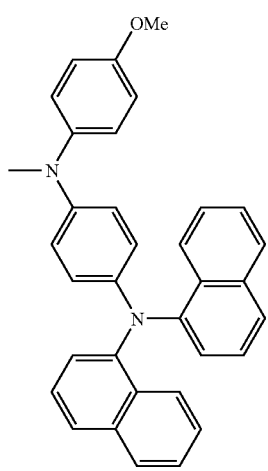
98 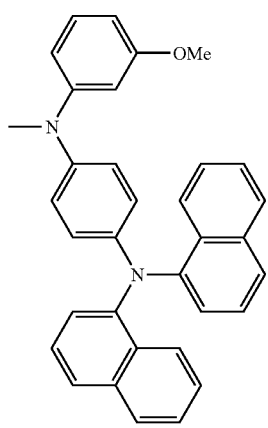
99 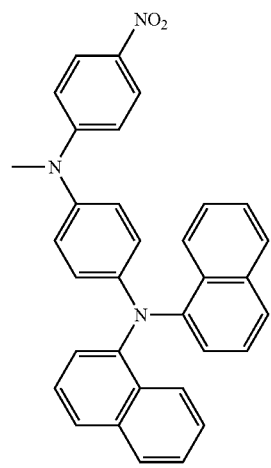
100 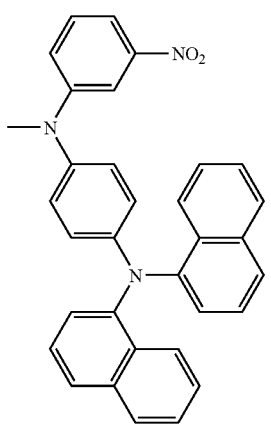
101 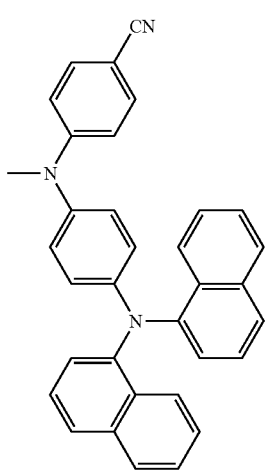

-continued
102
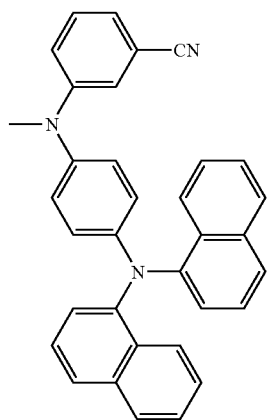
103
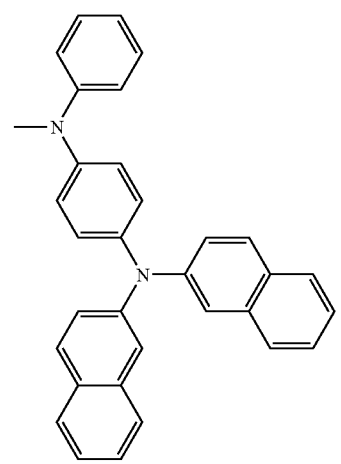
104
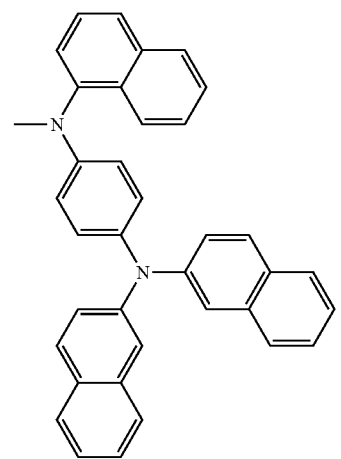
-continued
105
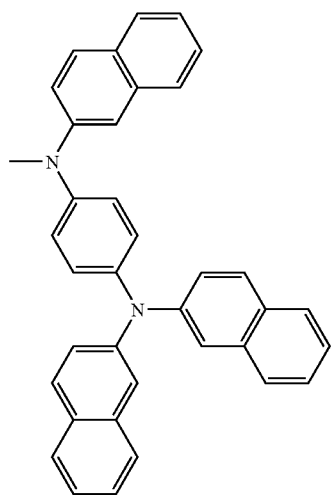
106
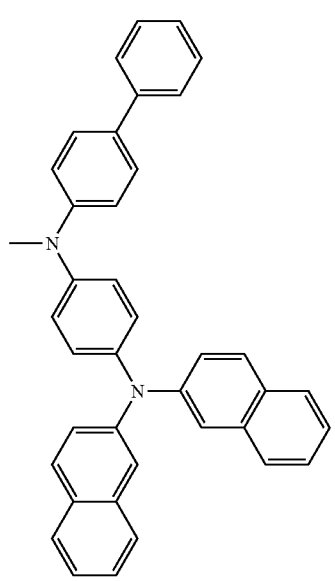
107
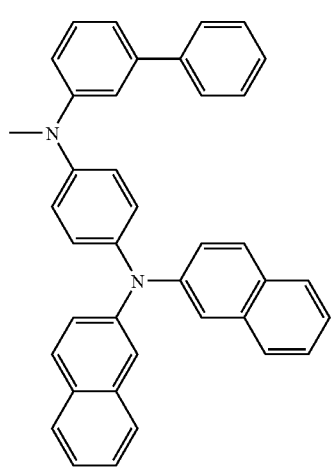

-continued
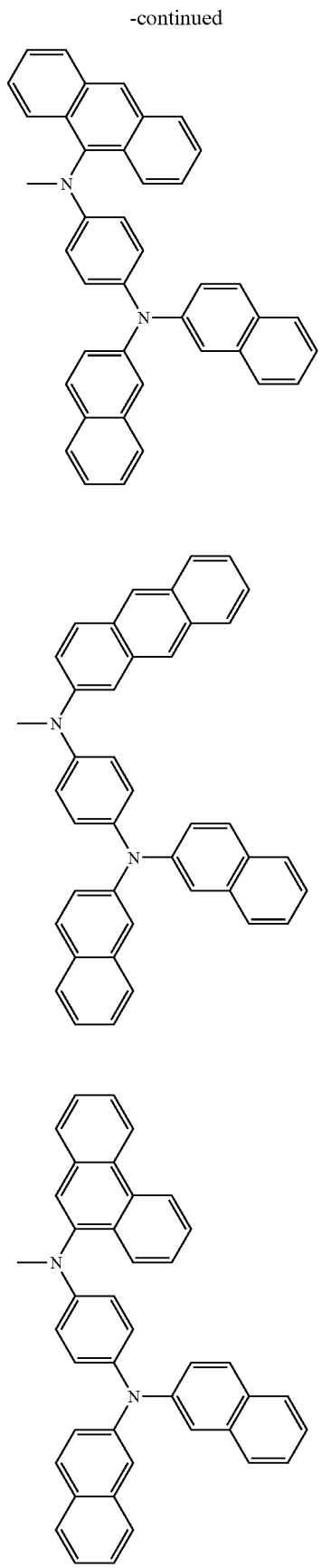
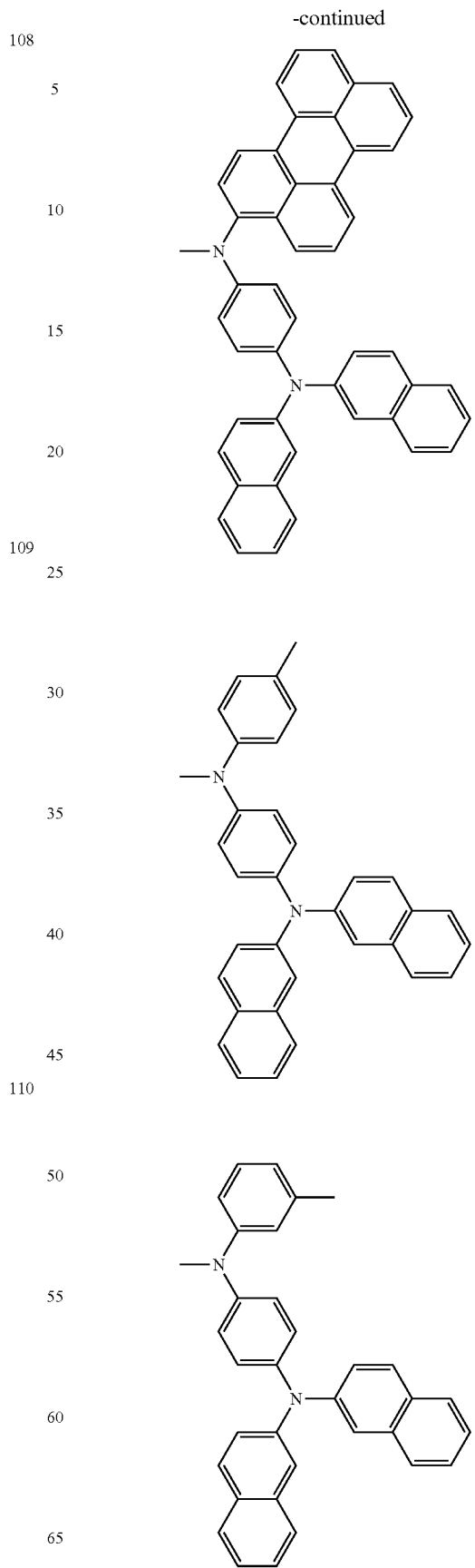

-continued
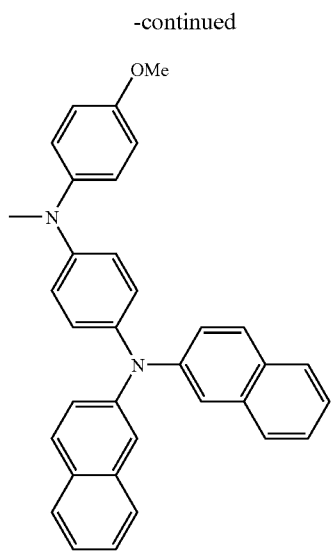
114
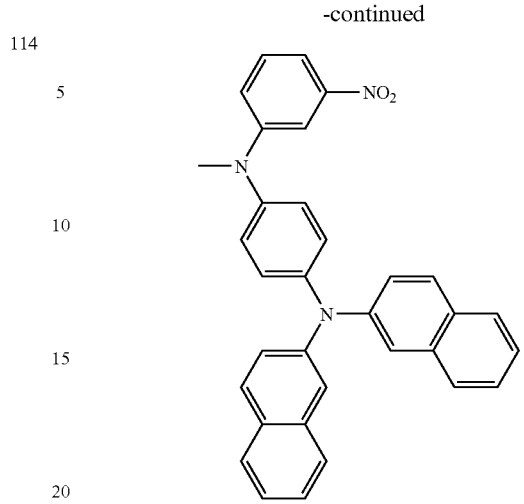
117
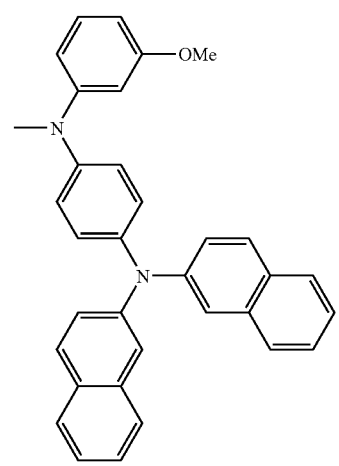
115
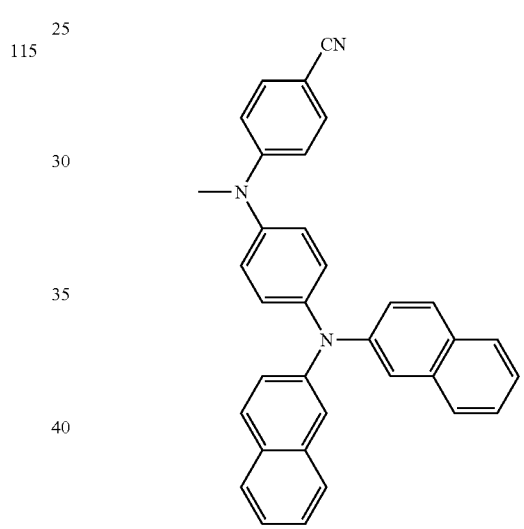
118
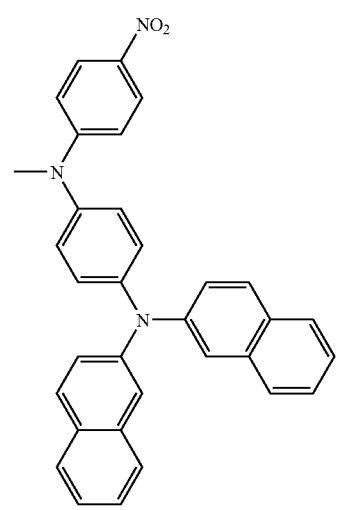
116
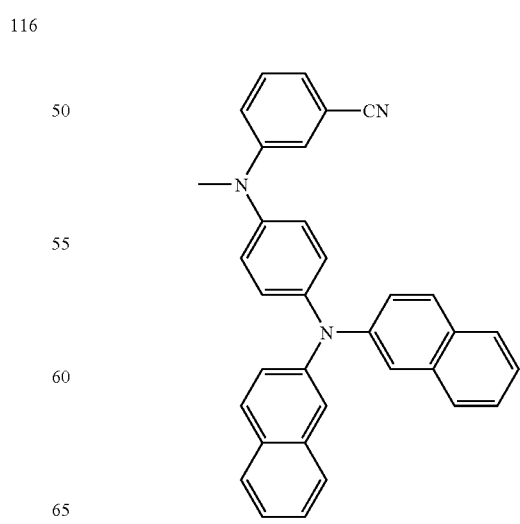
119

-continued
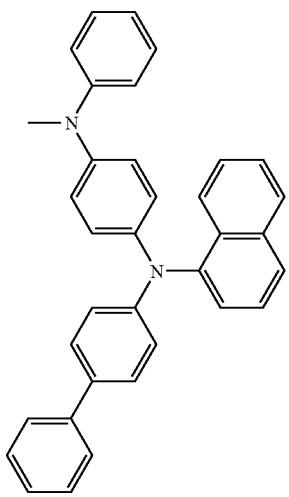
120
121
122
-continued
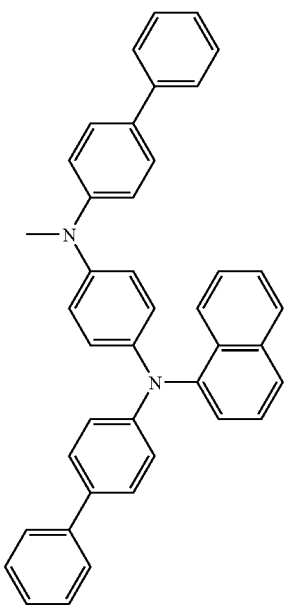
123
124
125

126
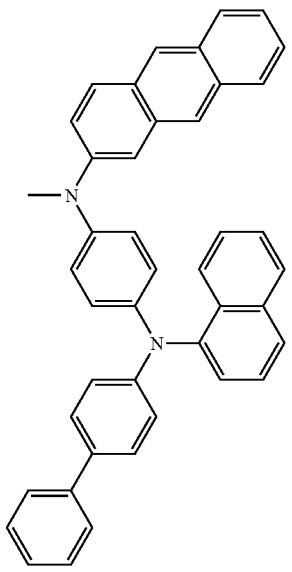
127
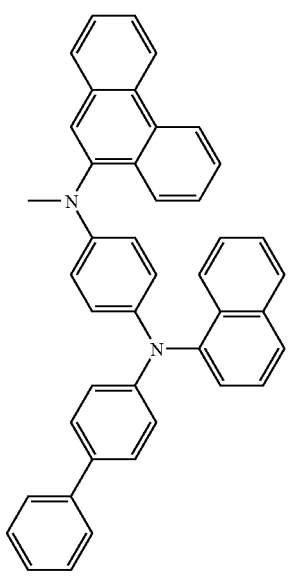
128
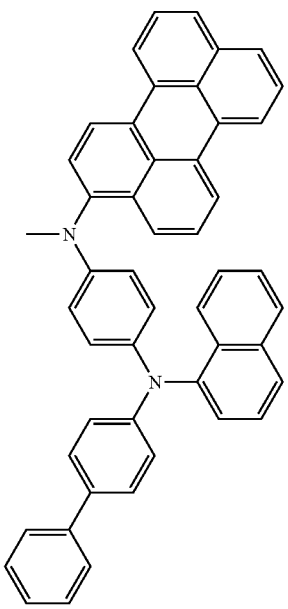
129
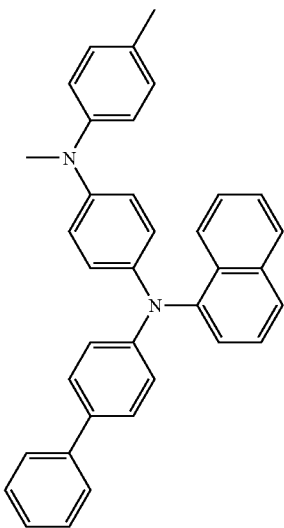
130
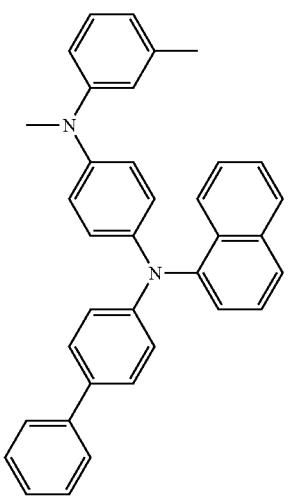

-continued
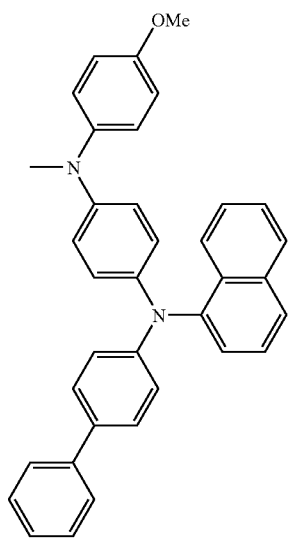
131
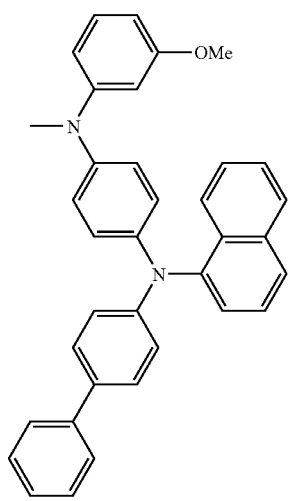
132
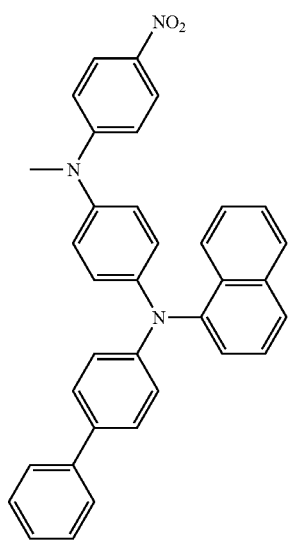
133
-continued
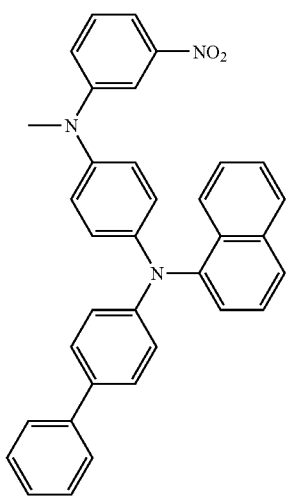
134
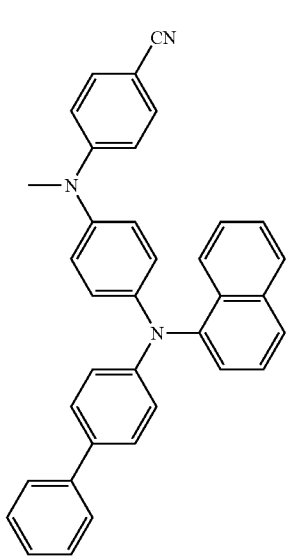
135
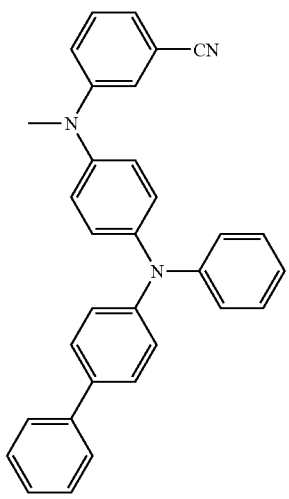
136

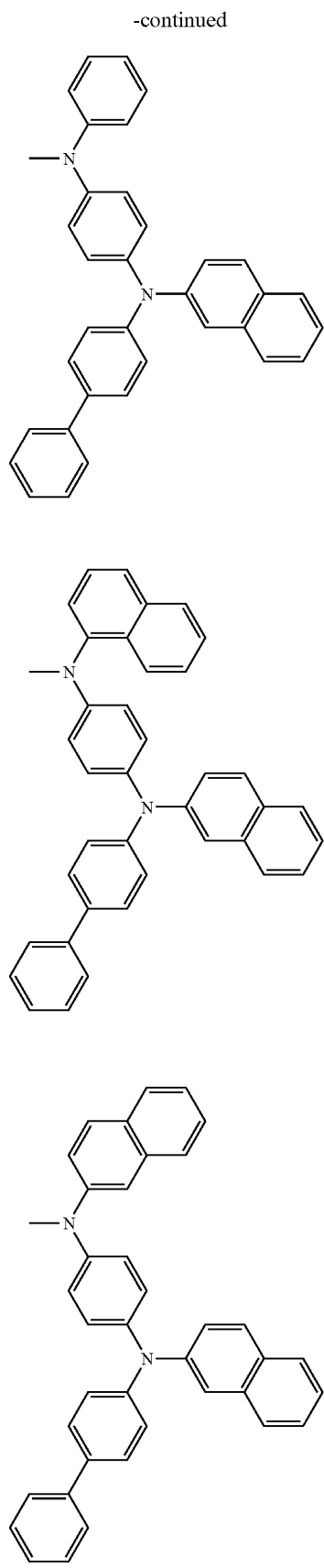
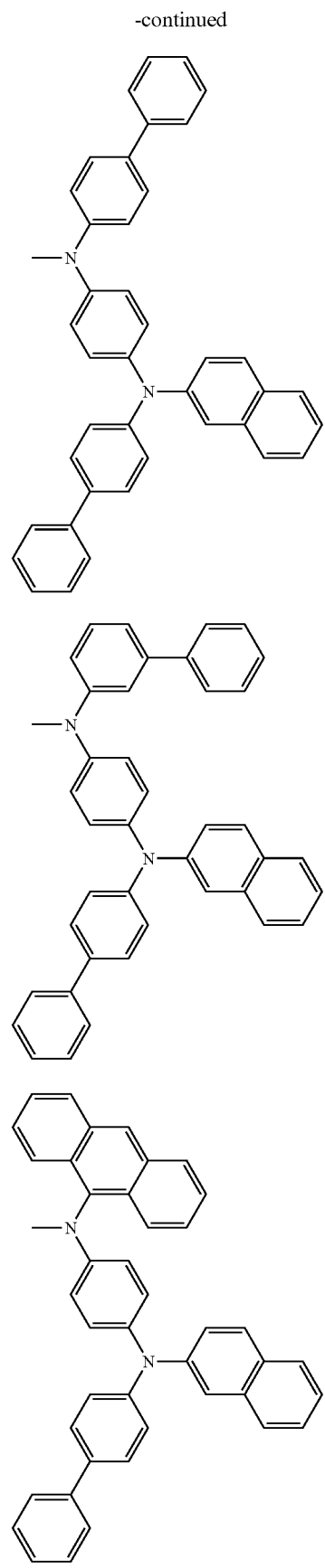

143
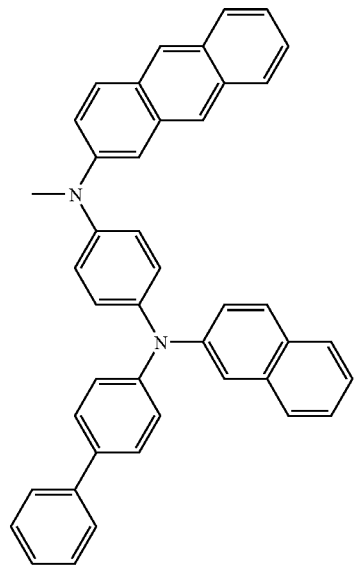
144
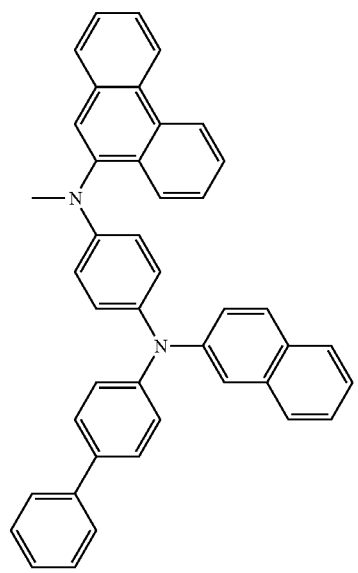
145
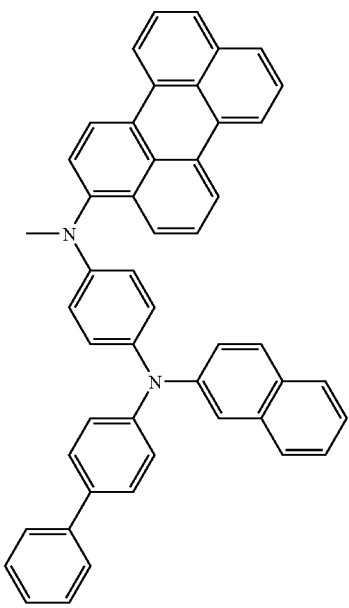
146
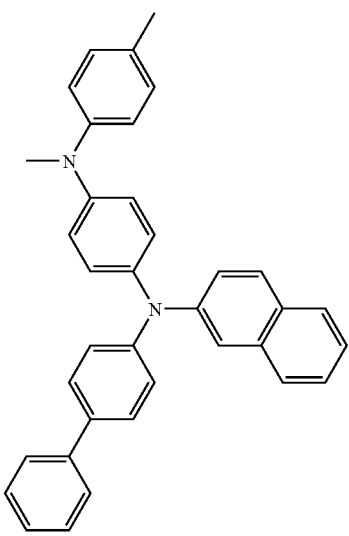
147
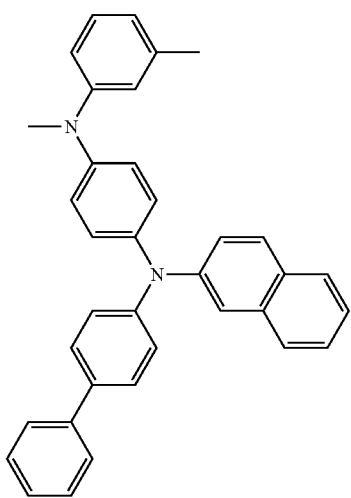

-continued
148
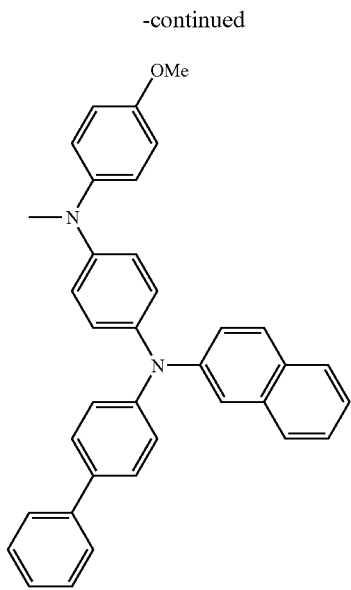
149
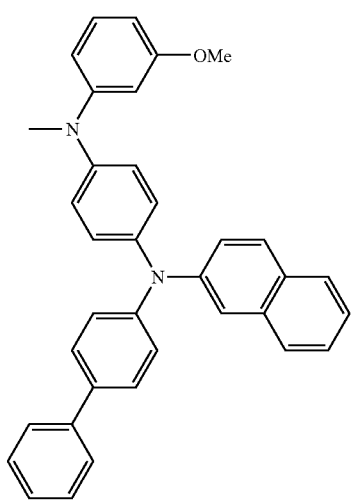
150
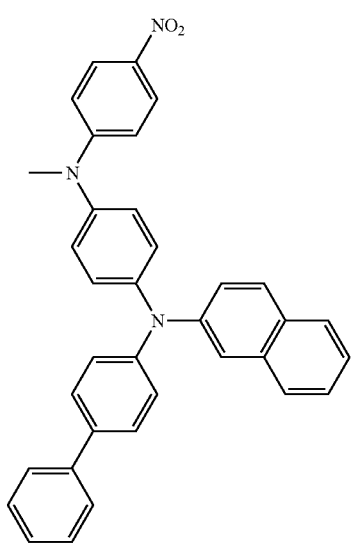
-continued
151
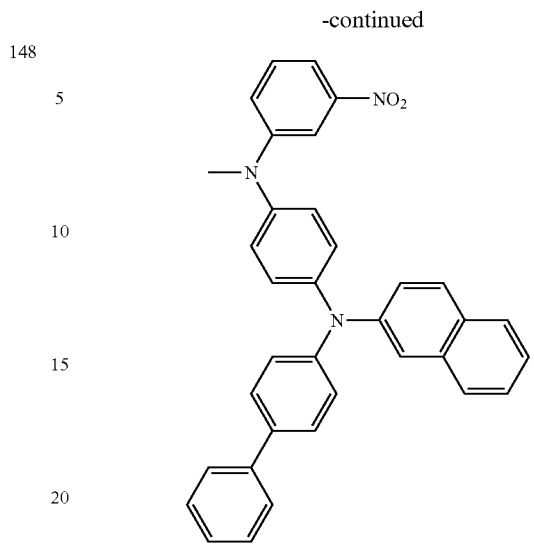
152
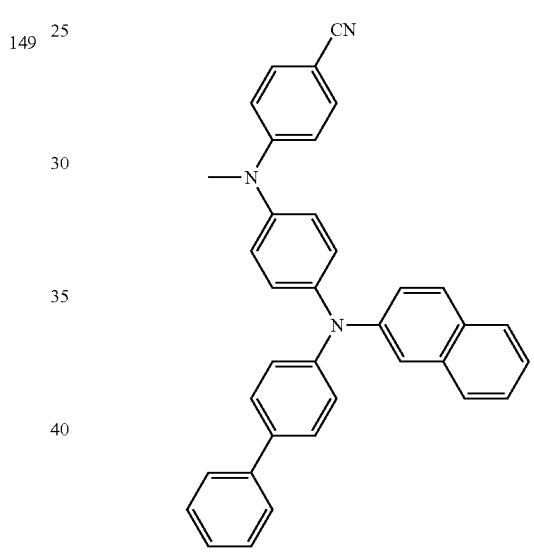
153
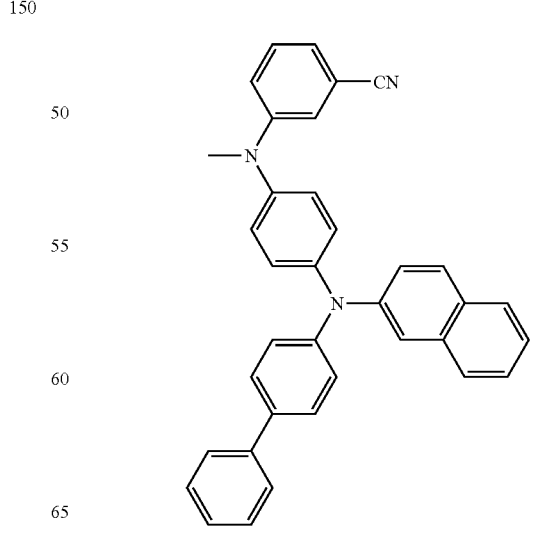

-continued
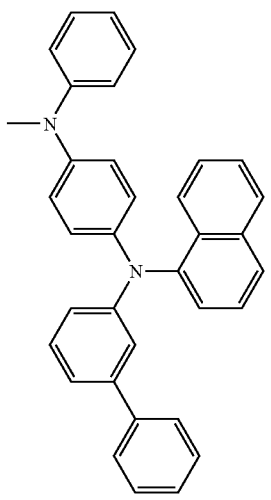
154
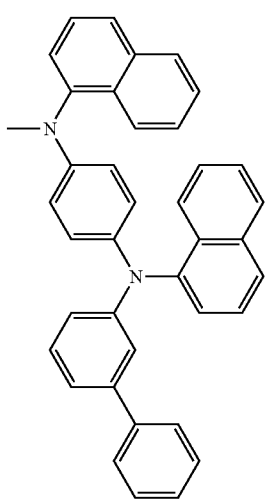
155
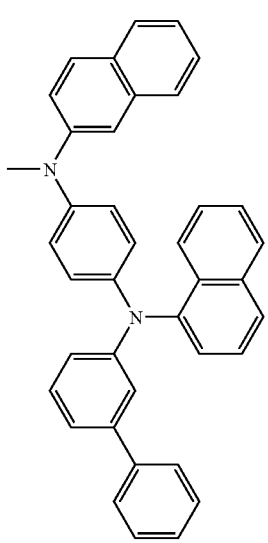
156
-continued
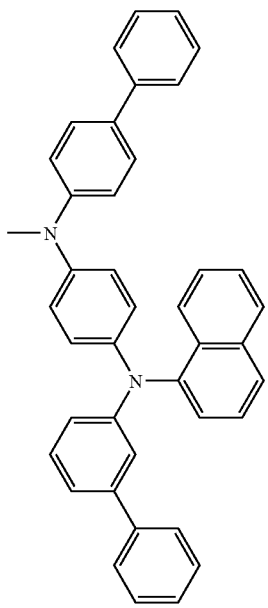
157
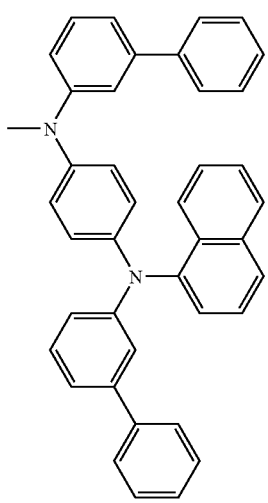
158
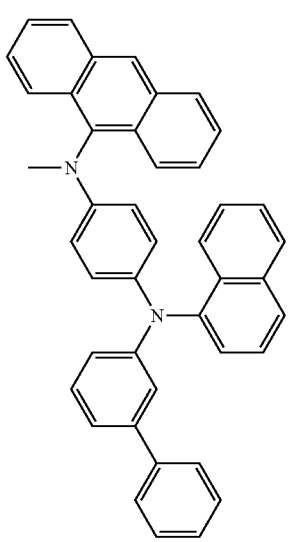
159

160
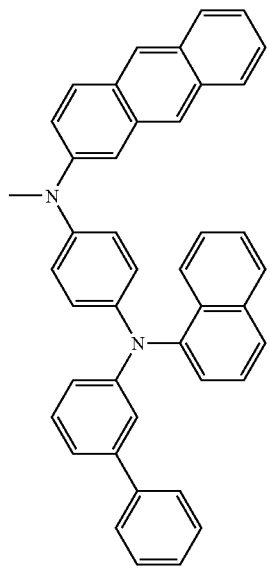
161
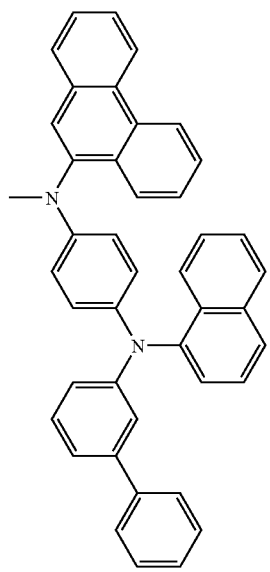
162
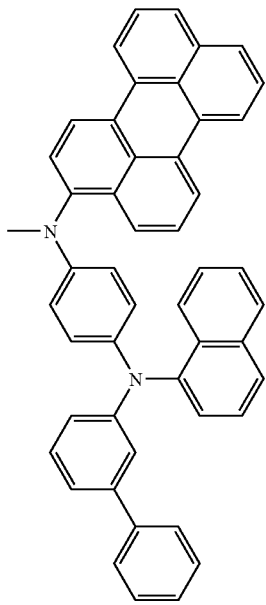
163
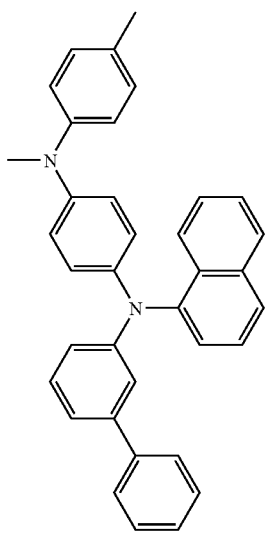
164
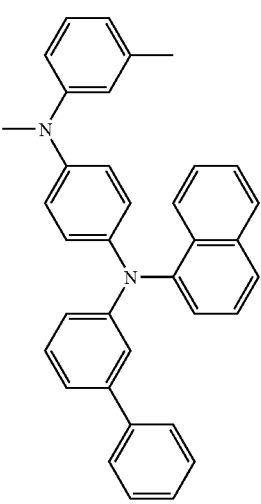

165
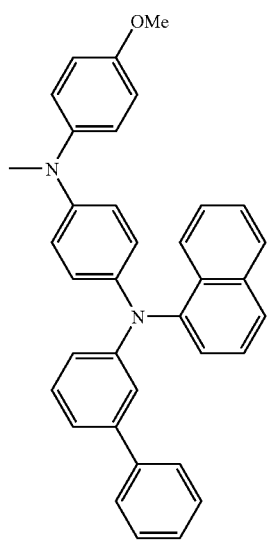
166
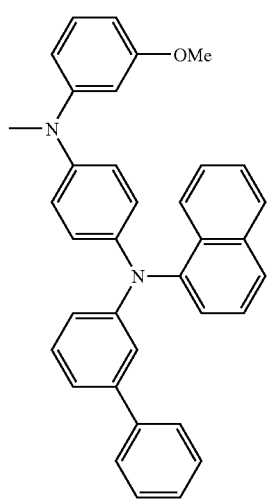
167
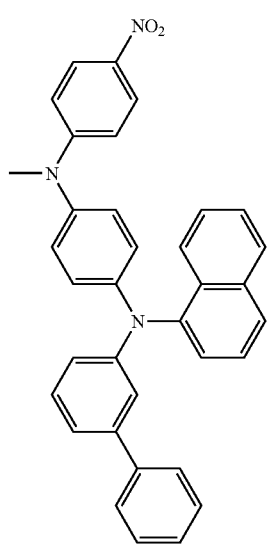
168
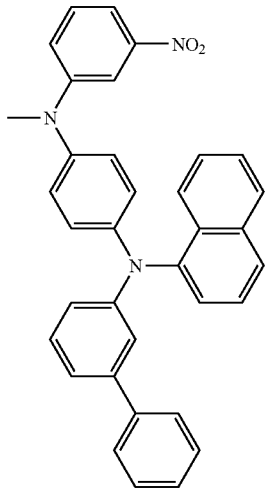
169
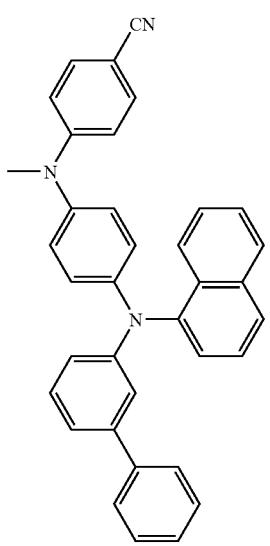
170
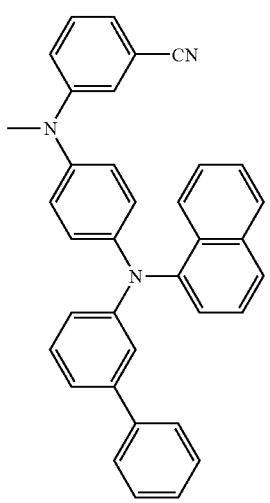

-continued
171 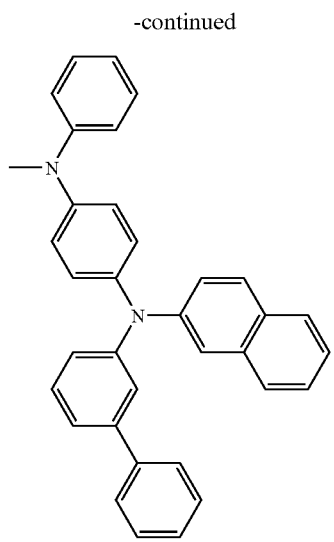
172 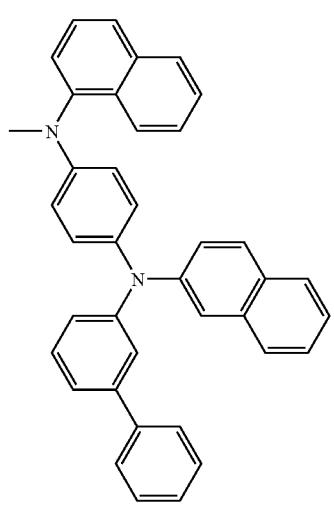
173 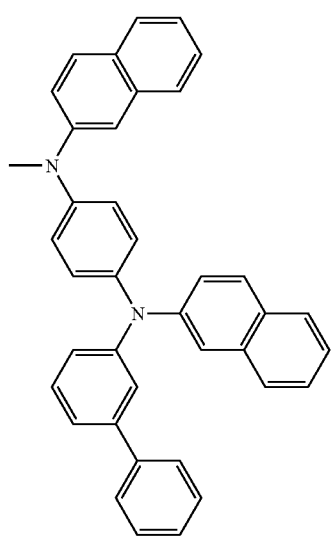
-continued
174 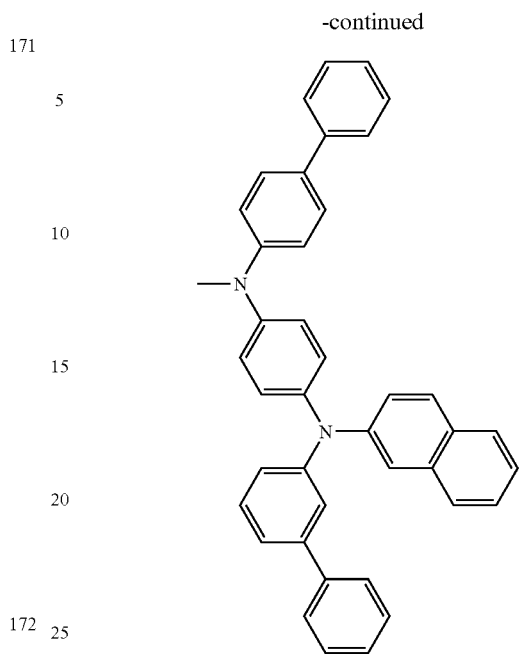
175
176 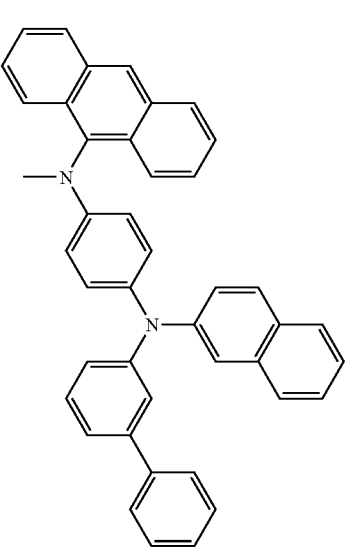

103
-continued
177 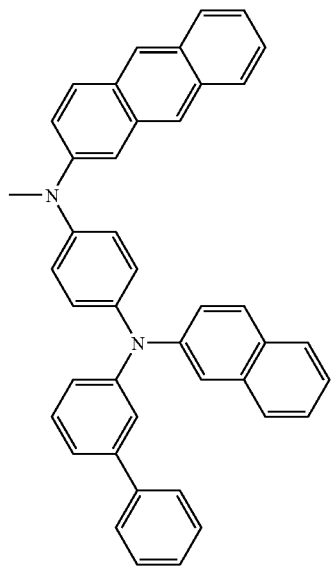
178 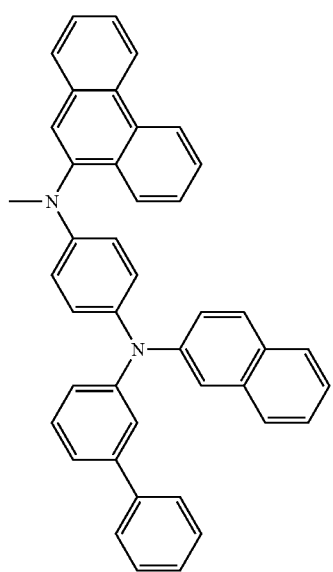
104
-continued
179 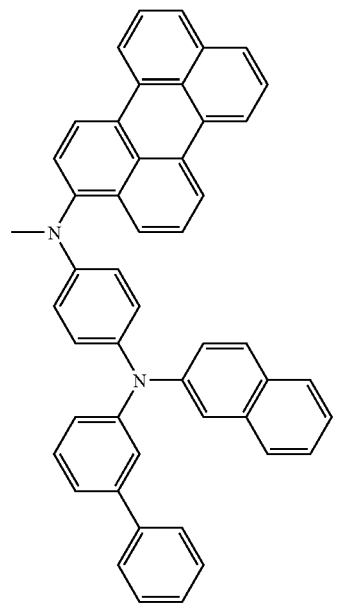
180 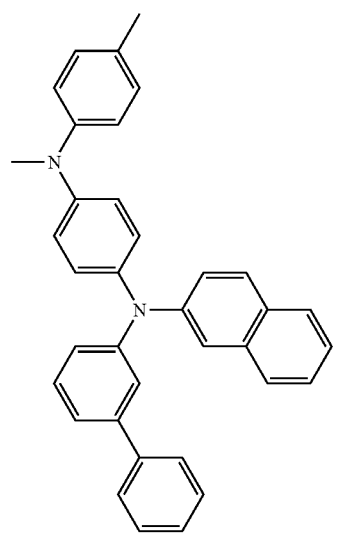
181 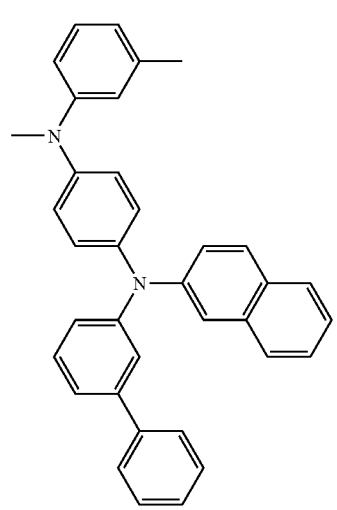

-continued
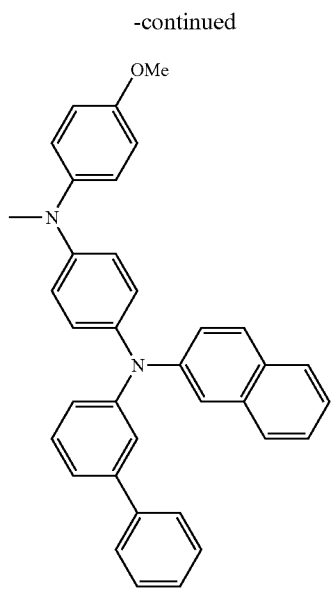
182
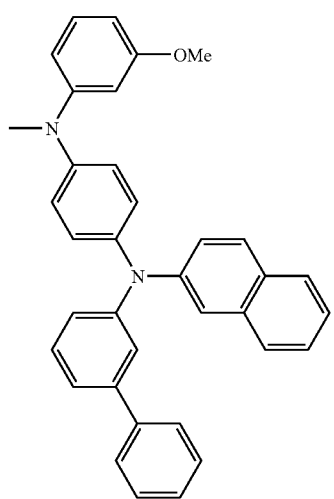
183
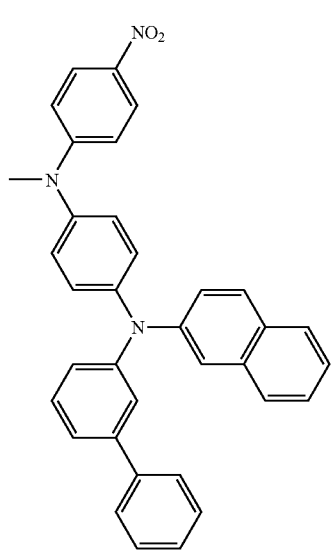
184
-continued
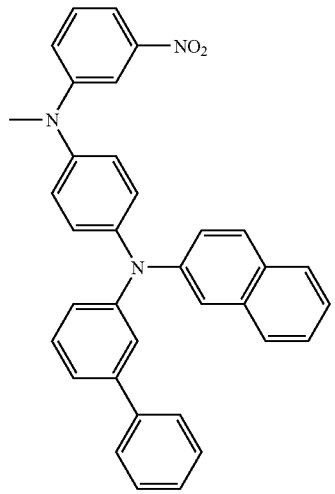
185
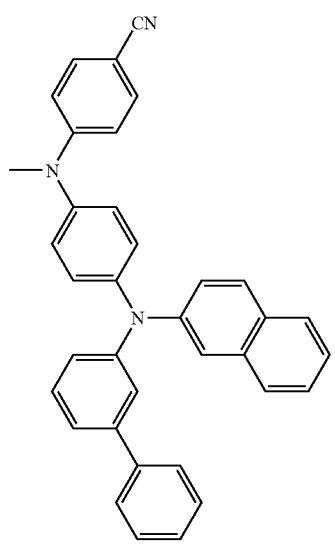
186
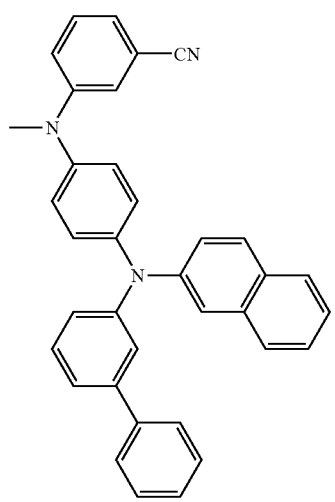
187

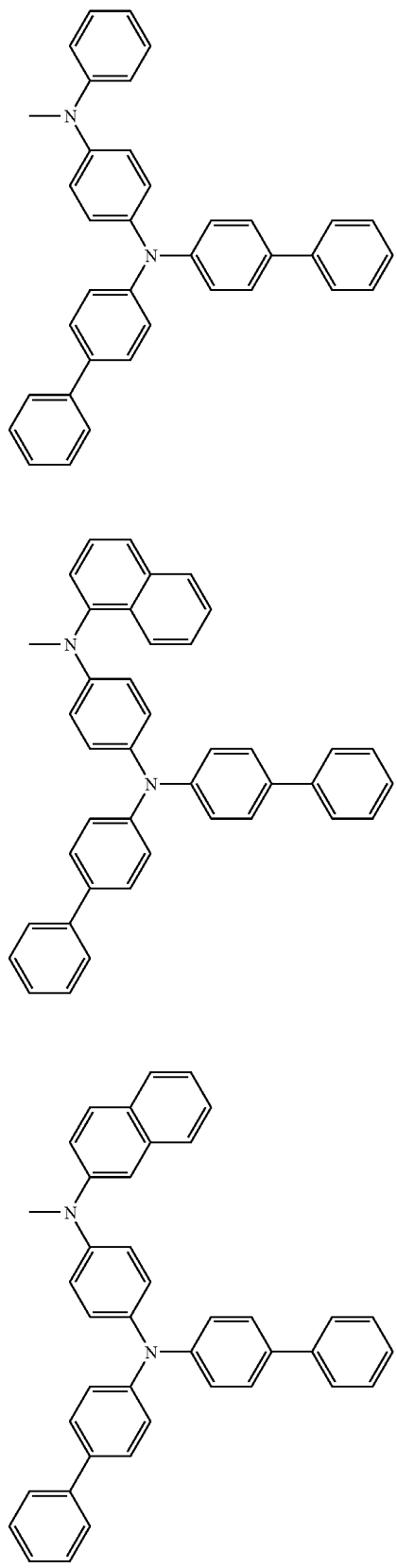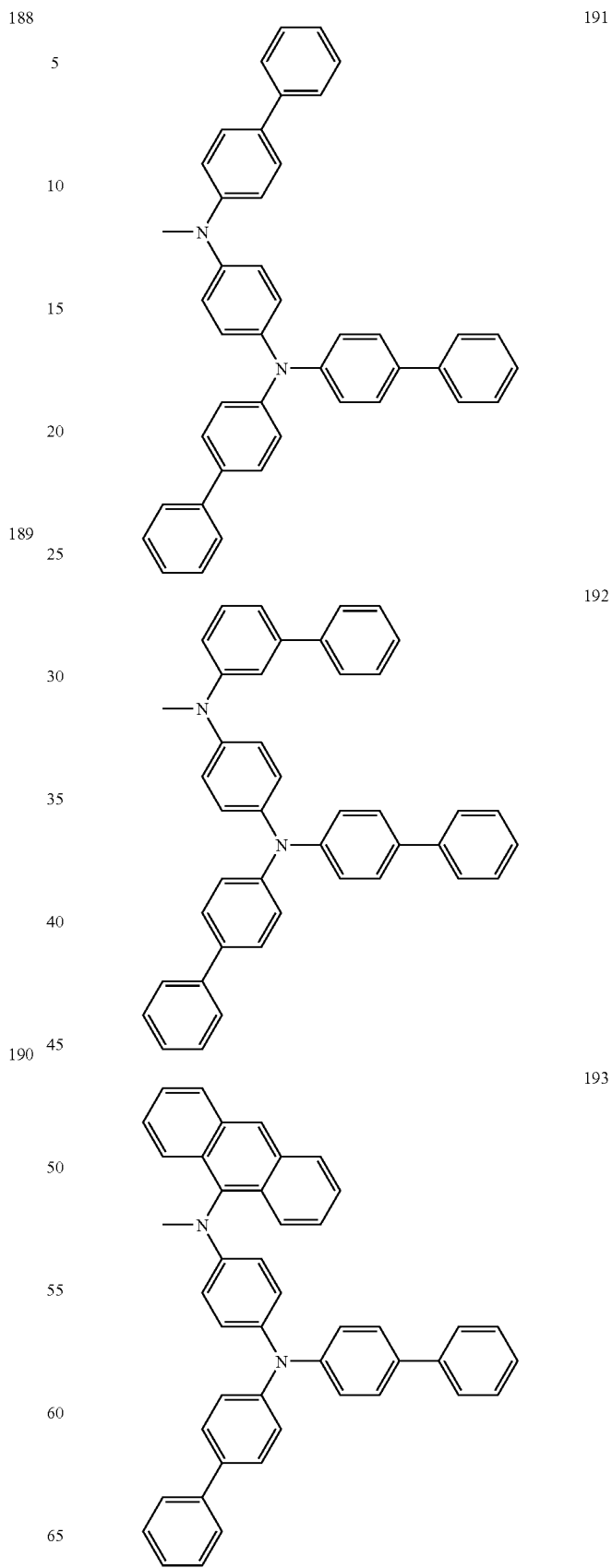

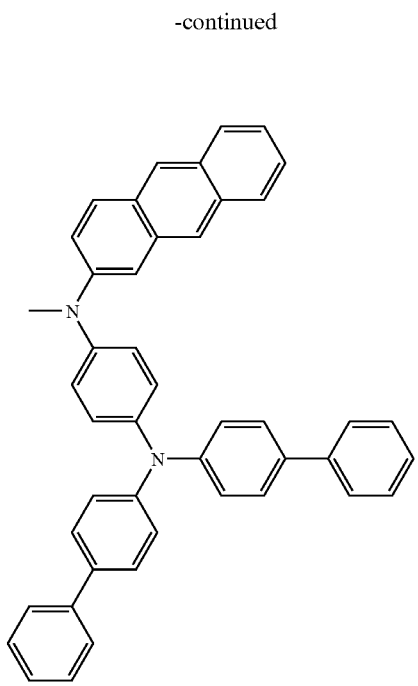
194
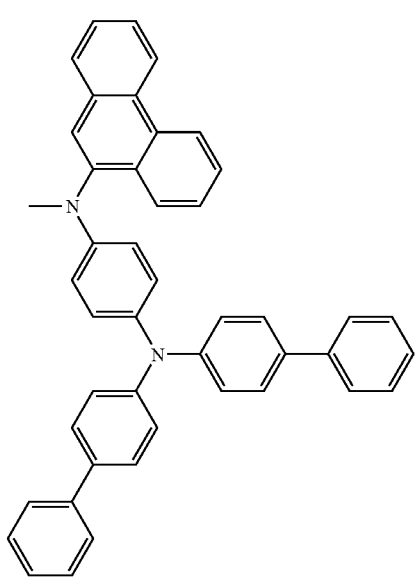
195
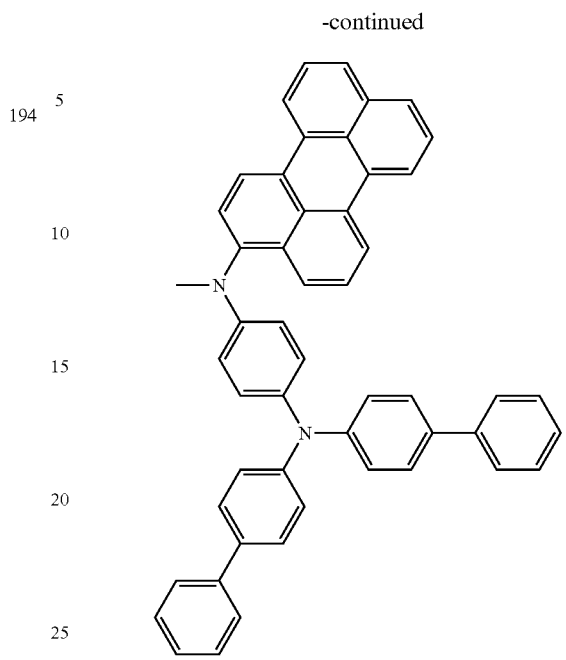
196
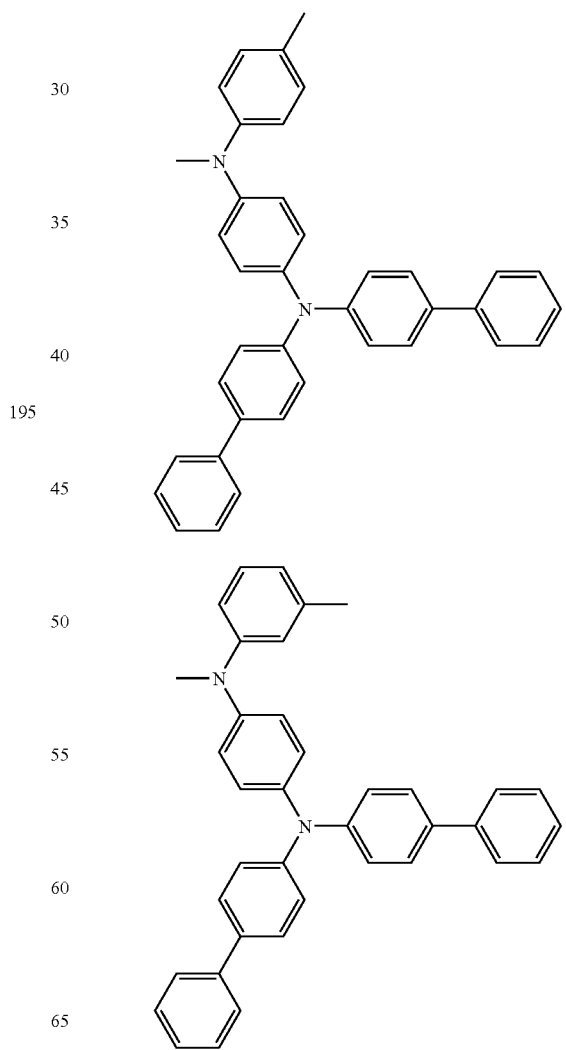

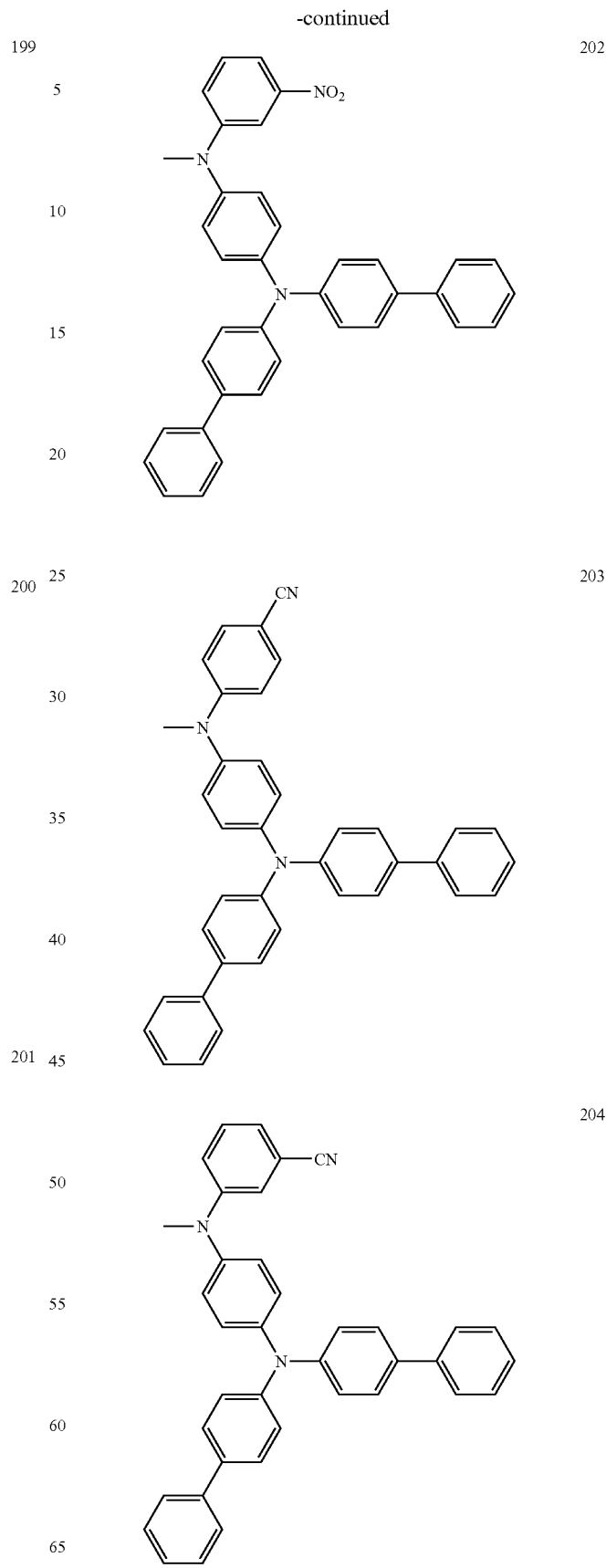

205
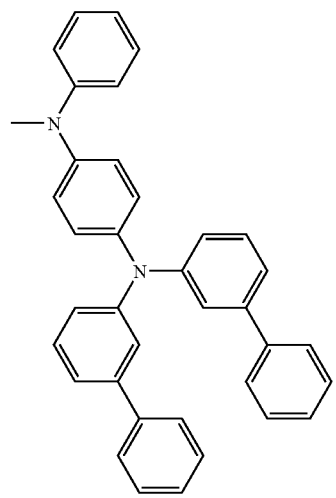
206
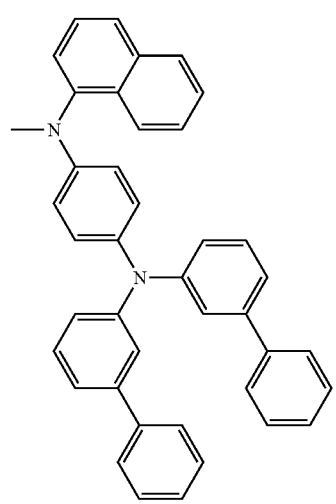
207
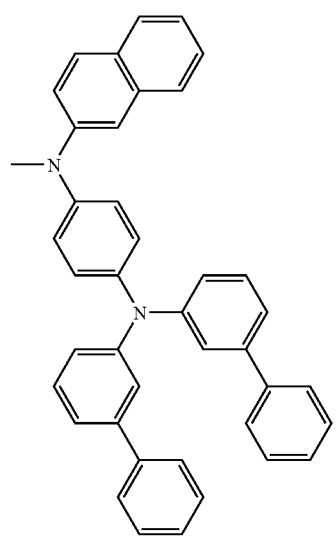
208
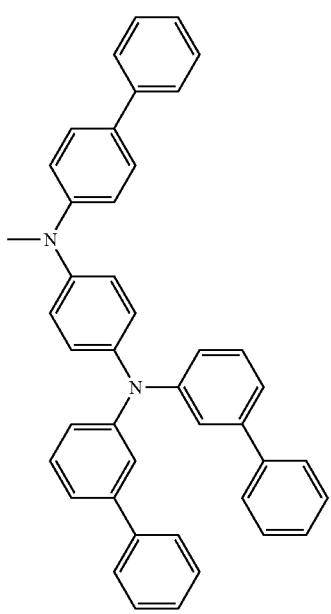
209
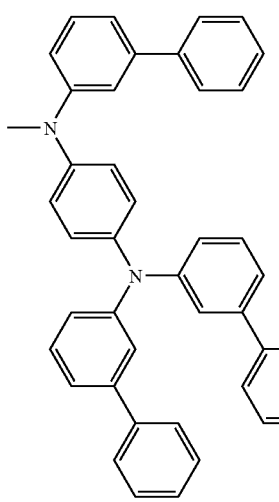
210
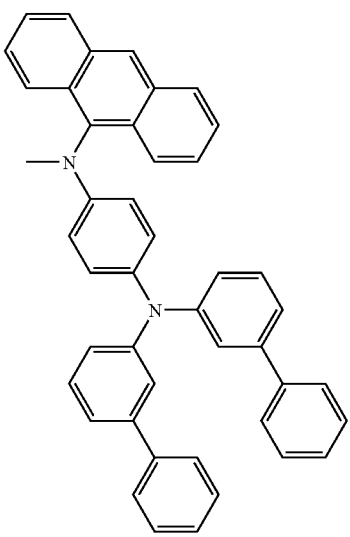

-continued
211
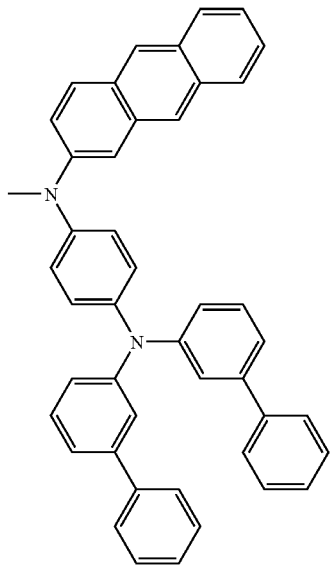
212
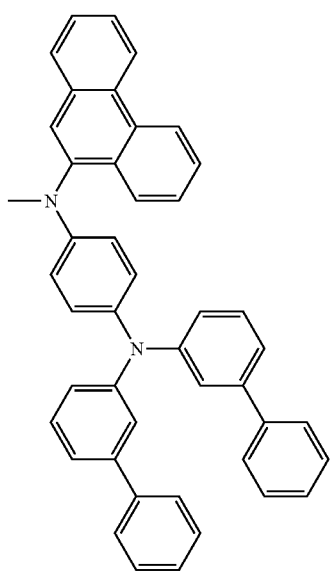
-continued
213
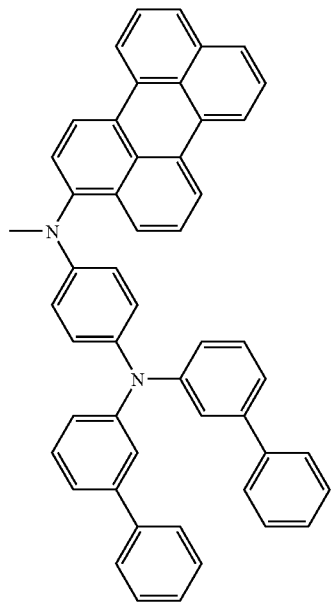
214
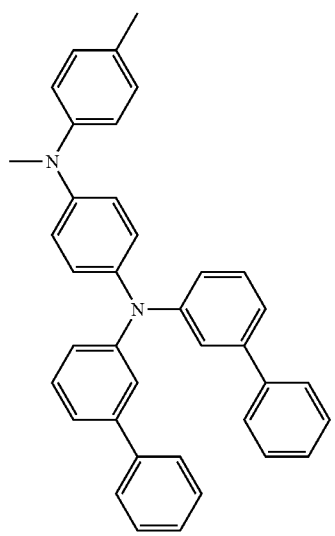
215
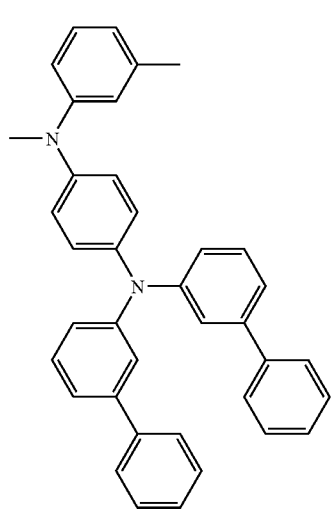

-continued
216
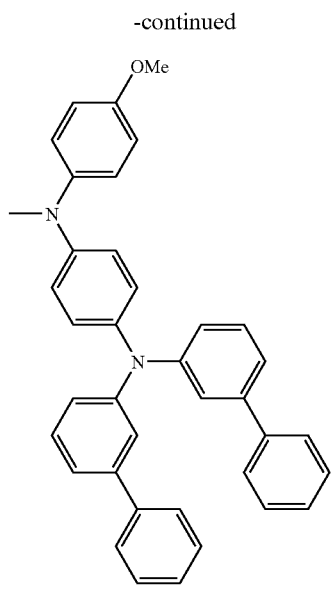
217
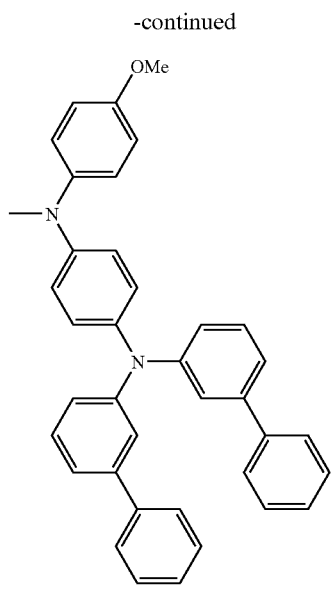
218
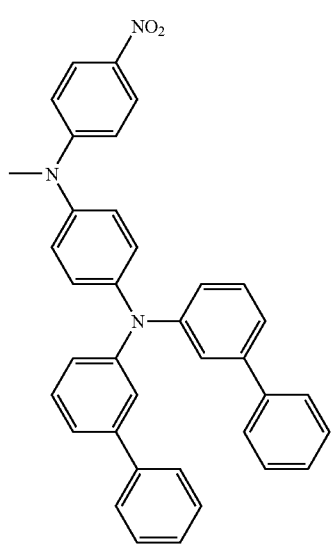
-continued
219
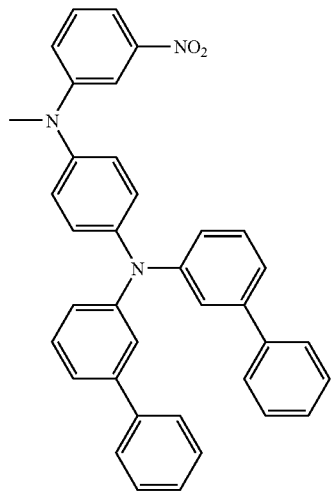
220
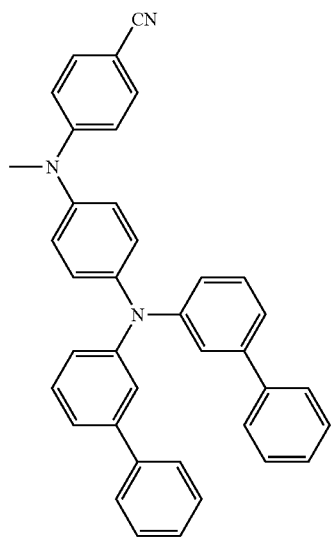
221
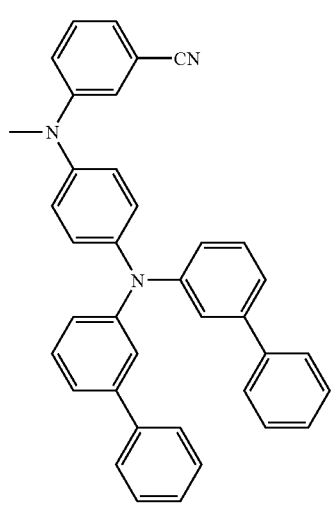

-continued
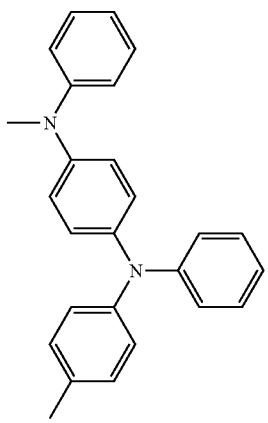
222
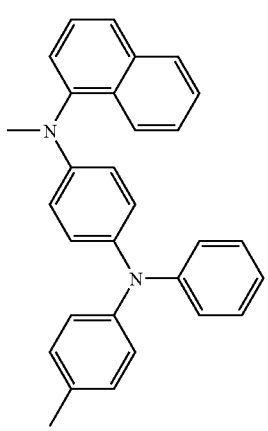
223
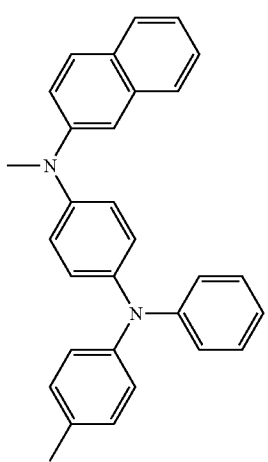
224
-continued
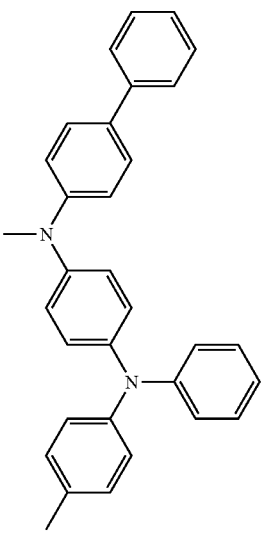
225
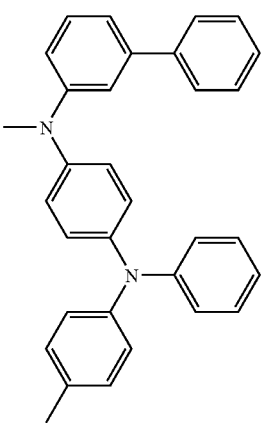
226
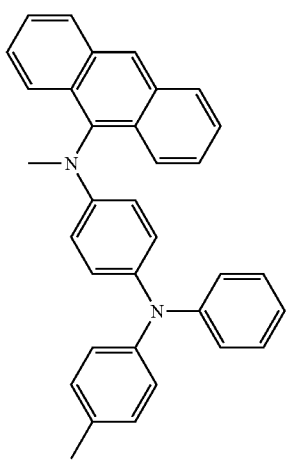
227

228
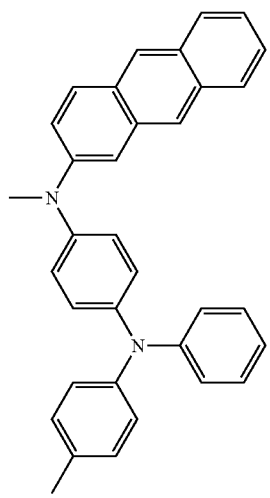
229
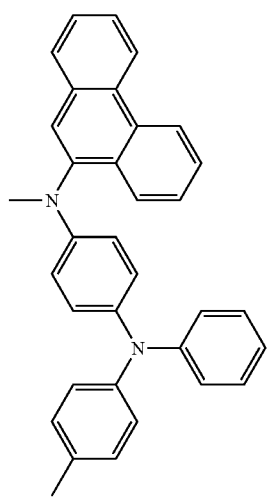
230
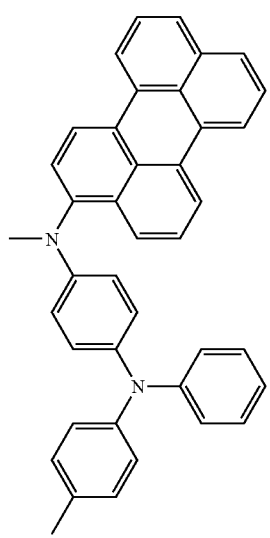
231
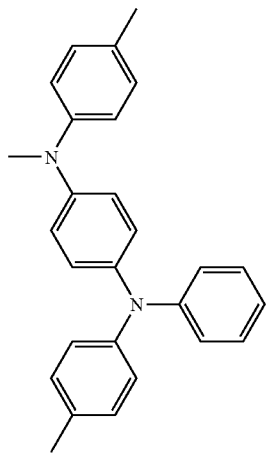
232
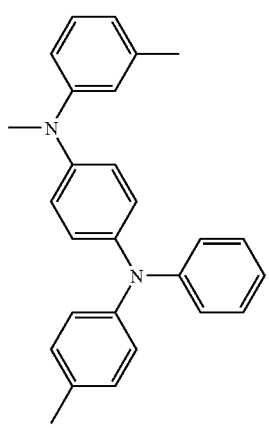
233
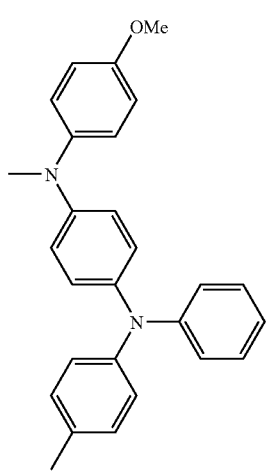

234
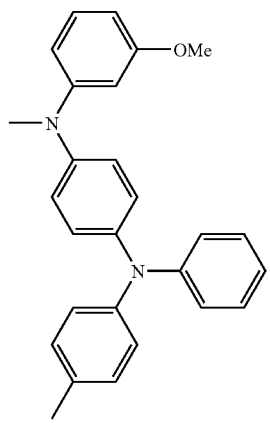
235
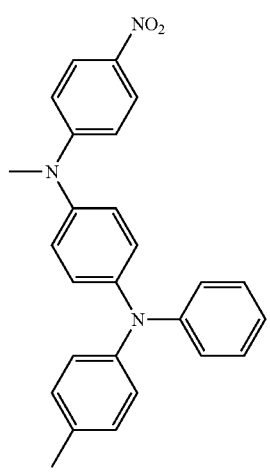
236
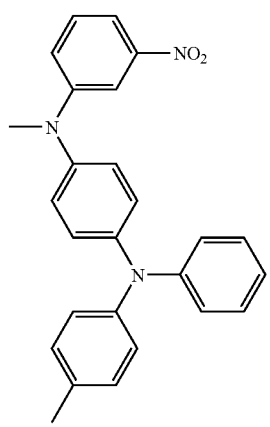
237
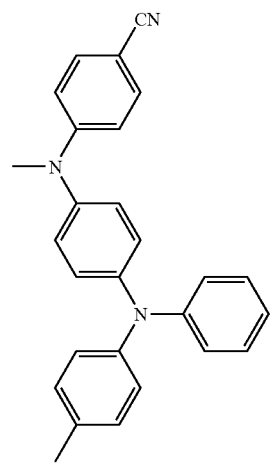
238
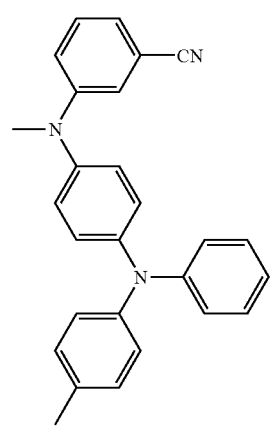
239
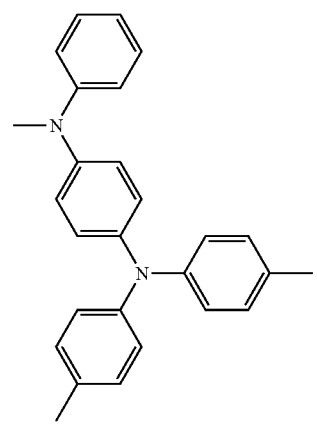

-continued
240
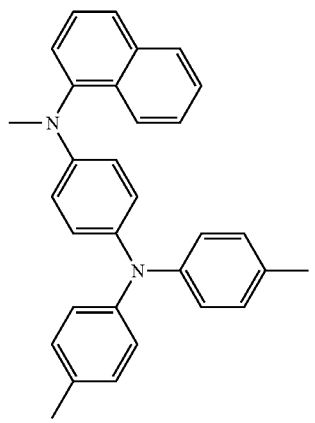
241
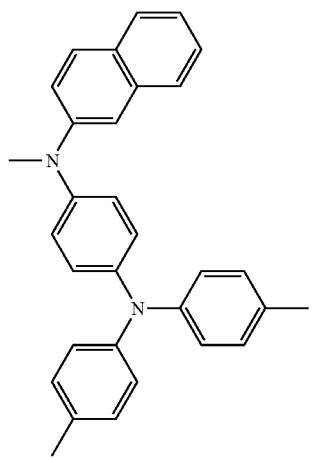
242
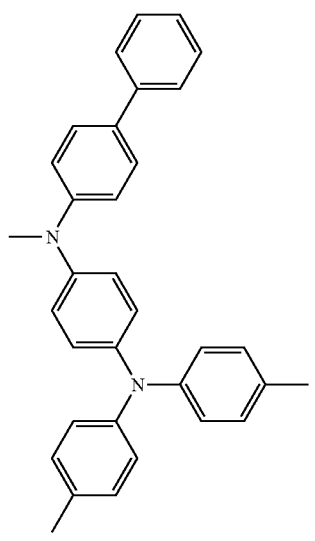
243
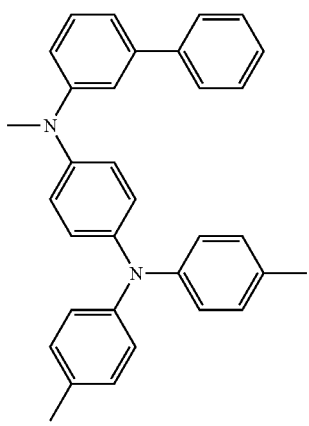
244
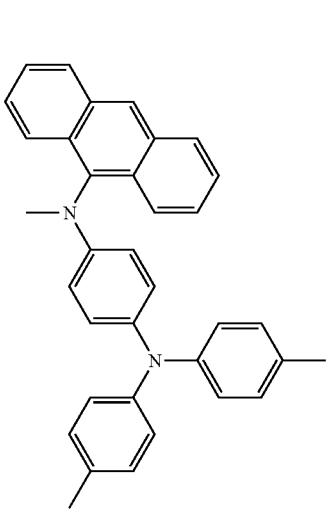
245
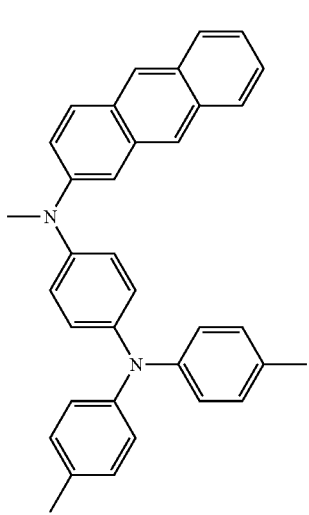

-continued
246
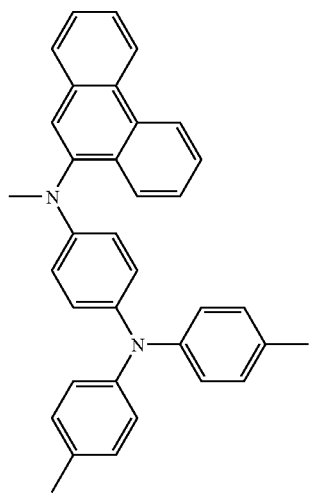
247
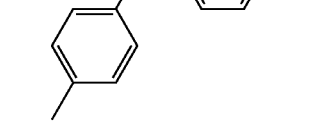
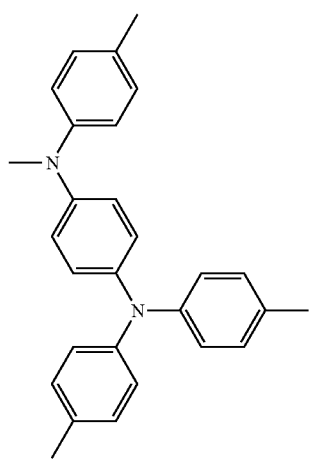
-continued
249
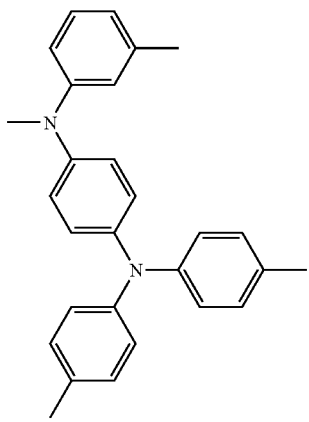
250
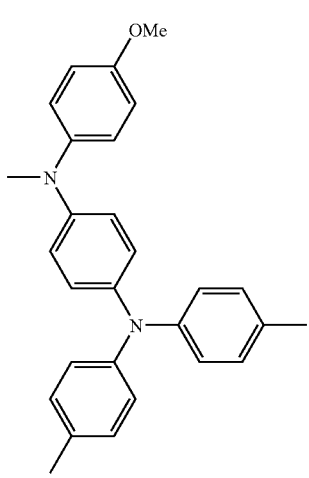
251
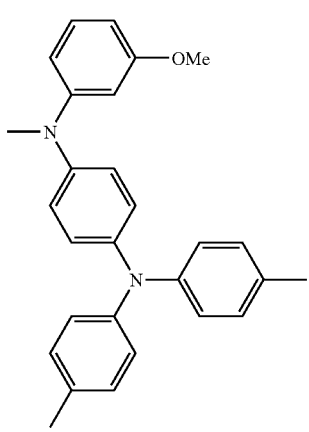

-continued
252
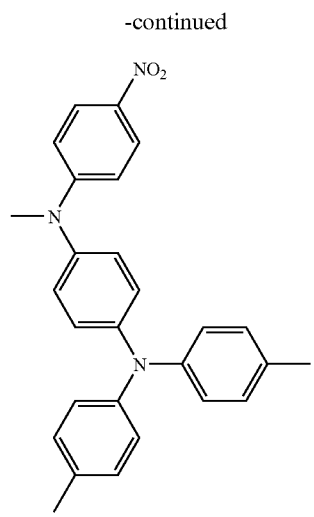
253
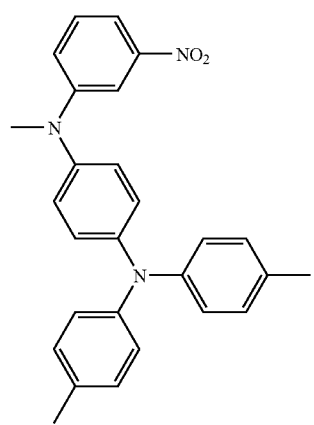
254
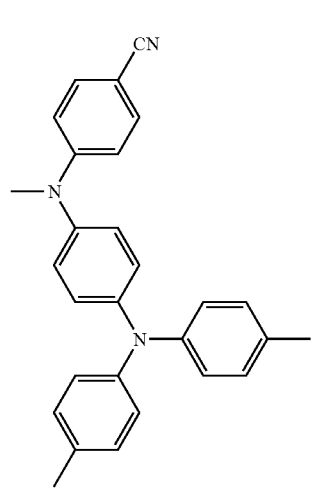
-continued
255
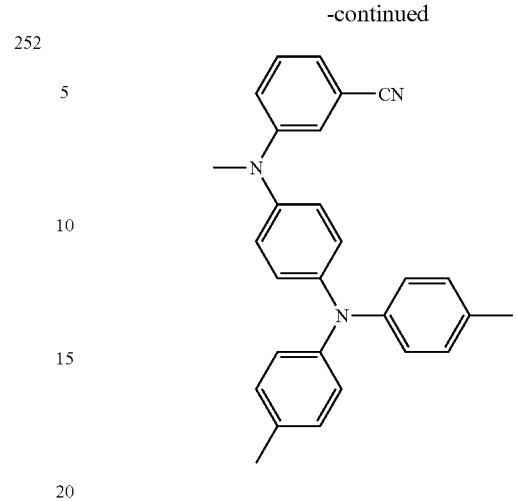
256
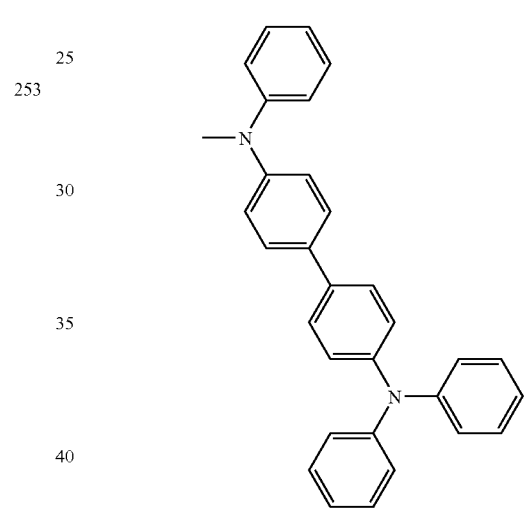
257
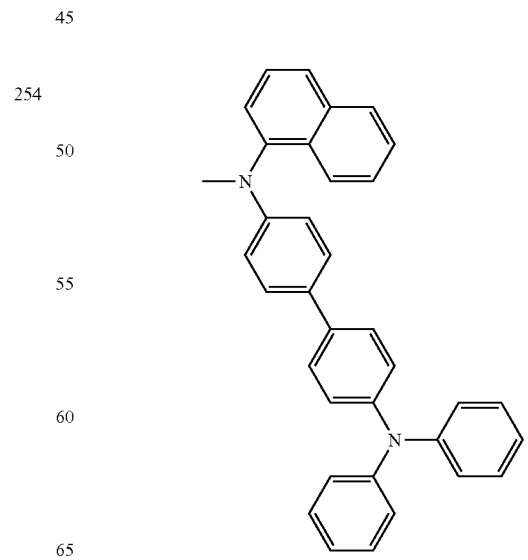

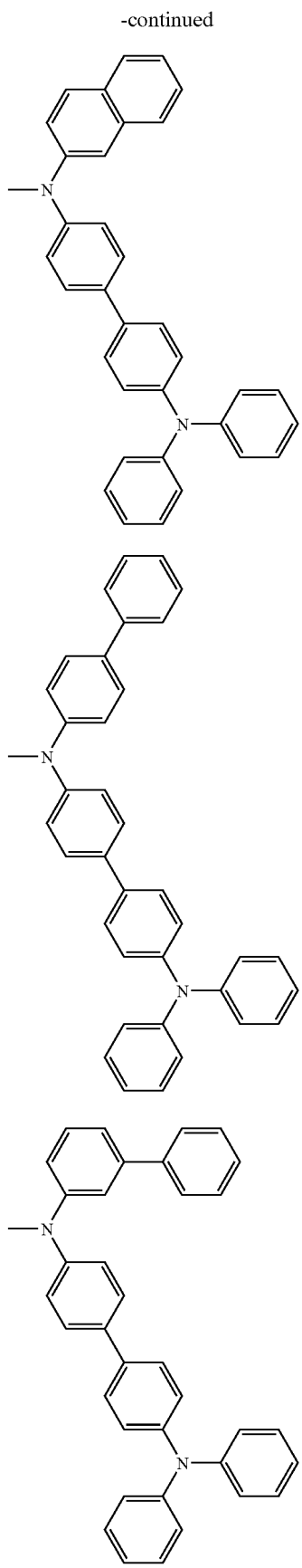
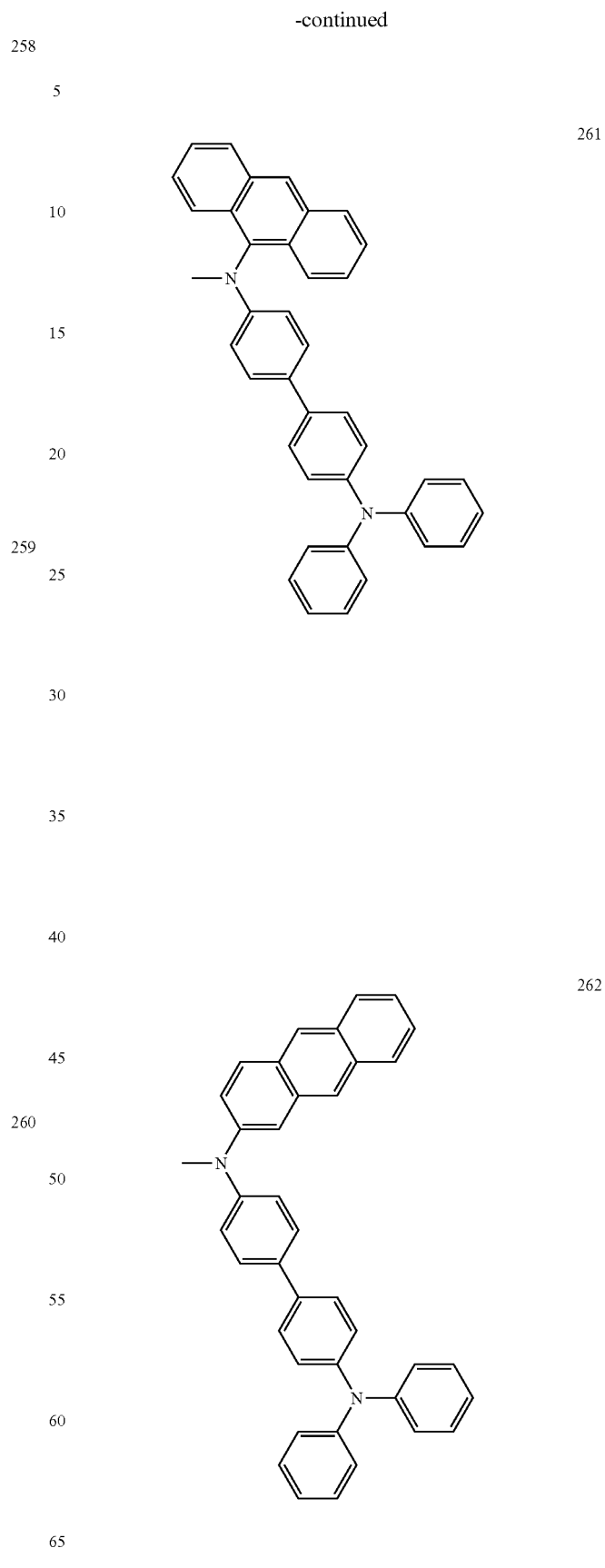

-continued
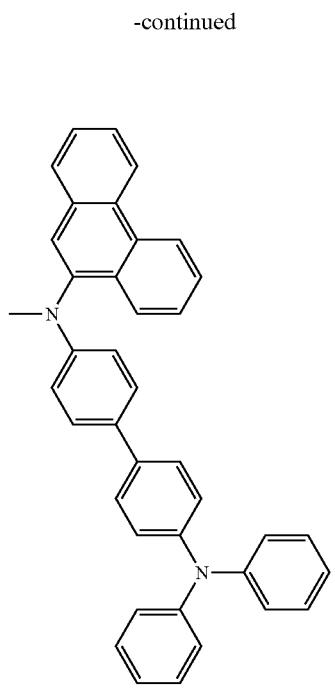
263
264
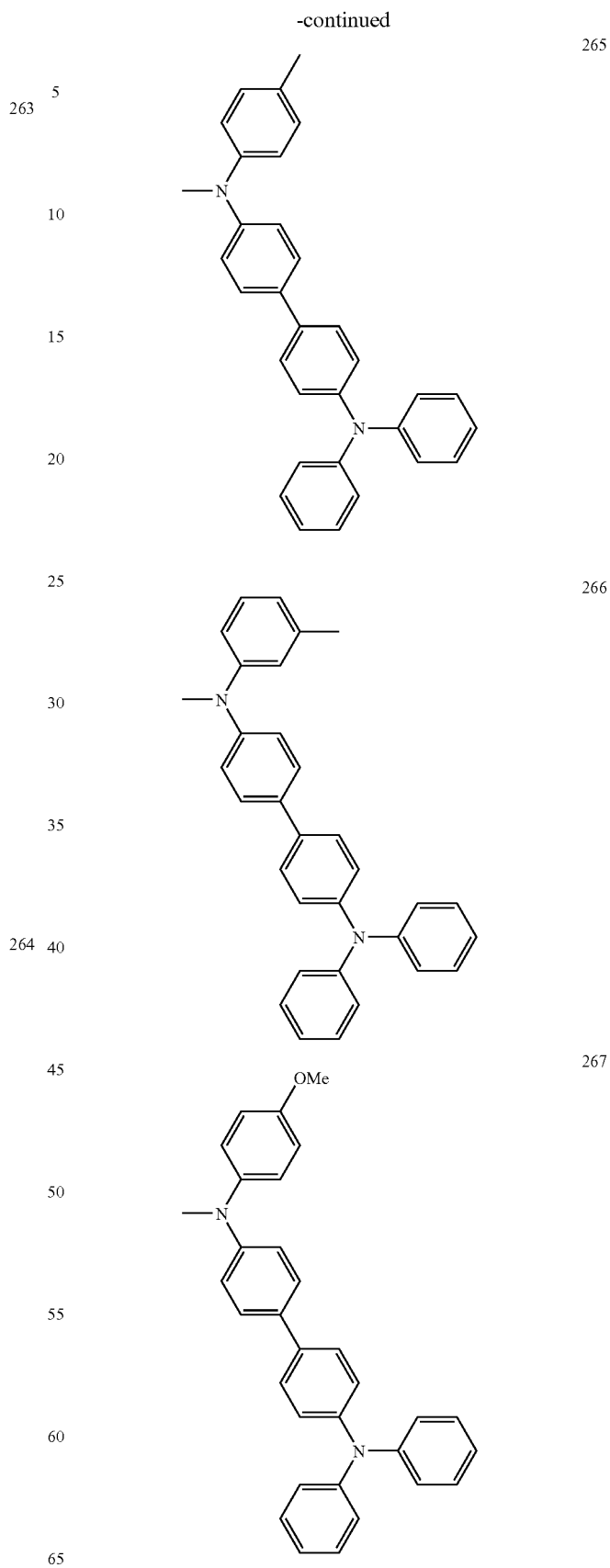
265
266
267

-continued
268
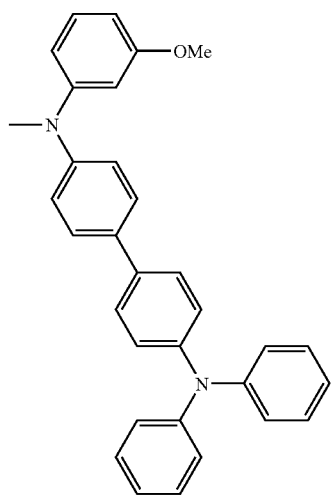
269
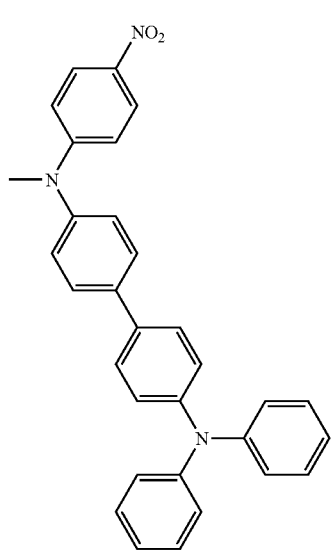
270
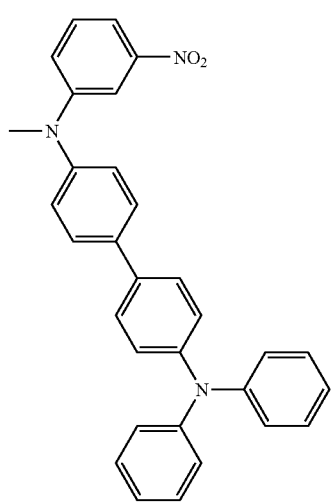
-continued
271
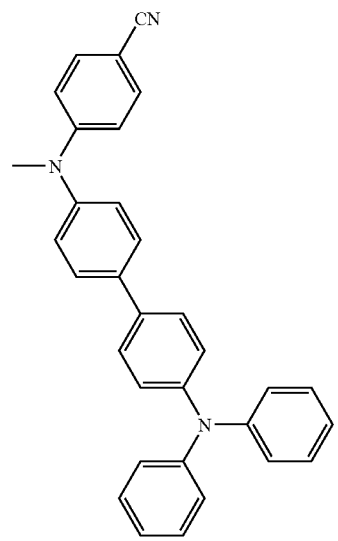
272
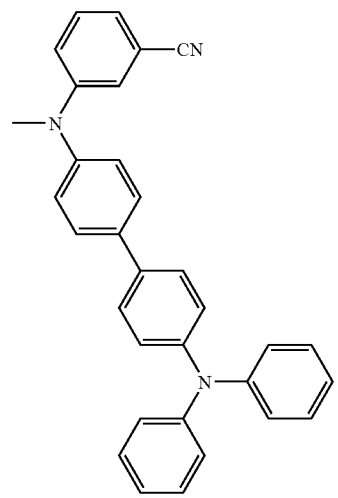
273
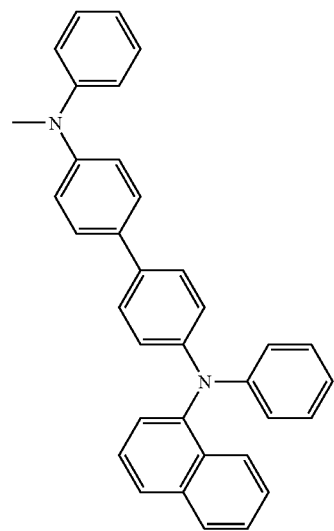

137
138
274
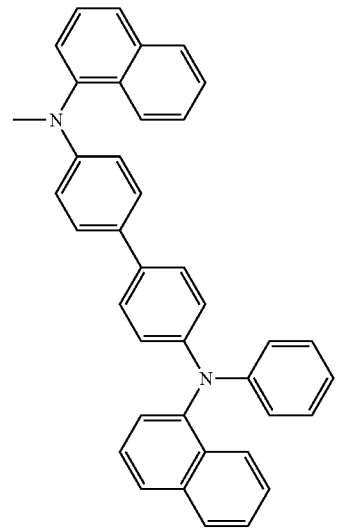
276
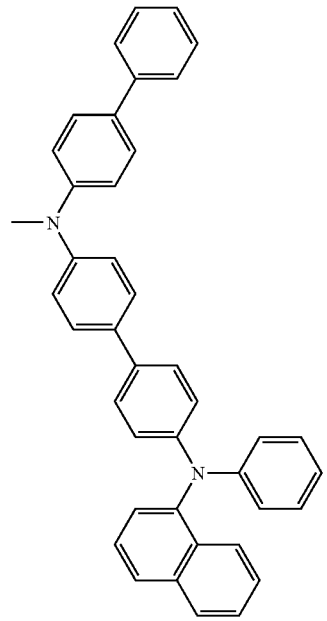
275
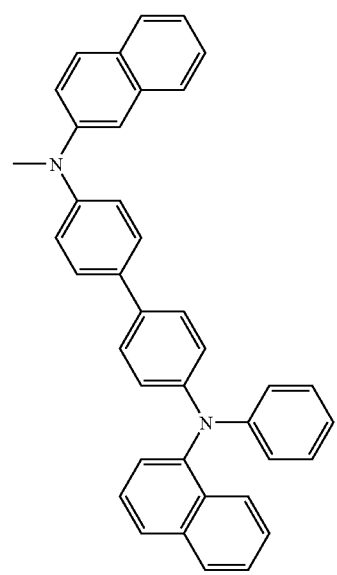
277
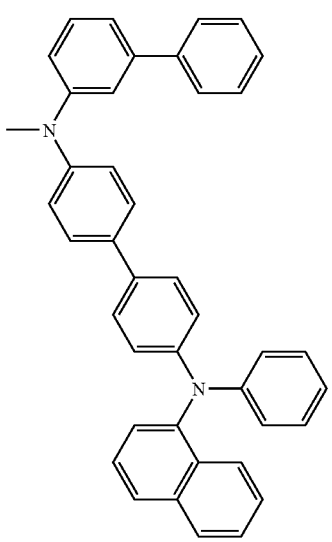

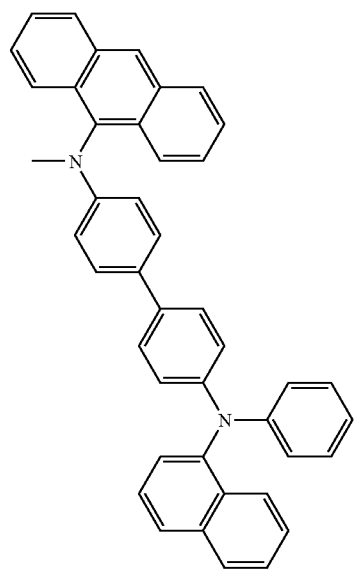
278
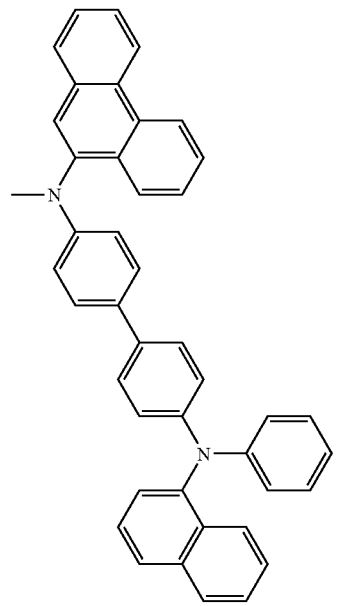
280
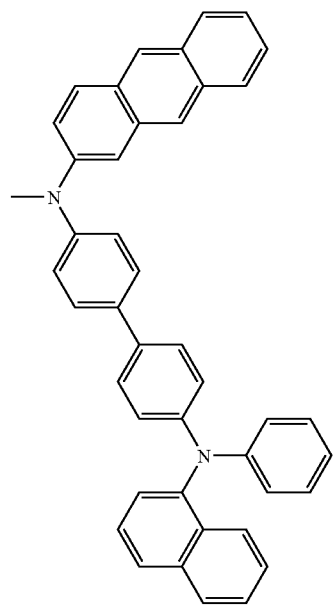
279
281

282
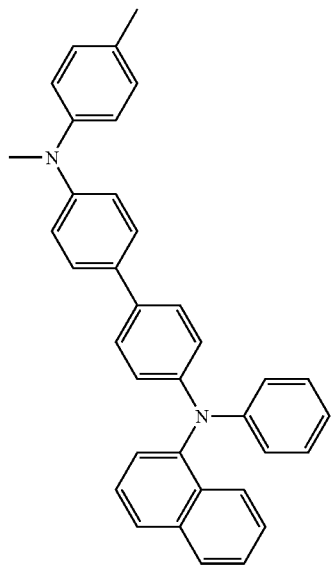
284
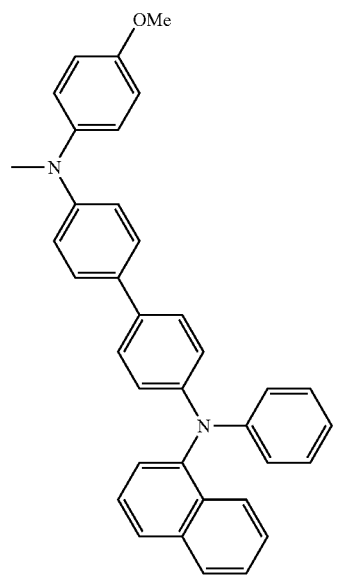
283
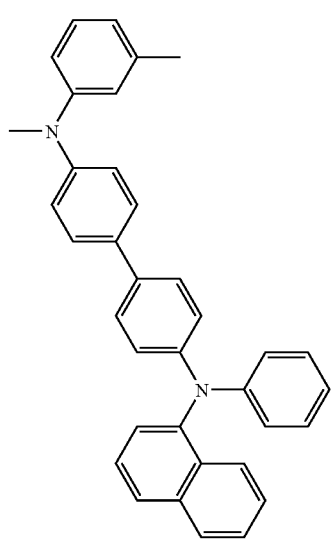
285
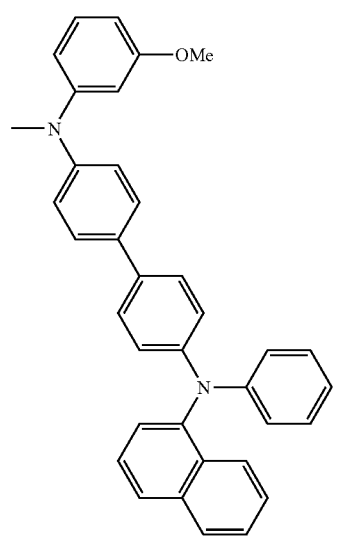

286
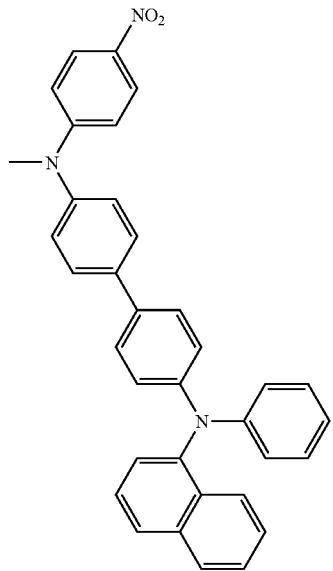
287
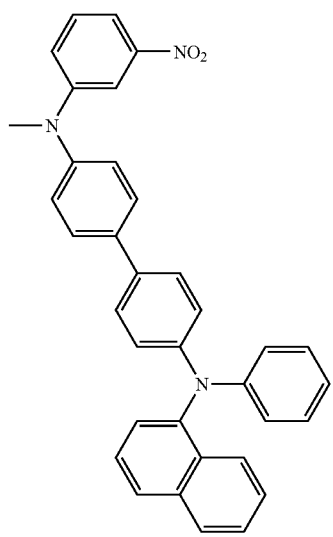
288
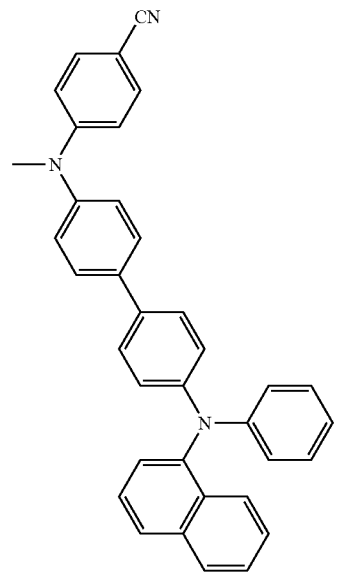
289
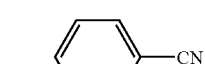
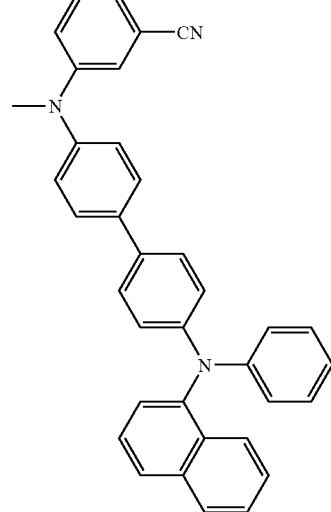
290
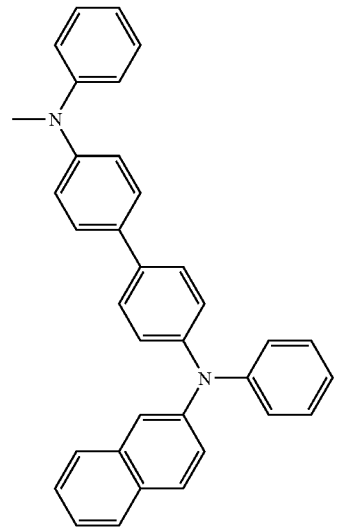

291 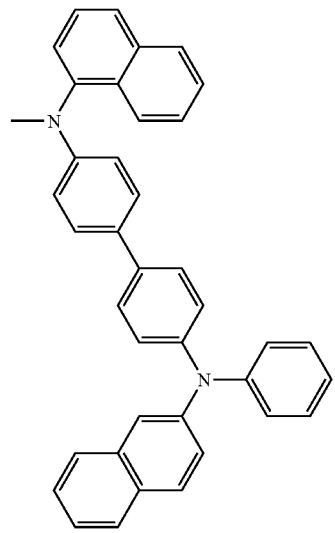
292 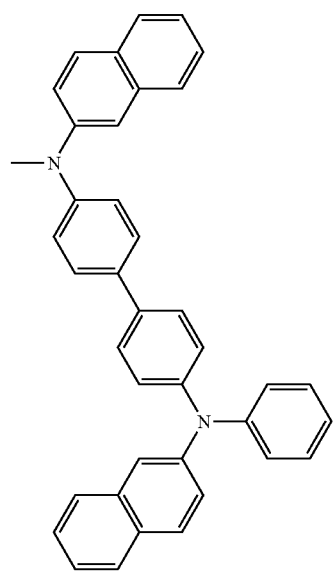
293 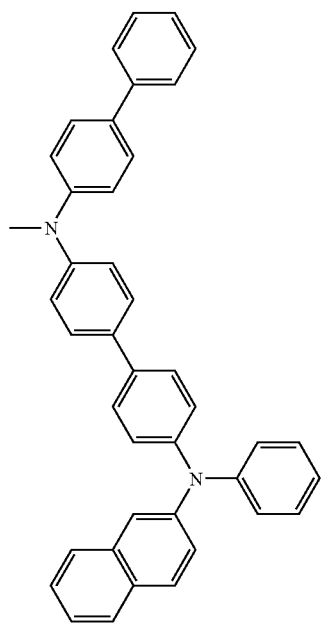
294 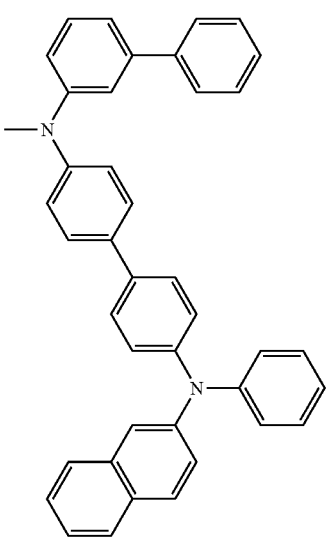

147 148
295 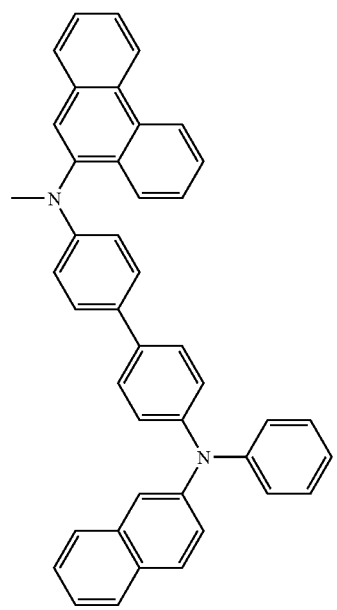
296 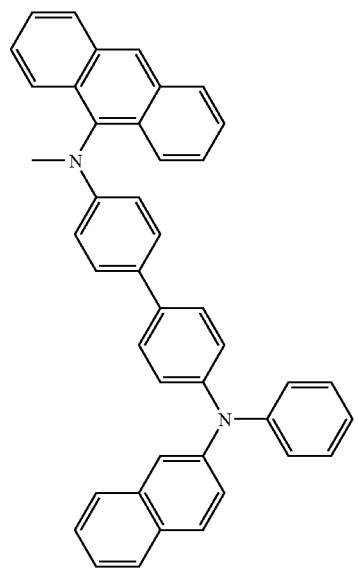
297 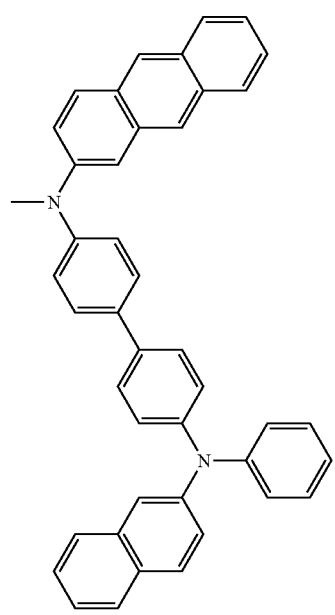
298 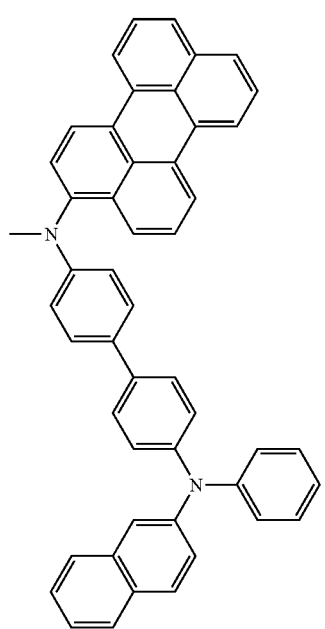

149
-continued
299
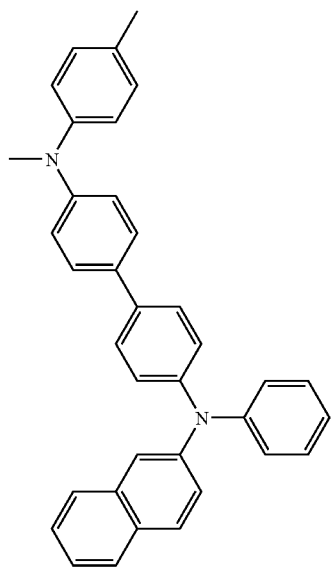
300
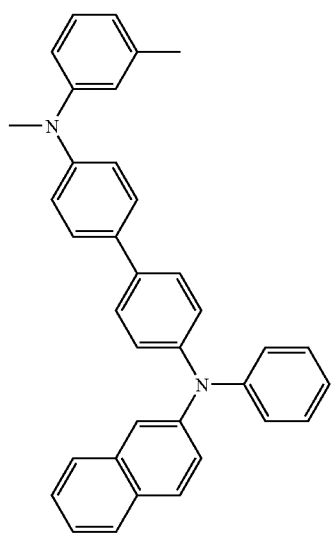
150
-continued
301
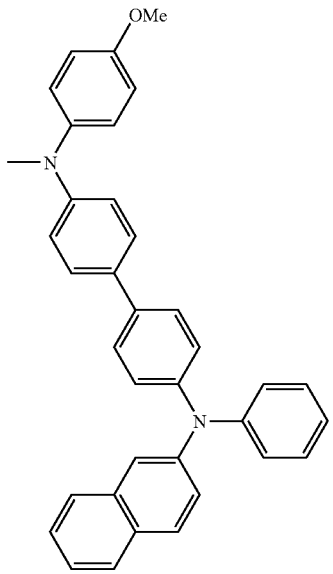
302
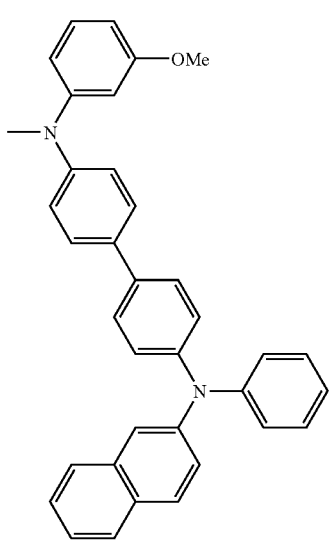

-continued
303
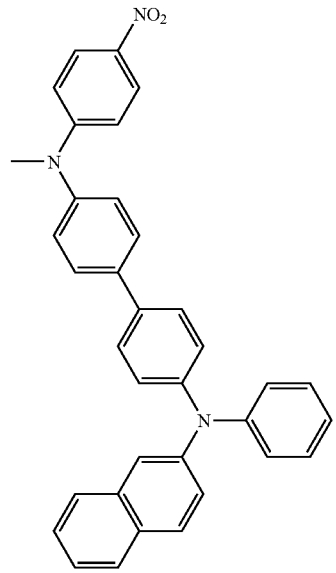
305
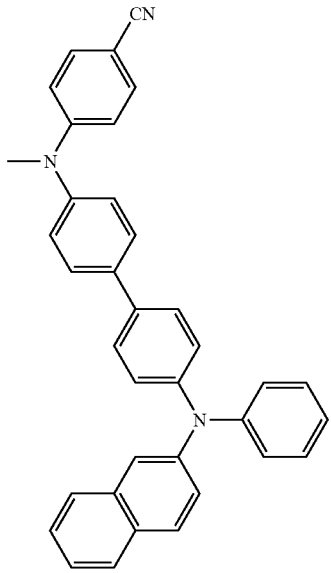
304
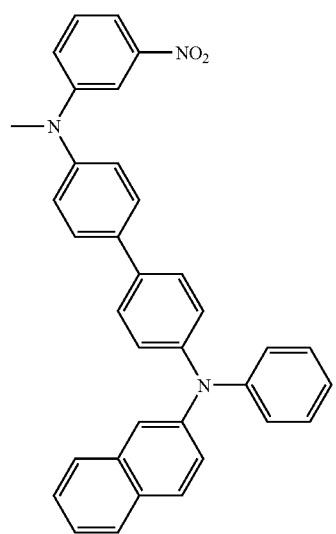
306
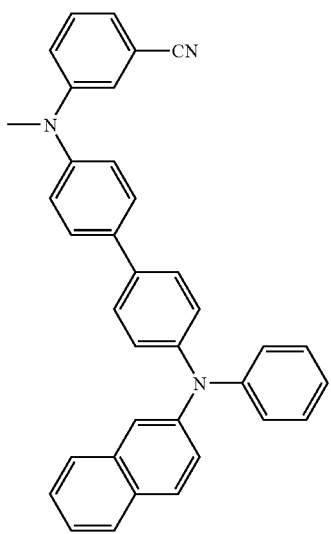

153
-continued
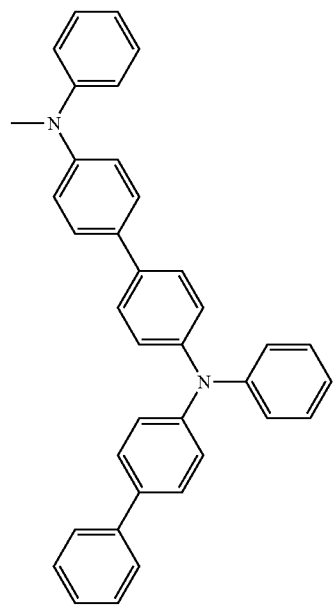
307
154
-continued
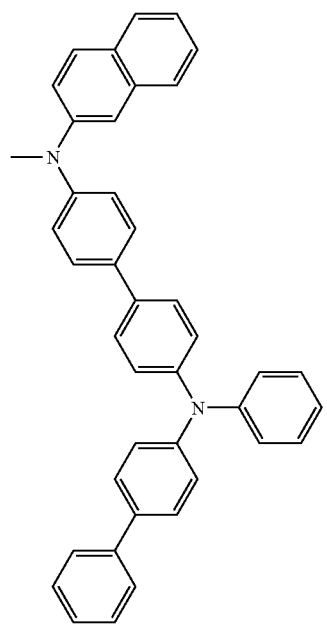
309
308
310

155 156
-continued
-continued
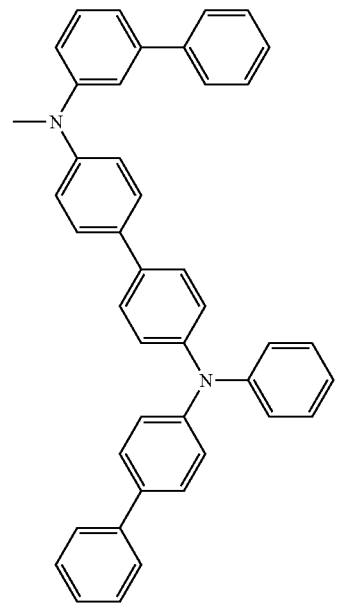
311
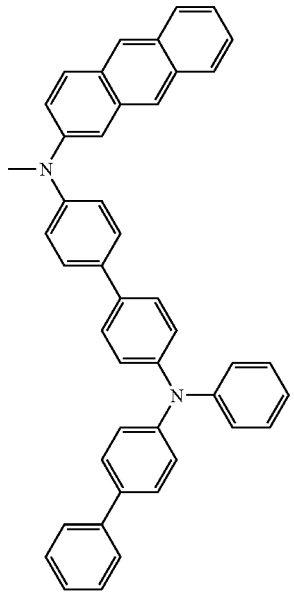
313
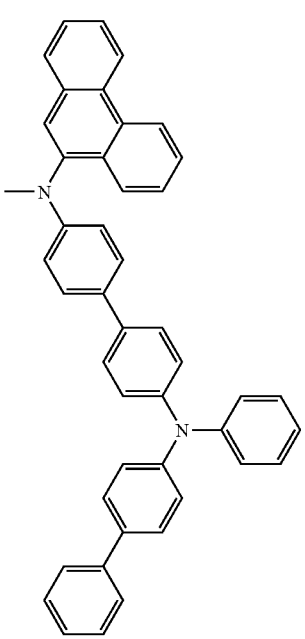
312
314

-continued
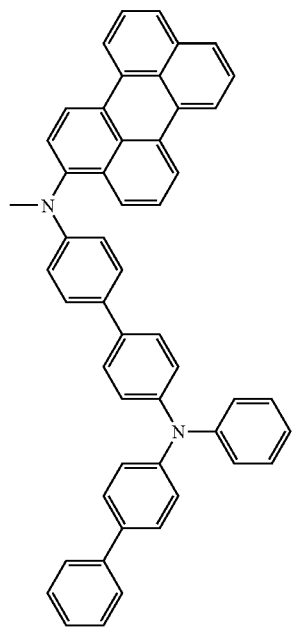
315
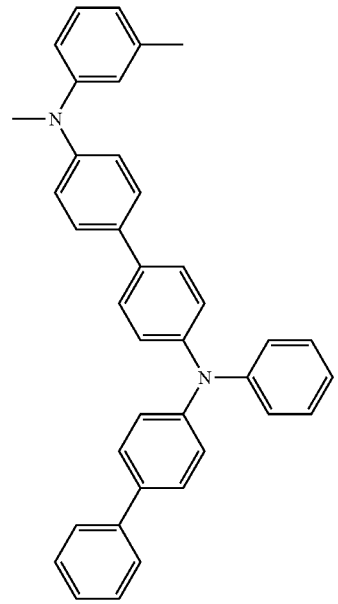
317
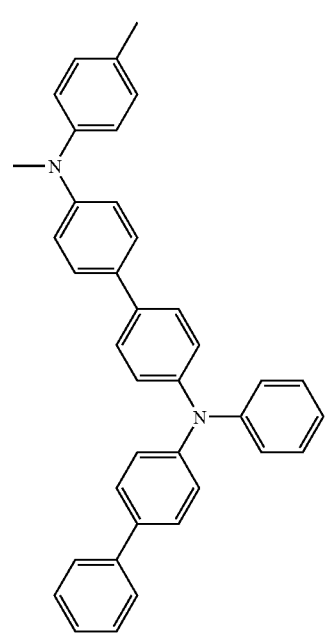
316
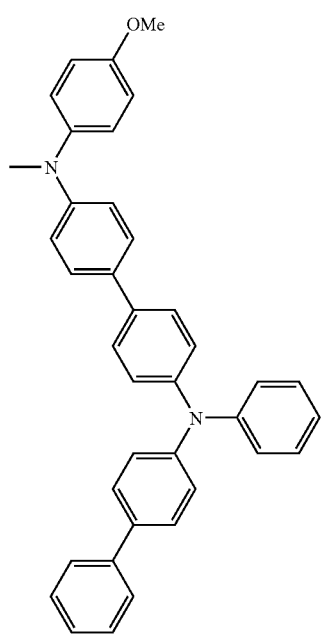
318

319
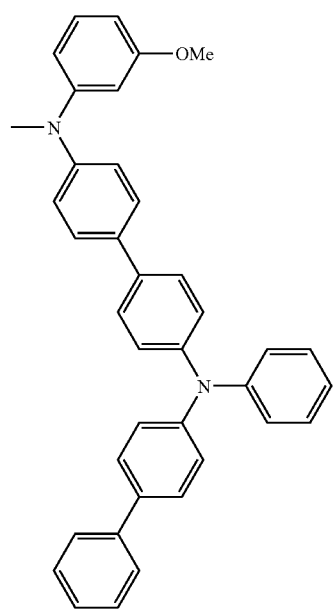
321
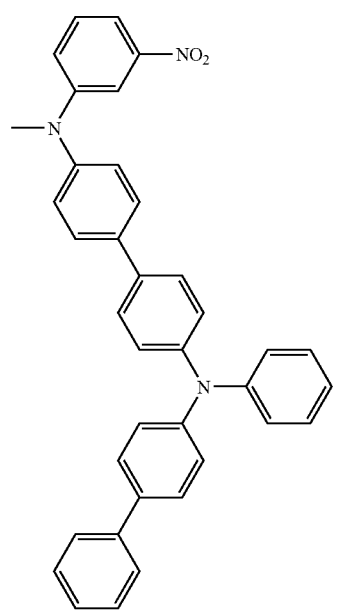
320
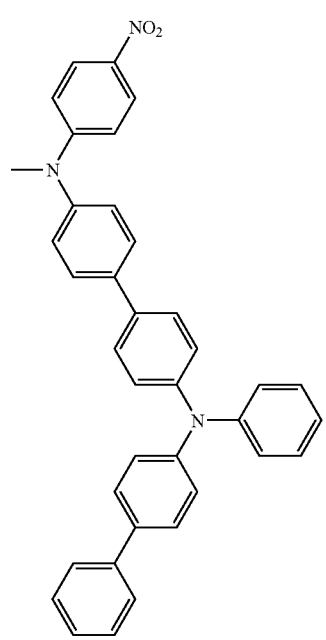
322
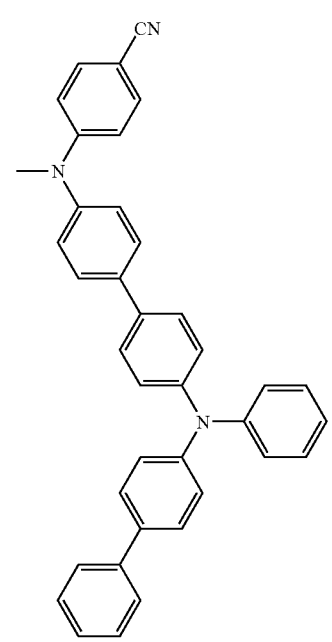

161                                     162
-continued                              -continued
323 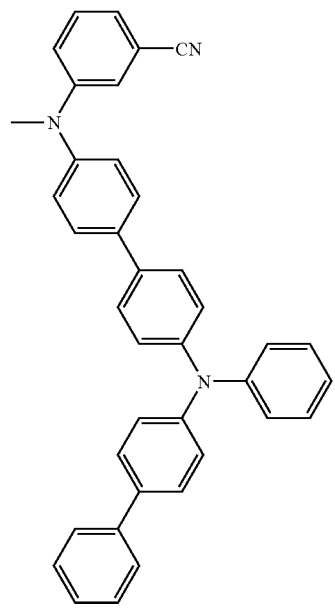
325 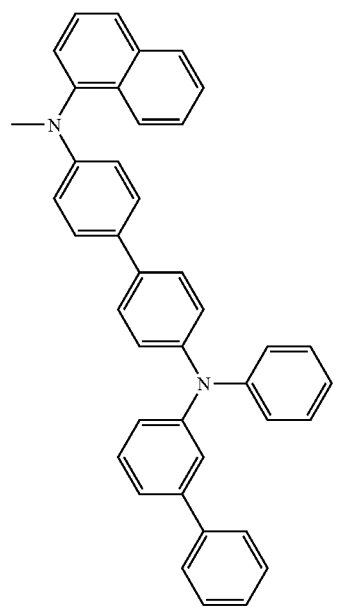
324 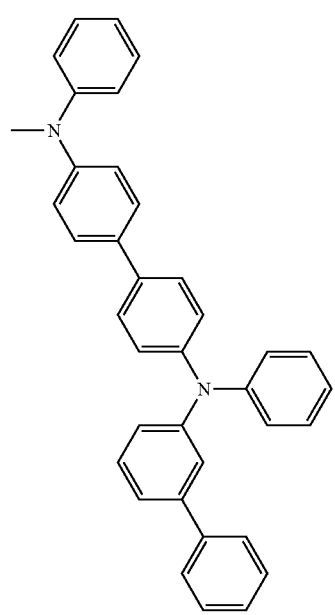
326 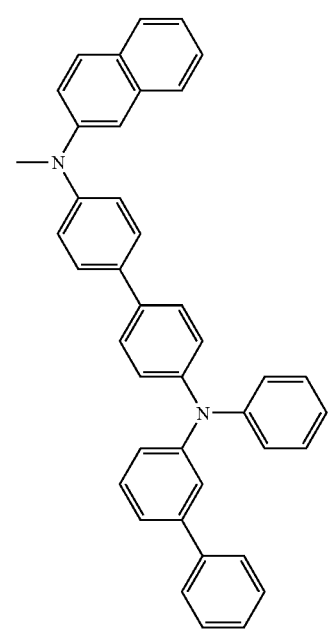

-continued
327
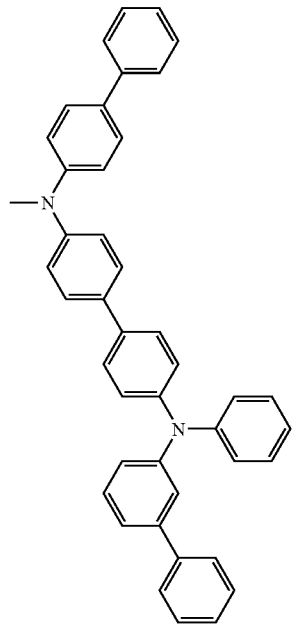
328
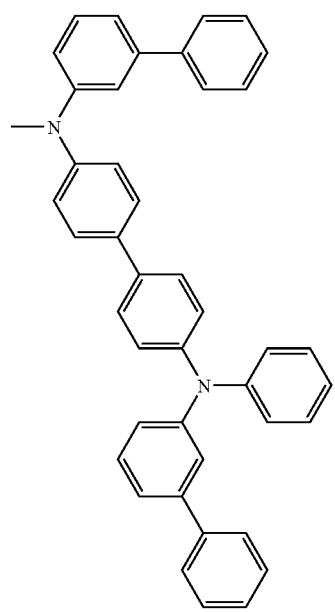
-continued
329
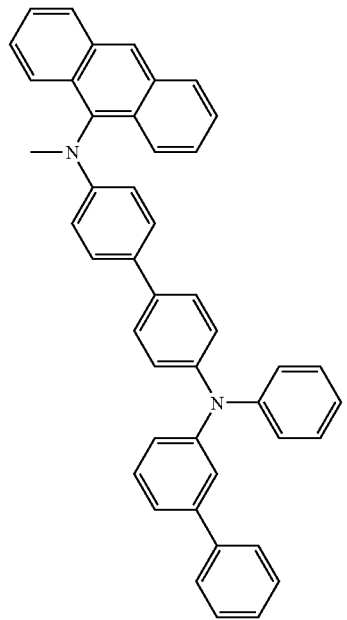
330
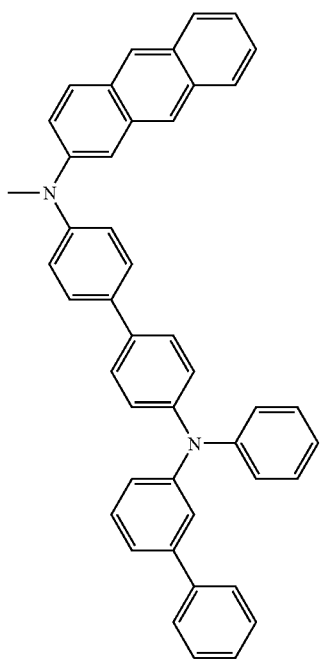

-continued
331
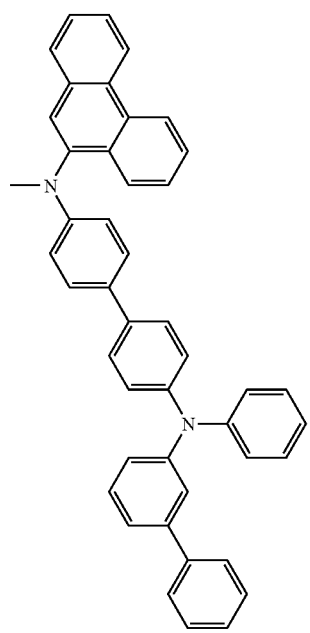
332
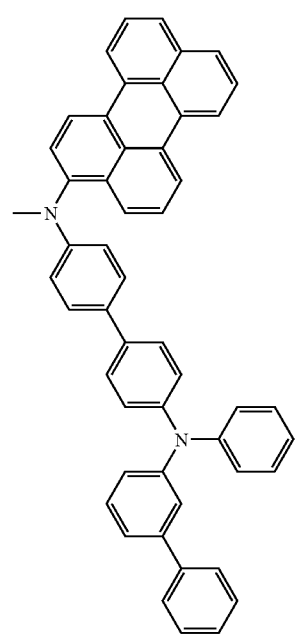
-continued
333
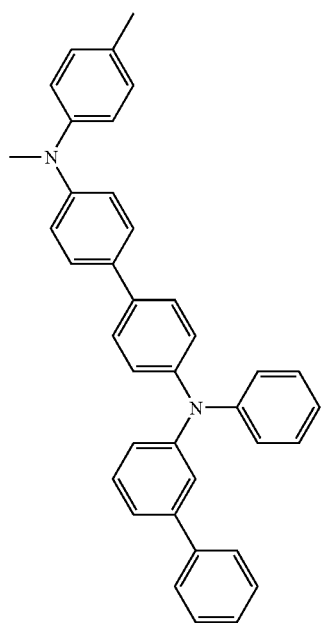
334
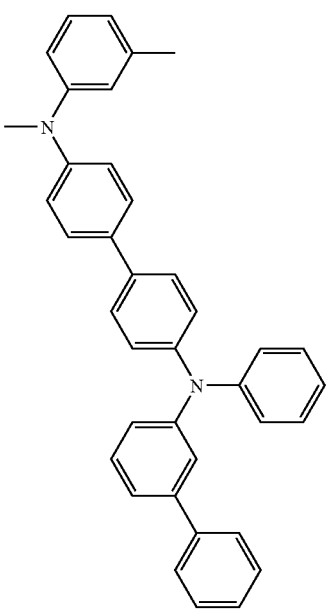

335
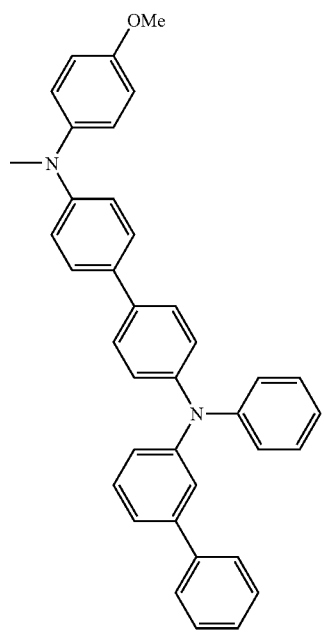
336
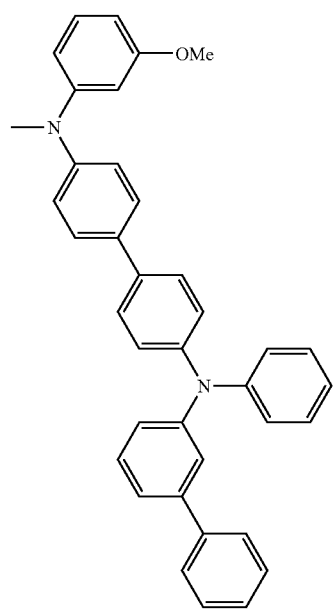
337
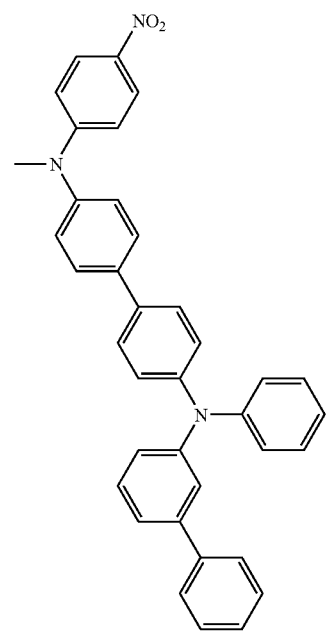
338
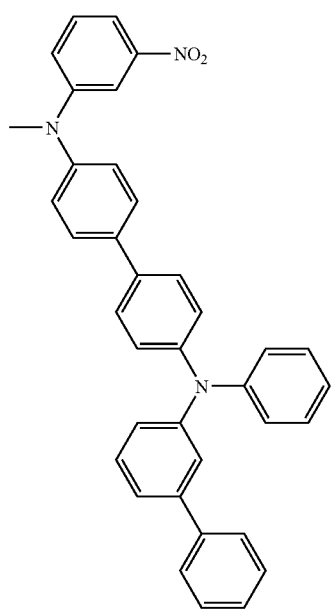

-continued
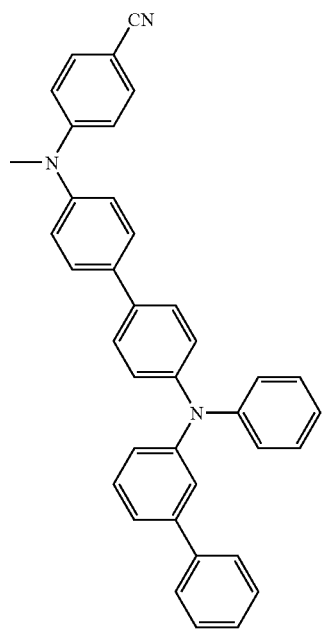
339
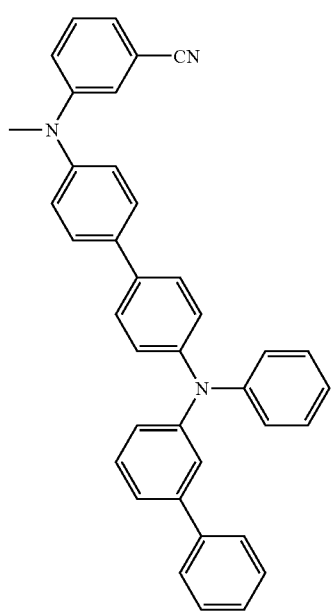
340
-continued
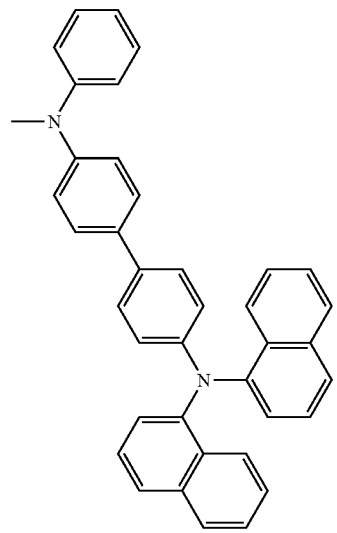
341
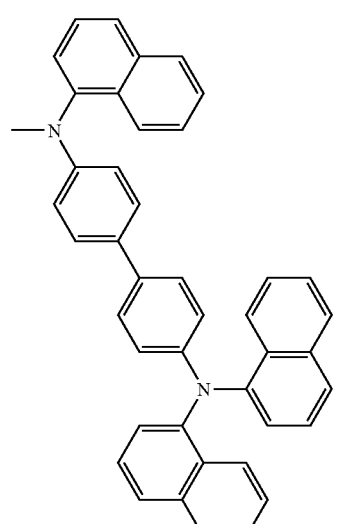
342
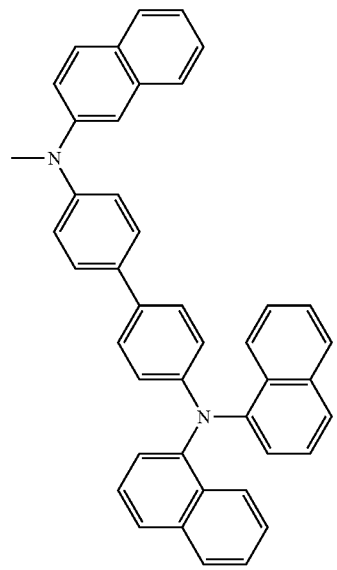
343

171
-continued
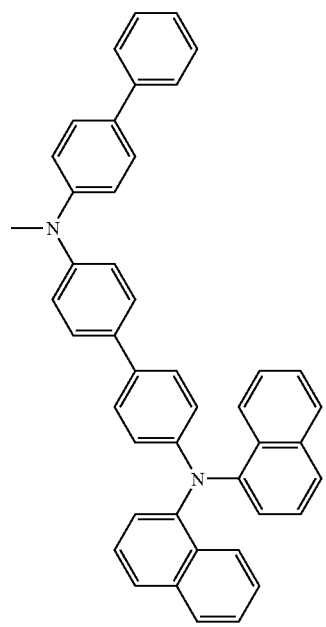
344
172
-continued
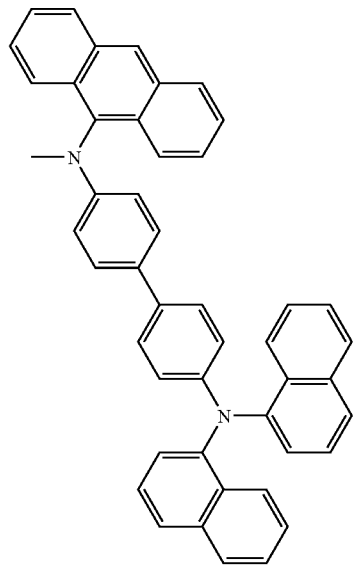
346
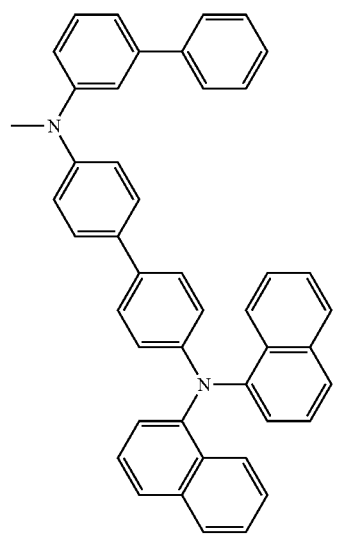
345
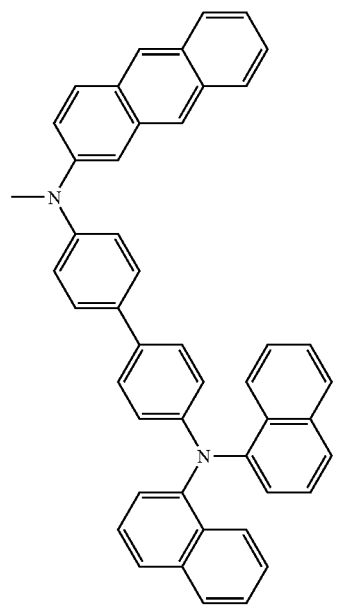
347

348
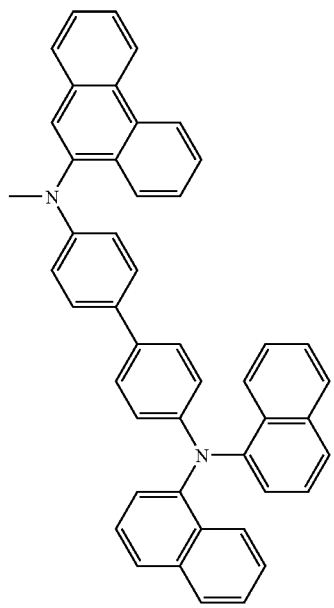
349
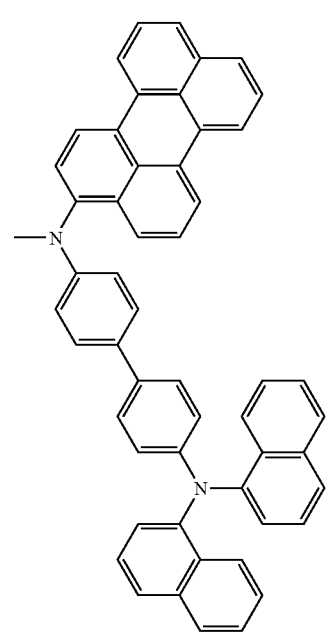
350
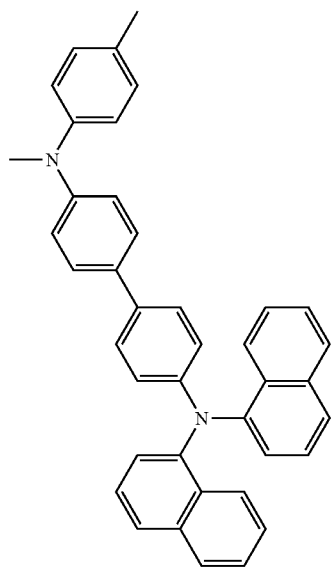
351
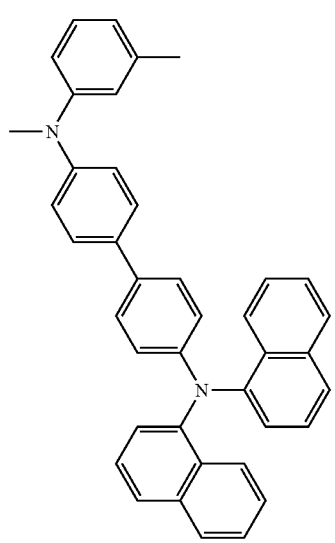

-continued
175
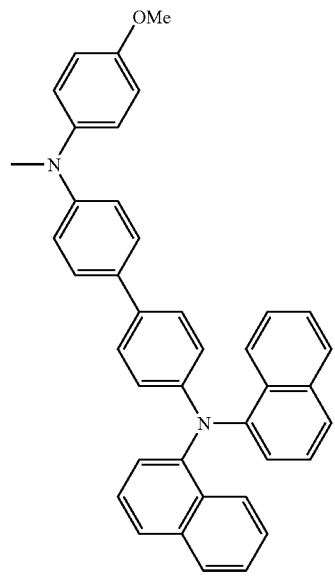
352
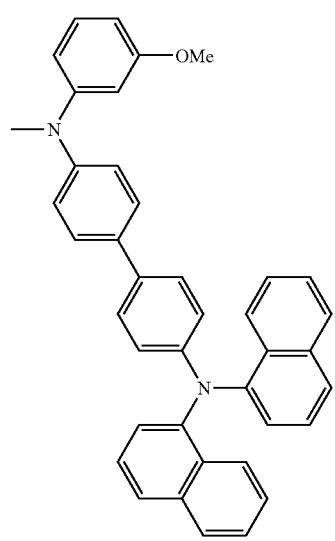
353
176
-continued
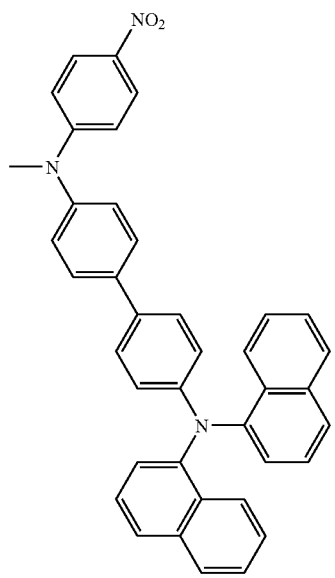
354
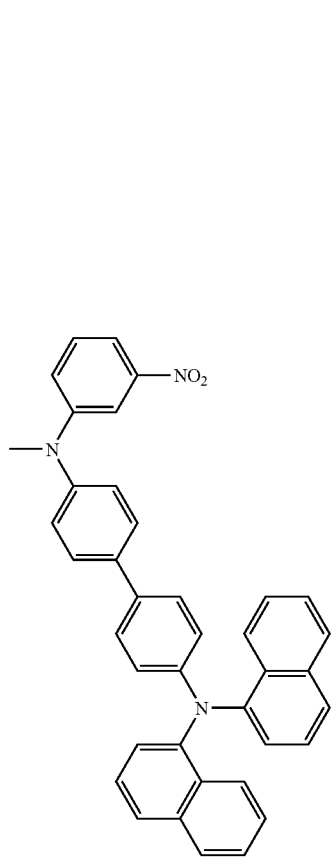
355

-continued
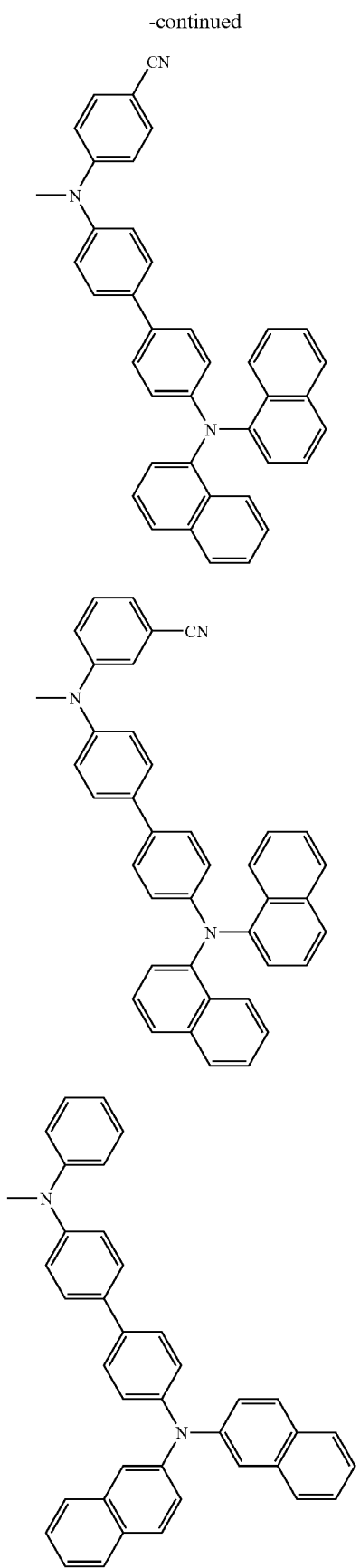
356
357
358
-continued
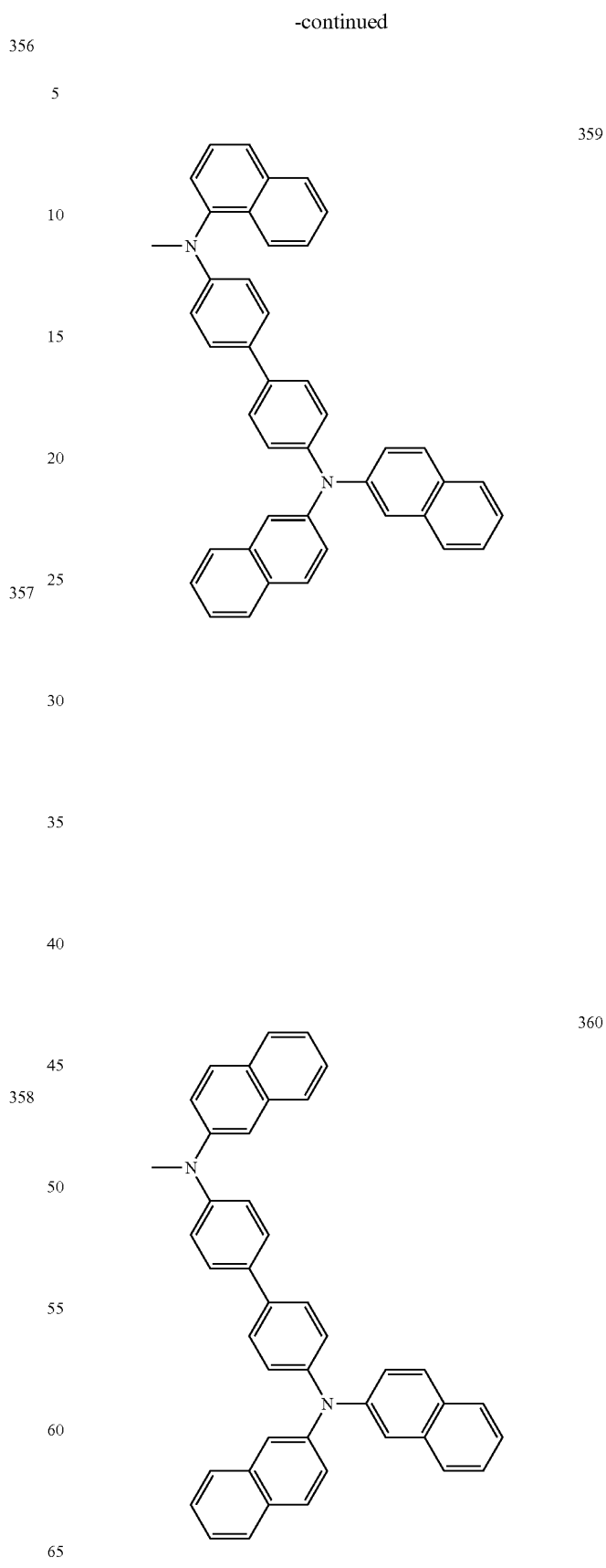
359
360

361
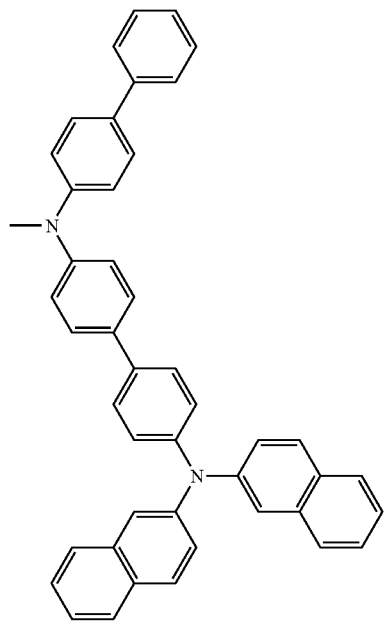
362
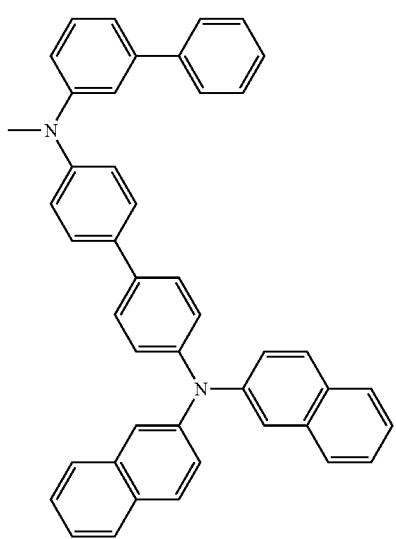
363
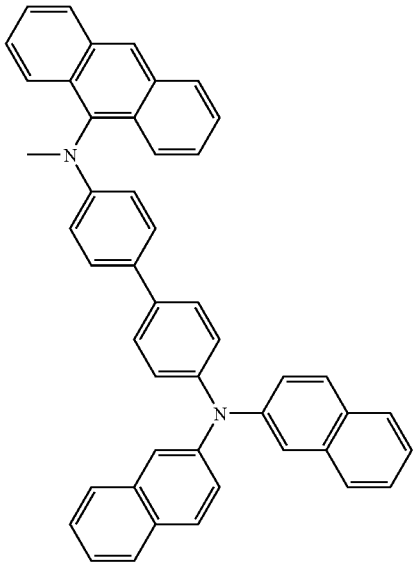
364
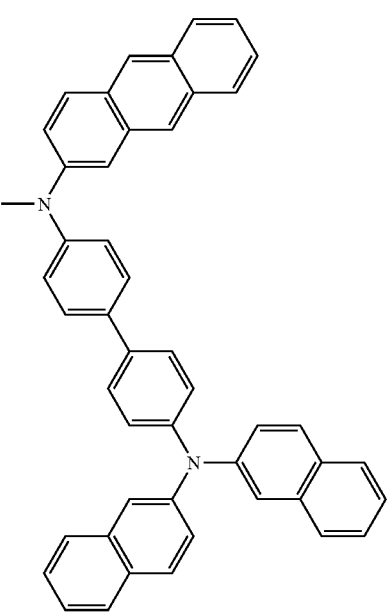

181   182
365 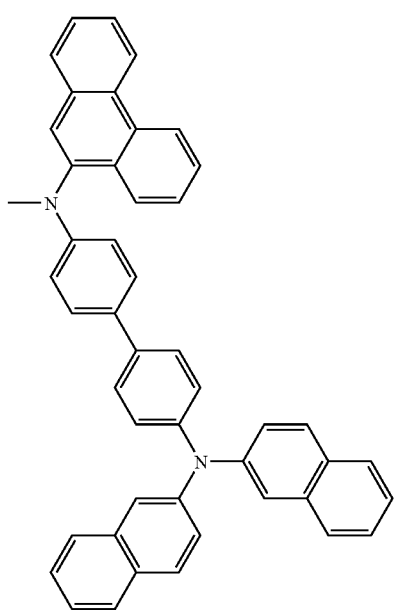 367 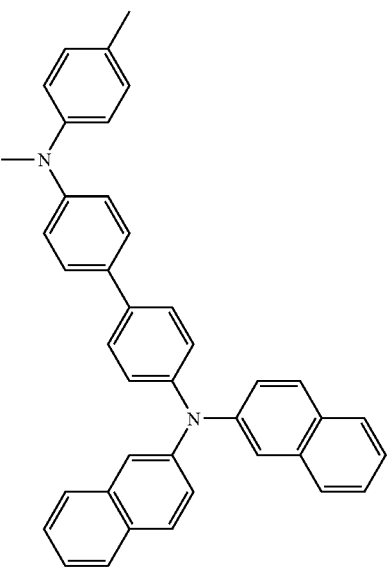
366 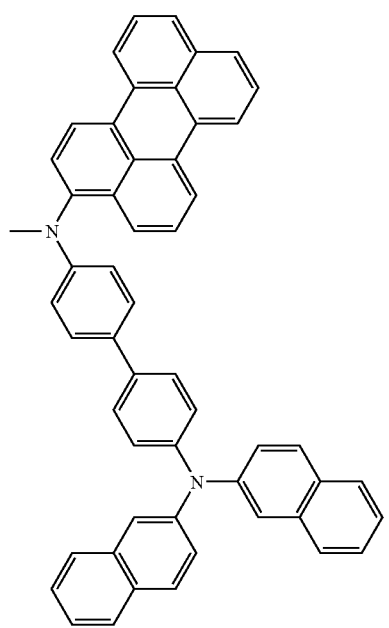 368 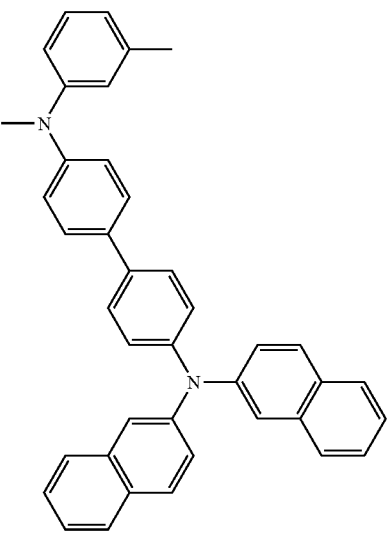

183
-continued
369
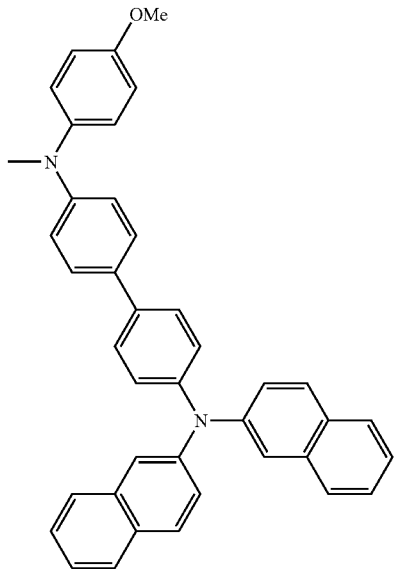
370
371
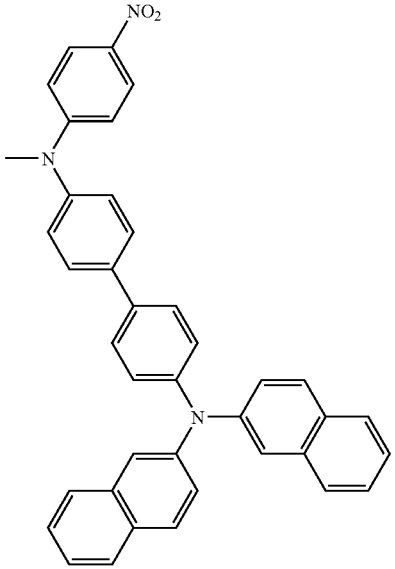
372
184
-continued 185 186
-continued -continued
373
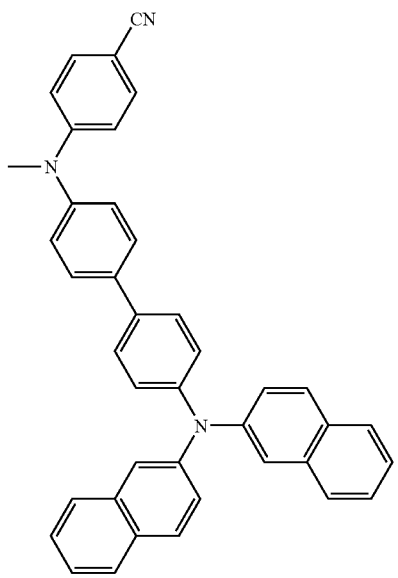
375
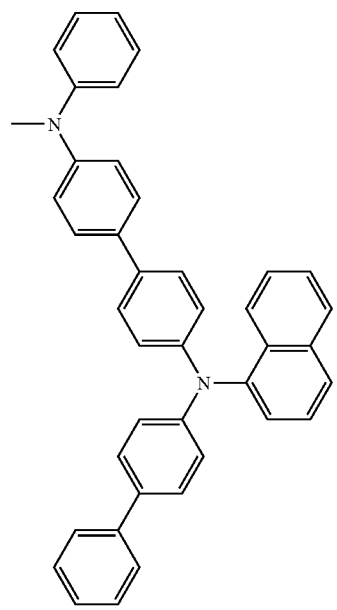
374
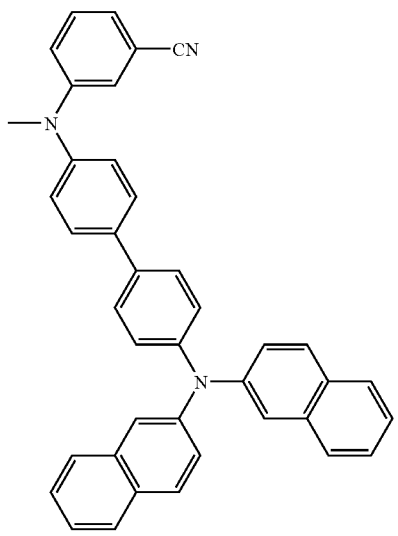
376
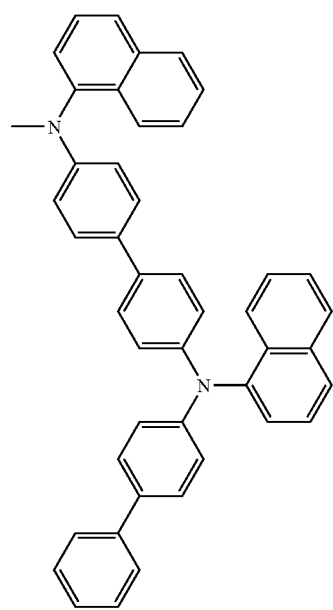

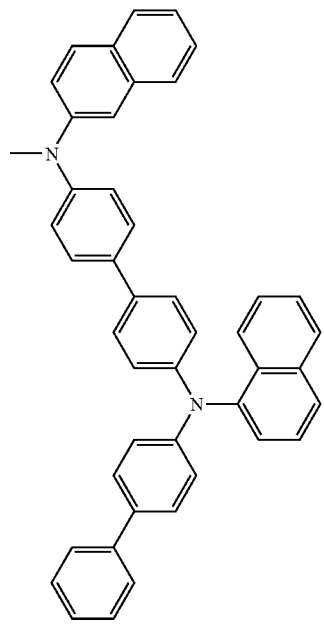
377
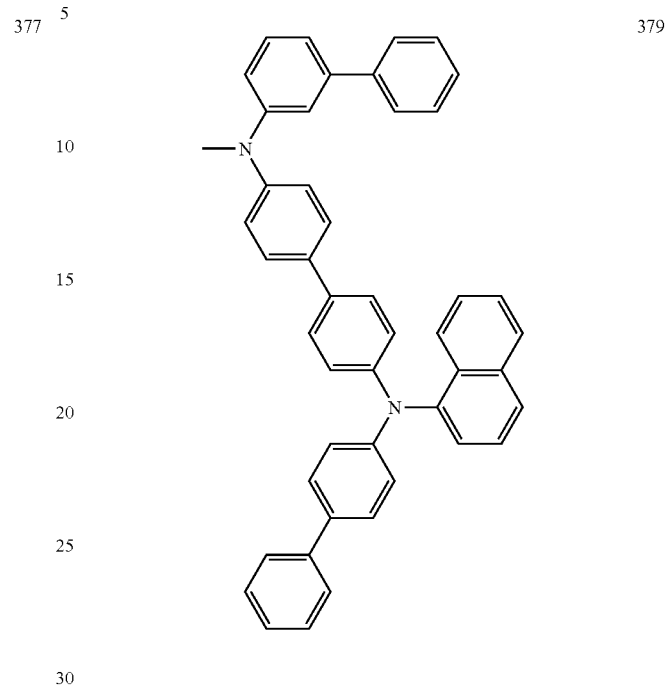
379
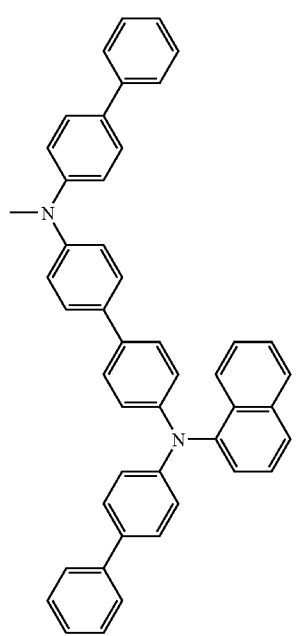
378
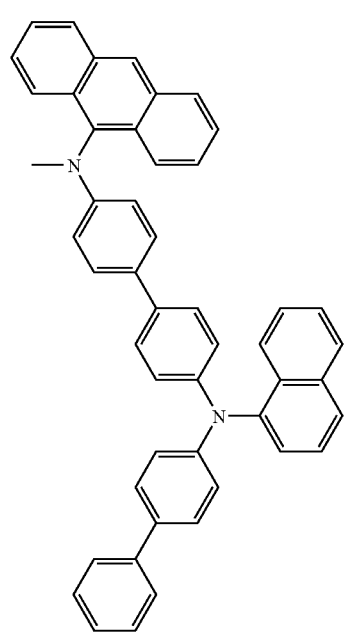
380

189
-continued
381
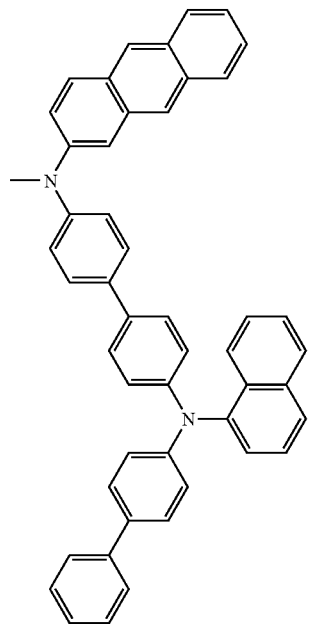
382
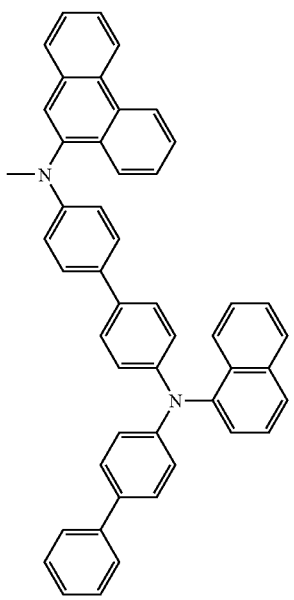
190
-continued
383
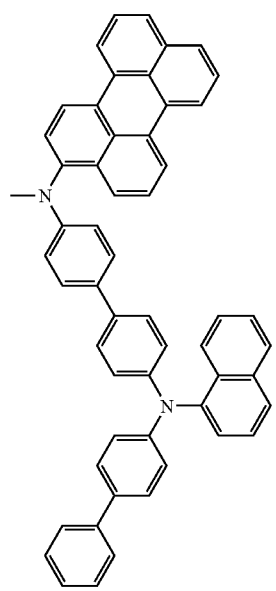
384
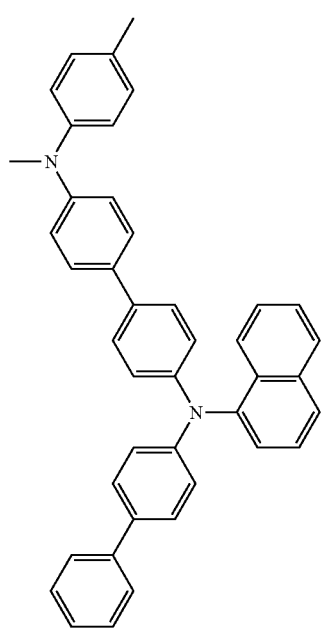

191
192
385 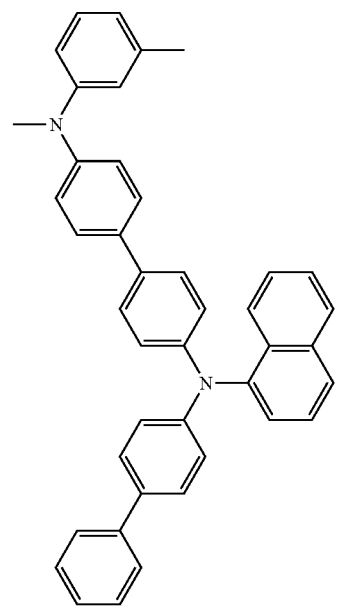
387 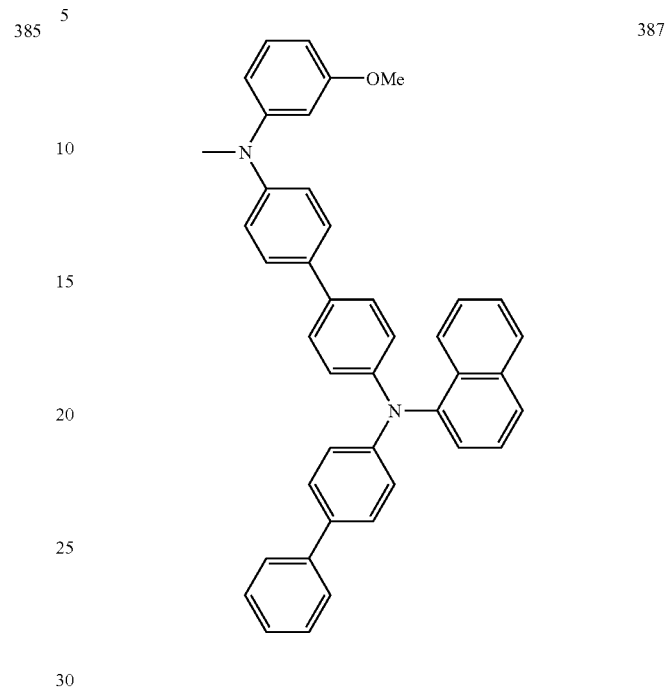
386 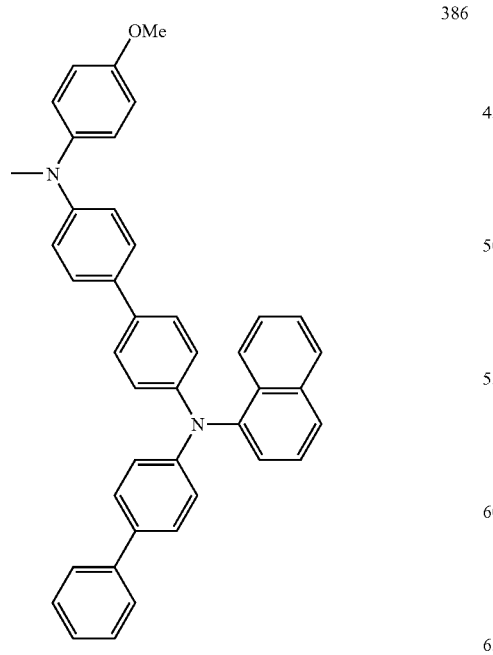
388 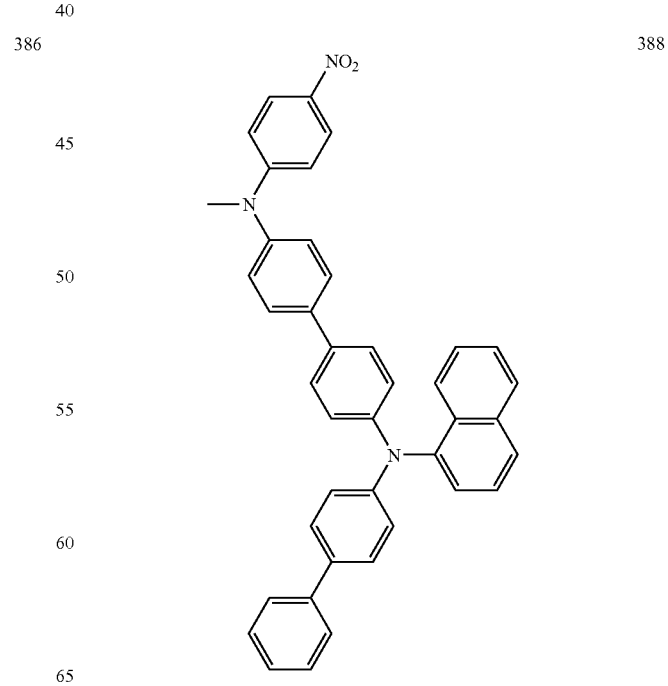

193
194
-continued
-continued
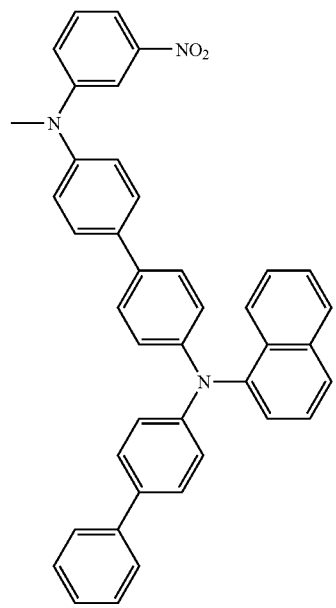
389
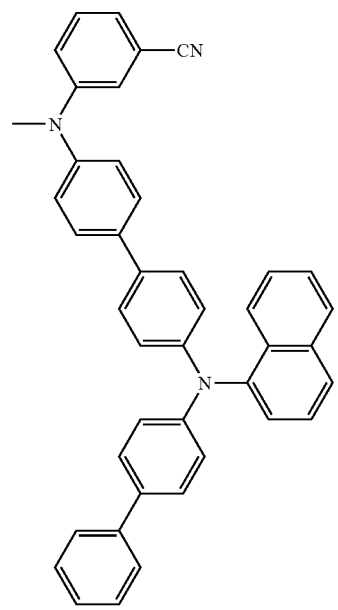
391
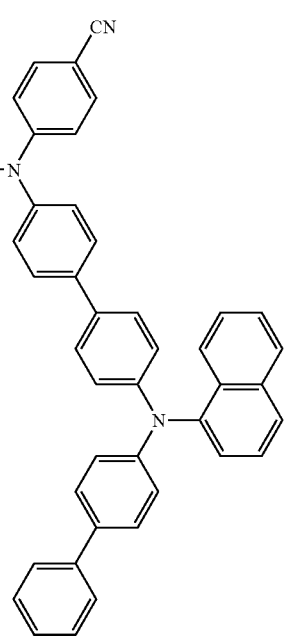
390
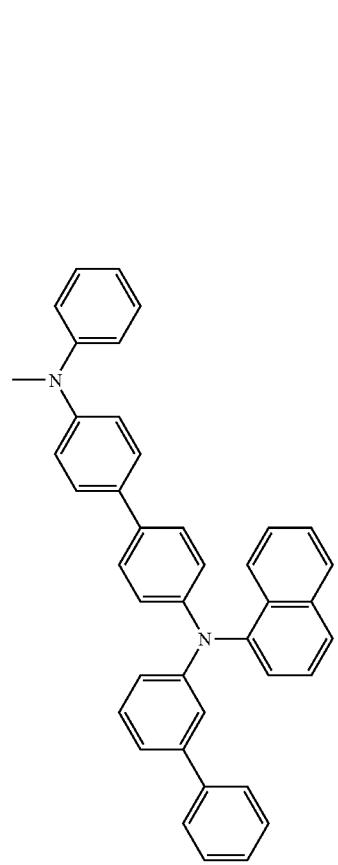
392

195
-continued
393
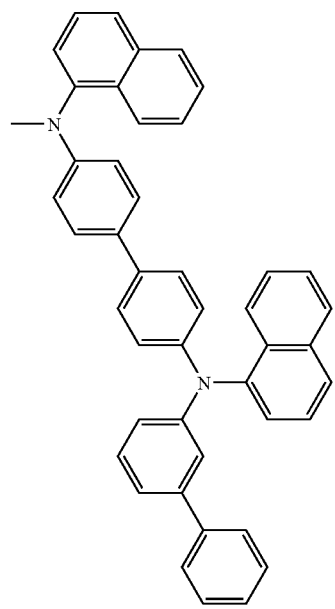
394
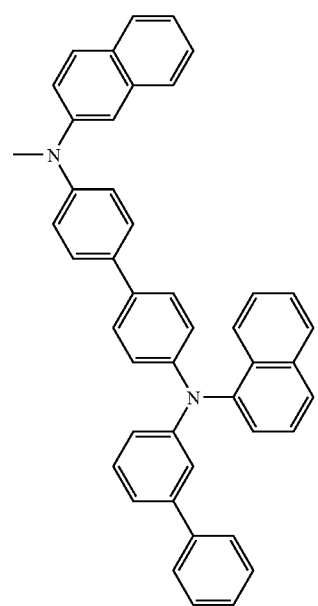
196
-continued
395
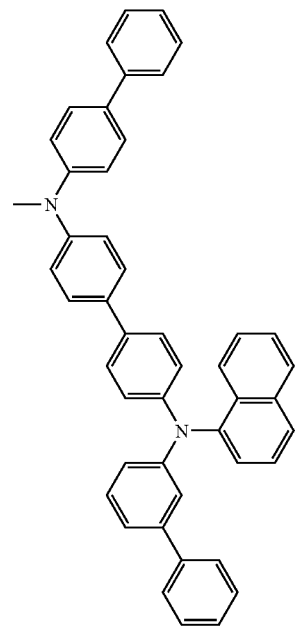
396
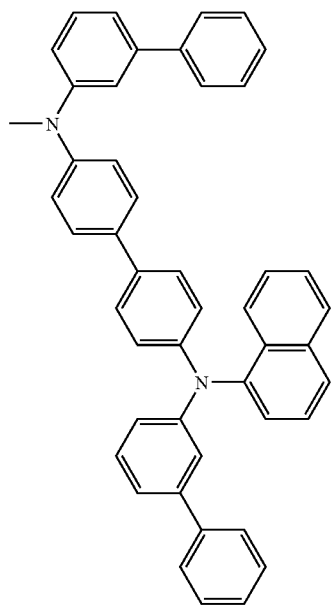

197
-continued
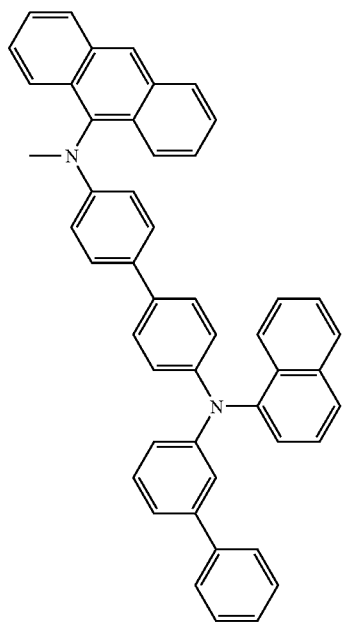
397
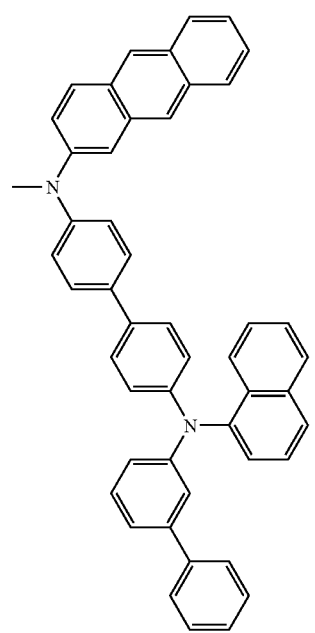
398
198
-continued
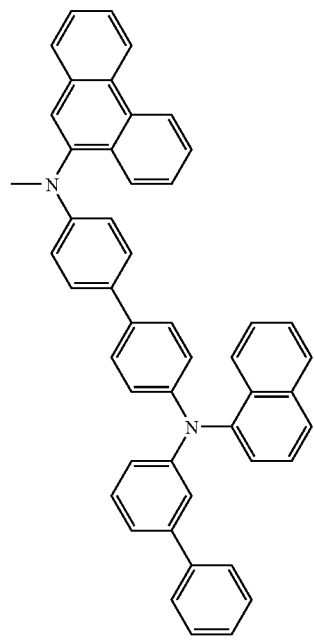
399
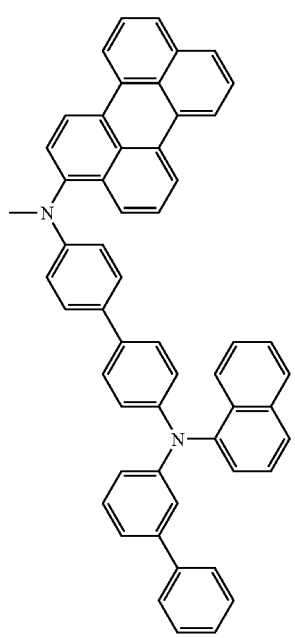
400

-continued
199
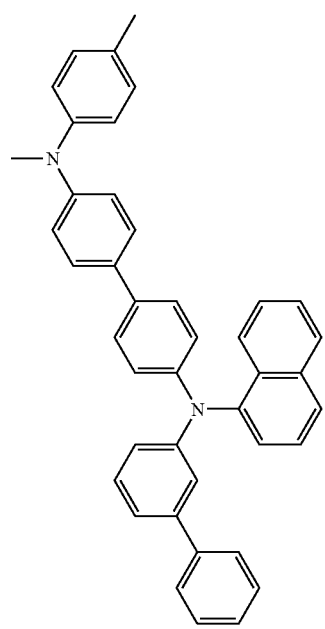
401
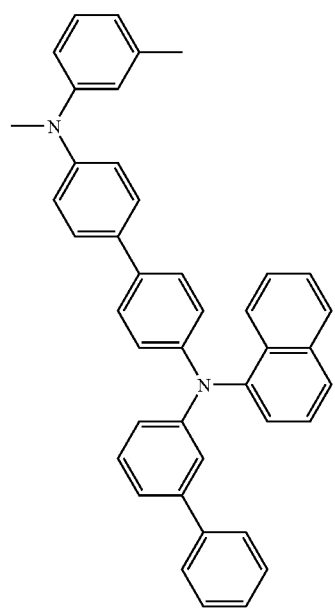
402
200
-continued
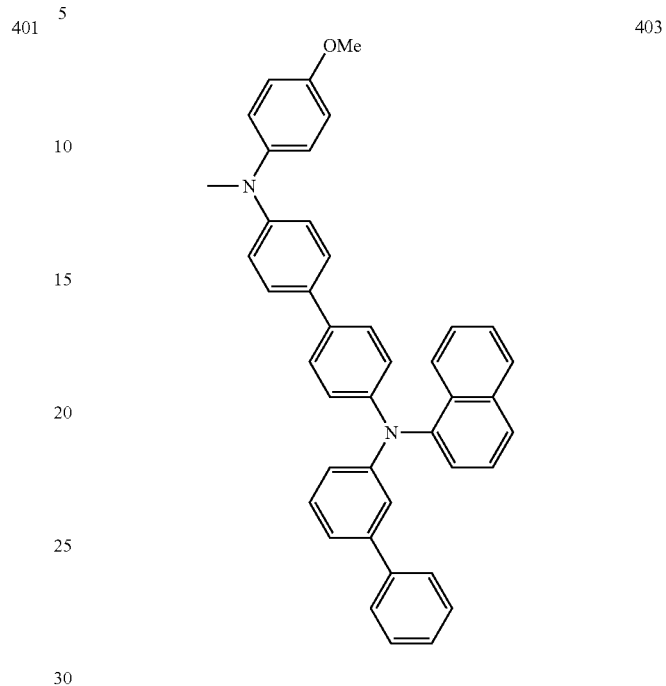
403
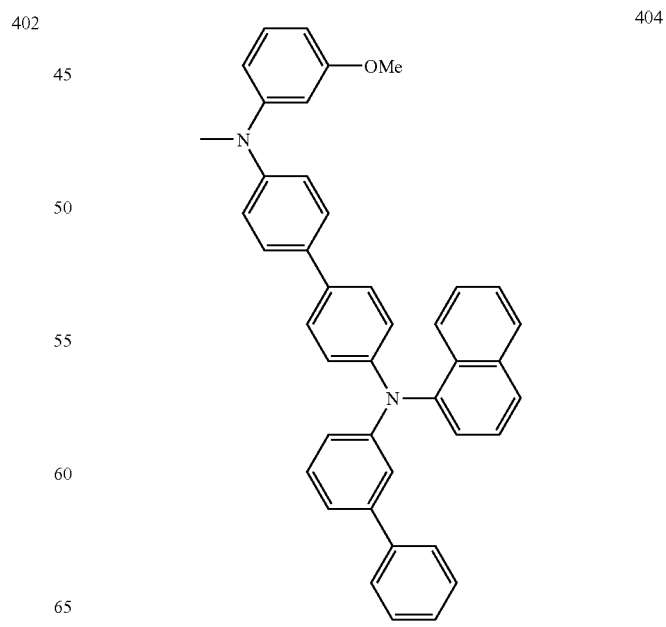
404

-continued
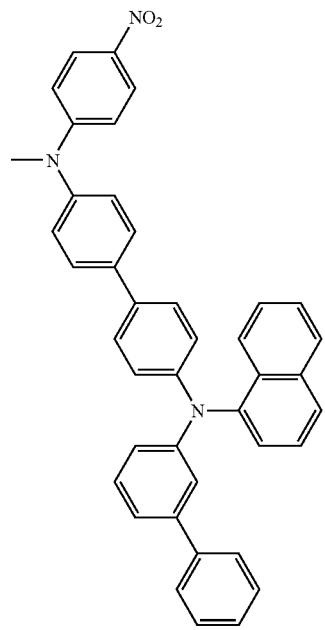
405
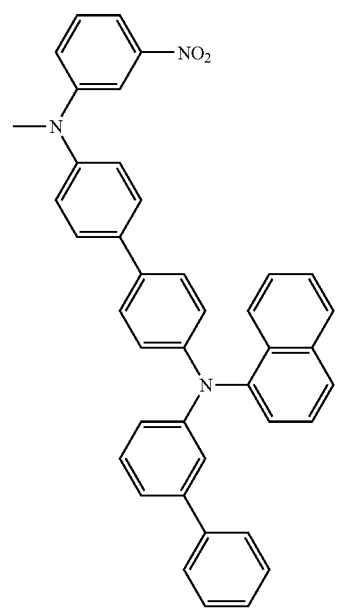
406
-continued
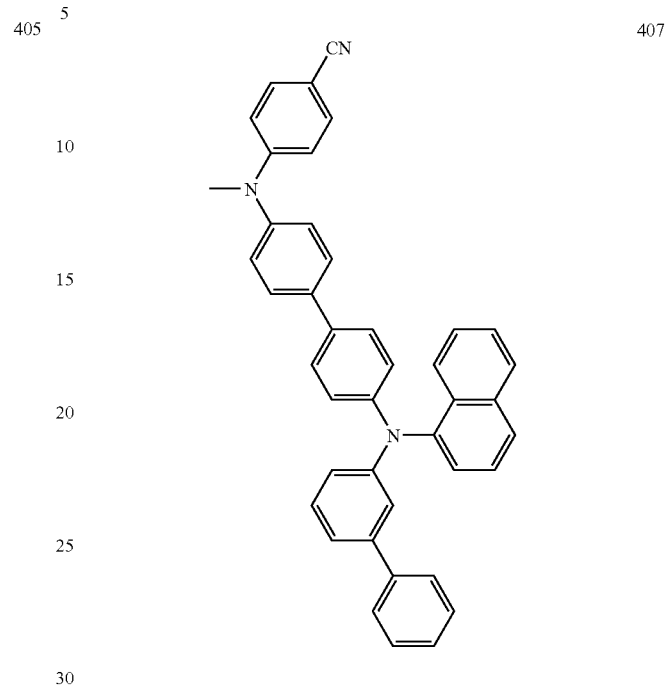
407
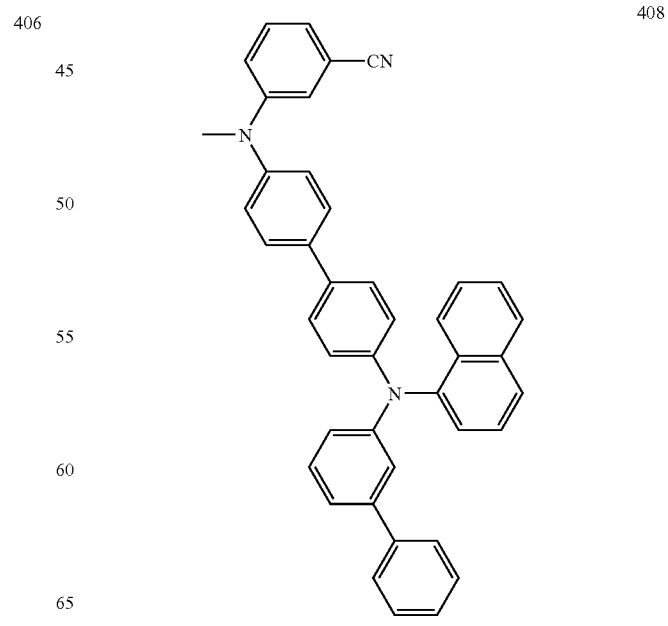
408

203
-continued
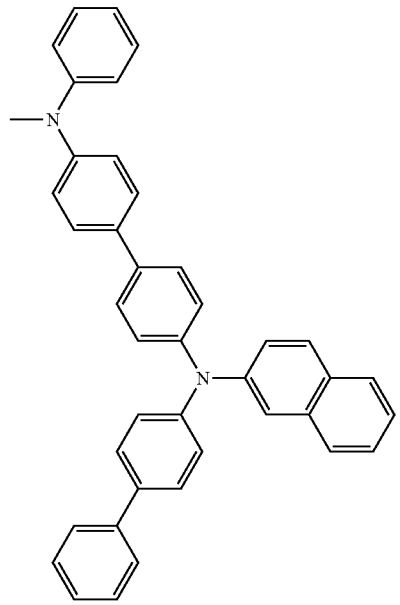
409
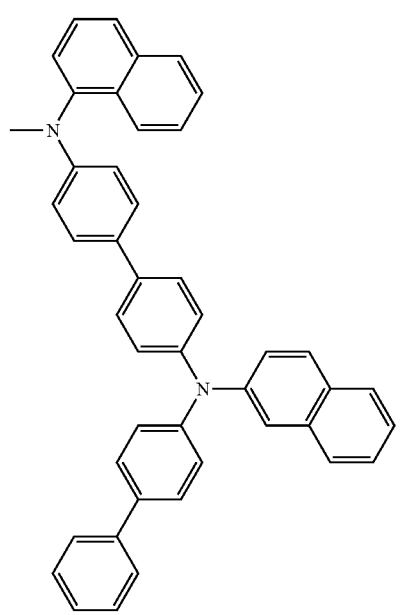
410
204
-continued
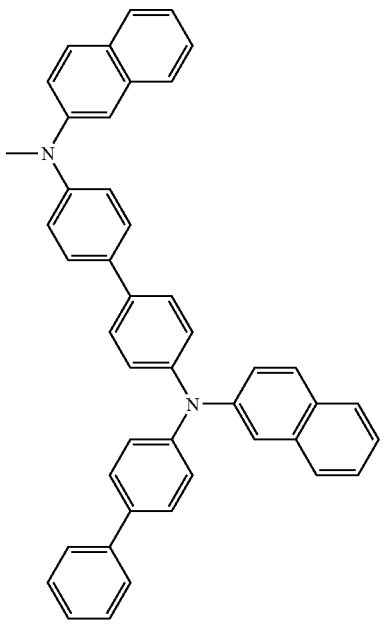
411
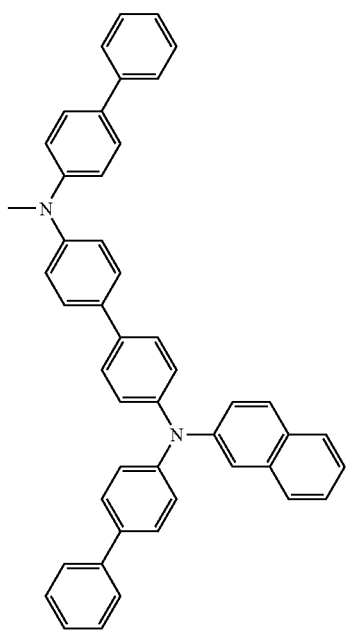
412

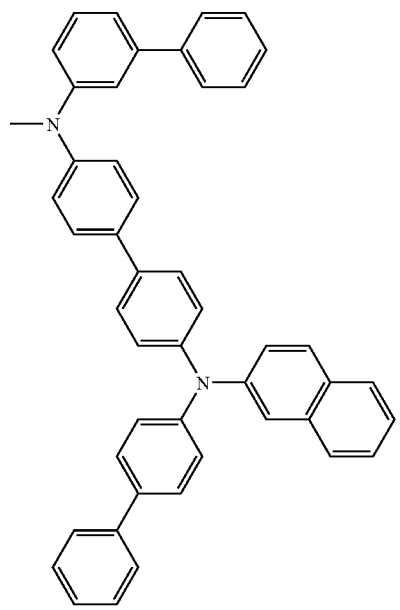
413
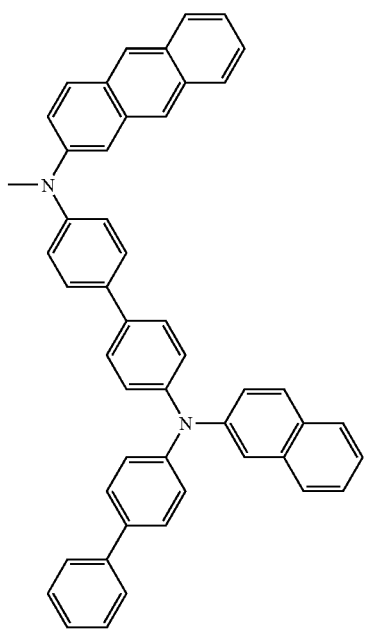
415
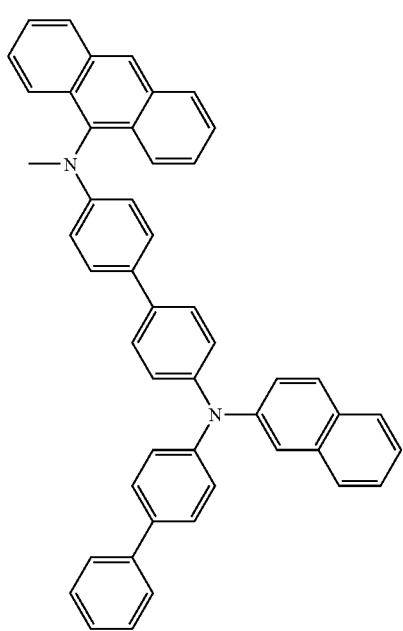
414
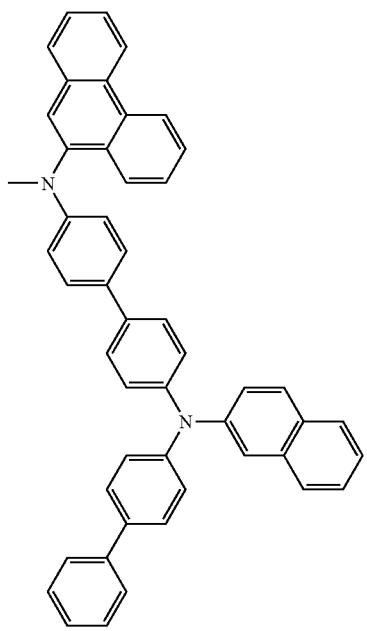
416

207
-continued
417
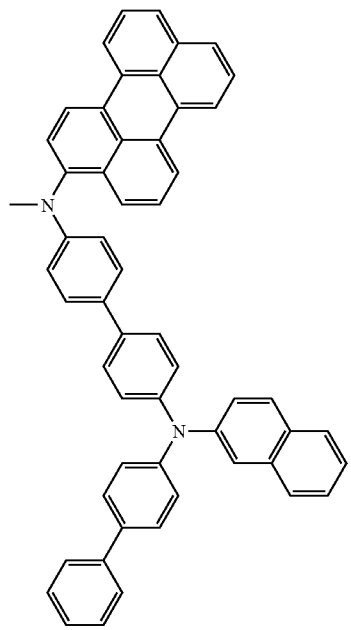
418
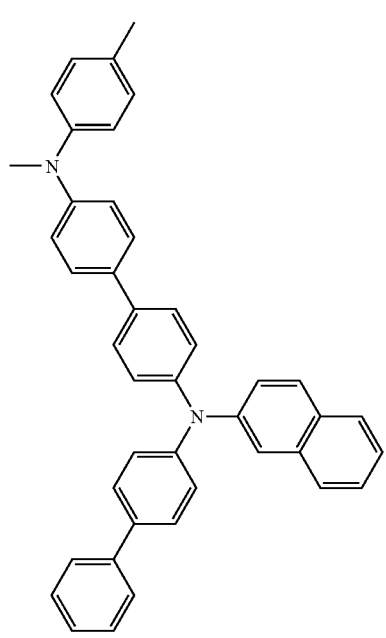
208
-continued
419
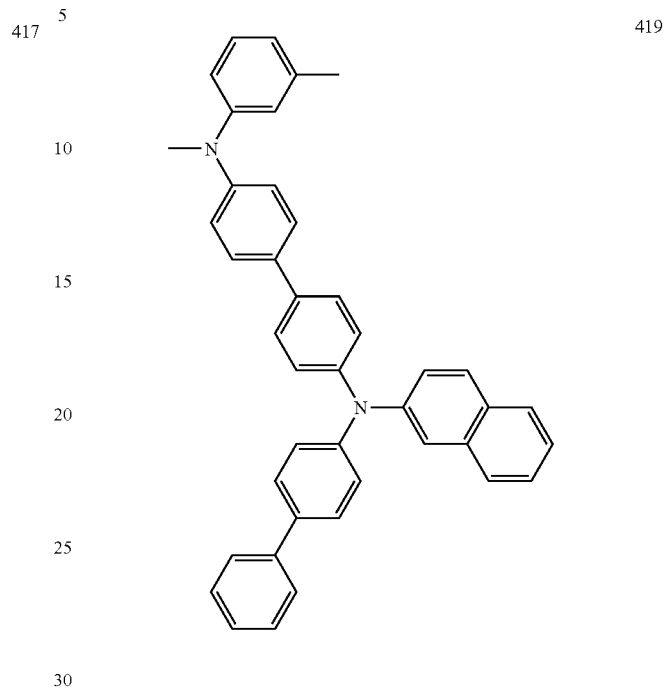
420
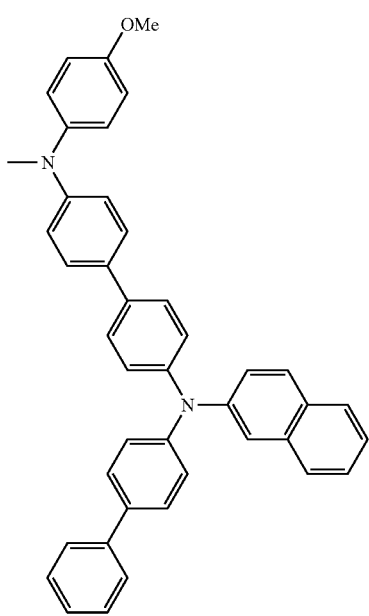

421
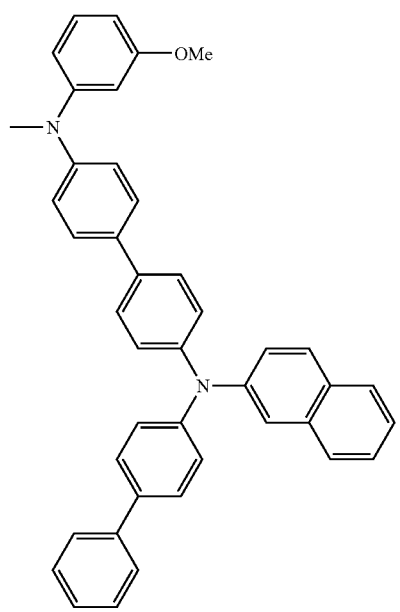
422
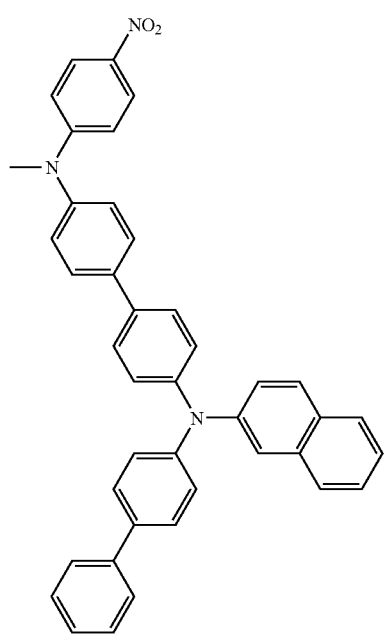
423
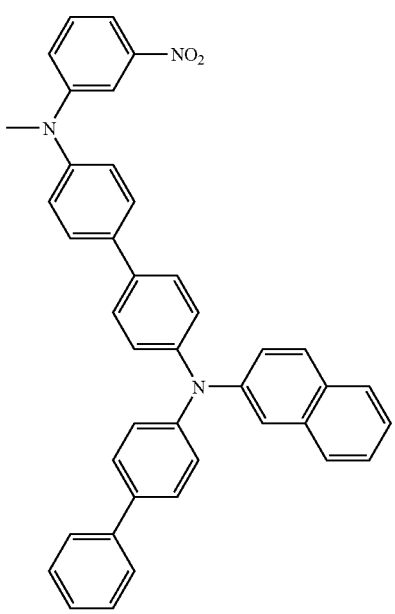
424
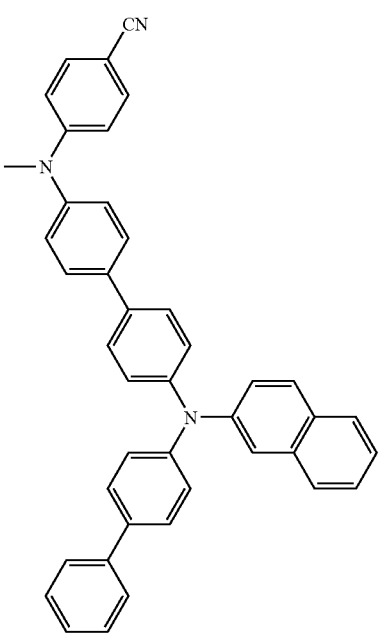

211
-continued
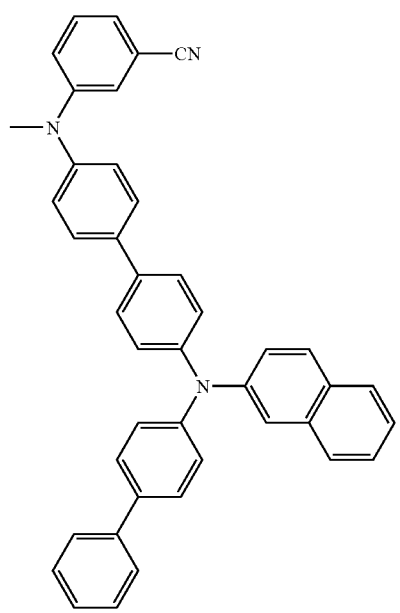
425
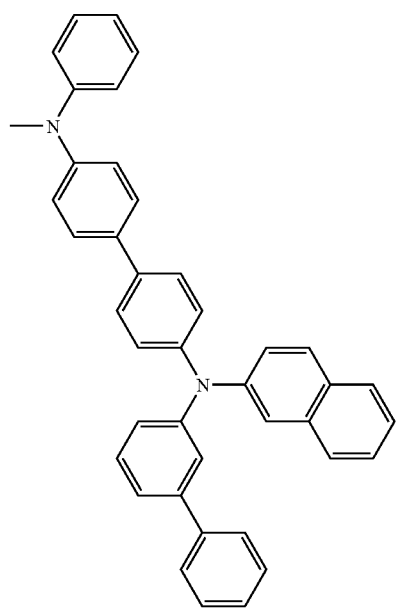
426
212
-continued
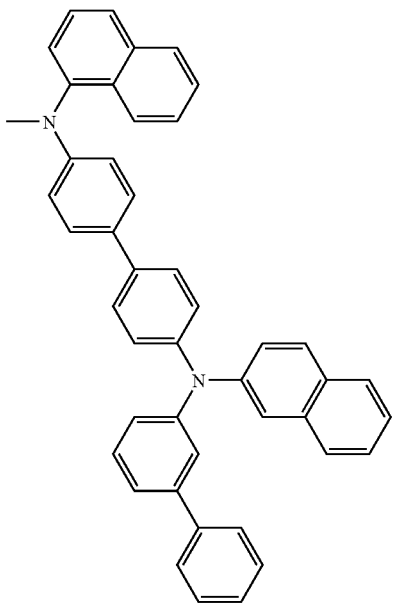
427
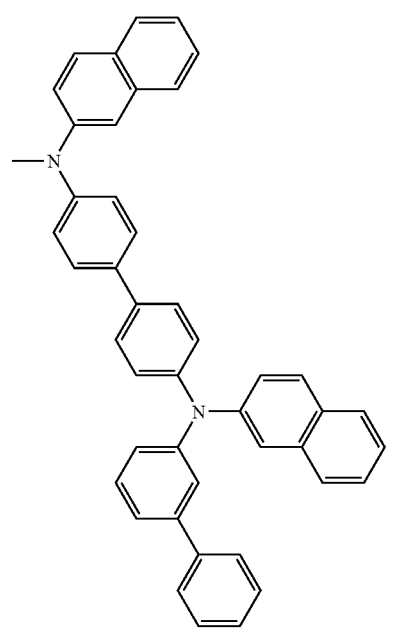
428

213 214
-continued -continued
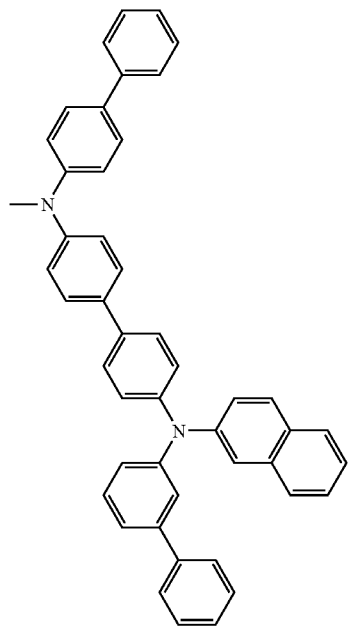
429
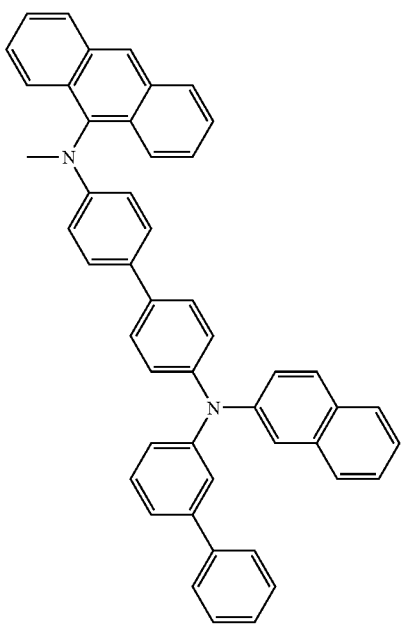
431
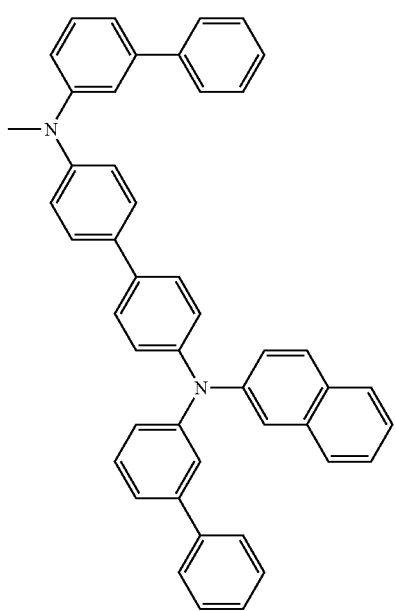
430
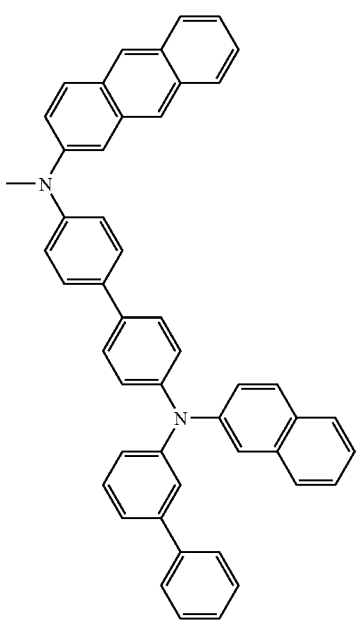
432

215
-continued
216
-continued
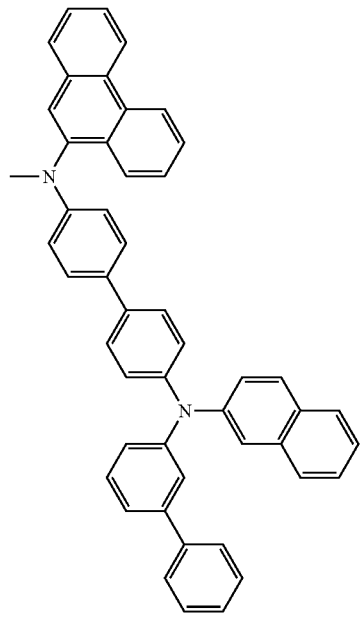
433
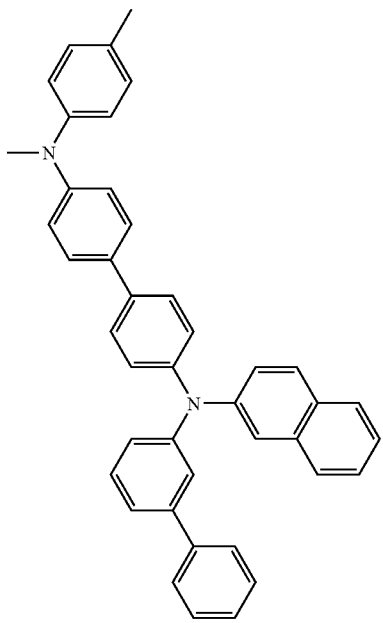
435
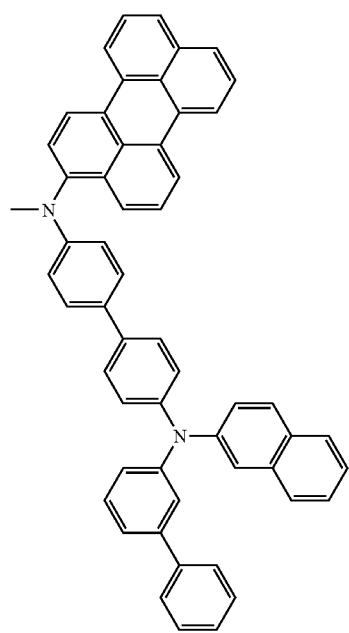
434
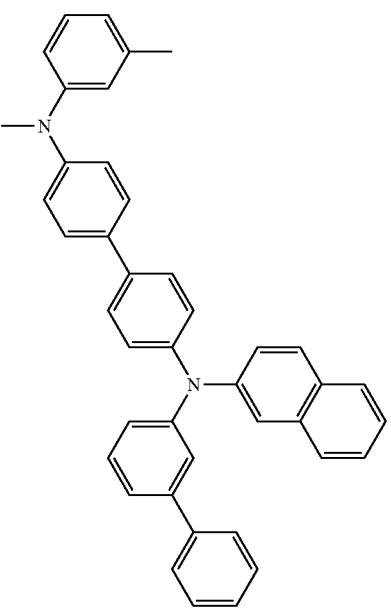
436

217
-continued
437
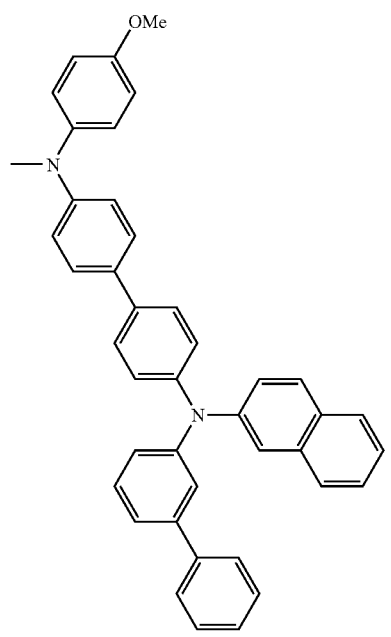
218
-continued
439
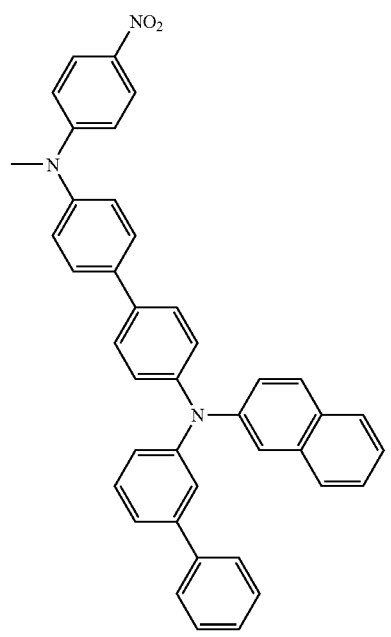
438
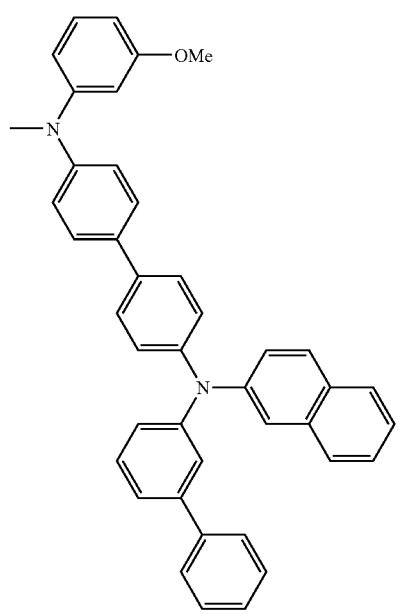
440
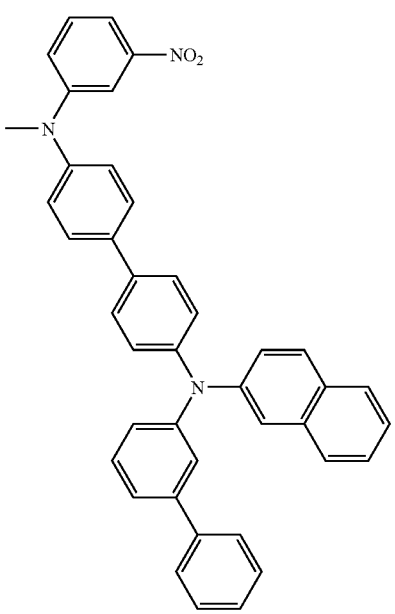

219 220
441 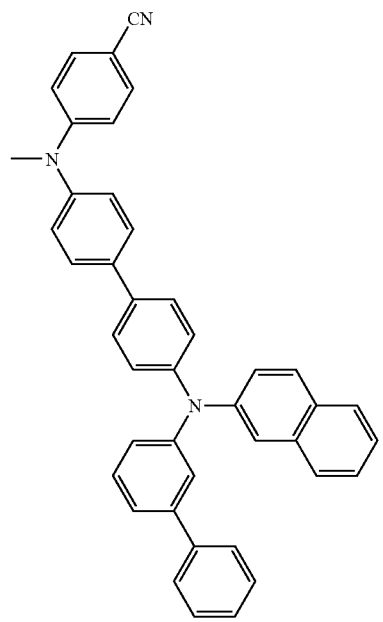
443 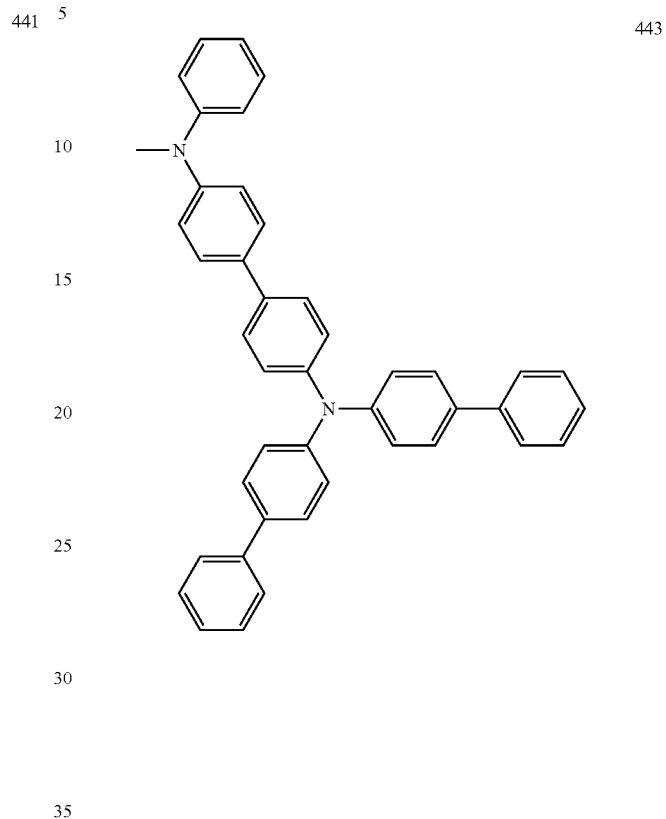
442 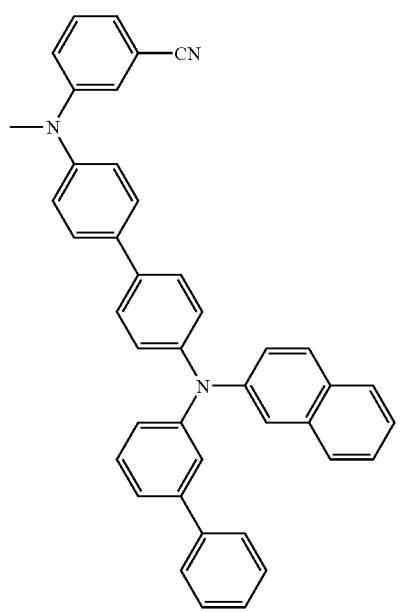
444 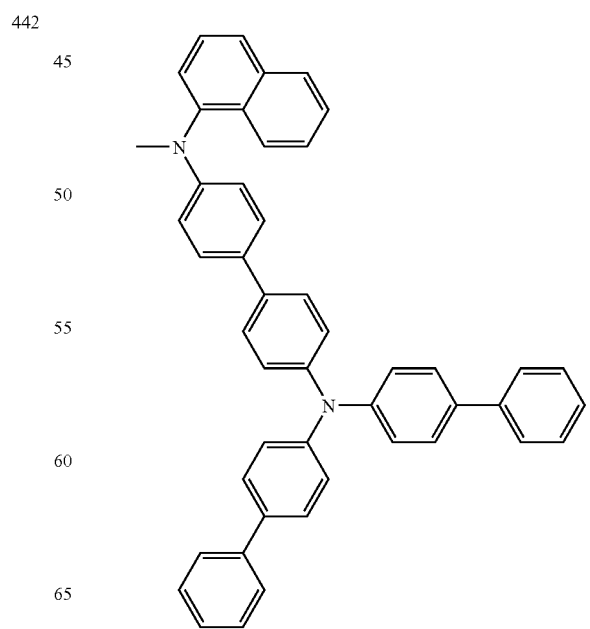

-continued
445
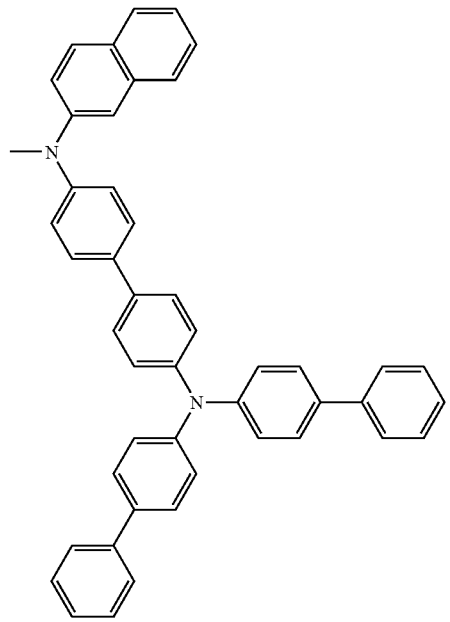
447
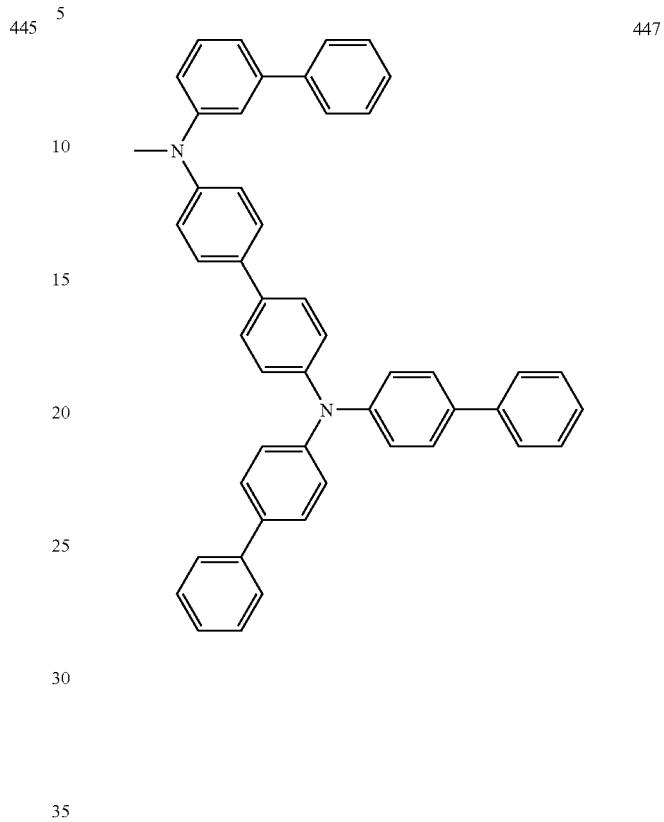
446
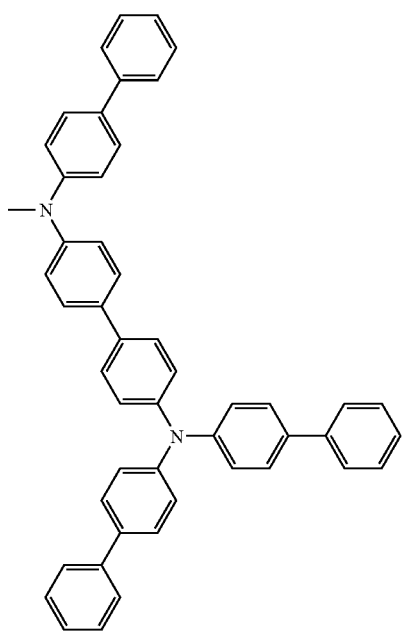
448
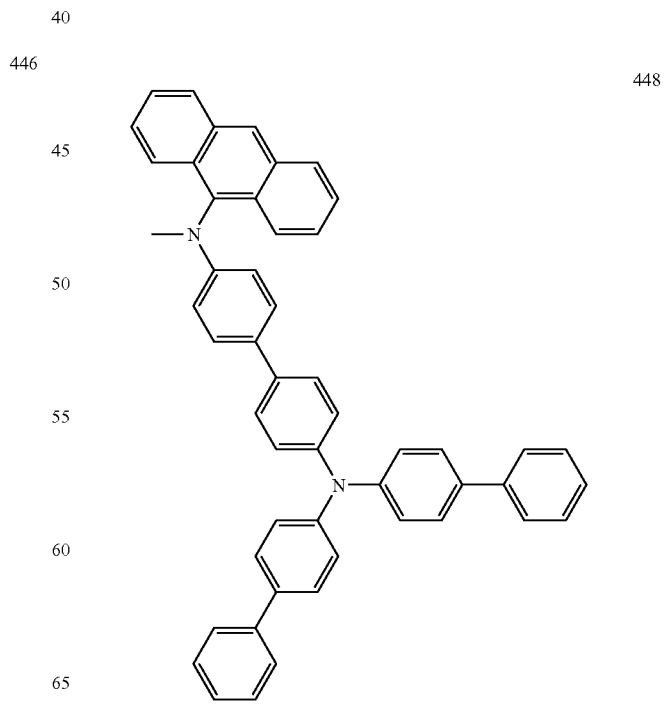

223
-continued
449 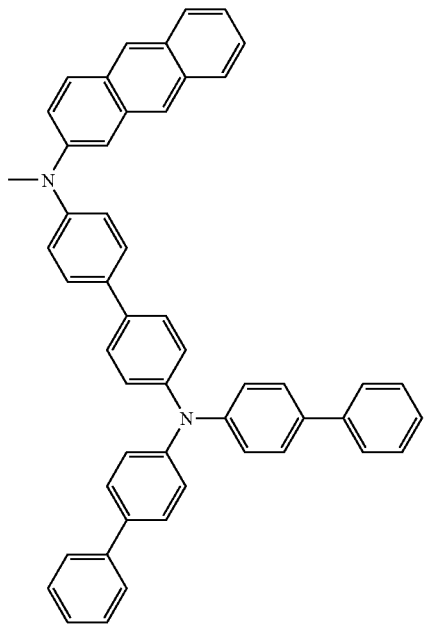
450 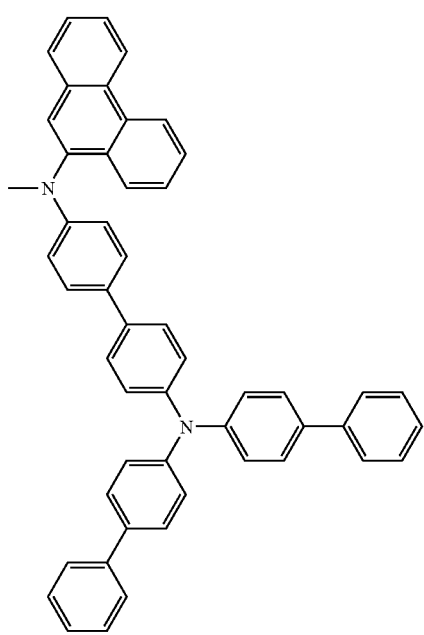
224
-continued
451 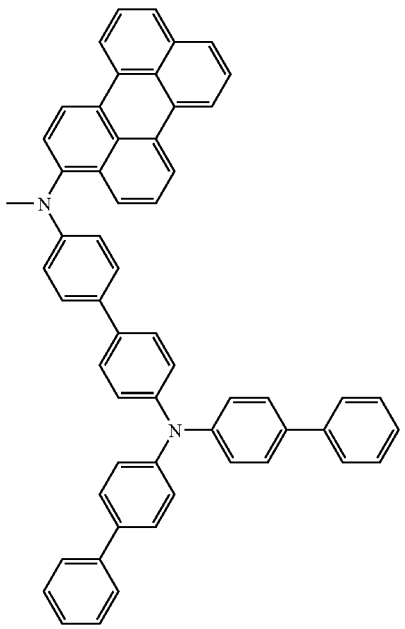
452 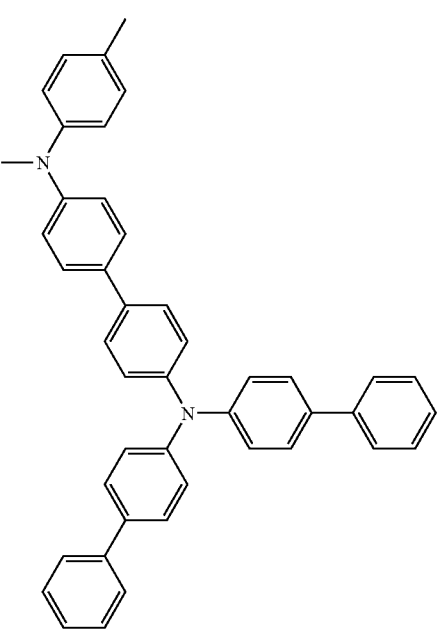

225 226
-continued
453
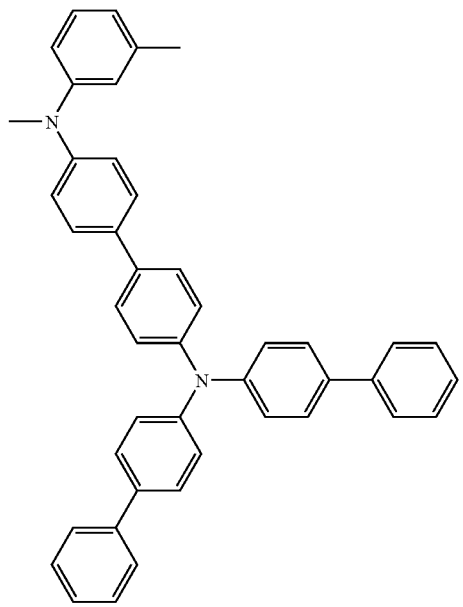
455
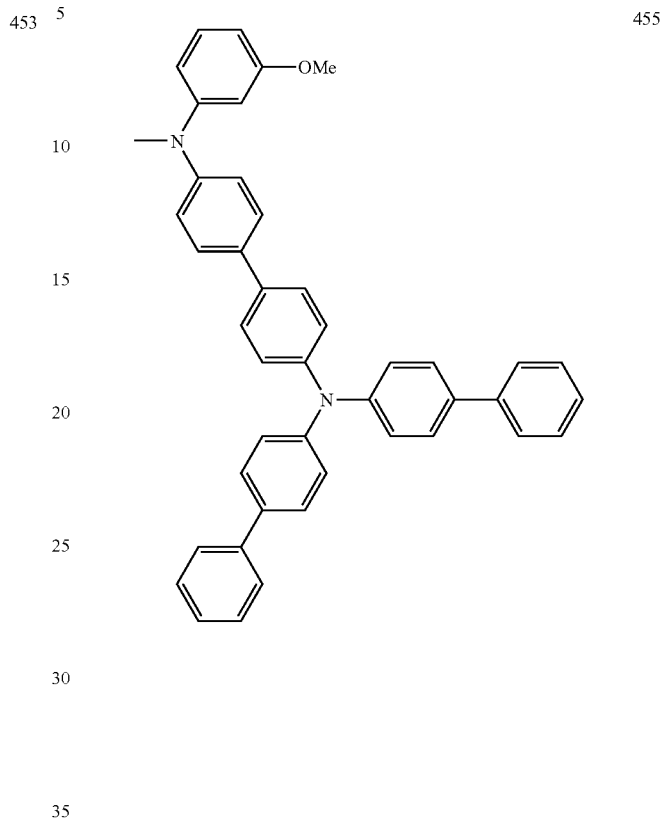
454
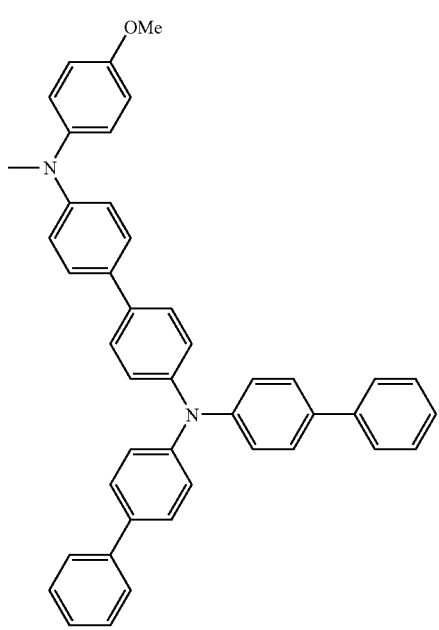
456
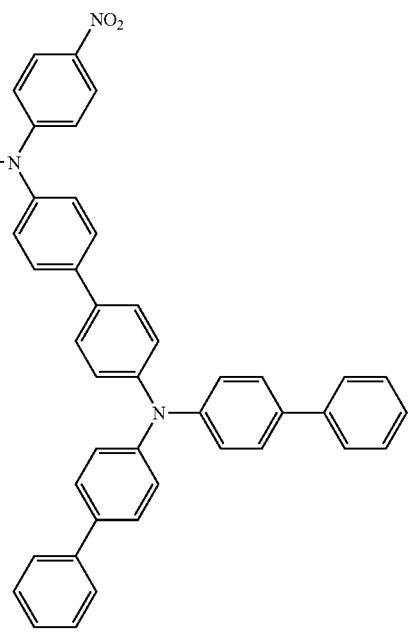

227 -continued
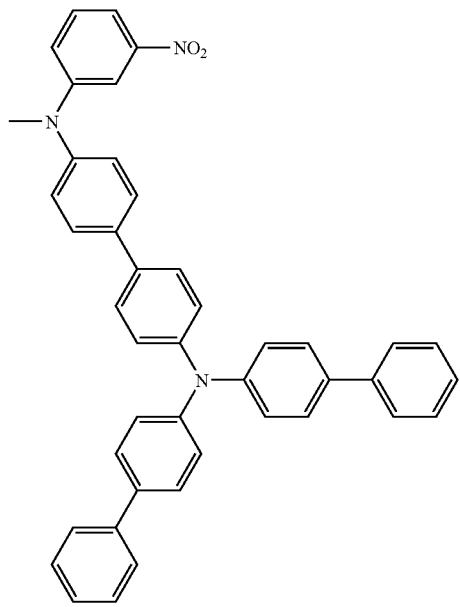
457
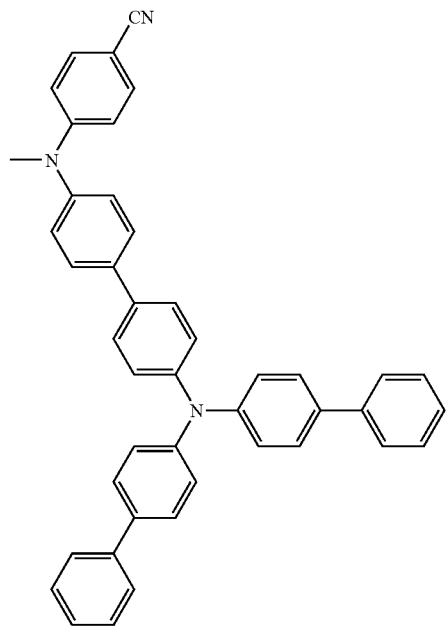
458
228 -continued
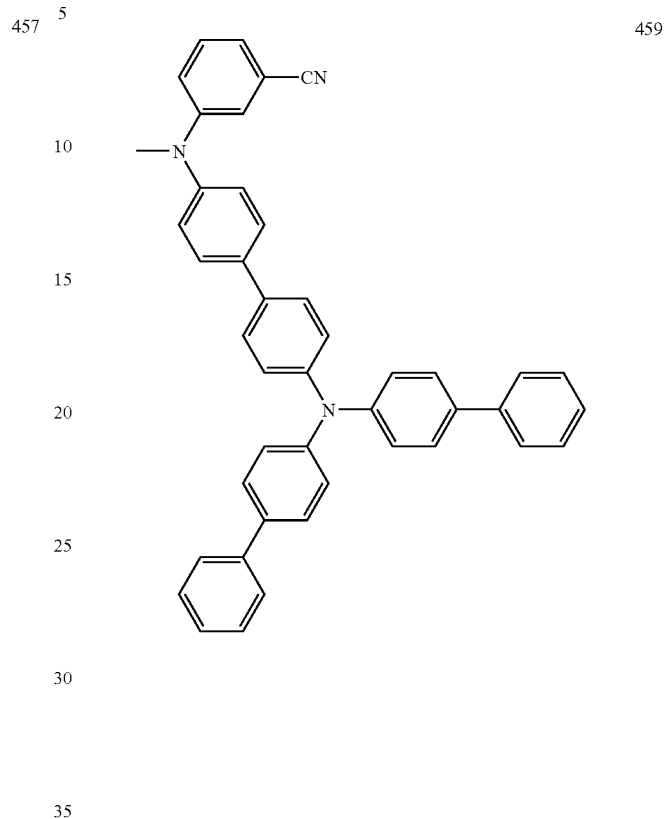
459
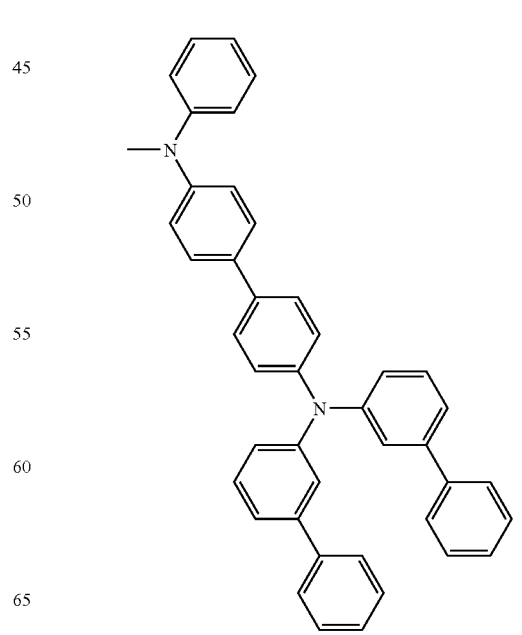
460

229
-continued
230
-continued
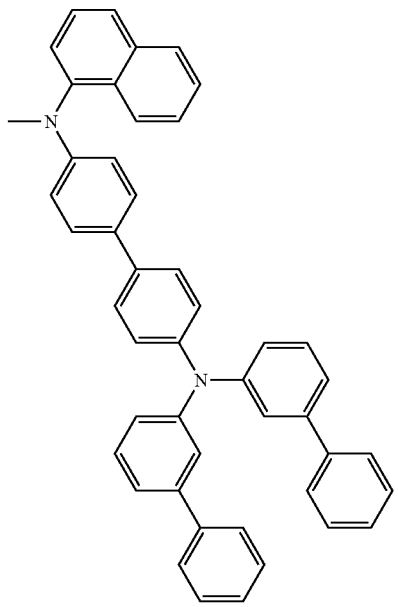
461
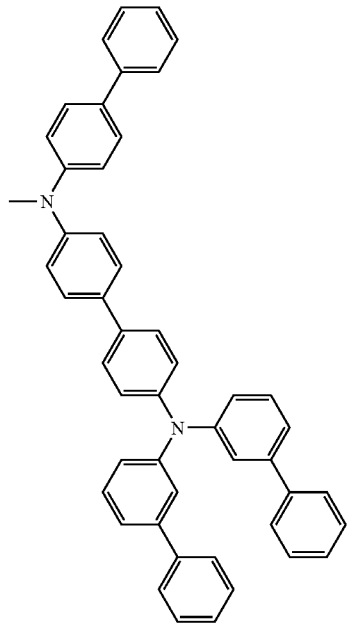
463
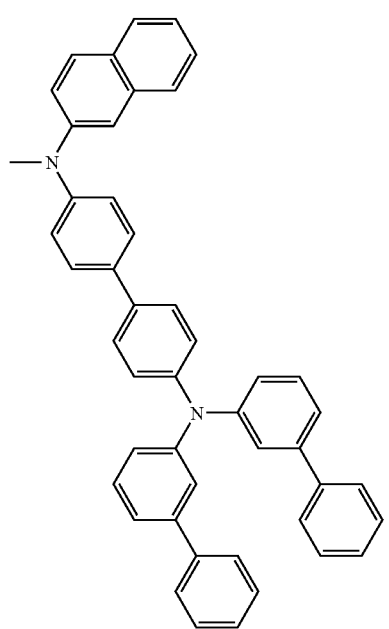
462
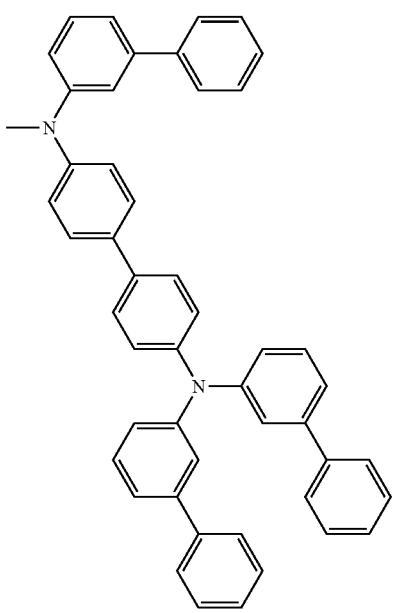
464

231
-continued
465
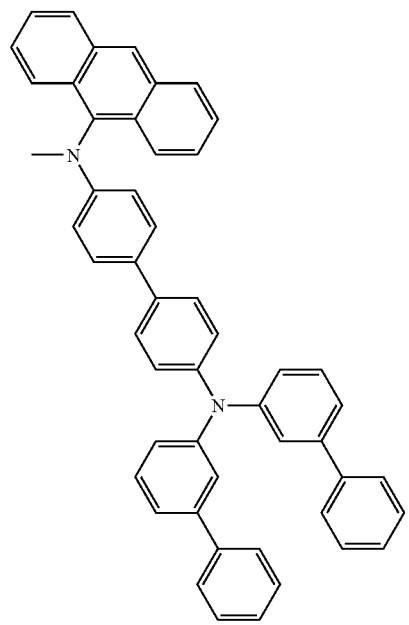
466
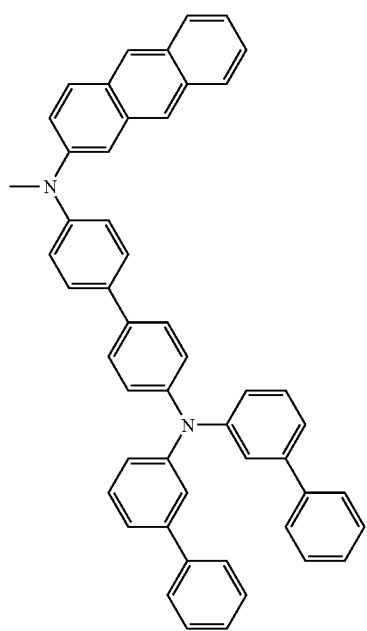
232
-continued
467
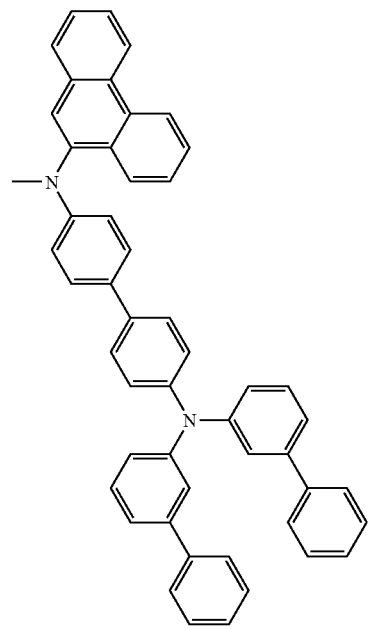
468
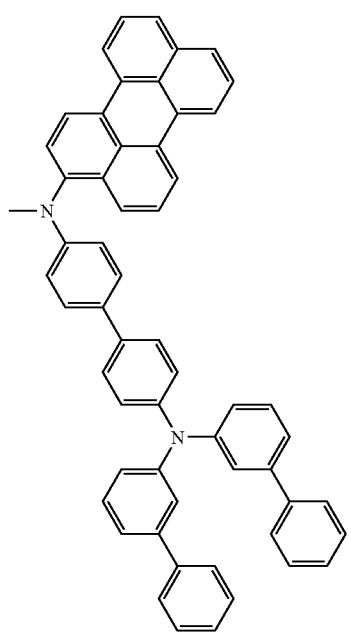

233 234
-continued -continued
469 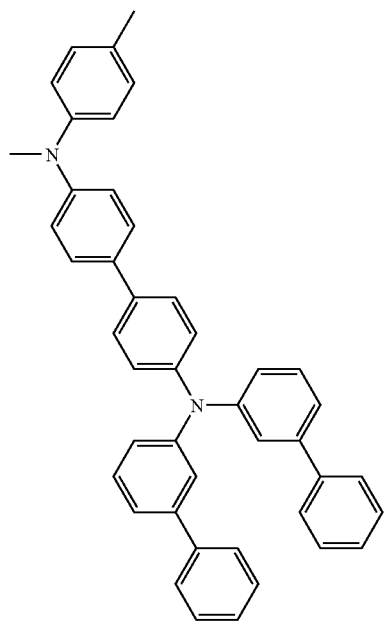 471 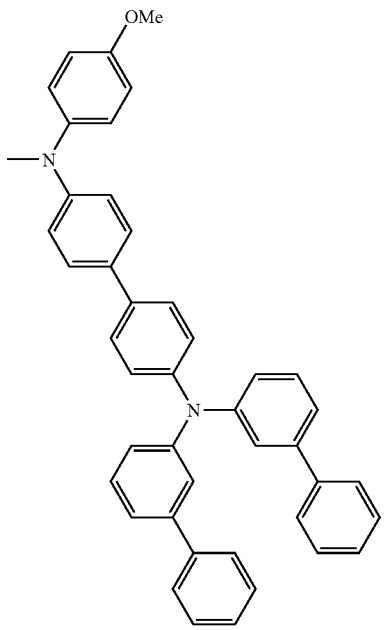
470 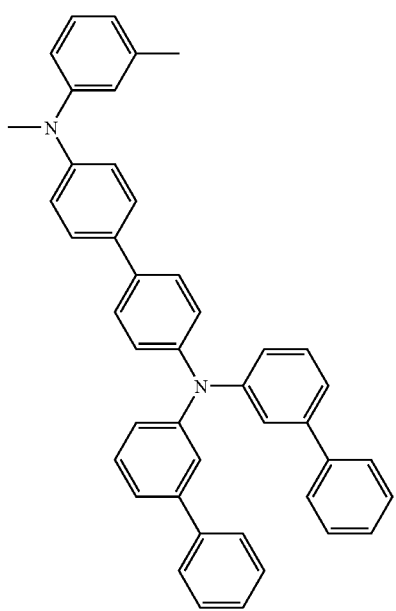 472 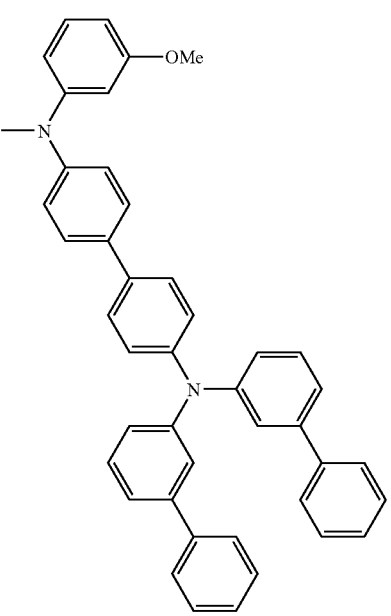

-continued

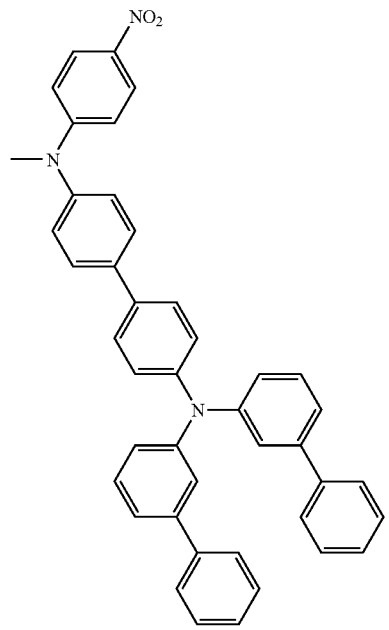

473

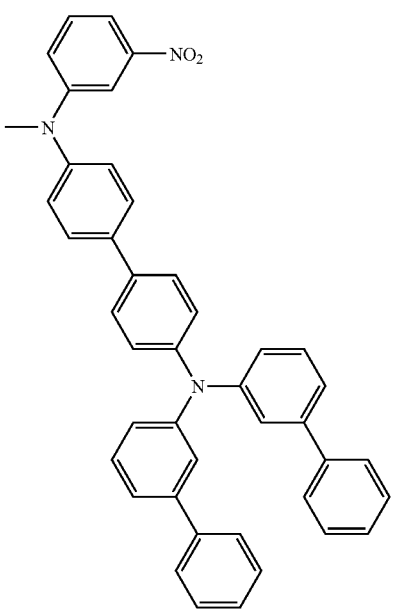

474

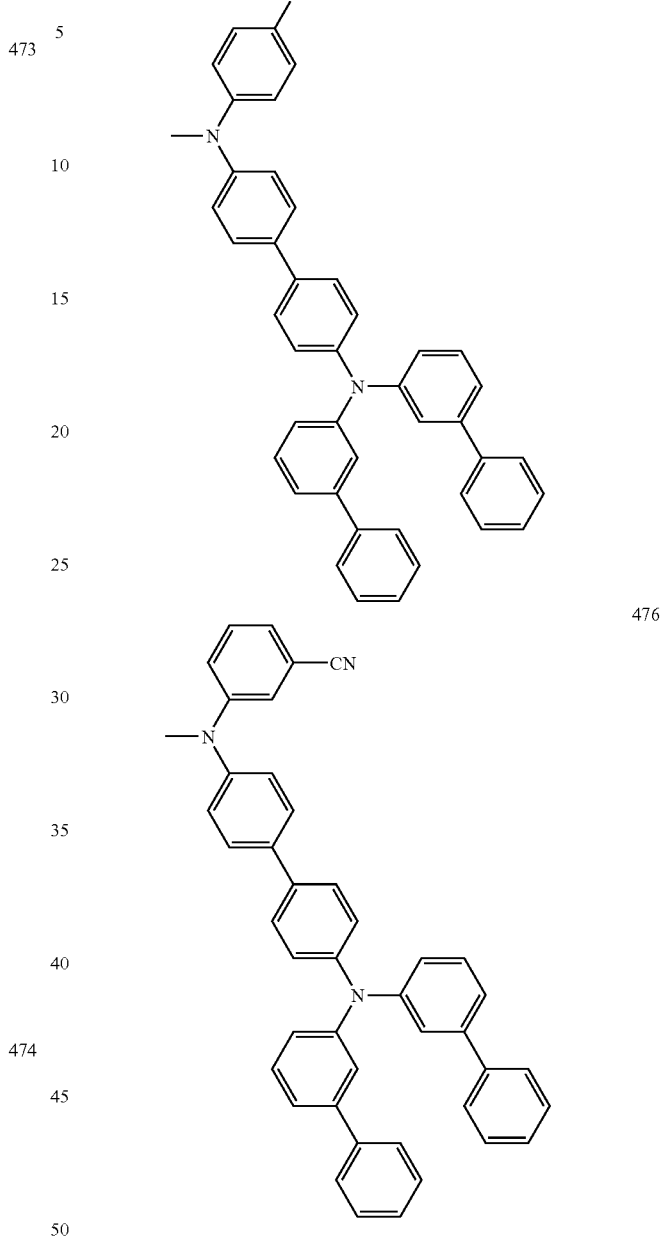

475

476

BEST MODE FOR CARRYING OUT THE INVENTION

Figure 1:
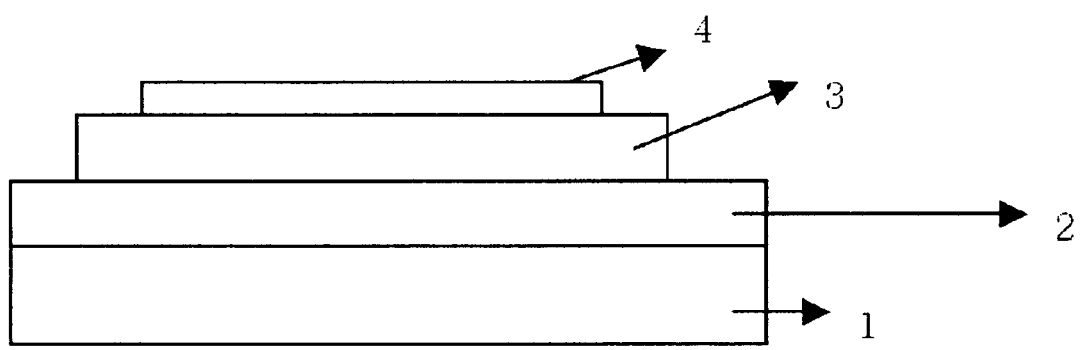
FIG. 1 illustrates an organic light emitting device comprising a substrate 1, an anode 2, a light emitting layer 3, and a cathode 4.
Figure 2:
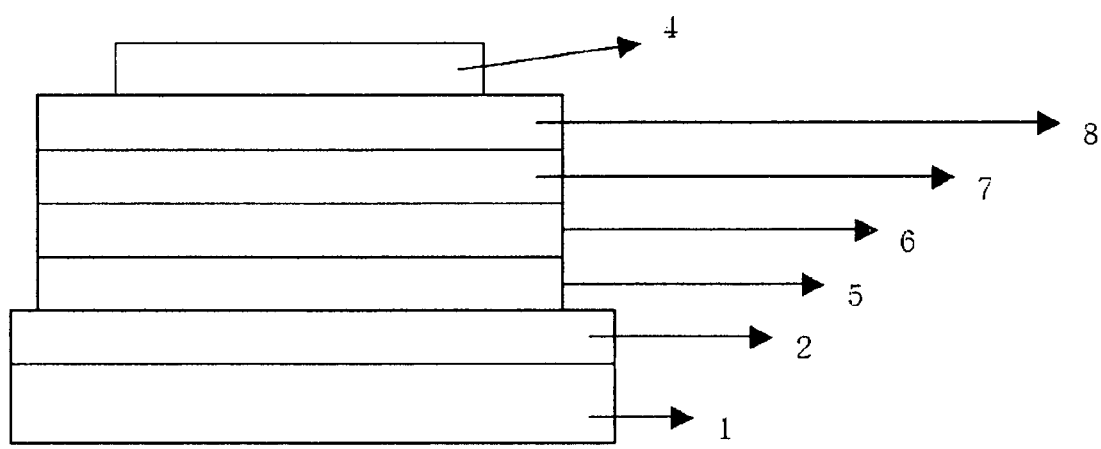
FIG. 2 illustrates an organic light emitting device comprising a substrate 1, an anode 2, a hole injection layer 5, a hole transport layer 6, a light emitting layer 7, an electron transport layer 8, and a cathode 4.

Hereinafter, a detailed description will be given of the present invention.

Various substituent groups are introduced into a core structure shown in Formula 1, in detail, the core structure in which a fluorene group is bonded to a combination of an acridine group and a carbazole group to form a spiro structure, thereby the compound of Formula 1 has characteristics suitable for application to an organic material layer used in an organic light emitting device. This will be described in detail, below.

The steric core structure of the compound of Formula 1, for convenience of explanation, can be divided into two portions, A and B, as shown in the following Formula.

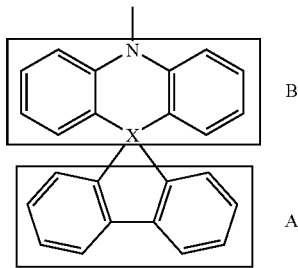

The compound of Formula 1 has the steric core structure in which a plane A meets with a plane B at right angles around X, and conjugation does not occur between the A and B portions around X. Furthermore, since one nitrogen atom is positioned among three aryl groups in the plane B, conjugation is limited in the plane B.

The conjugation length of the compound has a close relationship with an energy band gap. In detail, the energy band gap is reduced as the conjugation length of the compound increases. As described above, since a conjugation structure is limited in the core structure of the compound of Formula 1, the core structure has a large energy band gap.

As described above, in the present invention, various substituent groups are introduced to R1 to R13 positions and Z1 to Z2 positions of the core structure having the large energy band gap so as to produce compounds having various energy band gaps. Generally, it is easy to control the energy band gap by introducing substituent groups into a core structure having a large energy band gap, but it is difficult to significantly control the energy band gap by introducing substituent groups into a core structure having a small energy band gap. Furthermore, in the present invention, it is possible to control HOMO and LUMO energy levels of the compound by introducing various substituent groups into R1 to R13 and Z1 to Z2 of the core structure.

Additionally, various substituent groups are introduced into the core structure to produce compounds having intrinsic characteristics of the substituent groups. For example, substituent groups, which are frequently applied to hole injection layer, hole transport layer, light emitting layer, and electron transport layer materials during the production of the organic light emitting device, are introduced into the core structure so as to produce substances capable of satisfying the requirements of each organic material layer. Particularly, since the core structure of the compound of Formula includes the arylamine structure, it has an energy level suitable for the hole injection and/or hole transport materials in the organic light emitting device. In the present invention, the compound having the proper energy level is selected depending on the substituent group among the compounds represented by Formula 1 to be used in the organic light emitting device, thereby it is possible to realize a device having a low actuating voltage and a high light efficiency.

Furthermore, various substituent groups are asymmetrically introduced into the core structure (the A portion is located at one side of the core structure) so as to precisely control the energy band gap, improve interfacial characteristics with organic materials, and apply the compound to various fields.

As well, if the number of nitrogen contained in the substituent group A is set to 2 or more (if Y1 and Y2 and Z1 to Z4 are hetero aromatic amine compounds, the number of nitrogen contained in them is not counted), it is possible to precisely control the HOMO and LUMO energy levels and the energy band gap, and on the other hand interfacial characteristics with the organic materials is improved and thereby make it possible to apply the compound to various fields.

Additionally, various substituent groups are introduced into the steric structure of the compound of Formula 1 using spiro bonding to control the three-dimensional structure of the organic material so as to minimize π-π interaction in the organic material, thereby formation of excimers is prevented.

Meanwhile, since the compound of Formula 1 has a high glass transition temperature (Tg), it has excellent thermal stability. For example, the glass transition temperature of the compound of Formula 3-256 is 167° C., which is still higher than that of conventionally used NPB (Tg: 96° C.). An increase in thermal stability is an important factor providing actuating stability to the device.

Furthermore, the compound of Formula 1 may be used to form the organic material layer using a vacuum deposition process or a solution coating process during the production of the organic light emitting device. In connection with this, illustrative, but non-limiting, examples of the solution coating process include a spin coating process, a dip coating process, an inkjet printing process, a screen printing process, a spray process, and a roll coating process.

For example, the compound of Formula 1 has excellent solubility to a polar solvent, such as xylene, dichloroethane, or NMP, which is used during the production of the device, and forms a thin film very well through the process using a solution, thus the solution coating process may be applied to produce the device.

Tertiary alcohol, which is produced by a reaction of a lithiated aryl and keto group, is heated in the presence of an acid catalyst to form a hexagonal cyclic structure while water is removed, thereby producing the compound having a spiro structure according to the present invention. The above-mentioned procedure for producing the compound is well known in the art, and those skilled in the art can change the production conditions during the production of the compound of Formula 1. The production will be described in detail in the preparation examples later.

In the organic light emitting device of the present invention, a compound, in which a thermosetting or photo-crosslinkable functional group is introduced into the compound of Formula 1, may be used instead of the compound of Formula 1. The former compound has the basic physical properties of the compound of Formula 1, and may be used to form a thin film using a solution coating process and then be cured so as to form an organic material layer during the production of the device.

The method of forming the organic material layer, which comprises introducing the curable functional group into the organic material during the production of the organic light emitting device, forming the organic thin film using the solution coating process, and curing the resulting film, is disclosed in US Pat. No. 2003-0044518 and EP Pat. No. 1146574A2.

The above documents state that, if the organic material layer is formed through the above-mentioned method using a material having a thermosetting or photo-crosslinkable vinyl or acryl group so as to produce an organic light emitting device, it is possible to produce an organic light emitting device having a low voltage and high brightness as well as an organic light emitting device having a multilayered structure using the solution coating process. This operation mechanism may be applied to the compound of the present invention.

In the present invention, the thermosetting or photo-crosslinkable functional group may be a vinyl or acryl group.

The organic light emitting device of the present invention can be produced using known materials through a known process, modified only in that at least one layer of organic material layer(s) include the compound of the present invention, that is, the compound of Formula 1.

The organic material layer(s) of the organic light emitting device according to the present invention may have a single layer structure, or alternatively, a multilayered structure in which two or more organic material layers are layered. For example, the organic light emitting device of the present invention may comprise a hole injection layer, a hole transport layer, a light emitting layer, an electron transport layer, or an electron injection layer as the organic material layer(s). However, the structure of the organic light emitting device is not limited to this, but may comprise a smaller number of organic material layers.

Furthermore, the organic light emitting device of the present invention may be produced, for example, by sequentially layering a first electrode, organic material layer(s), and a second electrode on a substrate. In connection with this, a physical vapor deposition (PVD) method, such as a sputtering method or an e-beam evaporation method, may be used, but the method is not limited to these.

A method of producing the compound of Formula 1 and the production of the organic light emitting device using the same will be described in detail in the following preparation examples and examples. However, the following preparation examples and examples are set forth to illustrate, but are not to be construed to limit the present invention.

MODE FOR THE INVENTION

A better understanding of a method of producing an organic compound represented by Formula 1 and the production of an organic light emitting device using the same may be obtained in light of the following preparation examples and examples which are set forth to illustrate, but are not to be construed to limit the present invention.

In order to produce the compound represented by Formula 1, compounds of the following Formulae, a or b, may be used as a starting material.

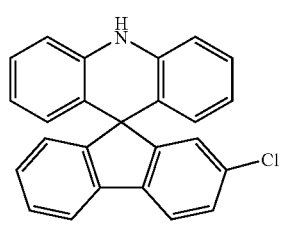

[Formula a]

-continued

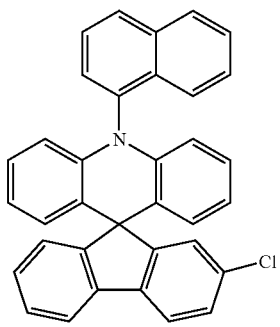

[Formula b]

PREPARATION EXAMPLE 1

Preparation of a Starting Material Represented by Formula a

1) After 10 g of diphenylamine (59 mmol) and 8.04 ml of bromomethyl methyl ether (88.6 mmol) were dissloved in 100 ml of tetrahydrofuran, 12.4 ml of triethylamine (88.6 mmol) were added thereto. Stirring was conducted in a nitrogen atmosphere for 5 hours, and an organic layer was then extracted using distilled water. The extracted organic layer was subjected to a column separation process at a ratio of n-hexane/tetrahydrofuran of 15:1, and vacuum dried to produce 12 g of tertiary amine (yield 90%).

2) The amine compound produced in 1) (12.0 g, 56.3 mmol) was dissolved in 100 ml of purified THF and cooled to −78° C., and n-BuLi (2.5 M hexane solution, 22.5 ml, 56.3 mmol) was slowly dropped thereon. Stirring was conducted at the same temperature for 30 min, and a 2-chloro-9-fluorenone compound (12.1 g, 56.3 mmol) was added thereto. After stirring was conducted at the same temperature for 40 min, the temperature was raised to normal temperature and stirring was carried out for an additional 3 hours. The reaction was completed in an ammonium chloride aqueous solution, and extraction was conducted with ethyl ether. Water was removed from an organic material layer using anhydrous magnesium sulfate, and an organic solvent was then removed therefrom. The produced solid was dispersed in ethanol, stirred for one day, filtered, and vacuum dried. After an intermediate material was dispersed in 100 ml of acetic acid, ten drops of concentrated sulfuric acid were added thereto and reflux was conducted for 4 hours. The resulting solid was filtered, washed with ethanol, and vacuum dried to produce 20 g of amine (97% yield). MS: $[M+H]^+=366$.

PREPARATION EXAMPLE 2

Preparation of a Starting Material Represented by Formula b

A compound of Formula a (8.23 g, 22.5 mmol), iodonaphthalene (11.4 g, 45.0 mmol), potassium carbonate (6.22 g, 45.0 mmol), copper iodide (214 mg, 1.13 mmol), and xylene (250 ml) were heated in a nitrogen atmosphere overnight. After cooling to normal temperature was conducted, a product was extracted with ethyl acetate, water was removed with anhydrous magnesium sulfate, and the solvent was removed at a reduced pressure. The resulting product was passed through a silica gel column using a hexane solvent to produce a compound, the solvent was removed at a reduced pressure, and vacuum drying was conducted to produce the compound of Formula b (5.2 g, 47% yield). M: [M+H]$^+$=493.

EXAMPLE 1

Preparation of the Compound Represented by Formula 3-256

1) Synthesis of arylamine (4-(N,N-diphenylamino)-biphenyl-N-phenylamine) to produce the compound represented by Formula 3-256: 4.00 g of 4-chlorobiphenyl-N,N-diphenylamine (11.2 mmol) and 1.13 ml of aniline (12.4 mmol) were dissolved in 100 ml of toluene, 2.70 g of sodium-tert-butoxide (28.1 mmol), 0.13 g of bis(dibenzylidene acetone)palladium (0) (0.23 mmol), and 0.17 ml of 50 wt % tri-tert-butylphosphine toluene solution (0.34 mmol) were added thereto, and reflux was conducted in a nitrogen atmosphere for 5 hours. Distilled water was added to the reaction solution to complete the reaction, and the organic layer was extracted. A column separation process was conducted using a solvent of n-hexane and tetrahydrofuran at a ratio of 10:1, stirring was conducted using petroleum ether, and vacuum drying was conducted to produce an arylamine connection group (3.8 g, yield 81%). MS: [M+H]$^+$=413.

2) 4.369 g of compound of Formula b (8.88 mmol) and 4.414 g of 4-(N,N-diphenylamino)-biphenyl-N-phenylamine (10.7 mmol) were dissolved in 120 ml of toluene, 2.90 g of sodium-tert-butoxide (30.2 mmol), 0.12 g of bis(dibenzylidene acetone)palladium(0) (0.21 mmol), and 0.16 ml of 50 wt % tri-tert-butylphosphine toluene solution (0.32 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 9:1, stirring was conducted using petroleum ether, and vacuum drying was conducted to produce the compound of Formula 3-256 (5.2 g, yield 65%). MS: [M+H]$^+$=869.

EXAMPLE 2

Preparation of the Compound Represented by Formula 3-259

1) Synthesis of arylamine (4-(N,N-diphenylamino)-biphenyl-N-biphenylamine) to produce the compound represented by Formula 3-259: 8.80 g of 4-chlorobiphenyl-N,N-diphenylamine (24.7 mmol) and 6.28 g of 4-aminobiphenyl (37.1 mmol) were dissolved in 200 ml of toluene, 5.94 g of sodium-tert-butoxide (61.8 mmol), 0.43 g of bis(dibenzylidene acetone)palladium(0) (0.74 mmol), and 0.61 ml of 50 wt % tri-tert-butylphosphine toluene solution (1.24 mmol) were added thereto, and reflux was conducted in a nitrogen atmosphere for 5 hours. Distilled water was added to the reaction solution to complete the reaction, and the organic layer was extracted. A column separation process was conducted using a solvent of n-hexane and tetrahydrofuran at a ratio of 10:1, stirring was conducted using petroleum ether, and vacuum drying was conducted to produce an arylamine connection group (7.0 g, yield 58%). MS: [M+H]$^+$=489.

2) 4.37 g of compound of Formula b (8.88 mmol) and 5.23 g of 4-(N,N-diphenylamino)-biphenyl-N-biphenylamine (10.7 mmol) were dissolved in 120 ml of toluene, 2.90 g of sodium-tert-butoxide (30.2 mmol), 0.12 g of bis(dibenzylidene acetone)palladium(0) (0.21 mmol), and 0.16 ml of 50 wt % tri-tert-butylphosphine toluene solution (0.32 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 9:1, stirring was conducted using petroleum ether, and vacuum drying was conducted to produce the compound of Formula 3-259 (5.4 g, yield 64%). MS: [M+H]$^+$=943.

EXAMPLE 3

Preparation of the Compound Represented by Formula 3-276

1) Synthesis of arylamine (4-(N-phenyl-N-naphthylamino)-biphenyl-N-biphenylamine) to produce the compound represented by Formula 3-276: 4.08 g of 4-chlorobiphenyl-N-phenyl-N-naphthylamine (10.1 mmol) and 2.55 g of 4-aminobiphenyl (15.1 mmol) were dissolved in 100 ml of toluene, 2.90 g of sodium-tert-butoxide (30.2 mmol), 0.17 g of bis(dibenzylidene acetone)palladium(0) (0.30 mmol), and 0.26 ml of 50 wt % tri-tert-butylphosphine toluene solution (0.53 mmol) were added thereto, and reflux was conducted in a nitrogen atmosphere for 7 hours. Distilled water was added to the reaction solution to complete the reaction, and the organic layer was extracted. A column separation process was conducted using a solvent of n-hexane and tetrahydrofuran at a ratio of 10:1, stirring was conducted using petroleum ether, and vacuum drying was conducted to produce an arylamine connection group (3.8 g, yield 70%). MS: [M+H]$^+$=539.

2) 4.369 g of compound of Formula b (8.88 mmol) and 5.76 g of 4-(N-phenyl-N-naphthylamino)-biphenyl-N-biphenylamine (10.7 mmol) were dissolved in 120 ml of toluene, 2.90 g of sodium-tert-butoxide (30.2 mmol), 0.12 g of bis(dibenzylidene acetone)palladium(0) (0.21 mmol), and 0.16 ml of 50 wt % tri-tert-butylphosphine toluene solution (0.32 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 9:1, stirring was conducted using petroleum ether, and vacuum drying was conducted to produce the compound of Formula 3-276 (4.9 g, yield 56%). MS: [M+H]$^+$=995.

EXAMPLE 4

Production of an Organic Light Emitting Device

A glass substrate (Corning 7059 glass), on which ITO (indium tin oxide) was applied to a thickness of 1000 Å to form a thin film, was put in distilled water, in which a detergent was dissolved, and washed using ultrasonic waves. In connection with this, a product manufactured by Fischer Inc. was used as the detergent, and distilled water was produced by filtering twice using a filter manufactured by Millipore Inc. After ITO was washed for 30 min, ultrasonic washing was conducted twice using distilled water for 10 min. After the washing using distilled water was completed, ultrasonic washing was conducted using isopropyl alcohol, acetone, and methanol solvents, and drying was then conducted. Next, it was transported to a plasma washing machine. The substrate was dry washed using oxygen plasma for 5 min, and then transported to a vacuum evaporator.

Hexanitrile hexaazatriphenylene (hereinafter, referred to as "HAT") of the following Formula was vacuum deposited to a thickness of 500 Å by heating on a transparent ITO electrode, which was prepared through the above procedure, so as to form an anode including an ITO conductive layer and an N-type organic material.

[HAT]

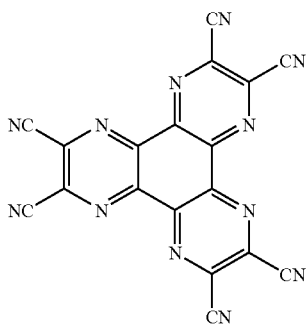

The compound of Formula 3-256 (400 Å) was vacuum deposited thereon to form a hole transport layer. Alq3 was vacuum deposited to a thickness of 300 Å on the hole transport layer to form a light emitting layer. An electron transport layer material of the following Formula was deposited to a thickness of 200 Å on the light emitting layer to form an electron transport layer.

Electron Transport Layer Material

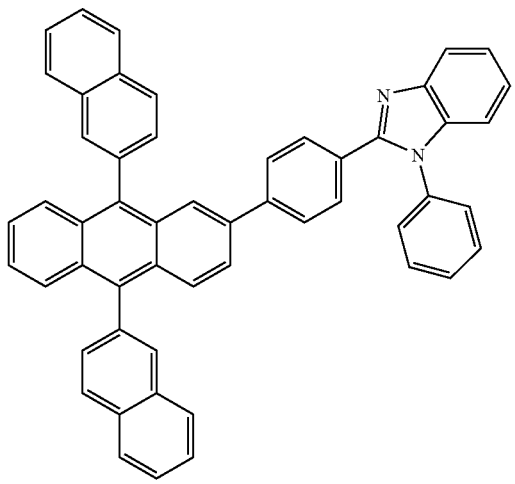

Lithium fluoride (LiF) having a thickness of 12 Å and aluminum having a thickness of 2000 Å were sequentially deposited on the electron transport layer to form a cathode.

In the above procedure, the deposition speed of an organic material was maintained at 0.3-0.8 Å/sec. Furthermore, lithium fluoride and aluminum were deposited at speeds of 0.3 Å/sec and 1.5-2.5 Å/sec, respectively, on the cathode. During the deposition, a vacuum was maintained at $1-3\times10^{-7}$.

The resulting device had an electric field of 4.54 V at a forward current density of 100 mA/cm$^2$, and a spectrum having a light efficiency of 1.89 lm/W. The operation and light emission of the device at the above-mentioned actuating voltage mean that the compound of Formula 3-256, which formed the layer between the hole injection layer and the light emitting layer, functions to transport holes.

EXAMPLE 5

Production of an Organic Light Emitting Device

The procedure of example 4 was repeated to produce a device except that the compound of Formula 3-256 used as a hole transport layer was substituted with the compound of Formula 3-259.

The resulting device had an electric field of 4.52 V at a forward current density of 100 mA/cm$^2$, and a spectrum having a light efficiency of 1.91 lm/W. The operation and light emission of the device at the above-mentioned actuating voltage mean that the compound of Formula 3-259, which formed a layer between a thin film on a substrate and the hole transport layer, functions to transport holes.

EXAMPLE 6

Production of an Organic Light Emitting Device

The procedure of example 4 was repeated to produce a device except that the compound of Formula 3-276 used as a hole transport layer was substituted with the compound of Formula 3-276.

The resulting device had an electric field of 4.31 V at a forward current density of 100 mA/cm$^2$, and a spectrum having a light efficiency of 1.96 lm/W. The operation and light emission of the device at the above-mentioned actuating voltage mean that the compound of Formula 3-276, which formed a layer between a thin film on a substrate and the hole transport layer, functions to transport holes.

INDUSTRIAL APPLICABILITY

The compound of the present invention can be used as an organic material layer material, particularly, hole injection and/or transport materials in an organic light emitting device, and when applied to an organic light emitting device it is possible to reduce the actuating voltage of the device, to improve the light efficiency thereof, and to improve the lifespan of the device through the thermal stability of the compound.

The invention claimed is:
1. An organic light emitting device, comprising:
a first electrode;
organic material layer(s) comprising a light emitting layer, wherein at least one layer of the organic material layer(s) includes the compound of Formula 1; and
a second electrode;
wherein the first electrode, the organic material layer(s), and the second electrode form a layered structure,

[Formula 1]

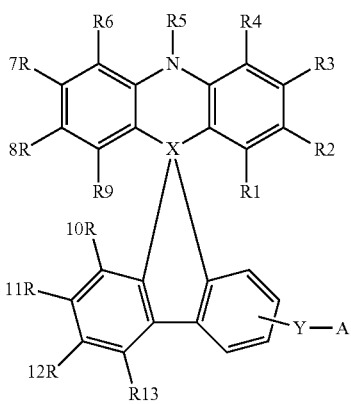

wherein X is C or Si;
A is

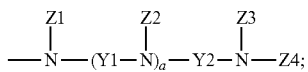

a is zero or positive integer;
Y is a bond; bivalent aromatic hydrocarbons; bivalent aromatic hydrocarbons which are substituted with at least one substituent group selected from the group consisting of nitro, nitrile, halogen, alkyl, alkoxy, and amino groups; a bivalent heterocyclic group; or a bivalent heterocyclic group which is substituted with at least one substituent group selected from the group consisting of nitro, nitrile, halogen, alkyl, alkoxy, and amino groups;
Y1 and Y2 are each independently bivalent aromatic hydrocarbons; bivalent aromatic hydrocarbons which are substituted with at least one substituent group selected from the group consisting of nitro, nitrile, halogen, alkyl, alkoxy, and amino groups; a bivalent heterocyclic group; or a bivalent heterocyclic group which is substituted with at least one substituent group selected from the group consisting of nitro, nitrile, halogen, alkyl, alkoxy, and amino groups;
Z1 to Z4 are each independently hydrogen; aliphatic hydrocarbons having a carbon number of 1-20; aromatic hydrocarbons; aromatic hydrocarbons which are substituted with at least one substituent group selected from the group consisting of the nitro, nitrile, halogen, alkyl, alkoxy, amino, aromatic hydrocarbon, and heterocyclic groups; a silicon group substituted with aromatic hydrocarbons; a heterocyclic group; a heterocyclic group which is substituted with at least one substituent group selected from the group consisting of the nitro, nitrile, halogen, alkyl, alkoxy, amino, aromatic hydrocarbon, and heterocyclic groups; a thiophene group which is substituted with hydrocarbons having a carbon number of 1-20 or aromatic hydrocarbons having a carbon number of 6-20; or a boron group which is substituted with aromatic hydrocarbons;
R1 to R4, and R6 to R13 are each independently selected from the group consisting of hydrogen, a substituted or unsubstituted alkyl group, a substituted or unsubstituted alkoxy group, a substituted or unsubstituted alkenyl group, a substituted or unsubstituted aryl group, a substituted or unsubstituted arylamine group, a substituted or unsubstituted heterocyclic group, an amino group, a nitrile group, a nitro group, a halogen group, an amide group, and an ester group, R1 to R4 and R6 to R13 may form aliphatic or hetero condensation rings along with adjacent groups;
R5 is selected from the group consisting of hydrogen, a substituted or un-substituted alkyl group, a substituted or unsubstituted cycloalkyl group, a substituted or unsubstituted alkenyl group, a substituted or unsubstituted aryl group, and a substituted or unsubstituted heterocyclic group; and
with a proviso that when R5 is the aryl group or the heterocyclic group, carbon at an ortho-position of the aryl or the heterocyclic group and R4 or R6 may form a condensation ring along with a group selected from the group consisting of O, S, NR, PR, C=O, CRR', and SiRR', wherein R and R' each independently are selected from the group consisting of hydrogen, a substituted or unsubstituted alkyl group, a substituted or unsubstituted alkoxy group, a substituted or un-substituted alkenyl group, a substituted or unsubstituted aryl group, a substituted or unsubstituted arylamine group, a substituted or unsubstituted heterocyclic group, a nitrile group, an amide group, and an ester group, and may form a condensation ring to form a spiro compound.

2. The organic light emitting device as set forth in claim 1, wherein R5 of Formula 1 is an aryl or a heterocyclic group.

3. The organic light emitting device as set forth in claim 2, wherein R5 of Formula 1 is an aryl or a heterocyclic group, and carbon at the ortho-position of the aryl or the heterocyclic group and R4 or R6 form the condensation ring along with a group selected from the group consisting of O, S, NR, PR, C=O, CRR', and SiRR'.

4. The organic light emitting device as set forth in claim 1, wherein the compound of Formula 1 is any one of compounds of Formulae 2 to 119:

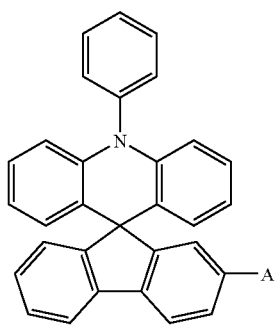

2

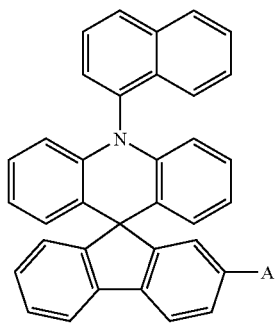

3

-continued
4
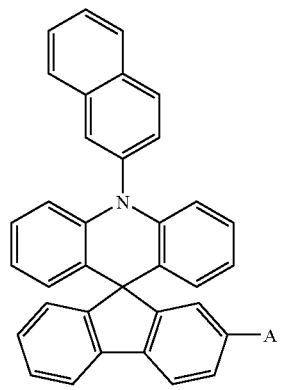
5
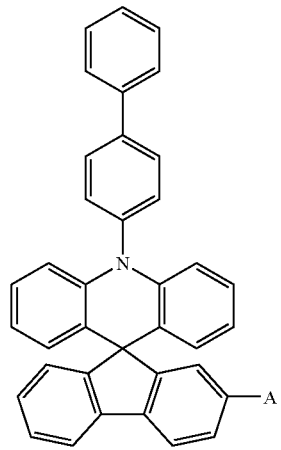
6
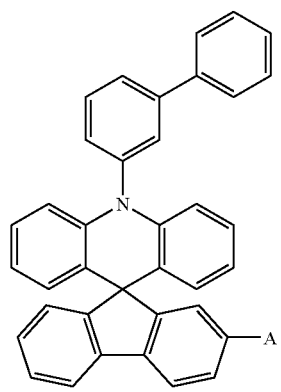
7
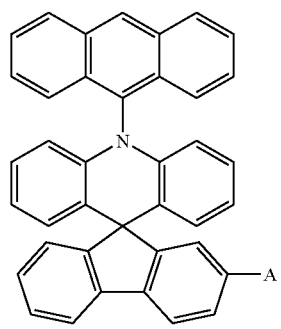
-continued
8
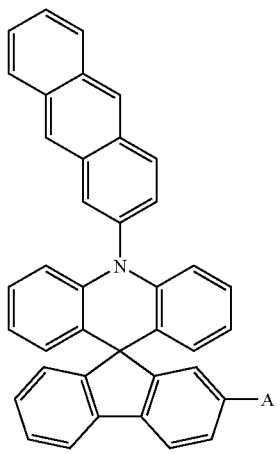
9
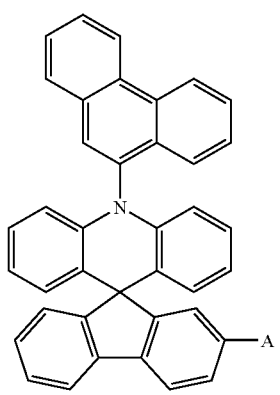
6
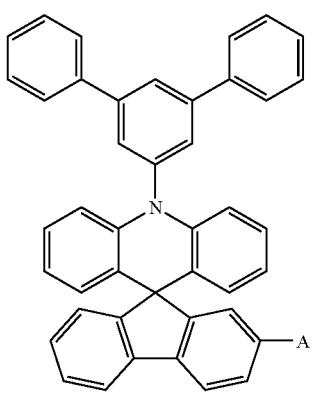

-continued
7
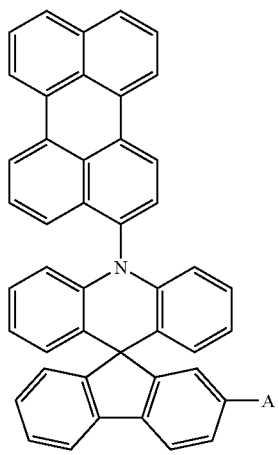
8
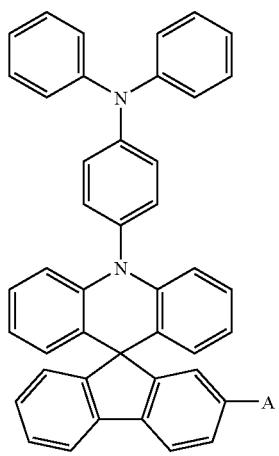
9
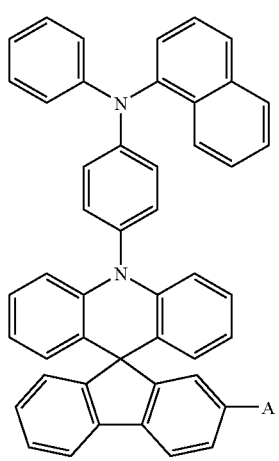
-continued
10
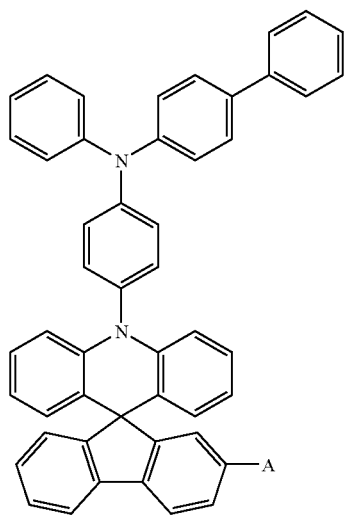
11
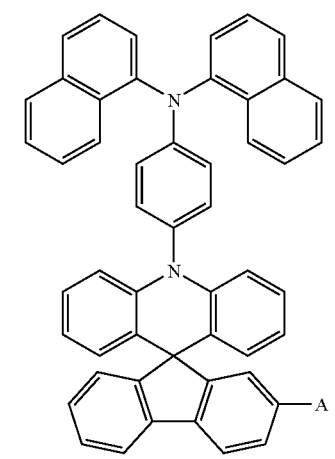
12
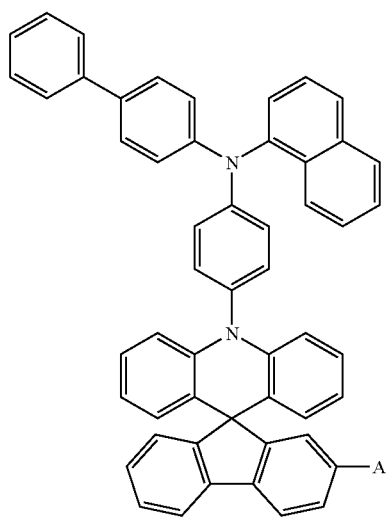

-continued
13
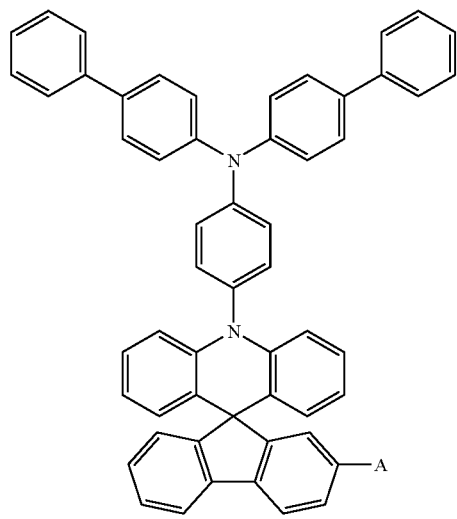
14
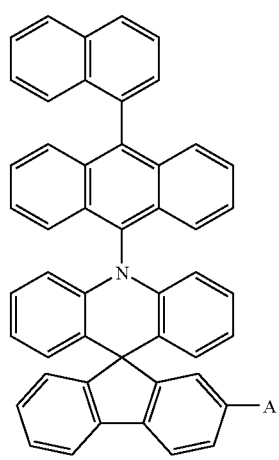
15
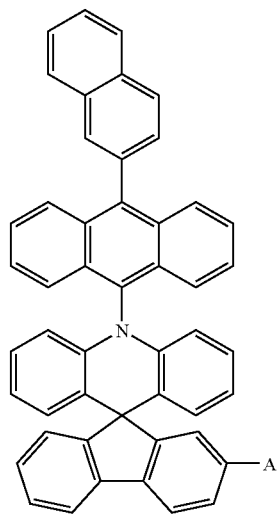
-continued
16
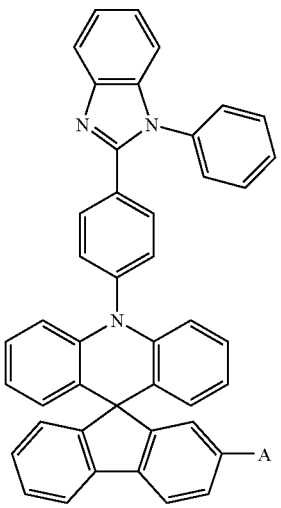
17
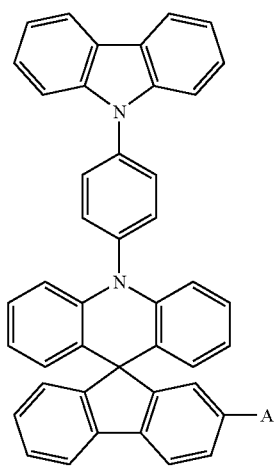
18
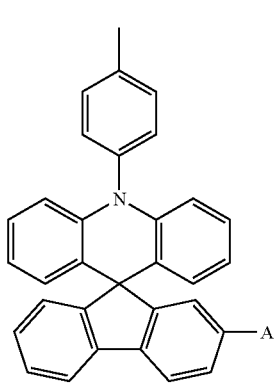

-continued
19
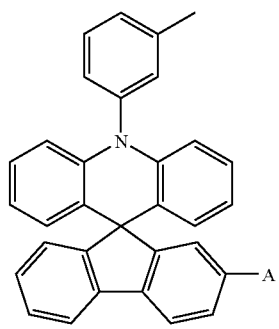
20
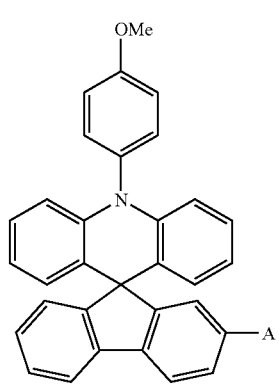
21
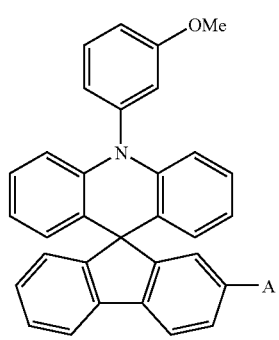
22
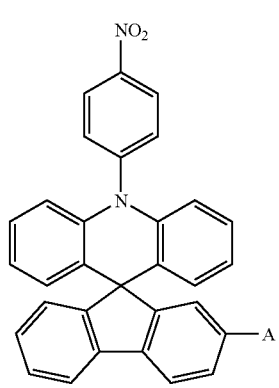
-continued
23
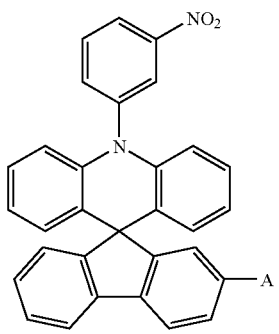
24
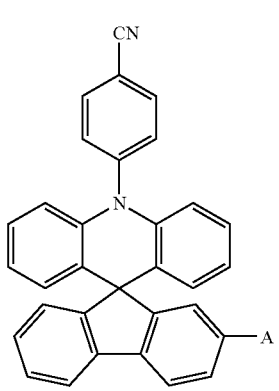
25
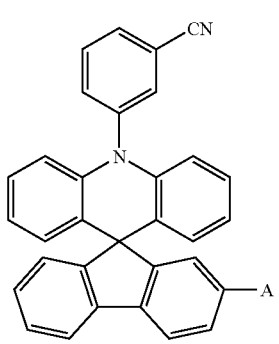
26
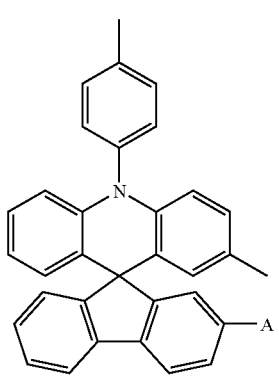

-continued
27
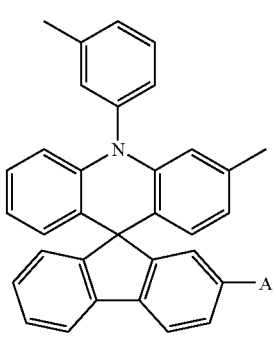
28
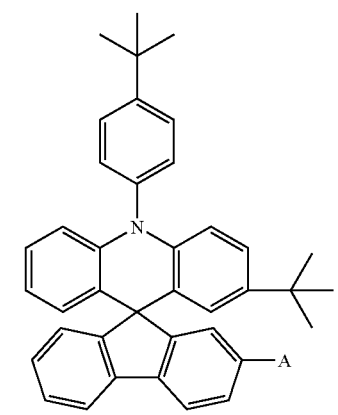
29
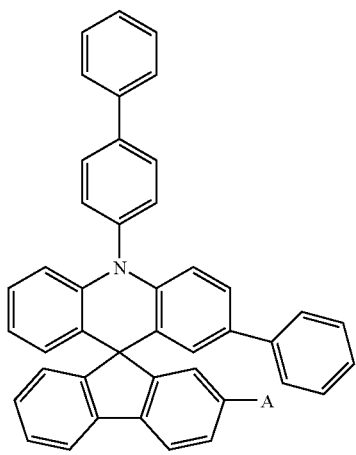
30
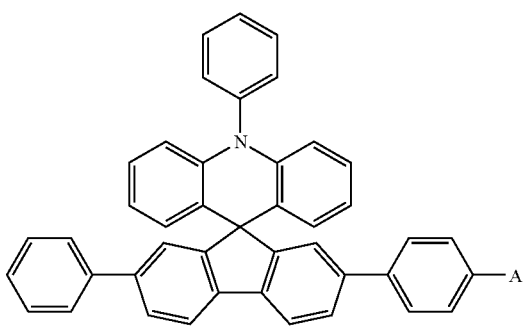
-continued
31
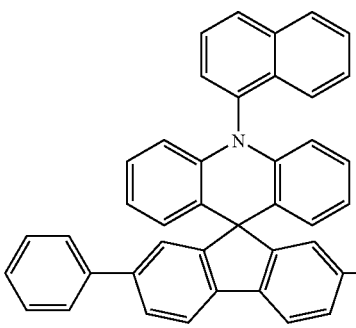
32
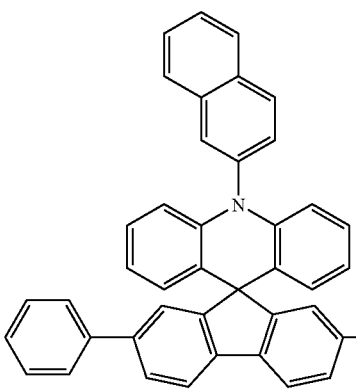
33
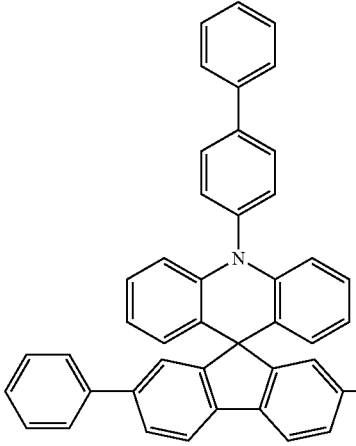
34
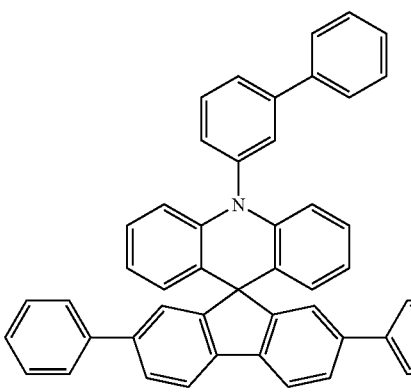

257
-continued
35
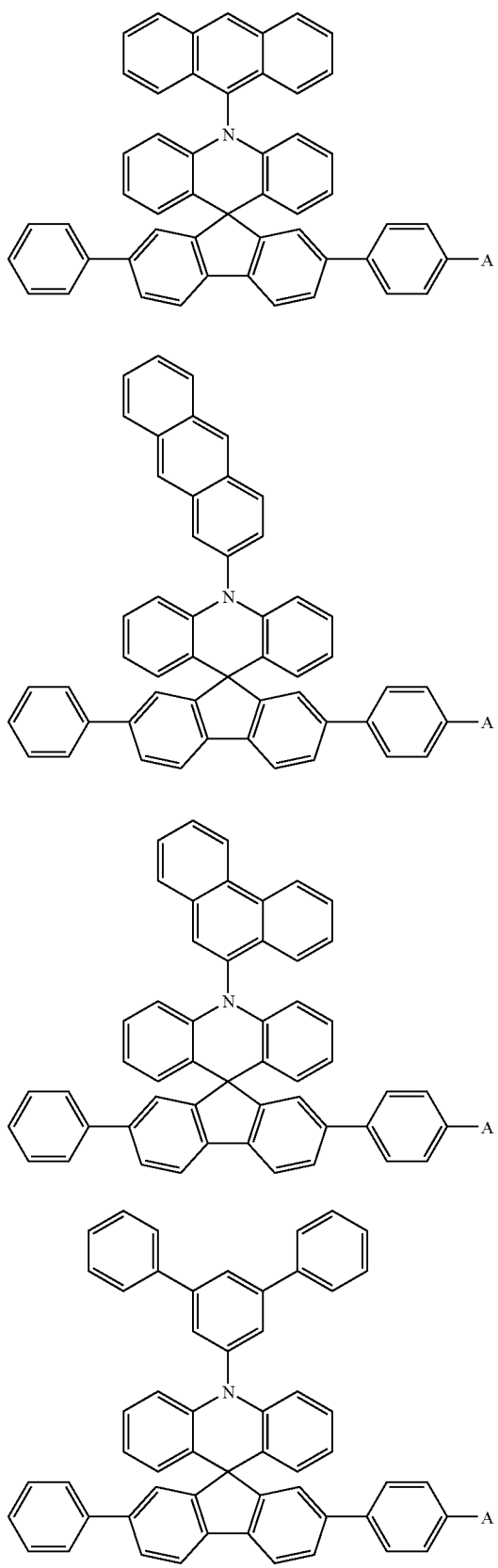
36
37
38
258
-continued
39
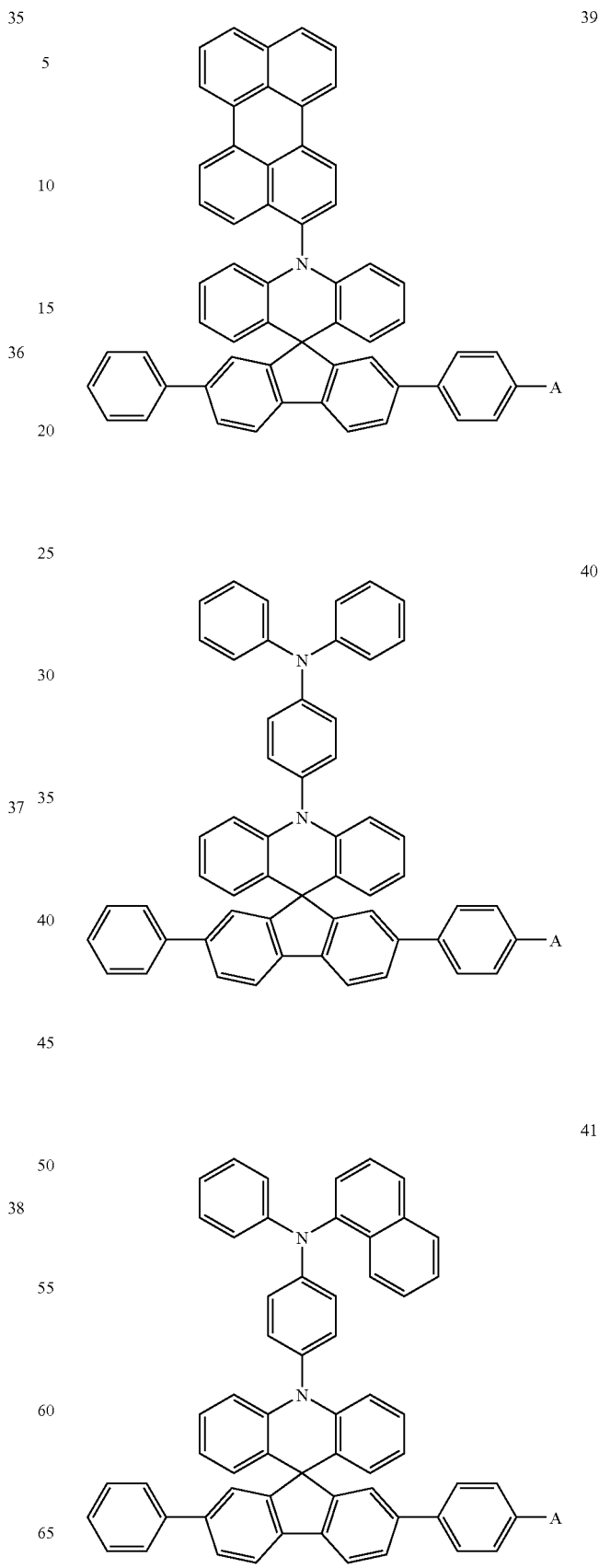
40
41

-continued
42
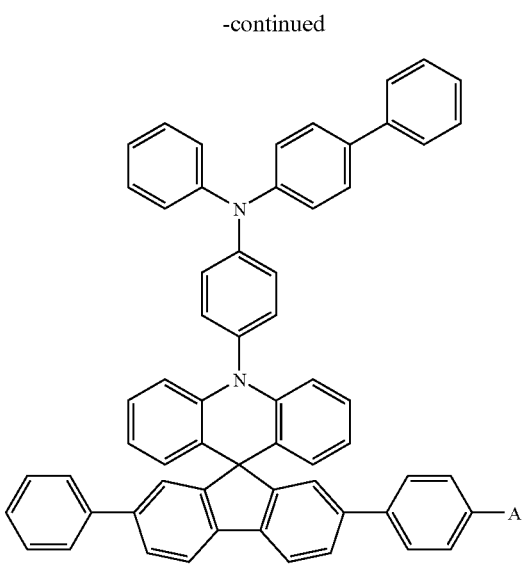
43
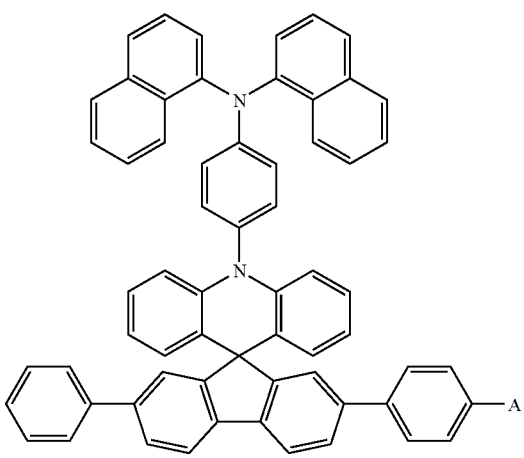
44
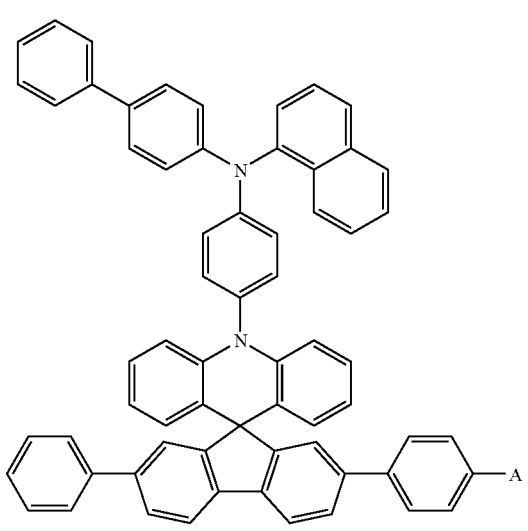
-continued
45
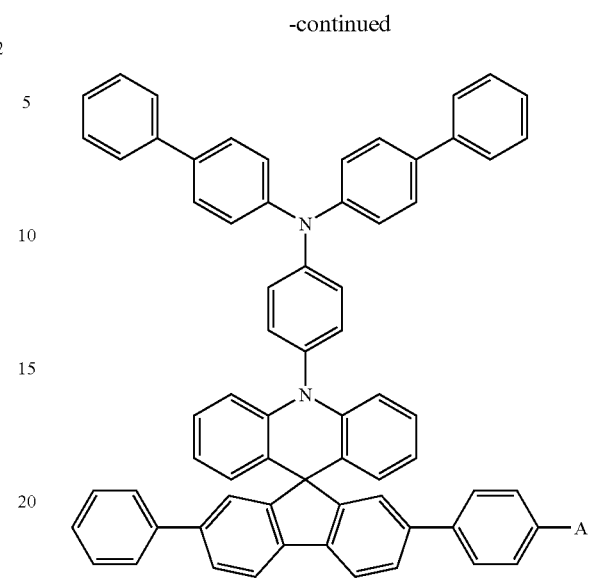
46
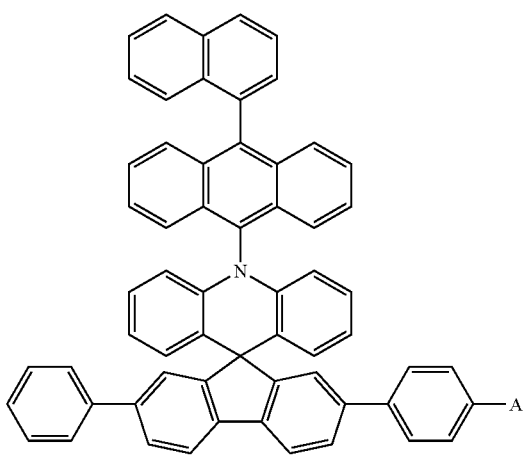
47
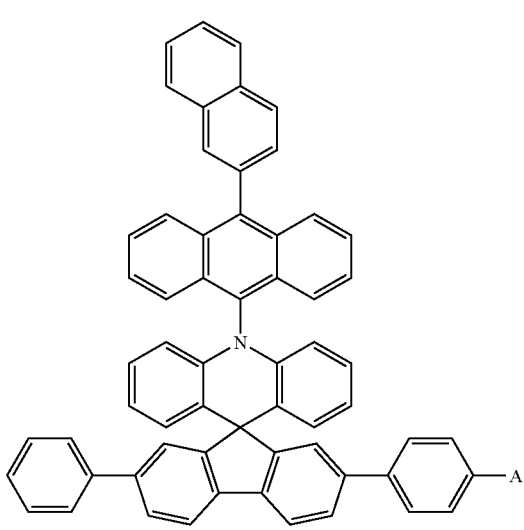

-continued
48
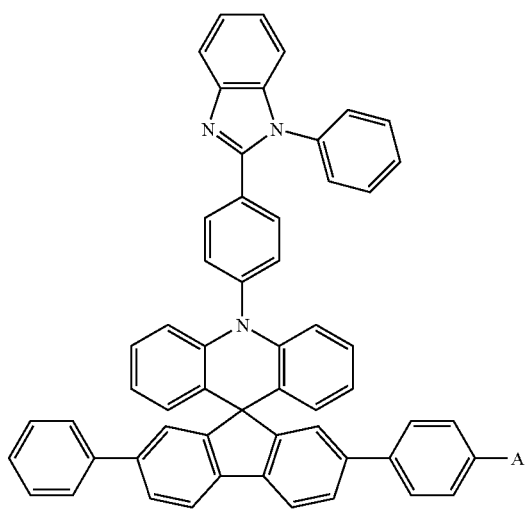
49
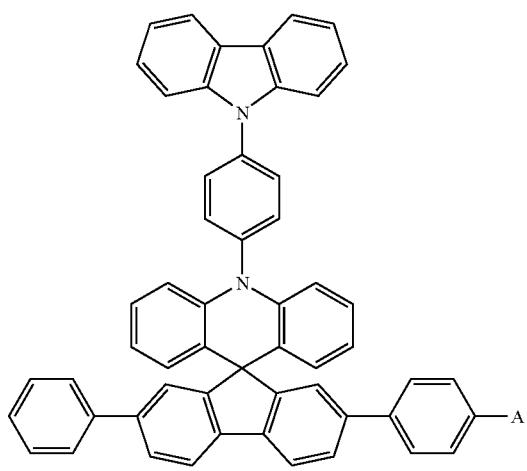
50
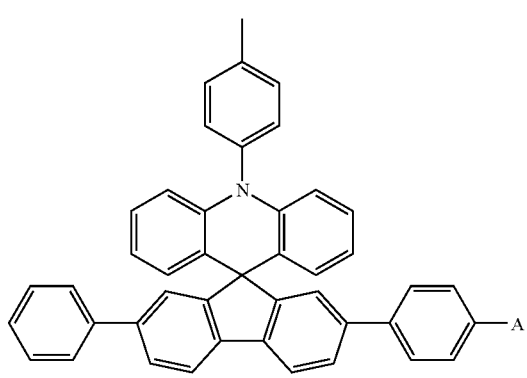
-continued
51
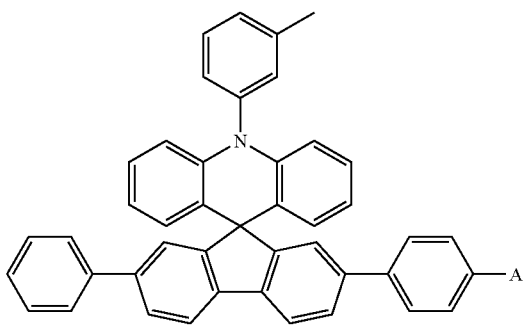
52
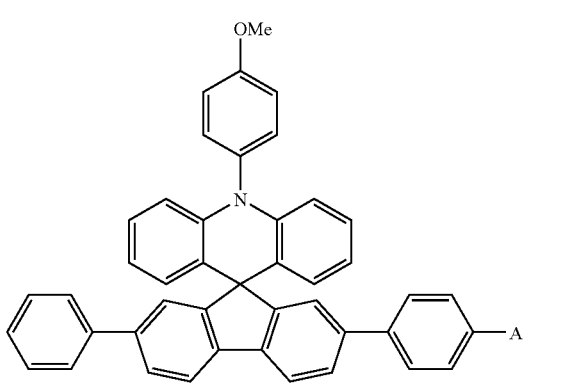
53
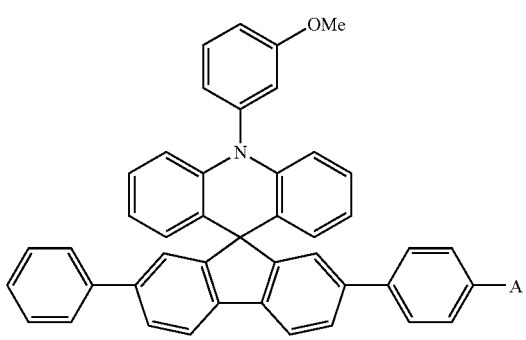
54
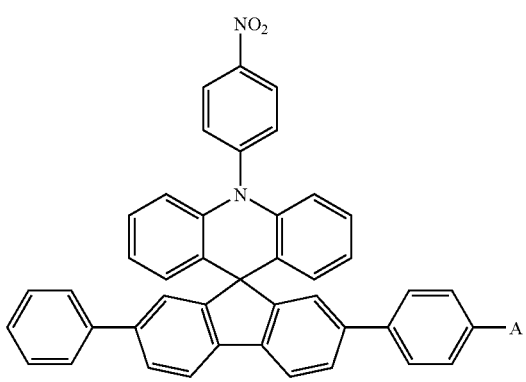

-continued
55
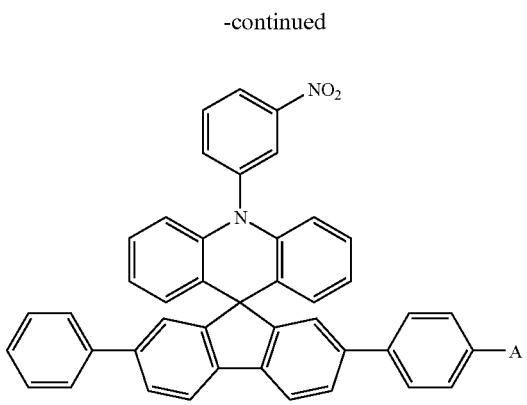
56
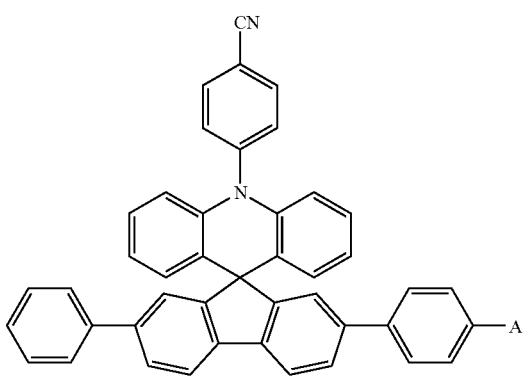
57
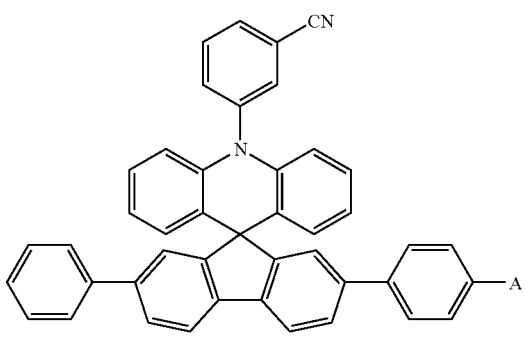
58
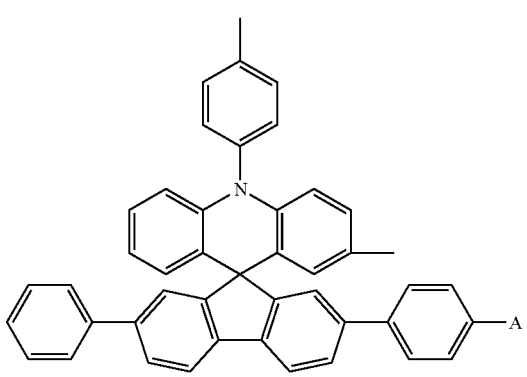
-continued
59
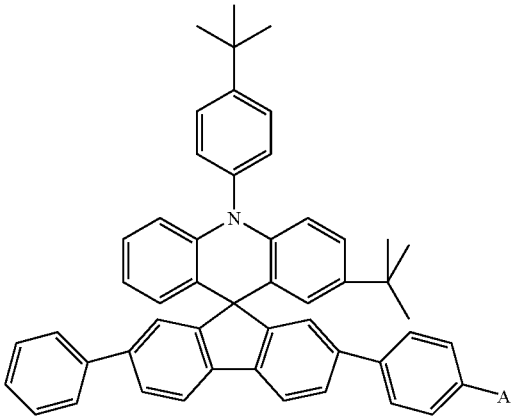
60
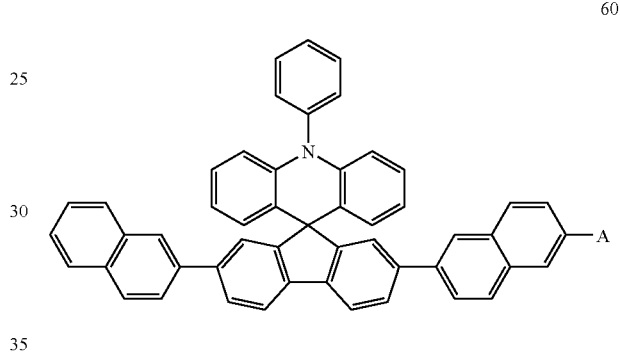
61
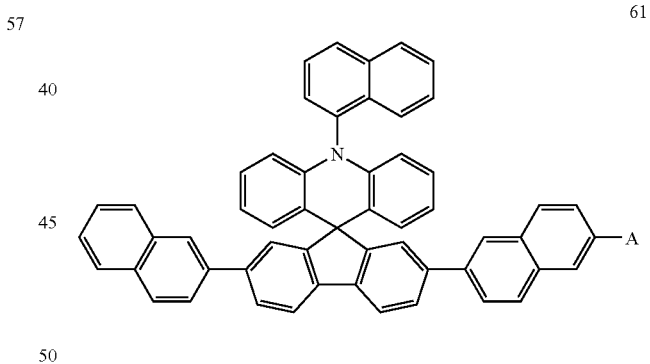
62
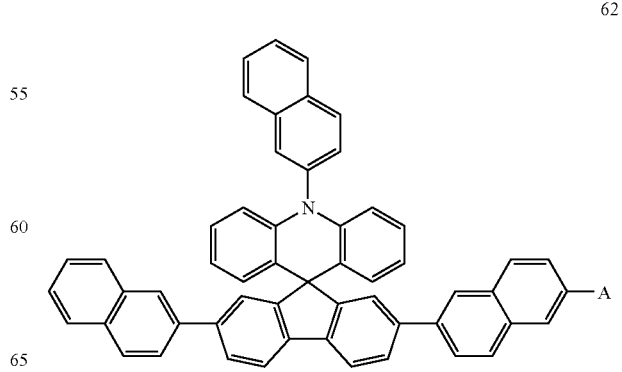

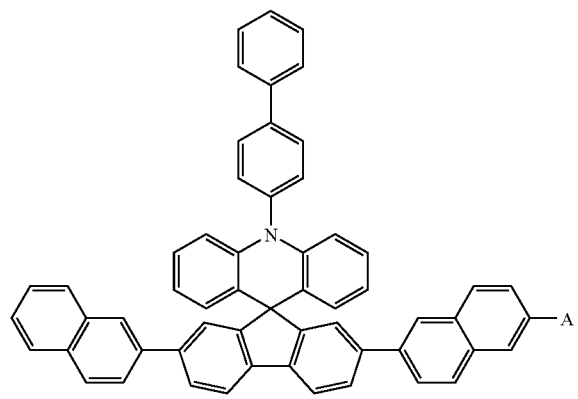
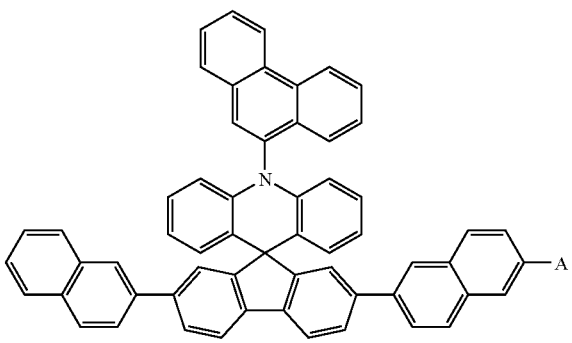

-continued
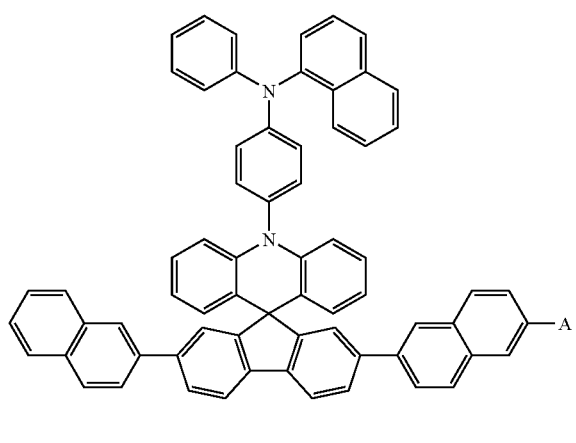
71
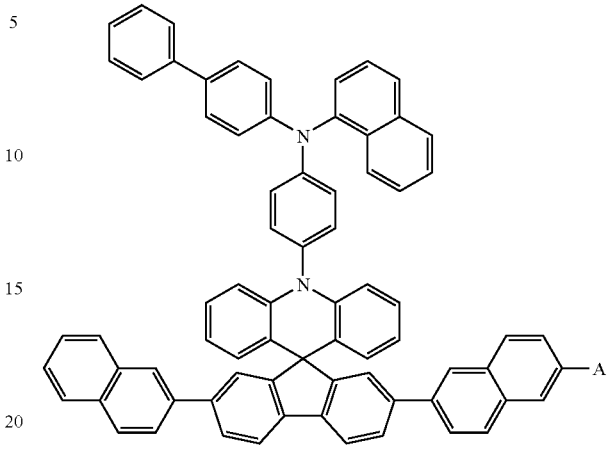
74
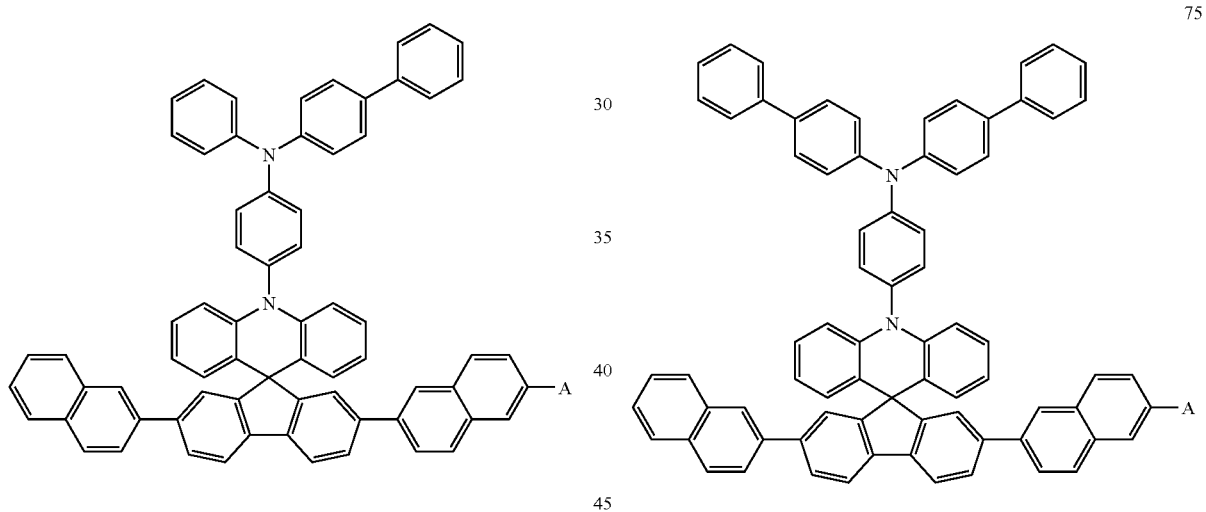
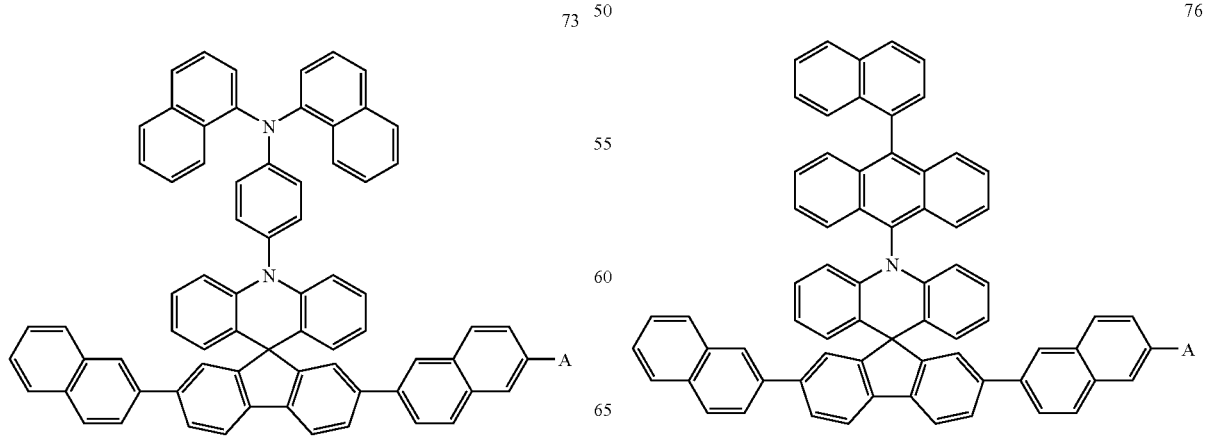
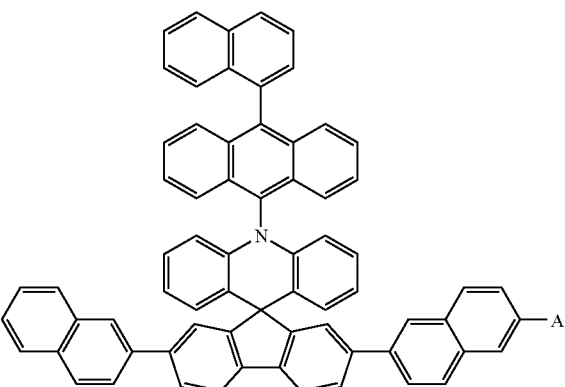

-continued
77
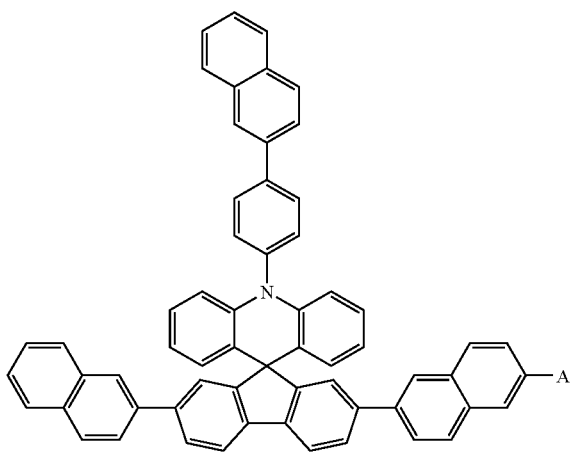
78
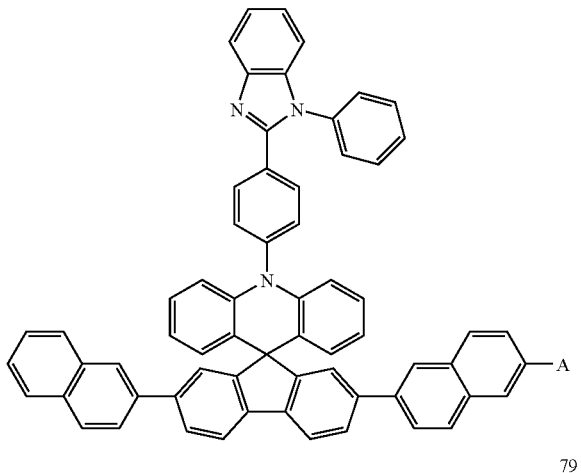
79
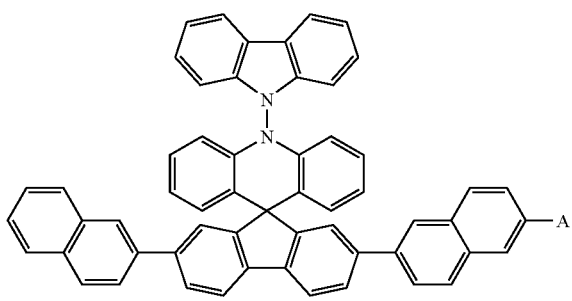
80
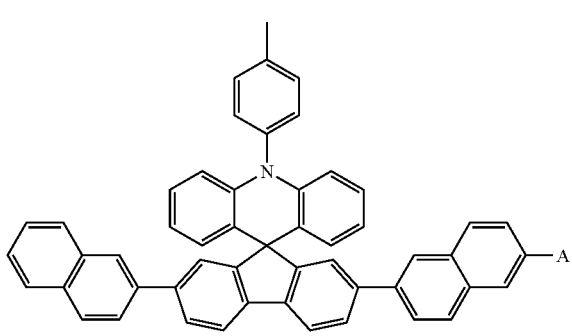
-continued
81
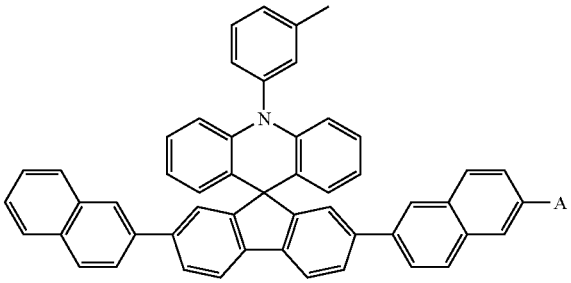
82
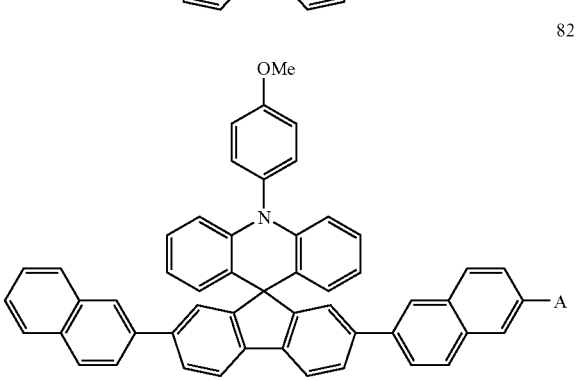
83
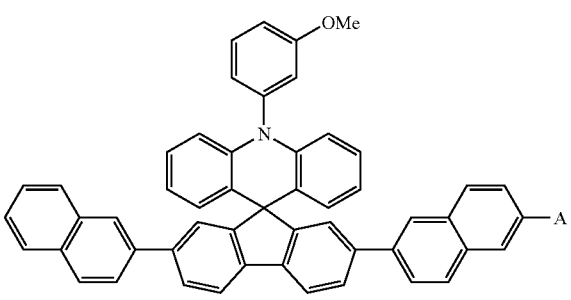
84
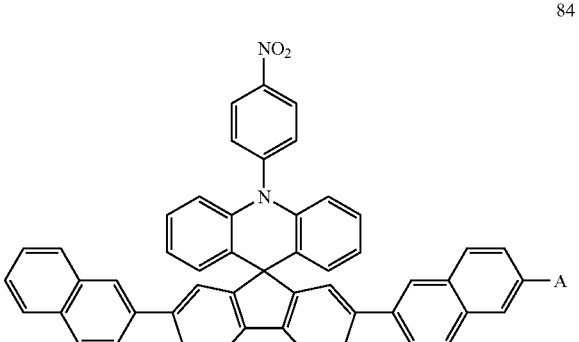
85
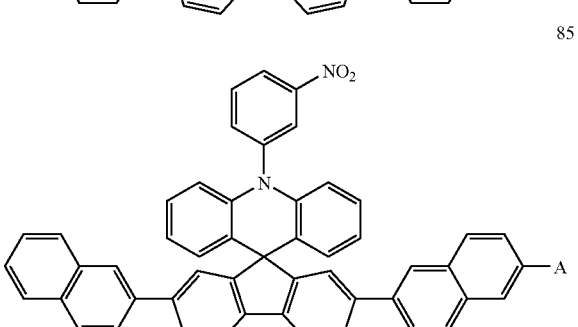

271 272
-continued
86
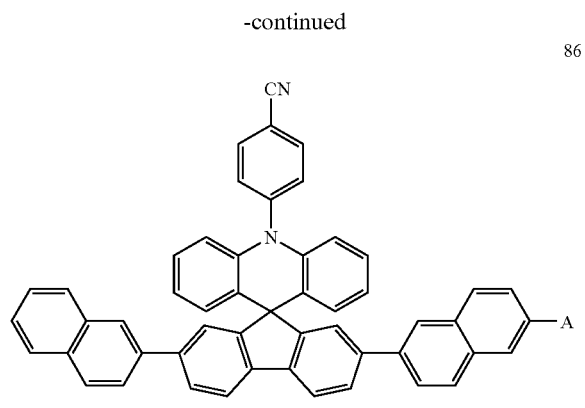
87
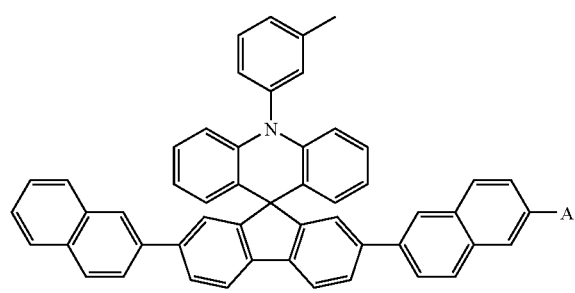
88
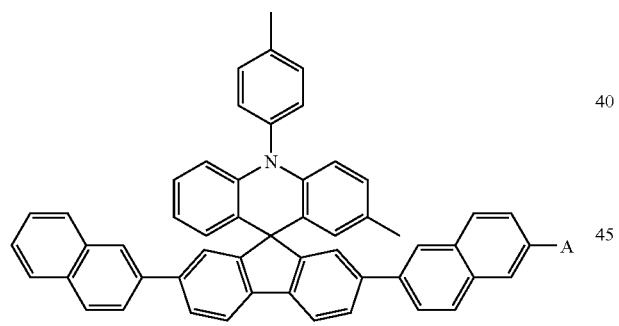
89
-continued
90
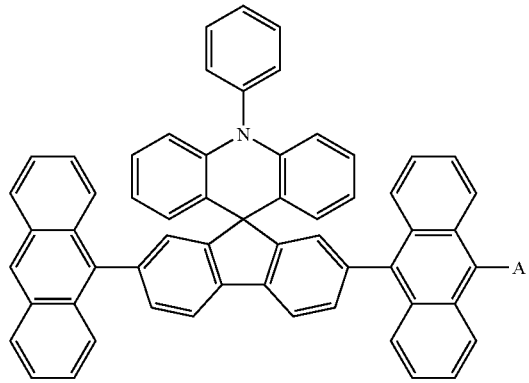
91
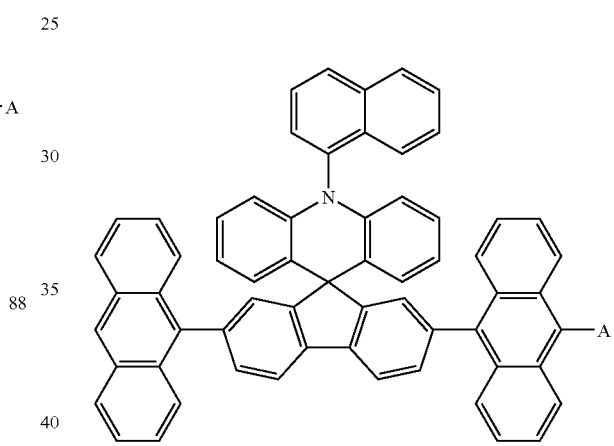
92
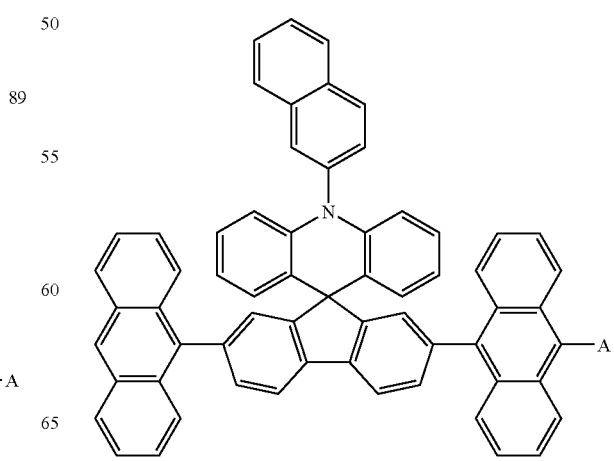

-continued
93
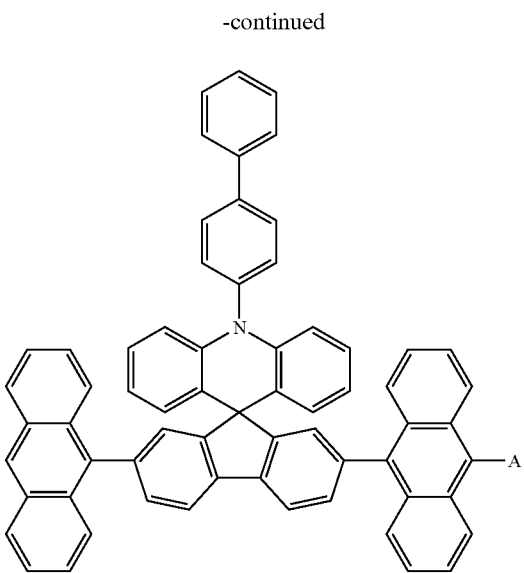
94
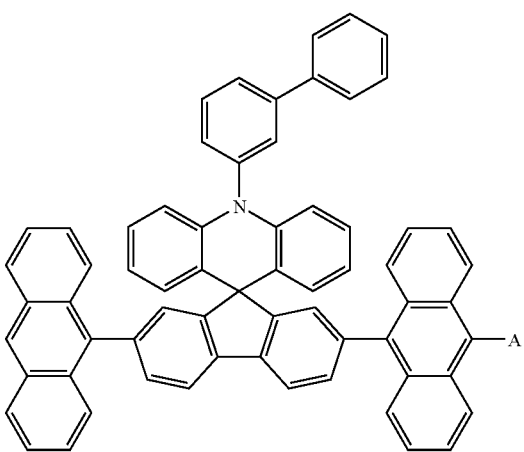
95
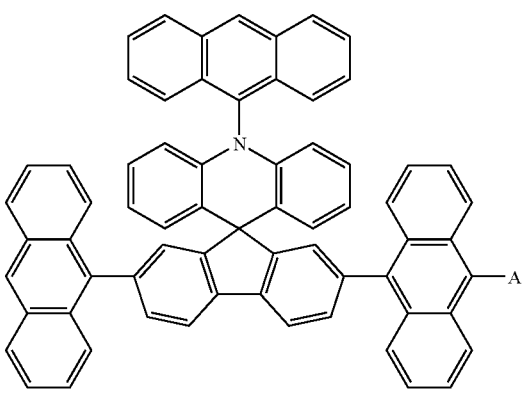
-continued
96
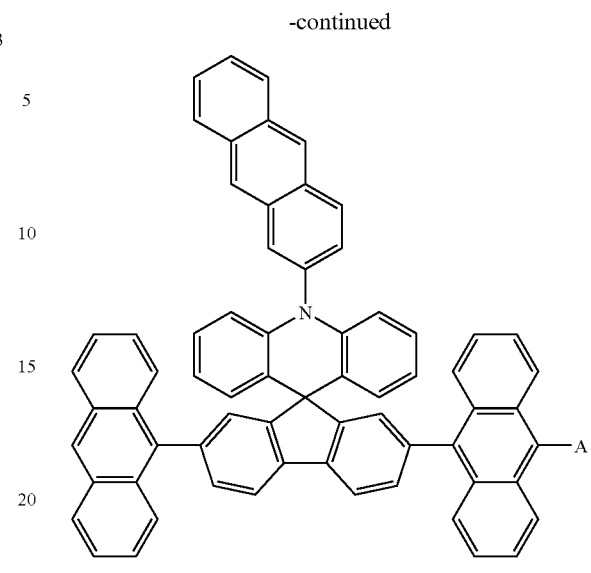
97
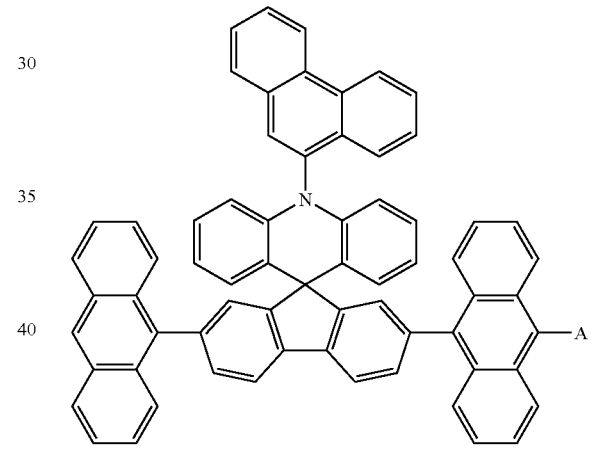
98
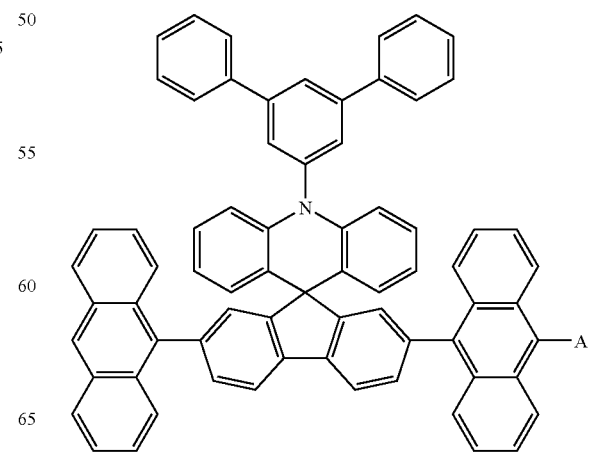

99
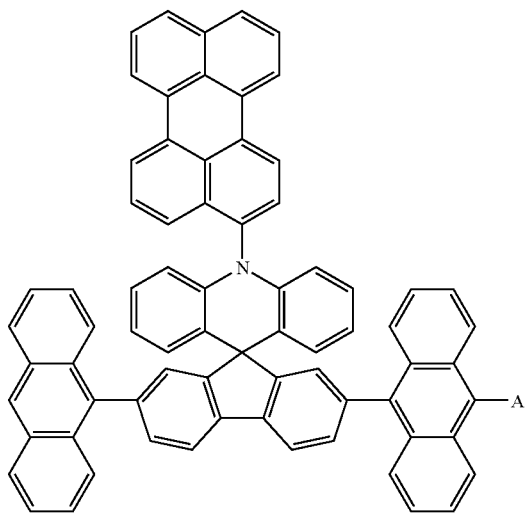
100
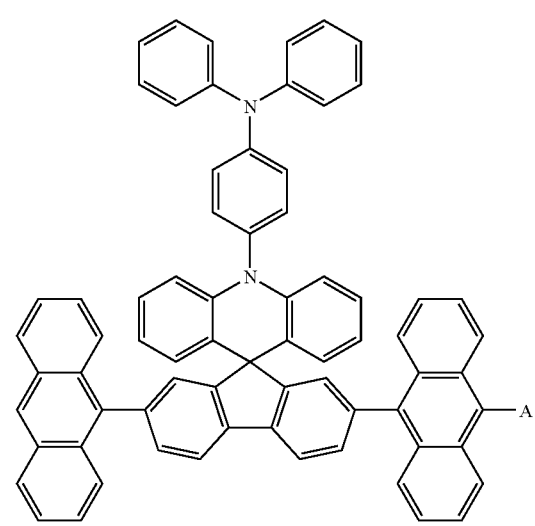
101
102
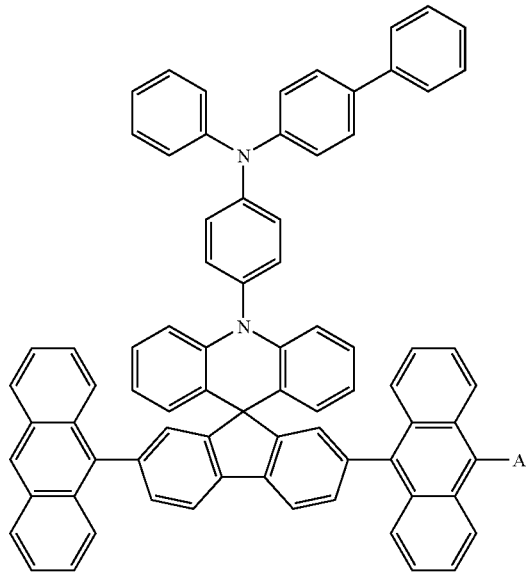
103
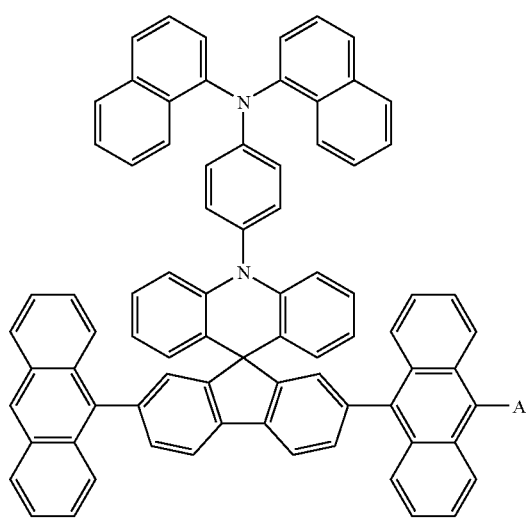

-continued
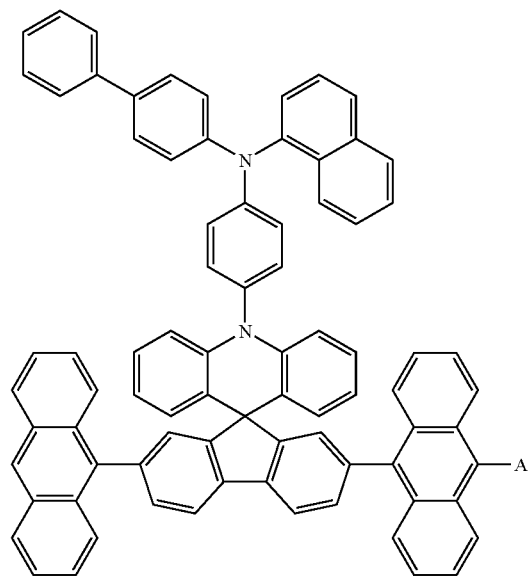
104
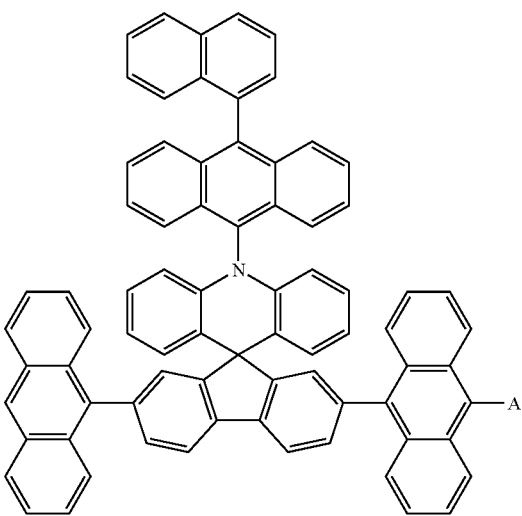
106
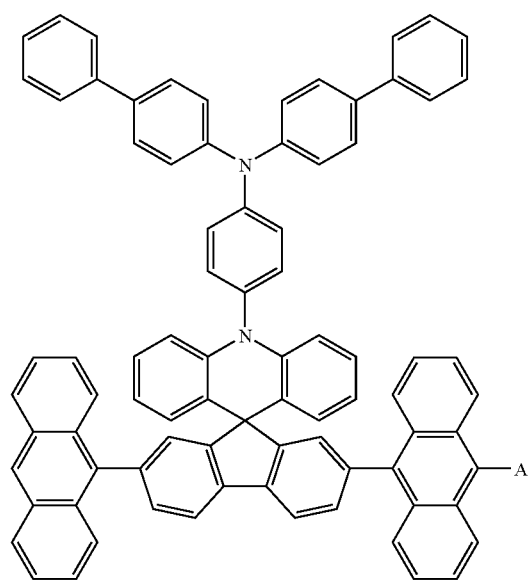
105
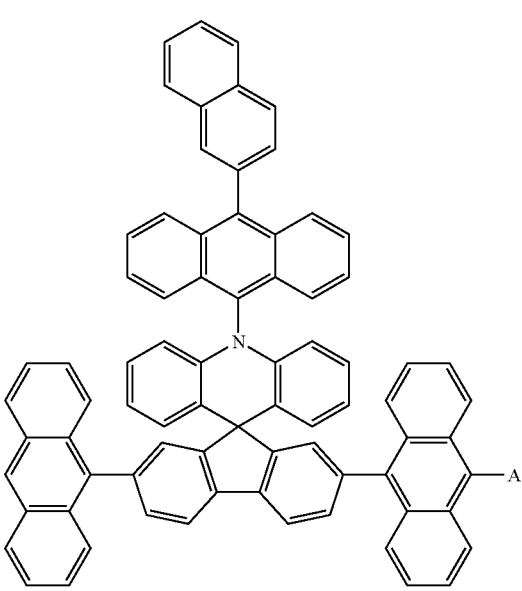
107

108
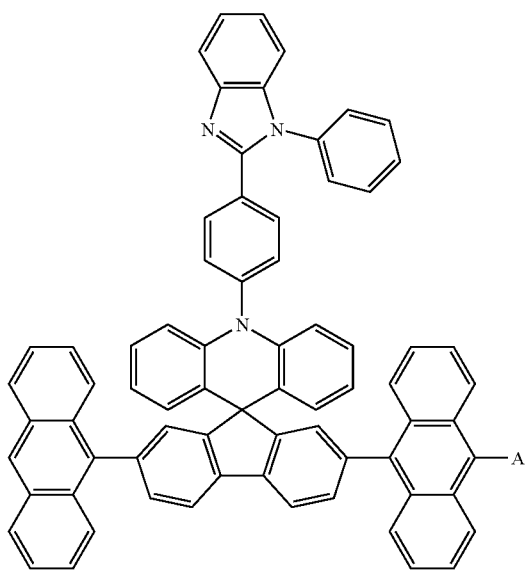
109
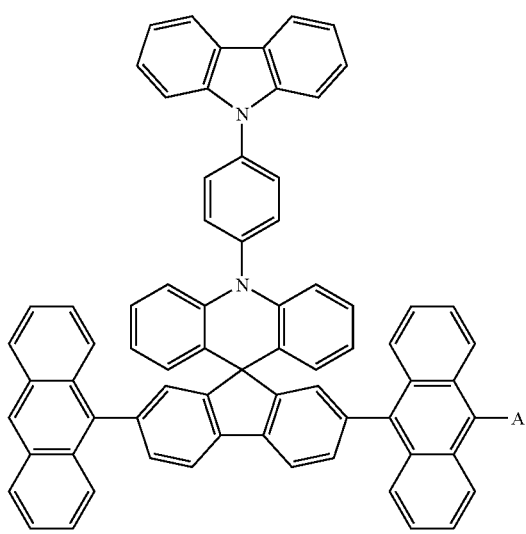
110
111
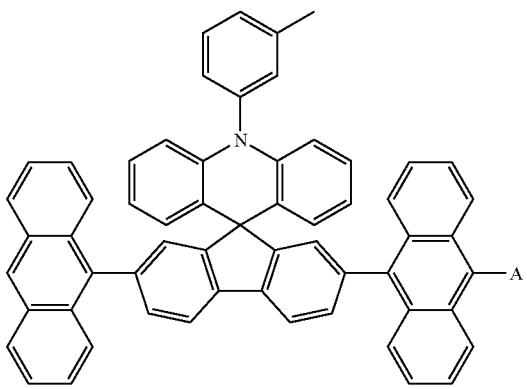
112
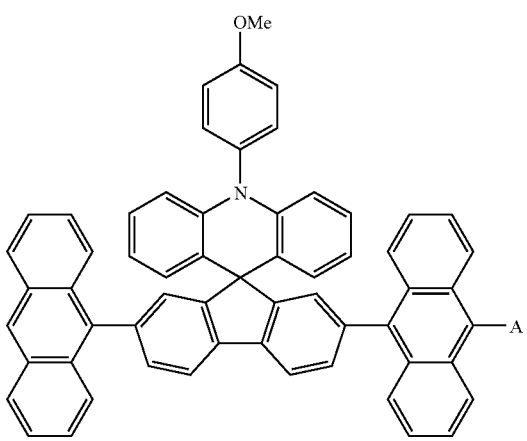
113
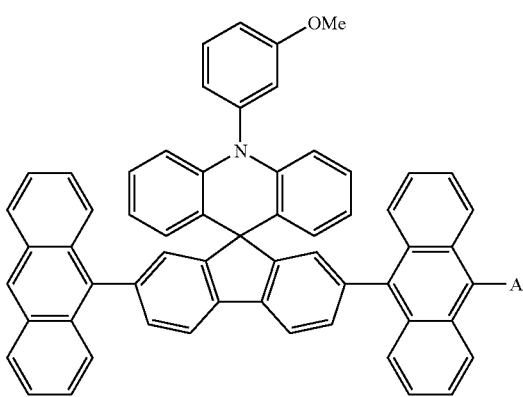

114
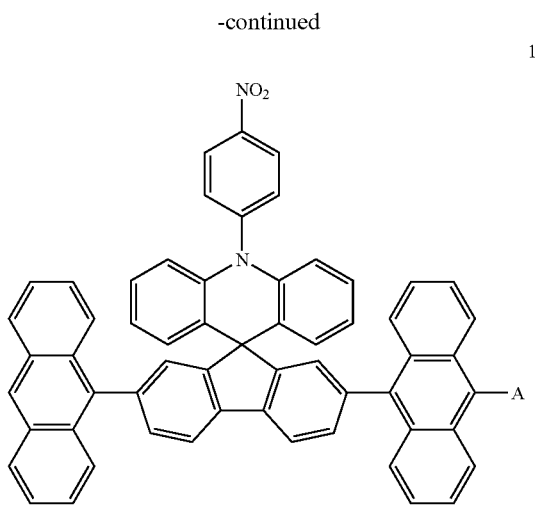
115
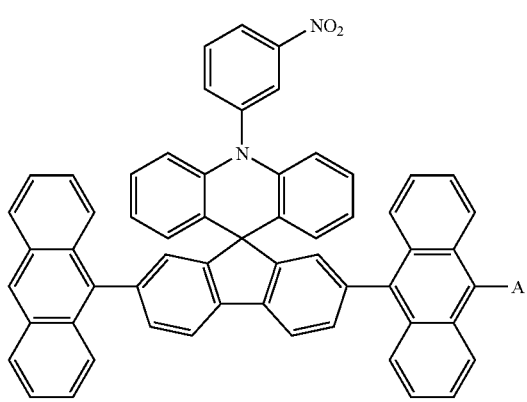
116
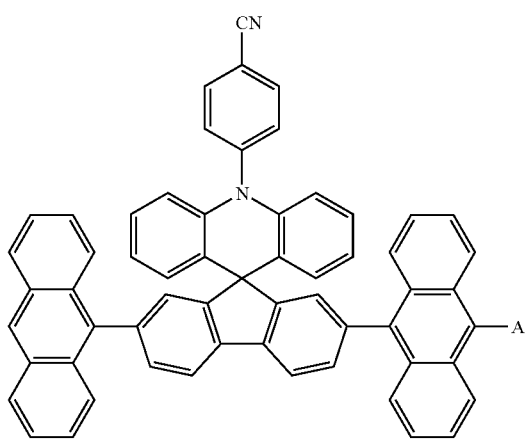
117
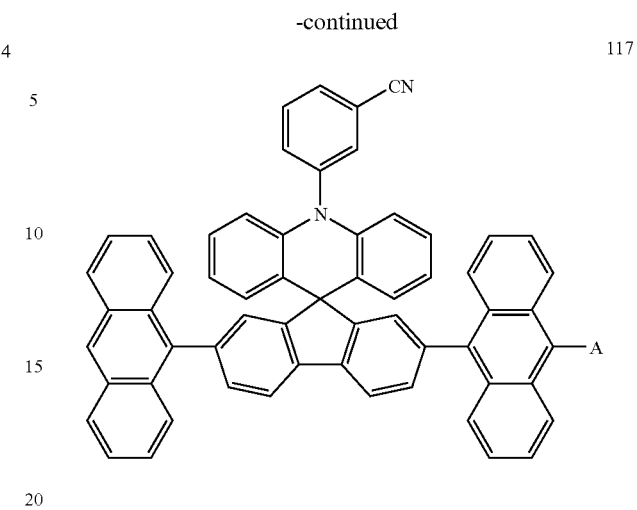
118
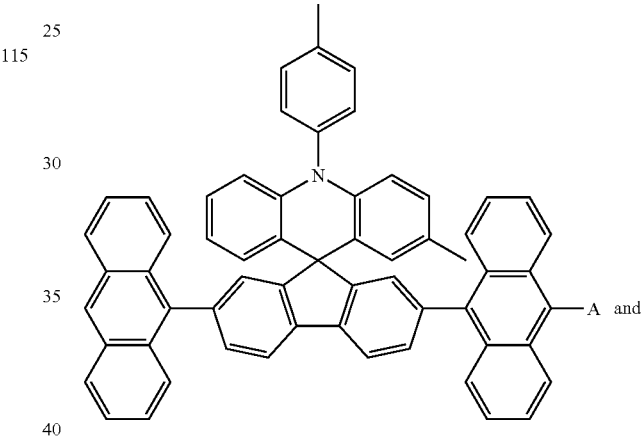
and
119
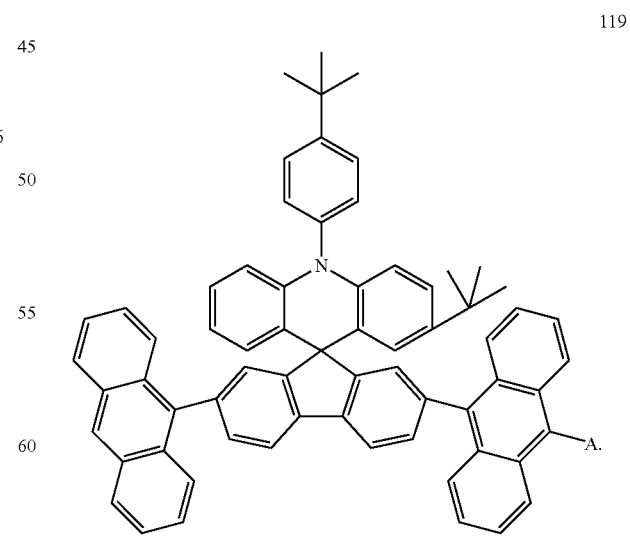
5. The organic light emitting device as set forth in claim 4, wherein A is independently any one of following groups:

1
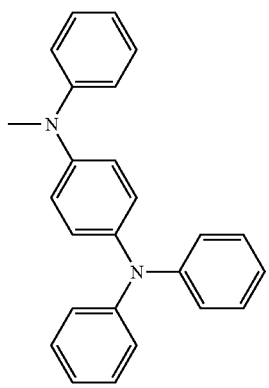
2
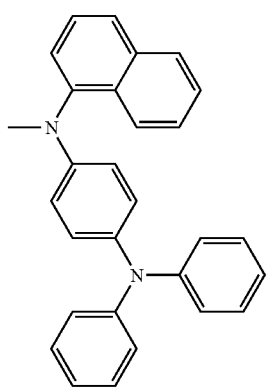
3
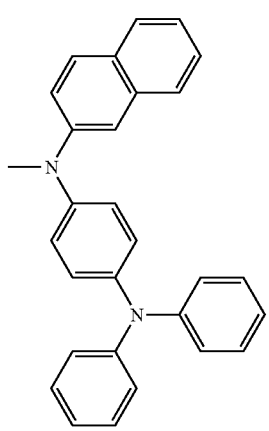
-continued
4
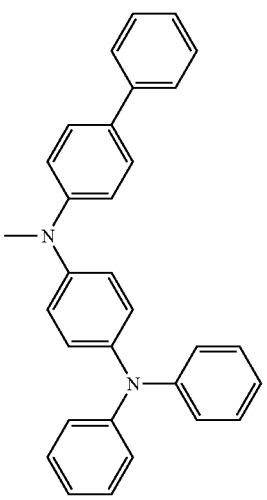
5
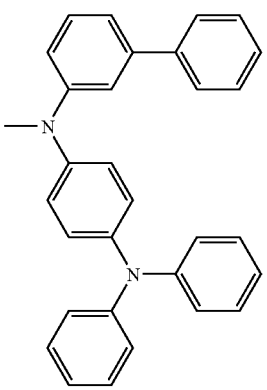
6
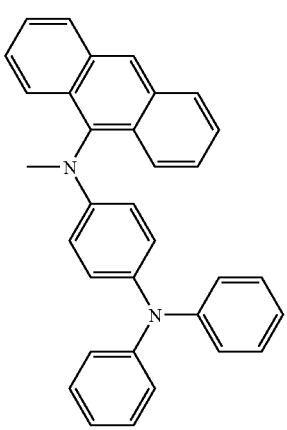

-continued
7
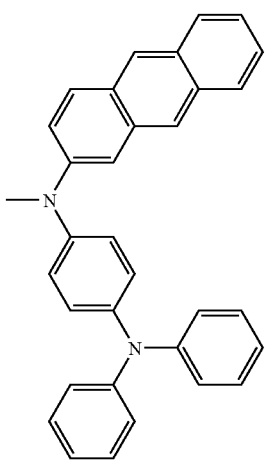
8
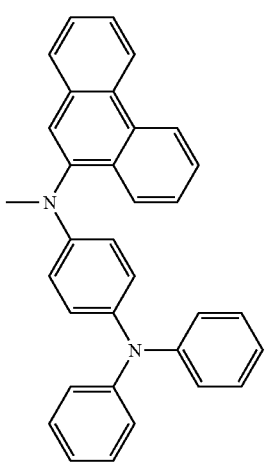
9
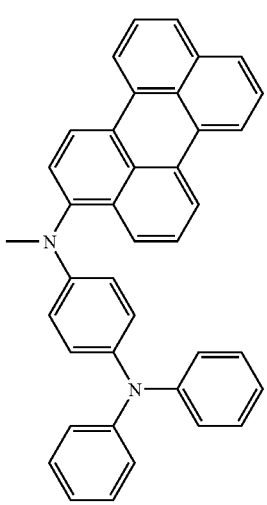
-continued
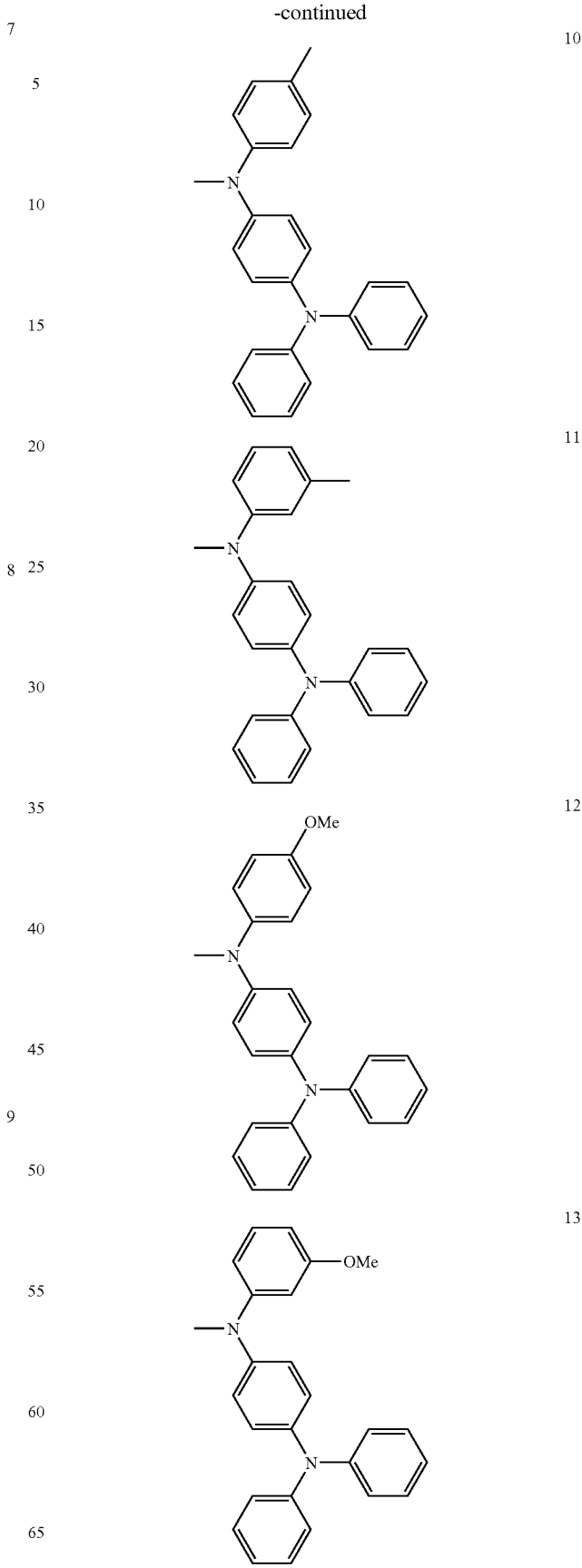

-continued
14
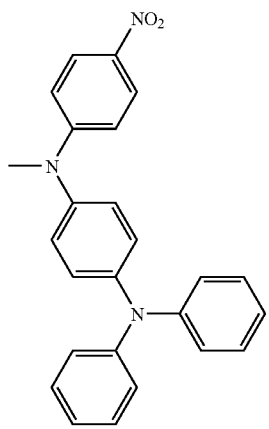
15
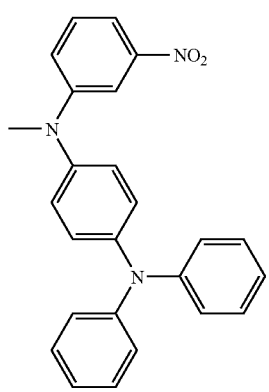
16
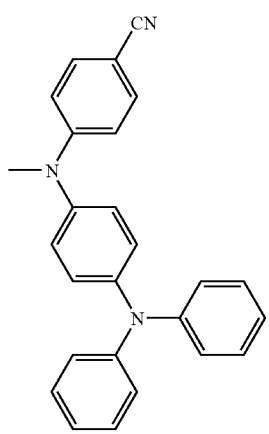
17
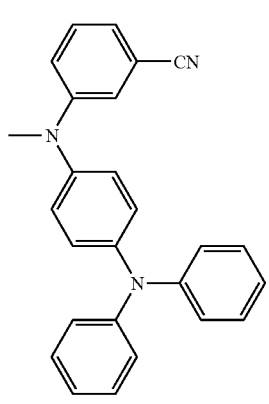
-continued
18
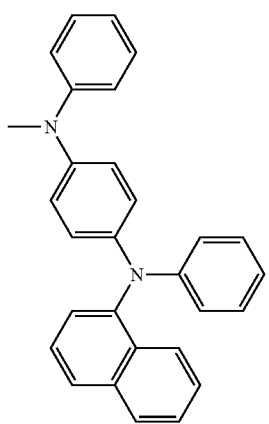
19
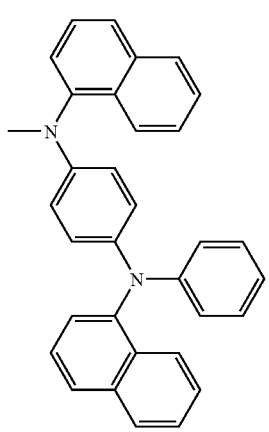
20
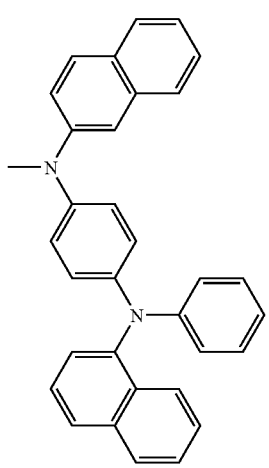

-continued
21
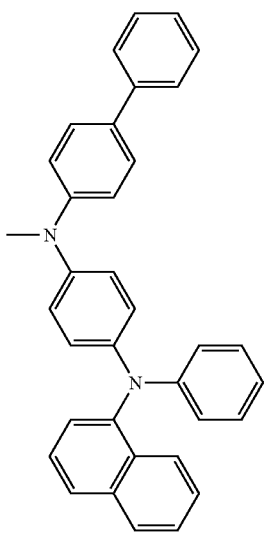
22
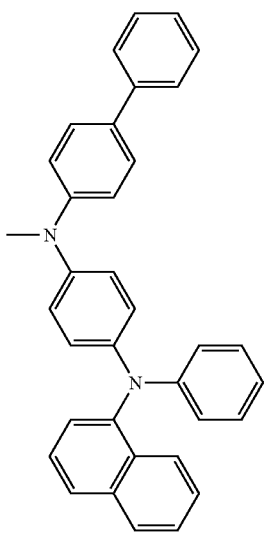
23
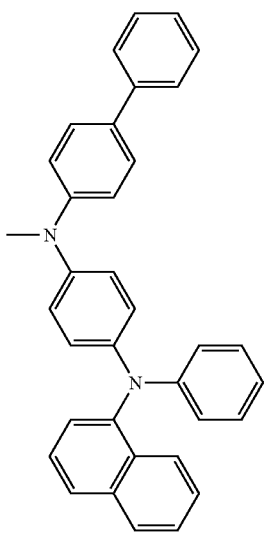
-continued
24
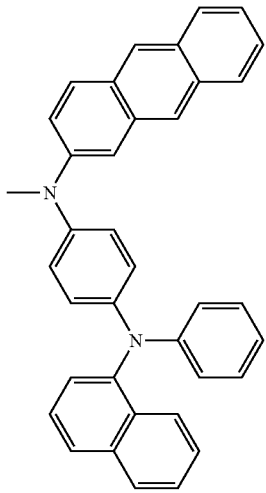
25
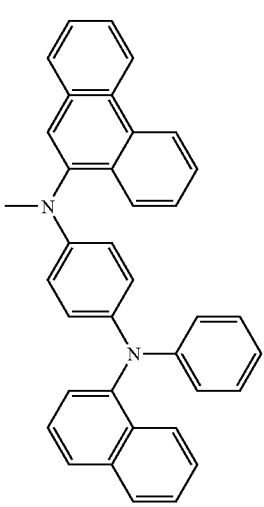
26
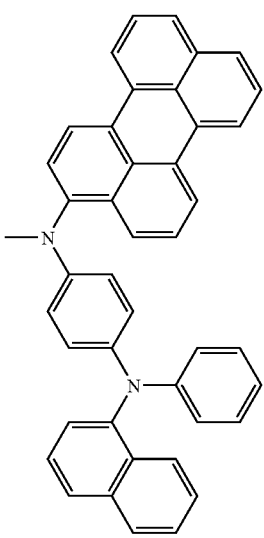

-continued
27
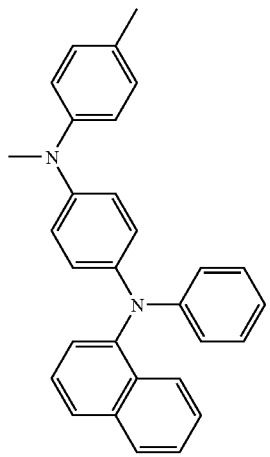
28
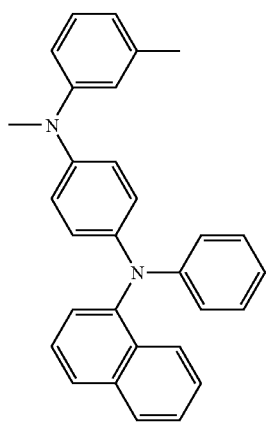
29
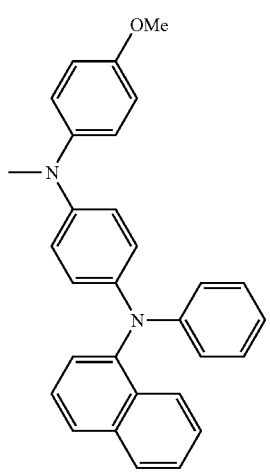
-continued
30
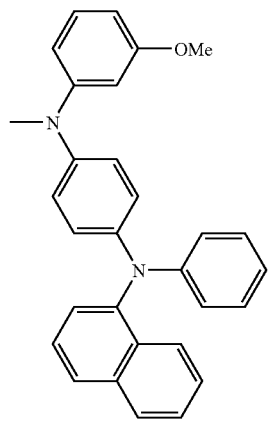
31
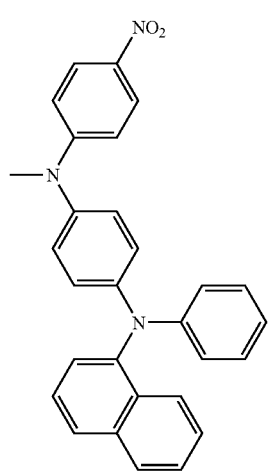
32
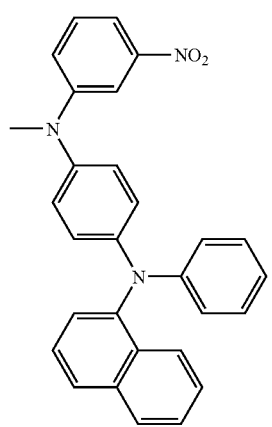

33
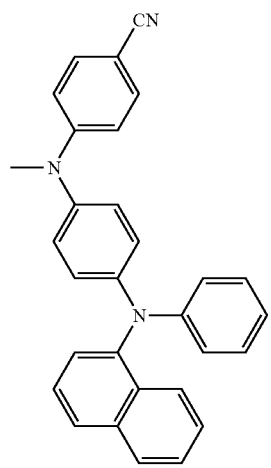
34
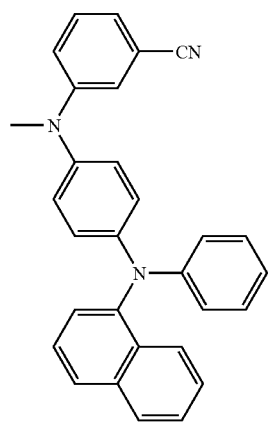
35
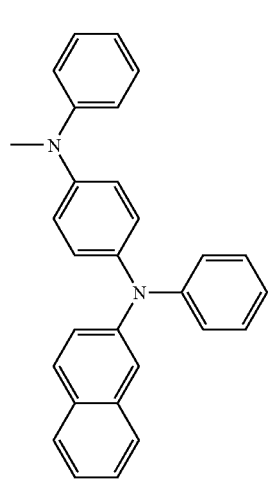
36
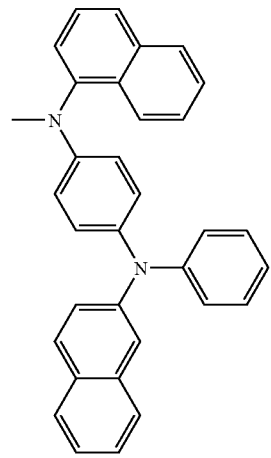
37
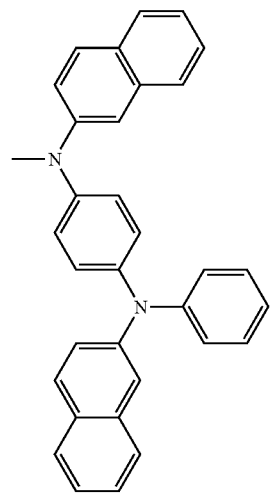
38
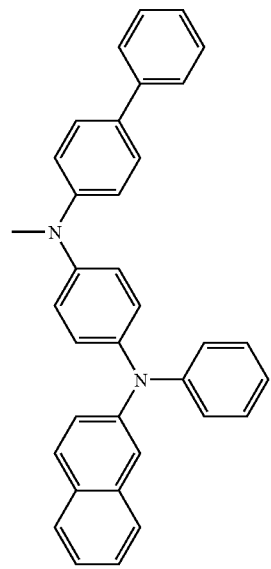

-continued
39
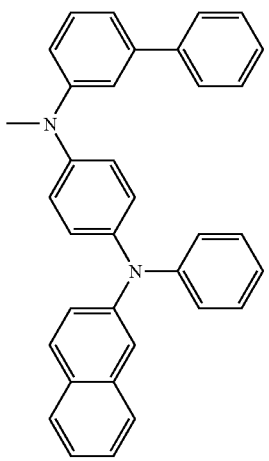
40
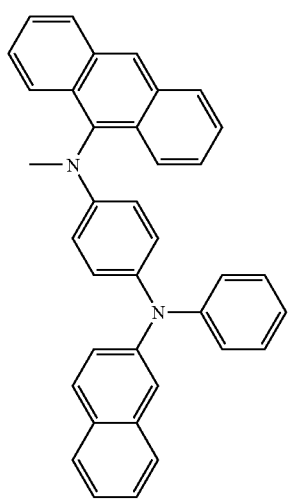
41
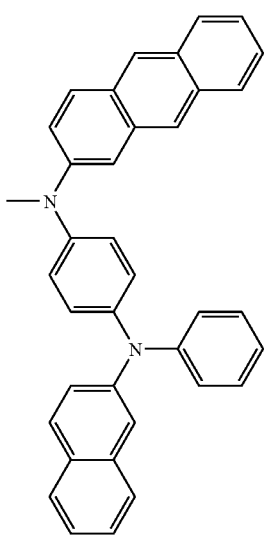
-continued
42
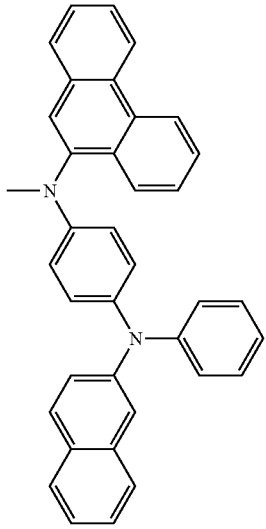
43
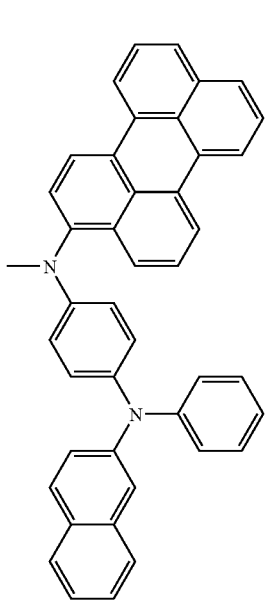
44
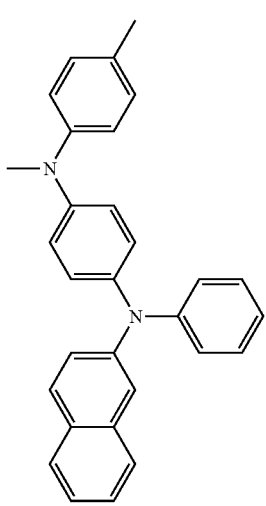

45
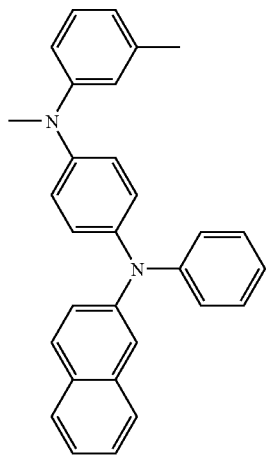
46
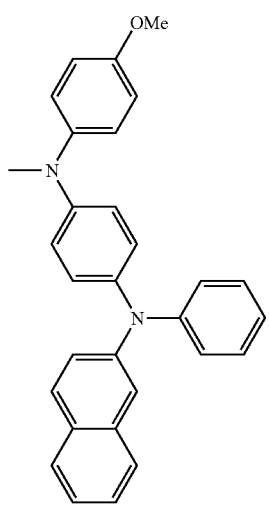
47
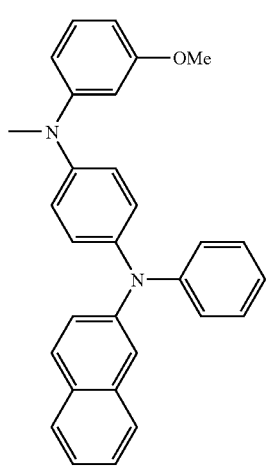
48
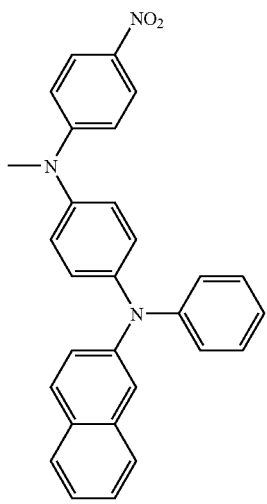
49
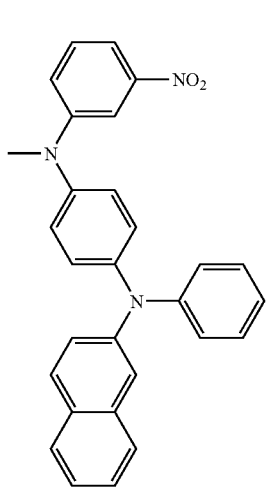
50
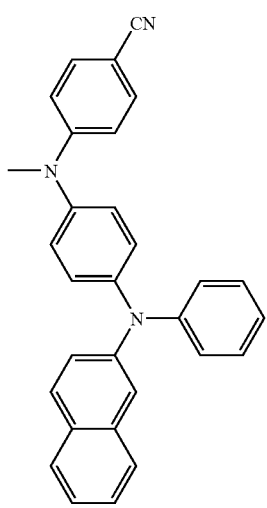

299
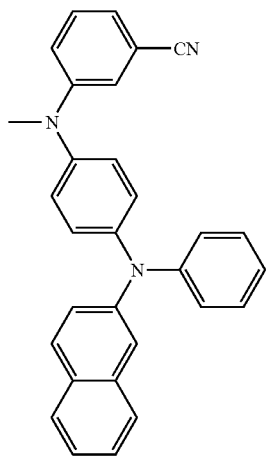
51
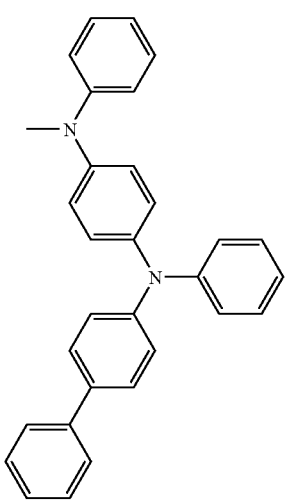
52
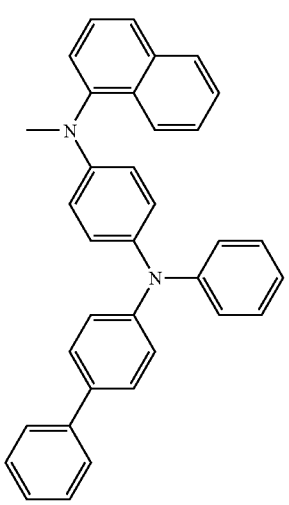
53
300
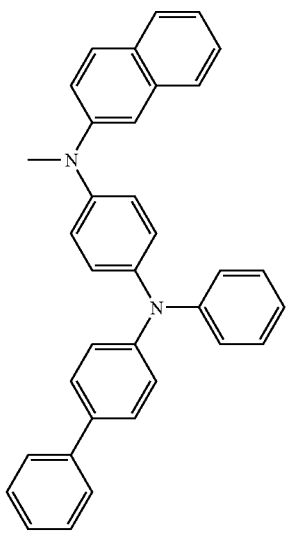
54
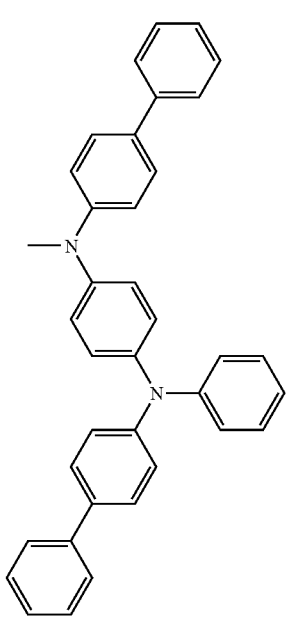
55
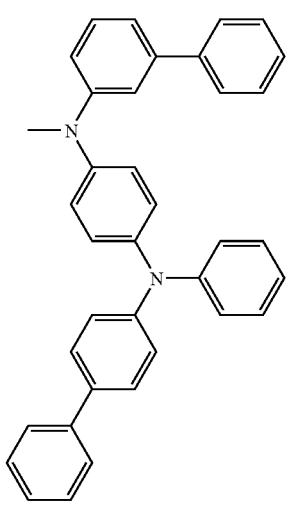
56

-continued
57
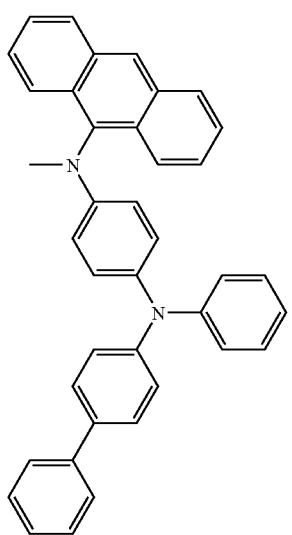
58
60
-continued
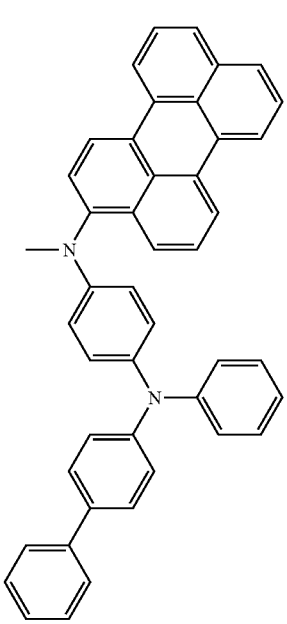
61
59
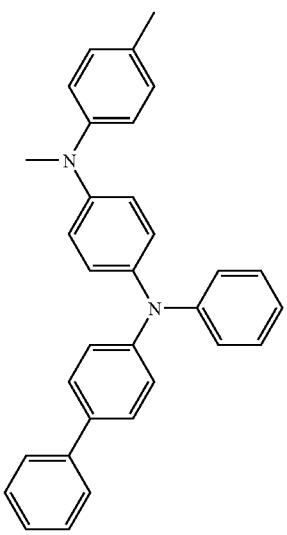
62
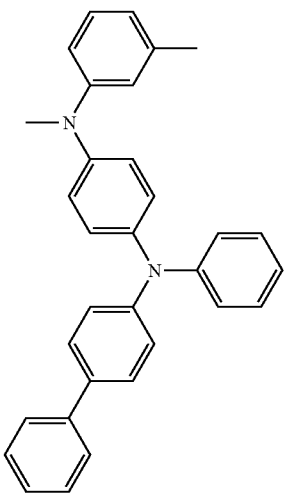

-continued
63
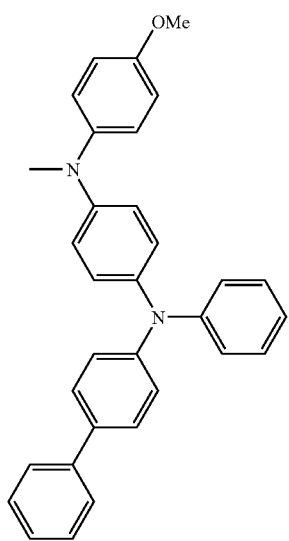
64
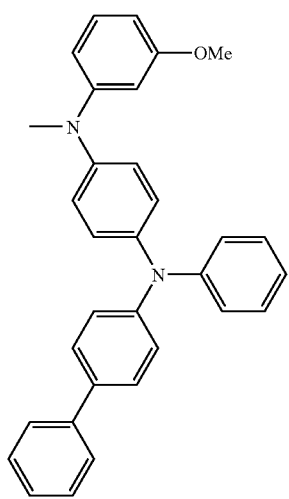
65
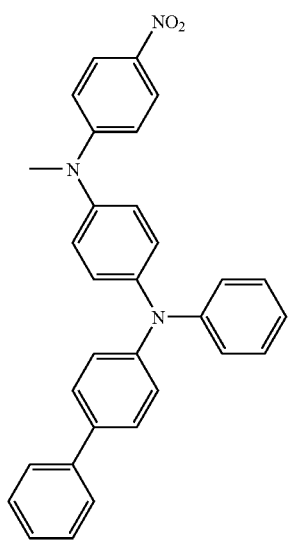
-continued
66
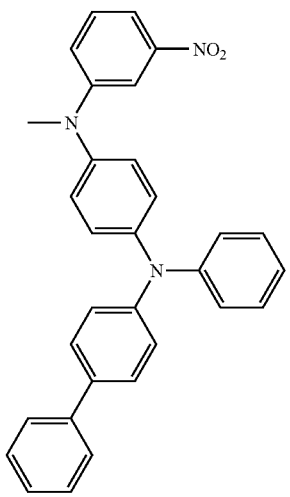
67
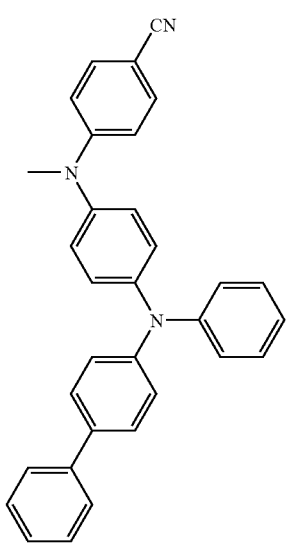
68
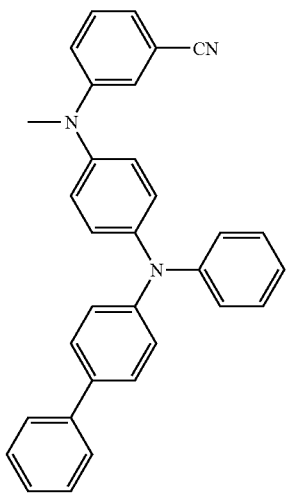

69
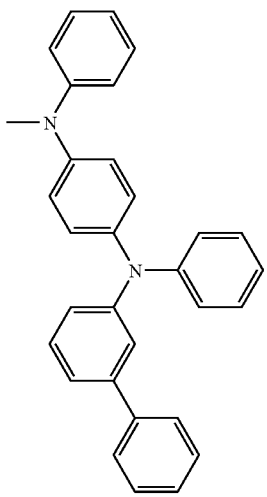
70
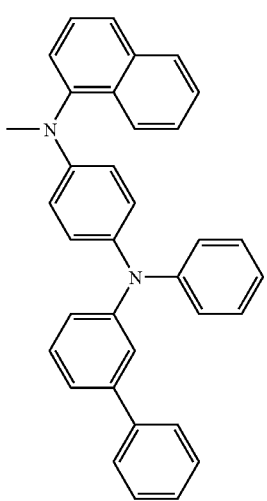
71
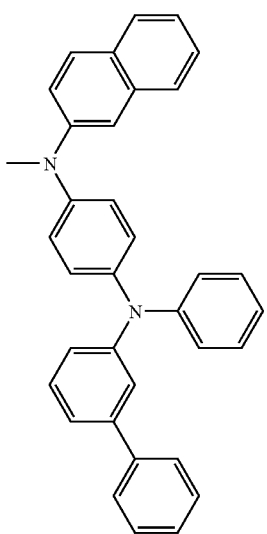
72
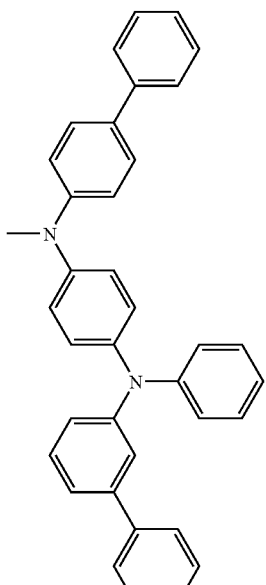
73
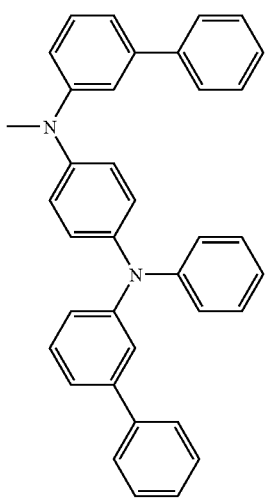
74
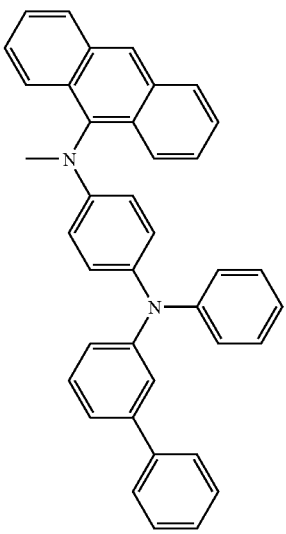

307
-continued
75
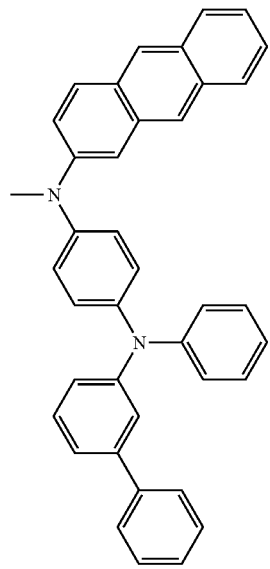
76
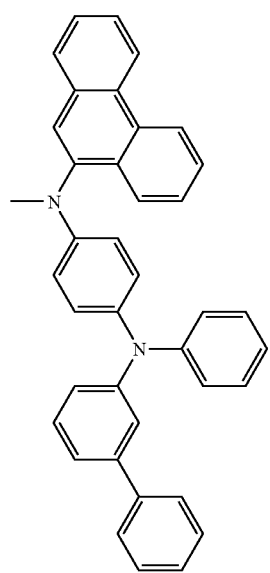
308
-continued
77
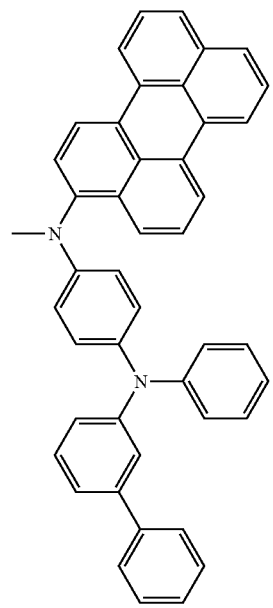
78
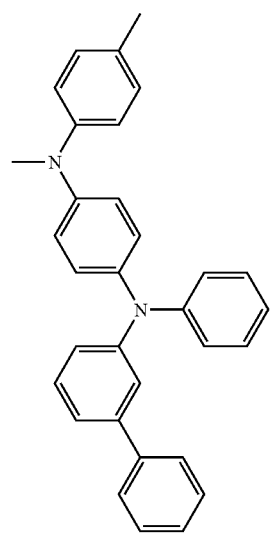
79

309 310
-continued
80 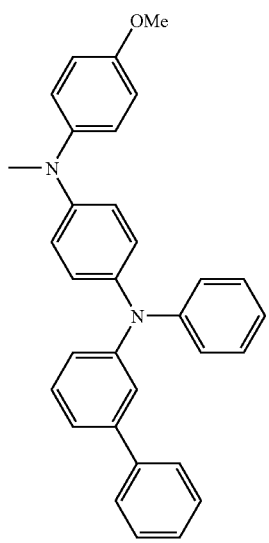
81 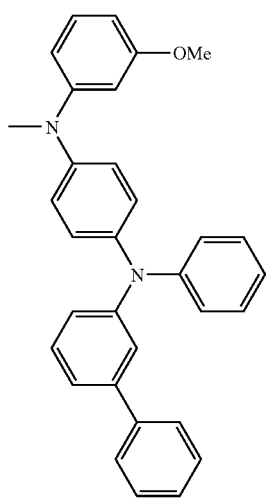
82 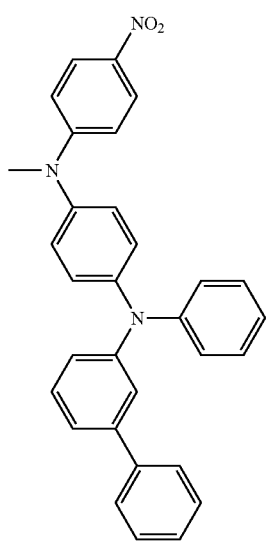
-continued
83 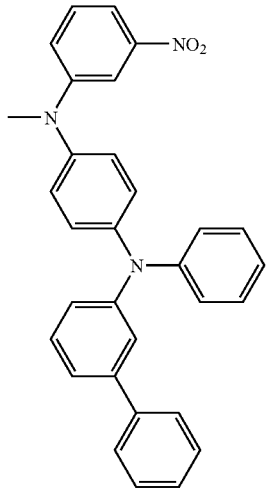
84 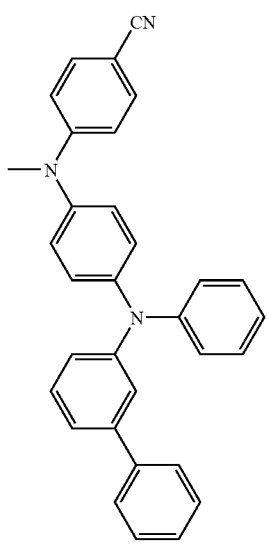
85 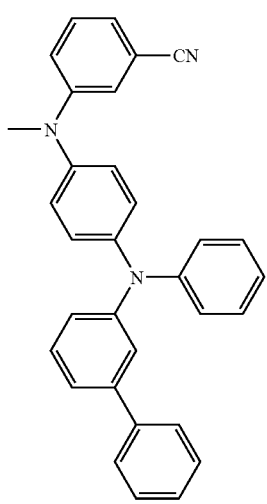

-continued
86
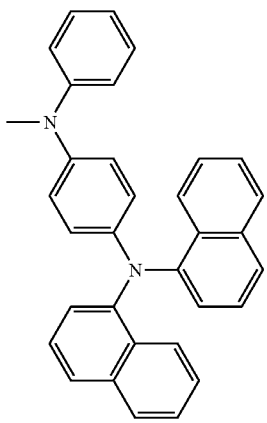
87
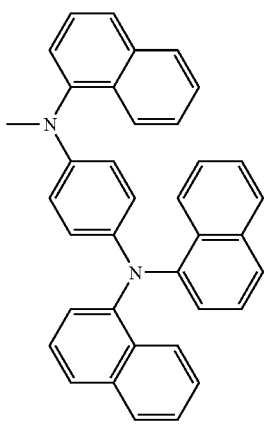
88
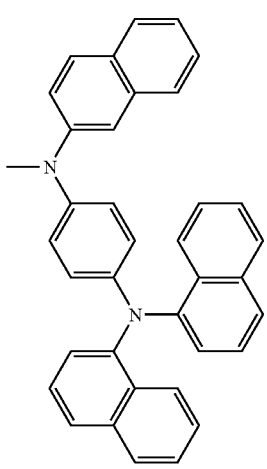
-continued
89
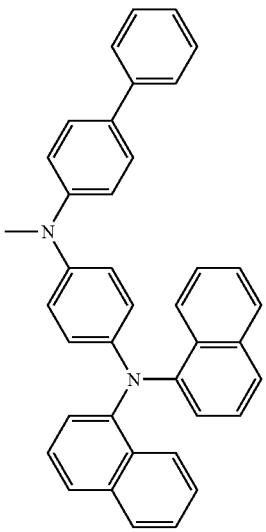
90
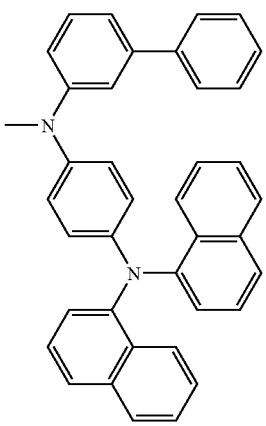
91
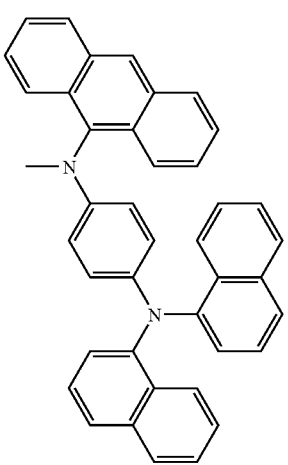

92
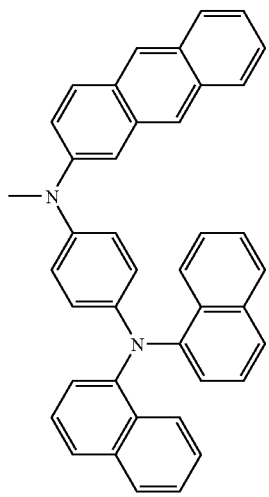
93
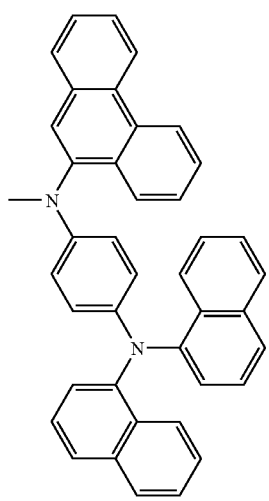
94
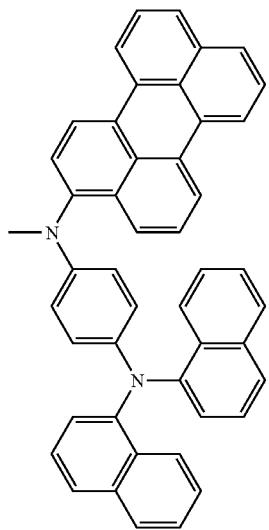
95
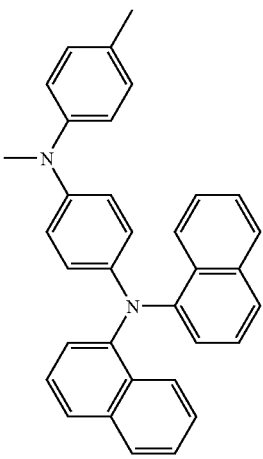
96
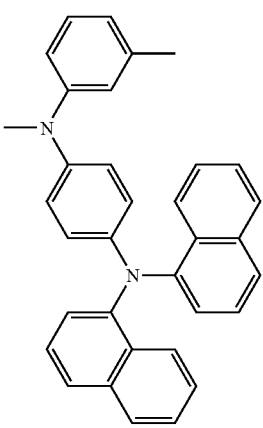
97
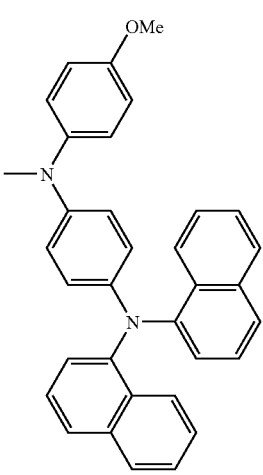

-continued
98
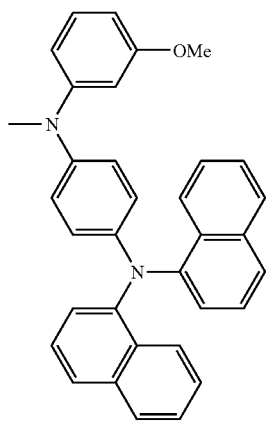
99
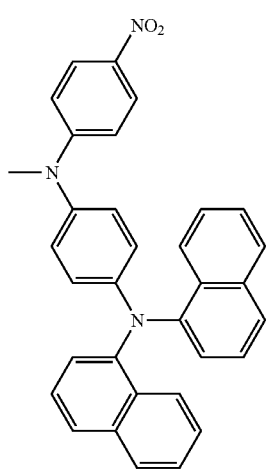
100
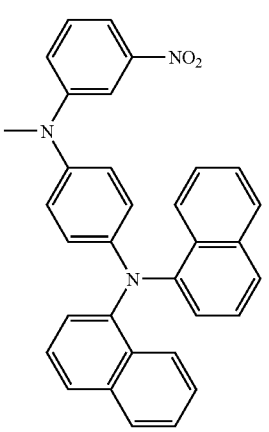
-continued
101
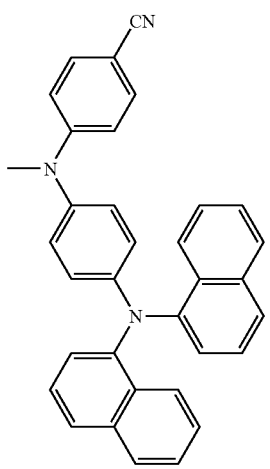
102
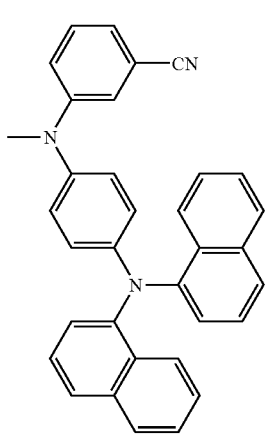
103
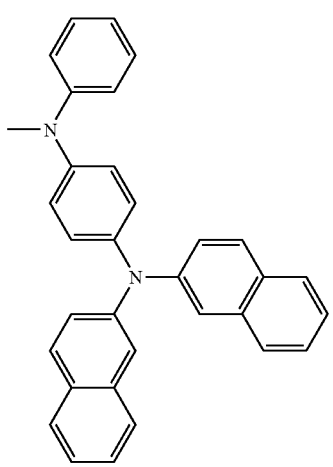

-continued
104
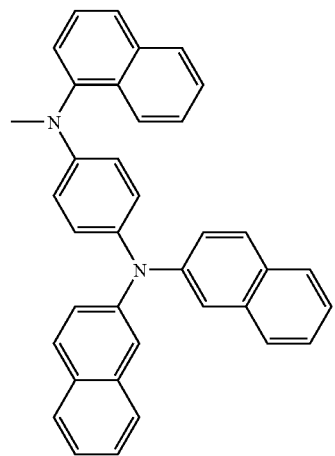
105
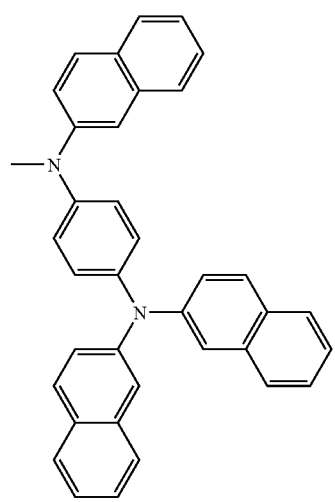
106
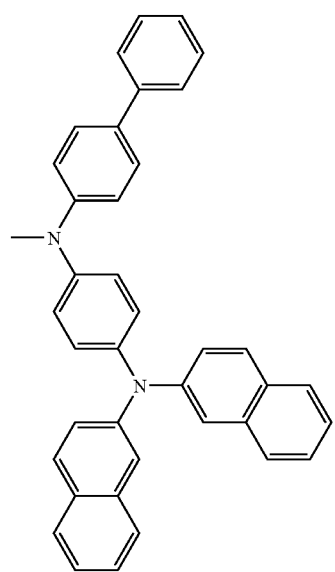
-continued
107
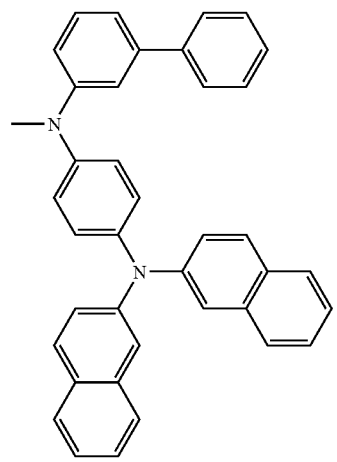
108
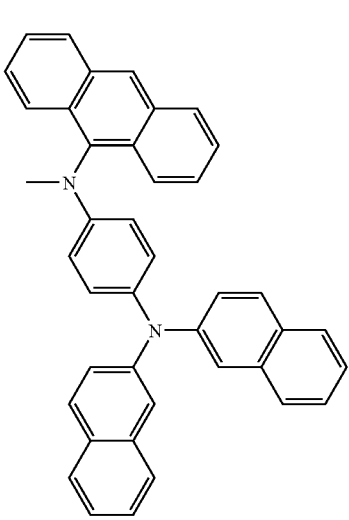
109
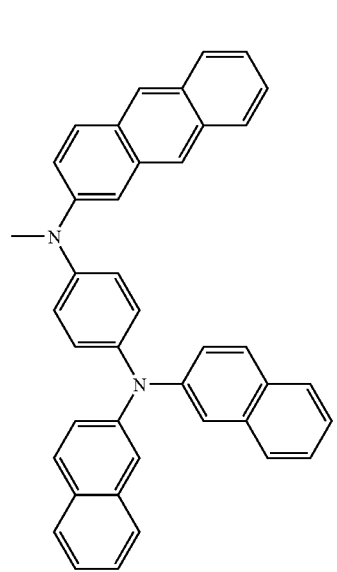

-continued
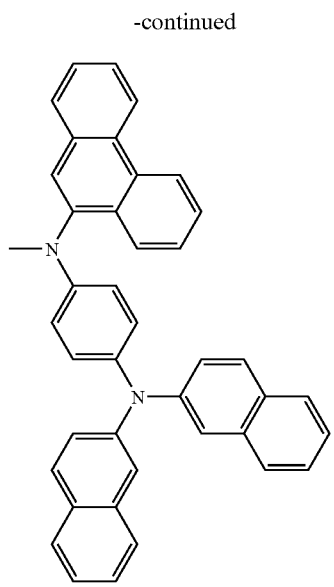
110
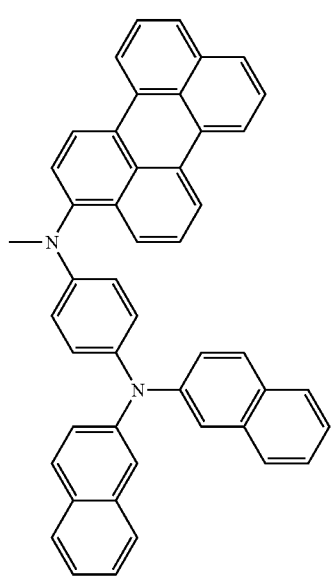
111
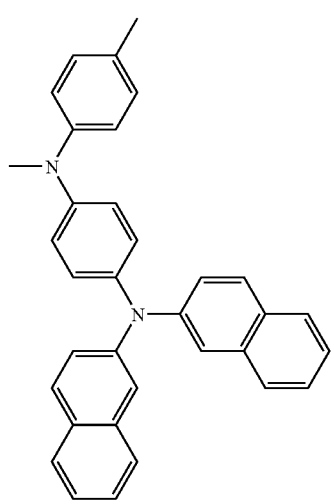
112
-continued
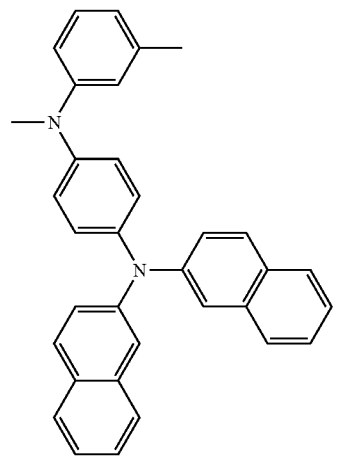
113
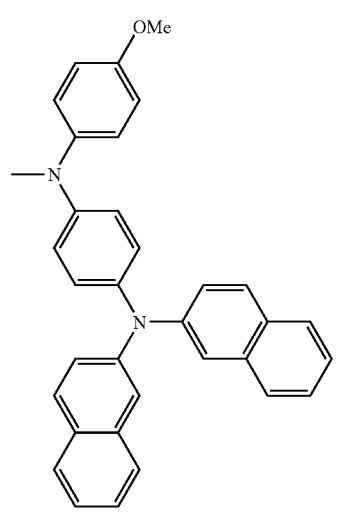
114
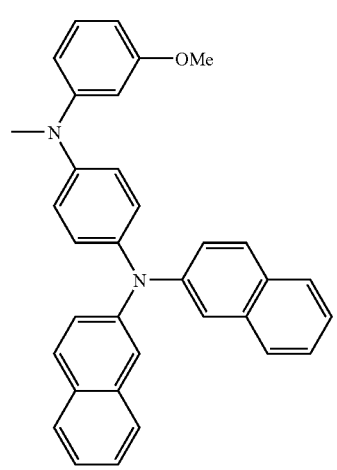
115

-continued
116
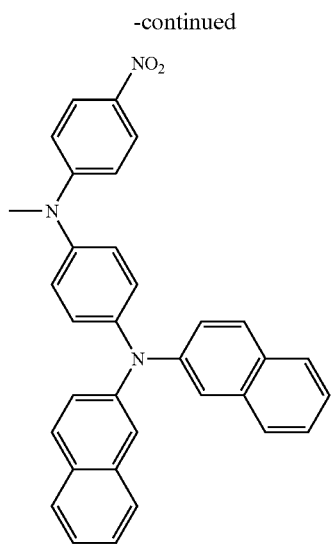
117
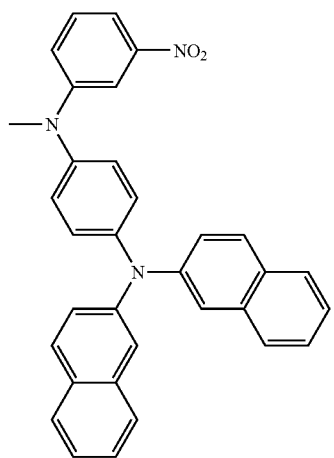
118
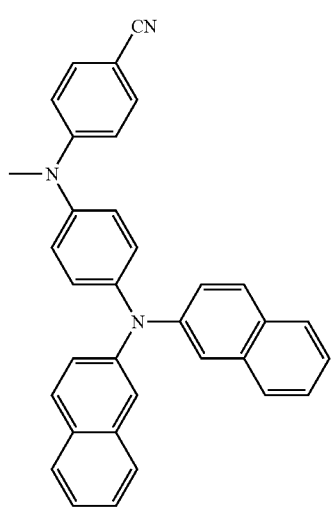
-continued
119
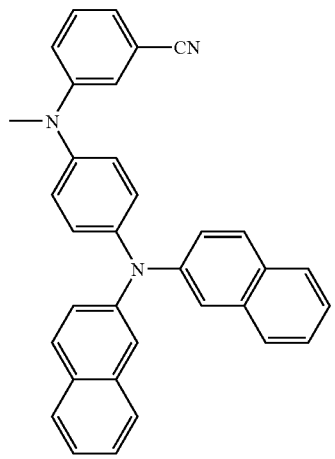
120
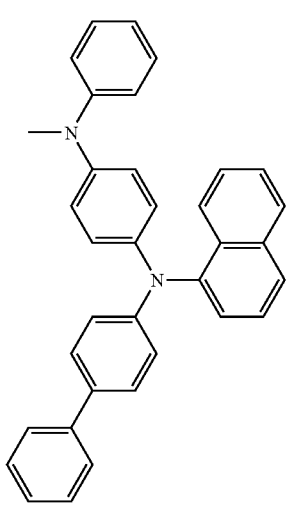
121
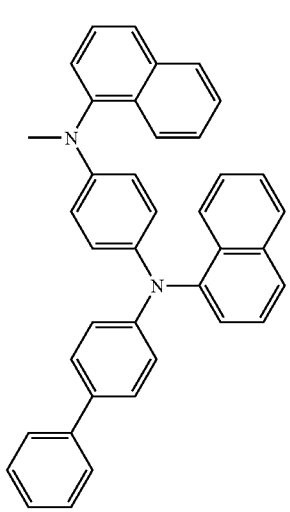

-continued
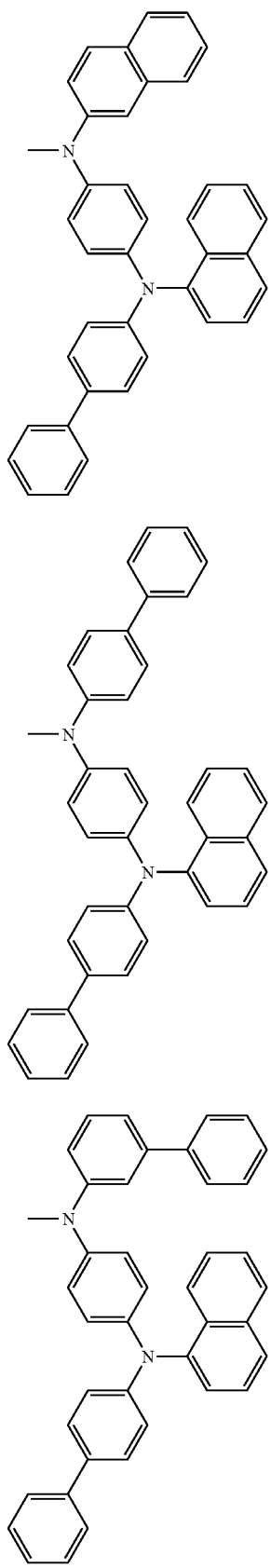
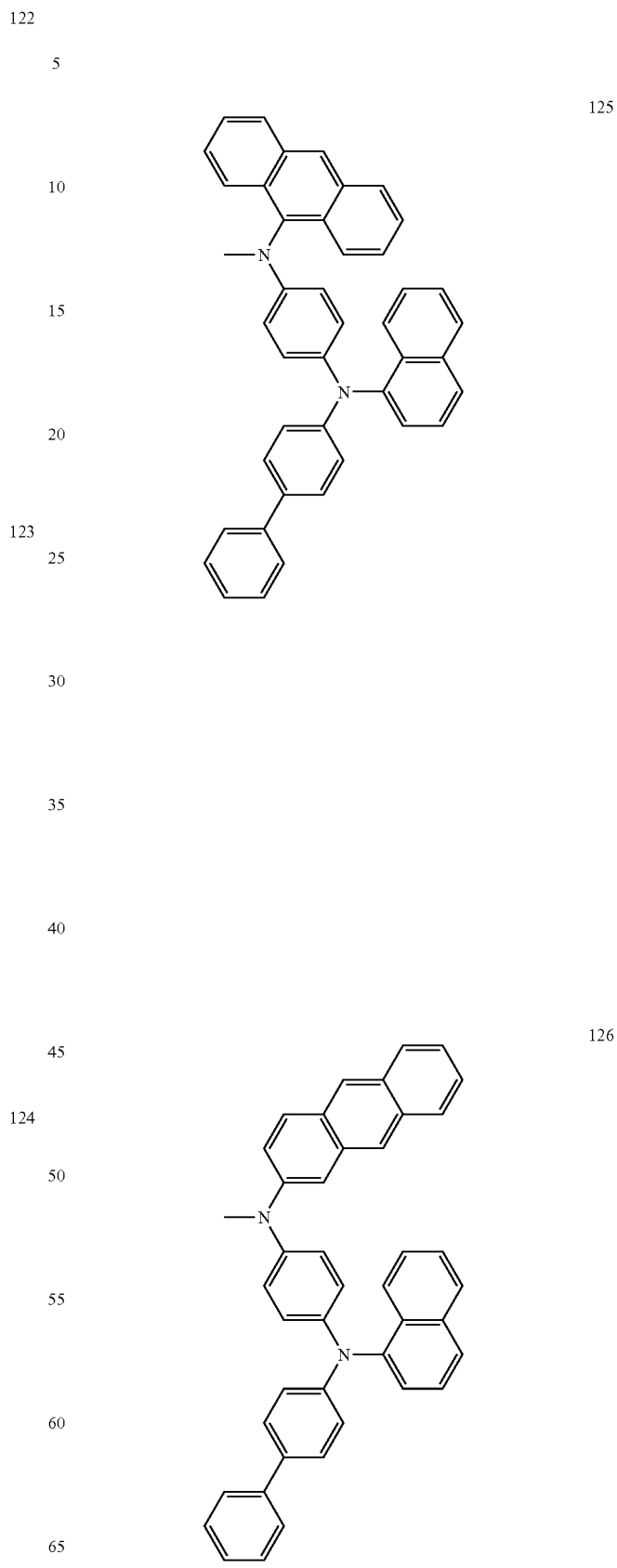

127
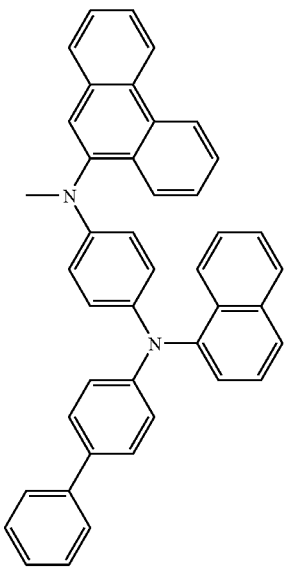
128
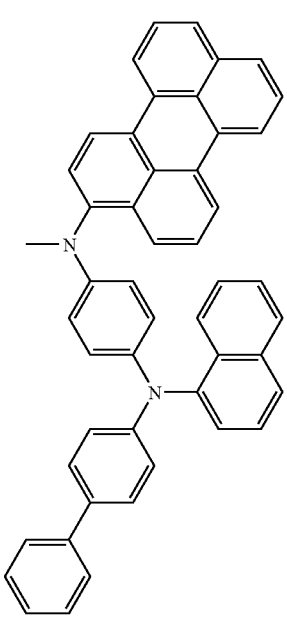
129
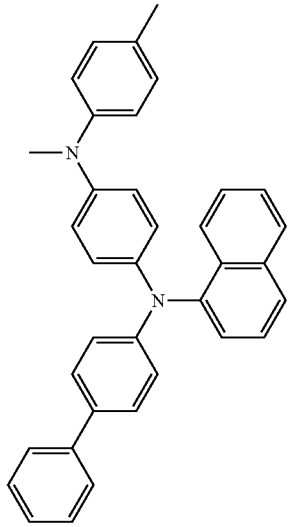
130
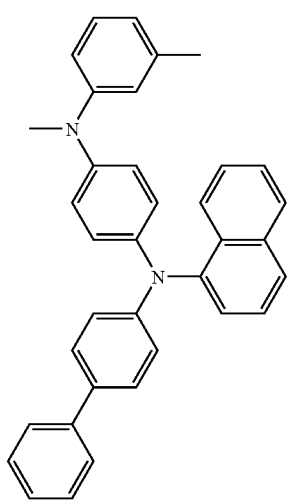
131
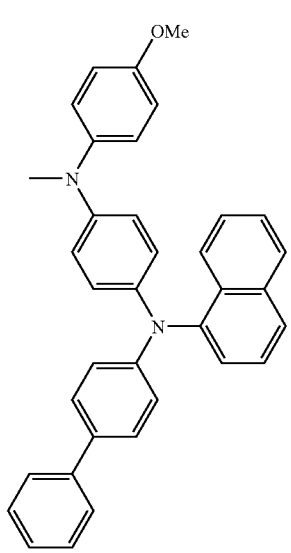

-continued
132
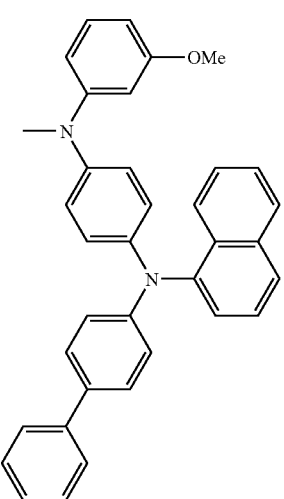
133
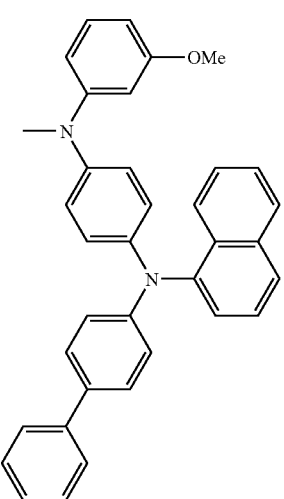
134
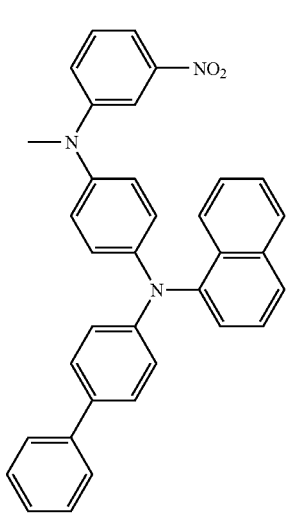
-continued
135
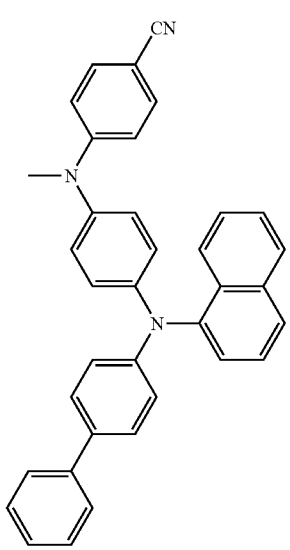
136
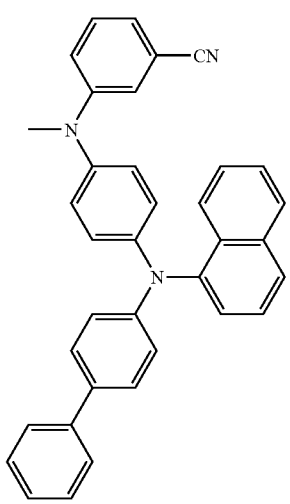
137
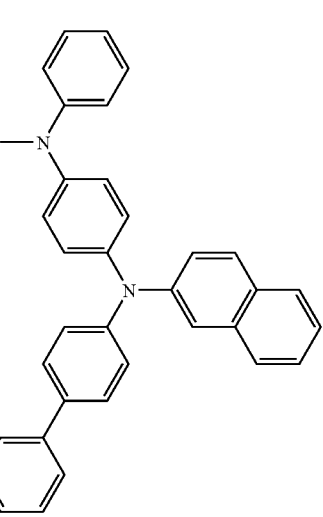

138
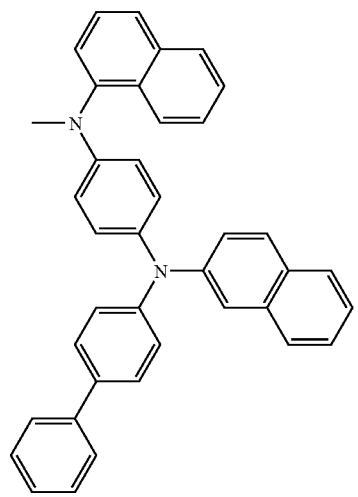
139
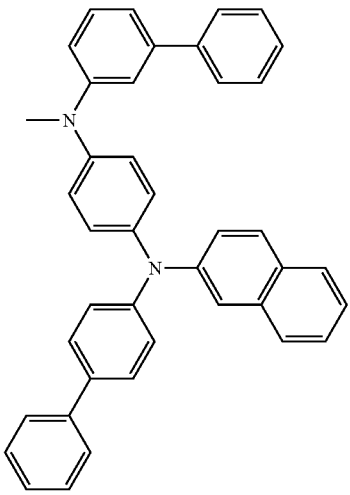
141
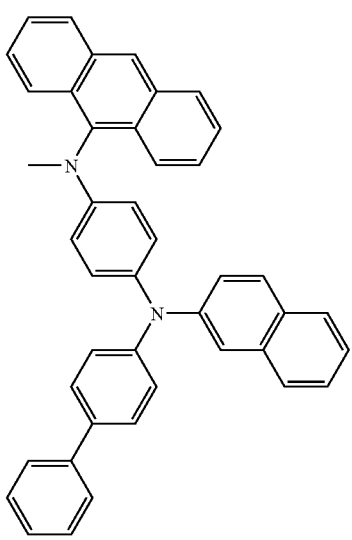
140
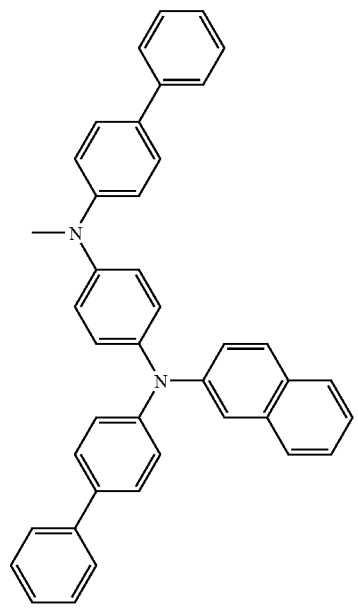
142
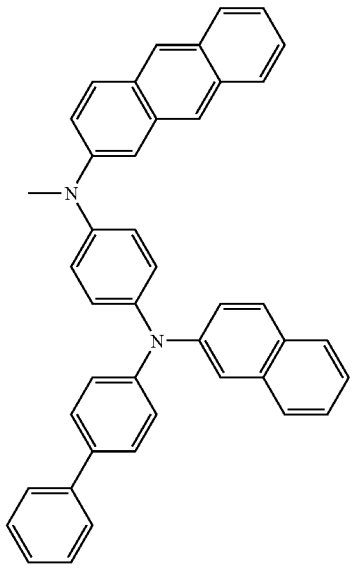
143

331
-continued
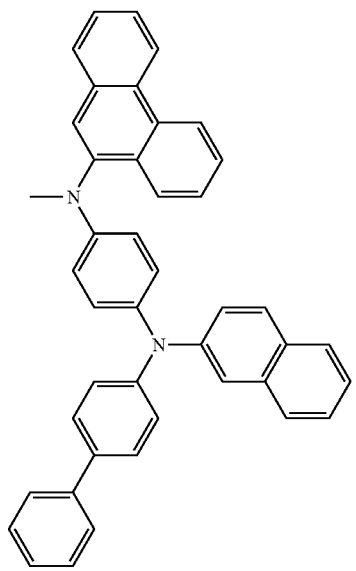
144
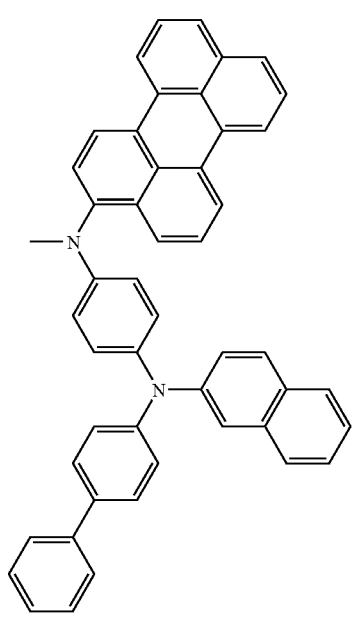
145
332
-continued
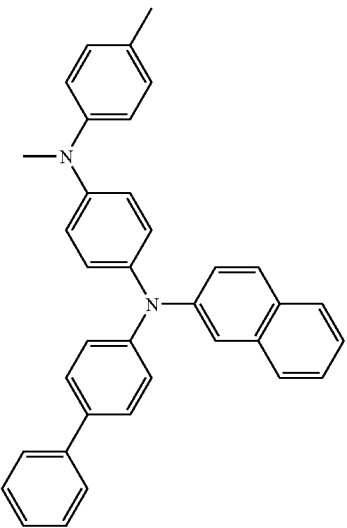
146
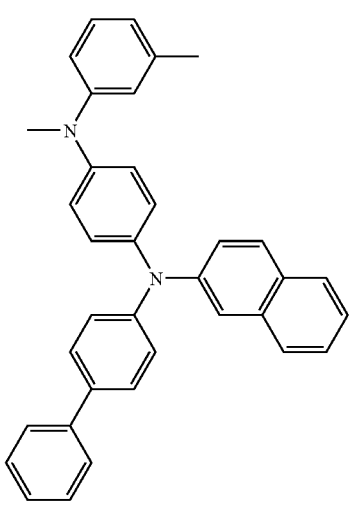
147
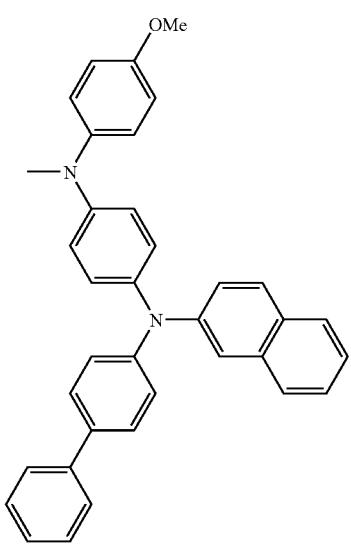
148

-continued
149
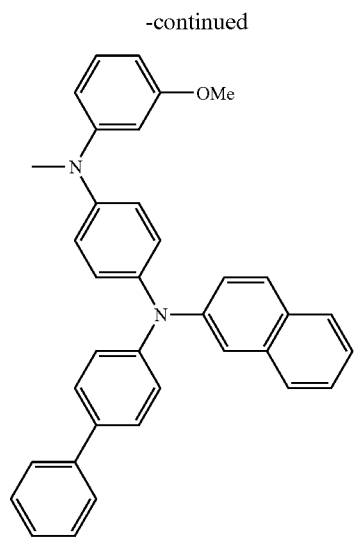
150
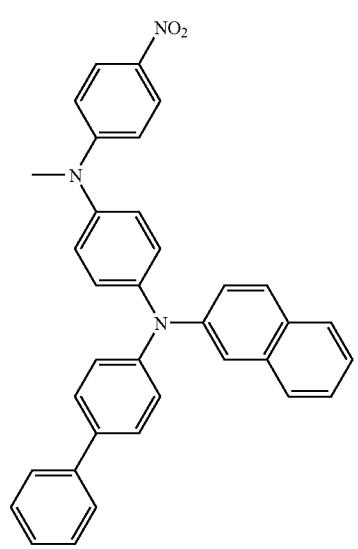
151
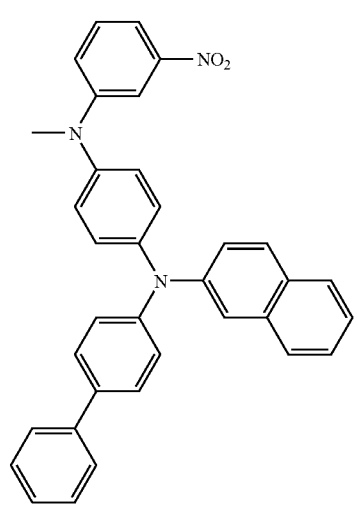
-continued
152
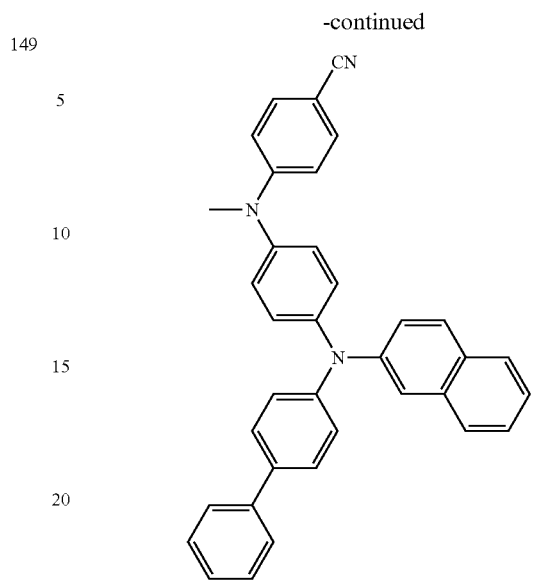
153
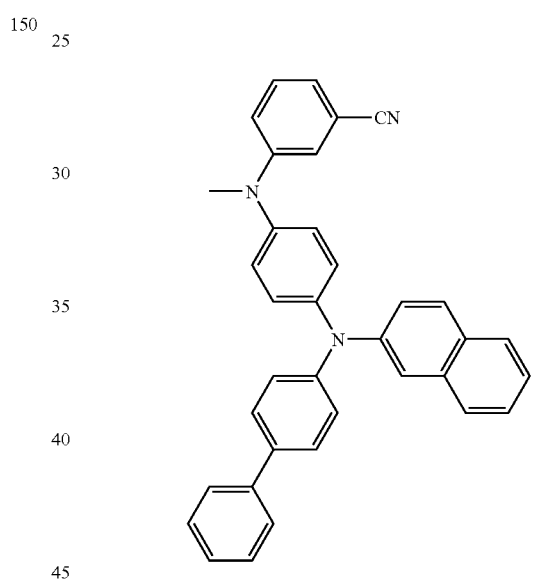
154
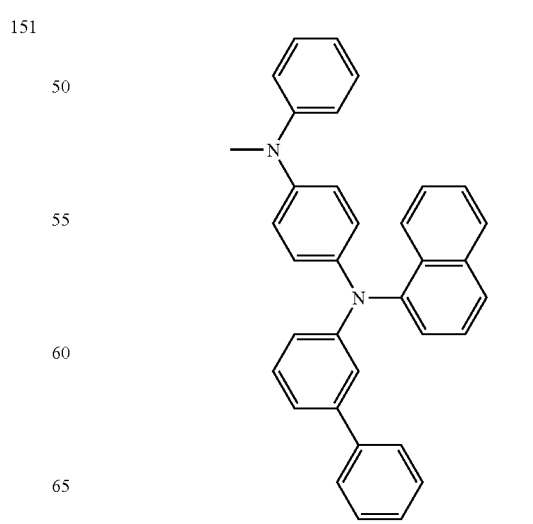

-continued
155
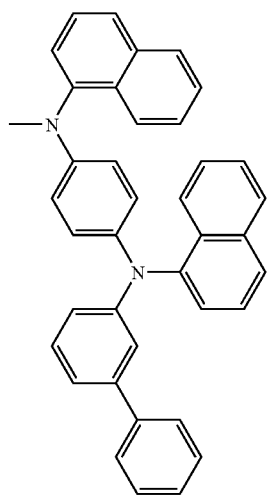
156
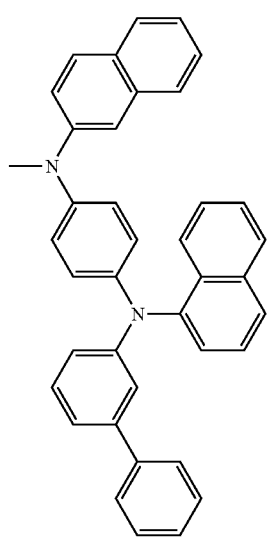
157
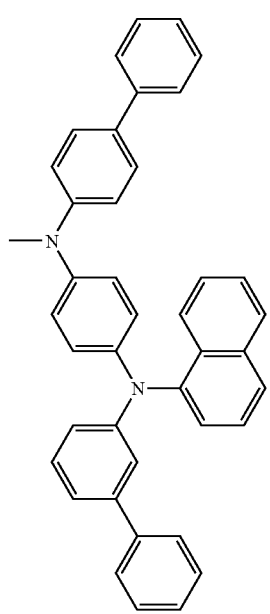
-continued
158
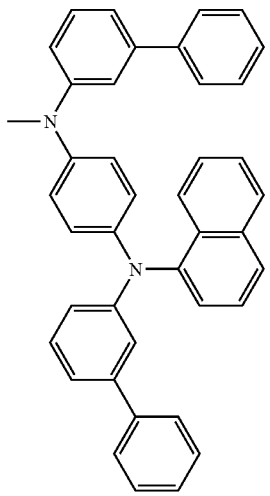
159
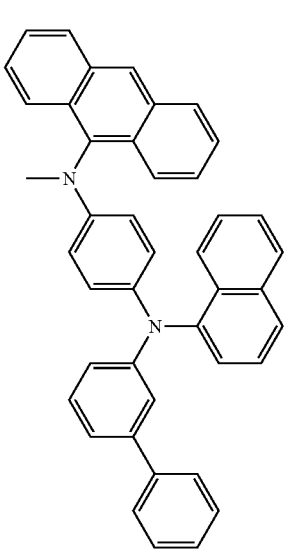
160
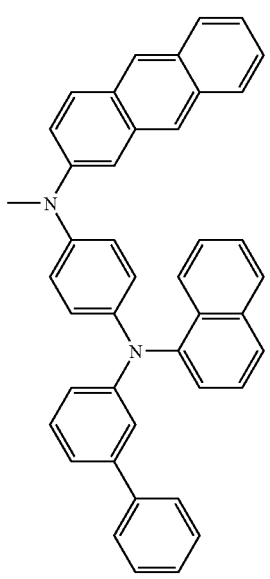

161
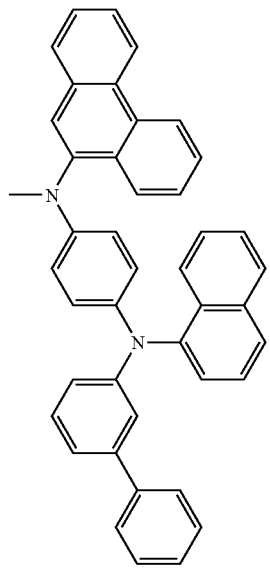
162
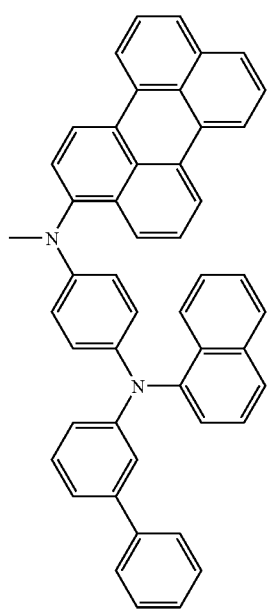
163
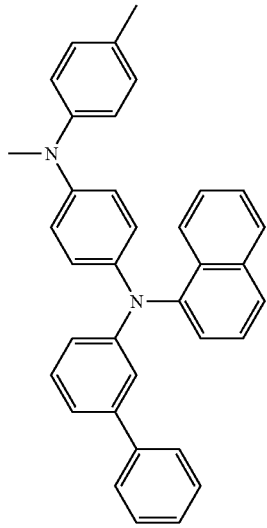
164
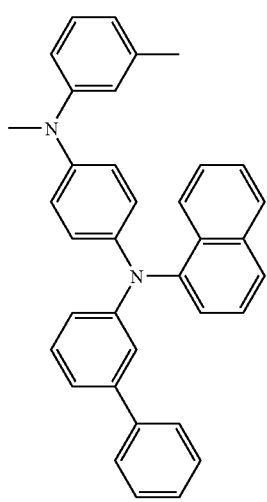
165
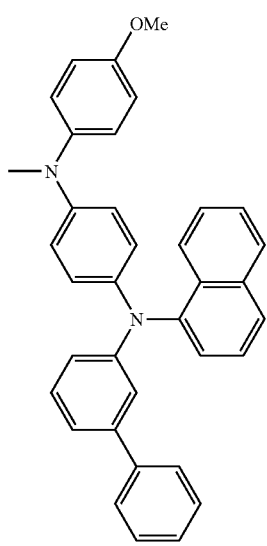

166
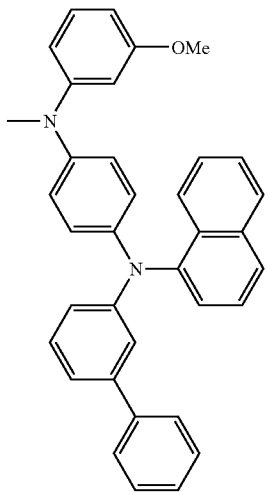
167
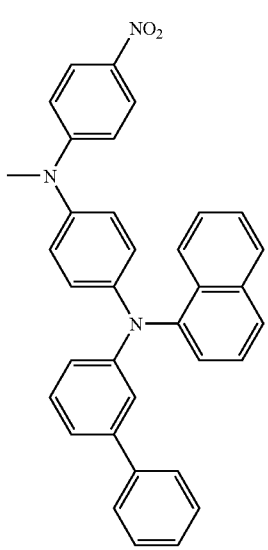
168
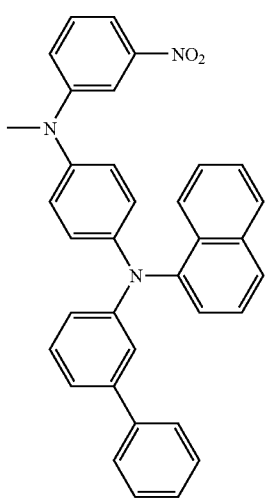
169
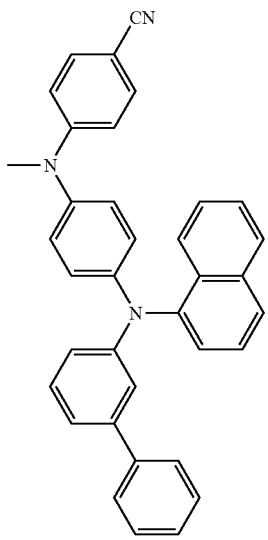
170
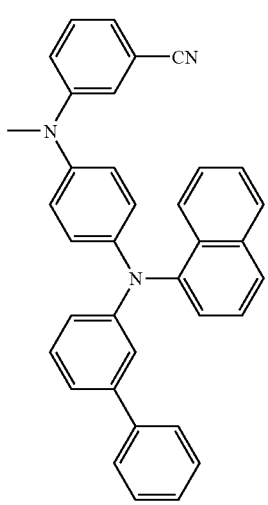
171
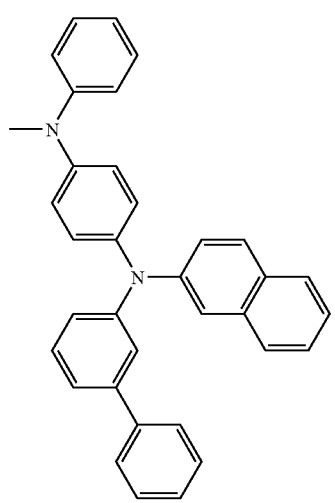

-continued
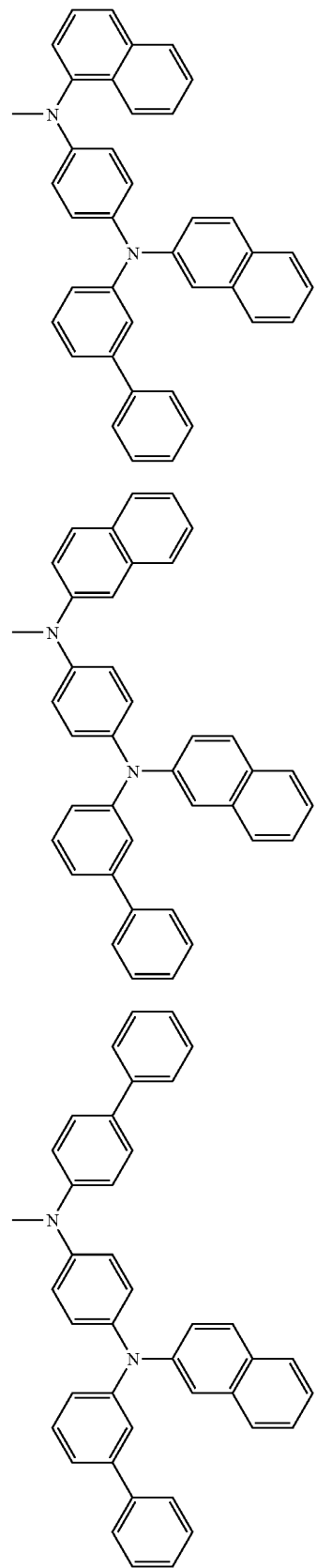
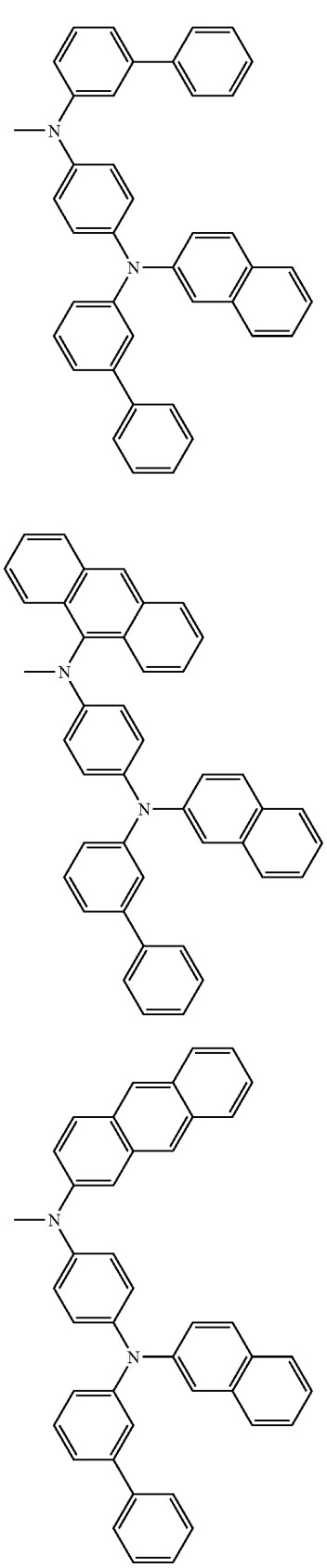

343
-continued
178
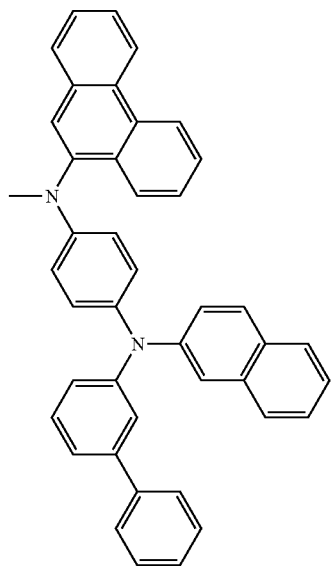
179
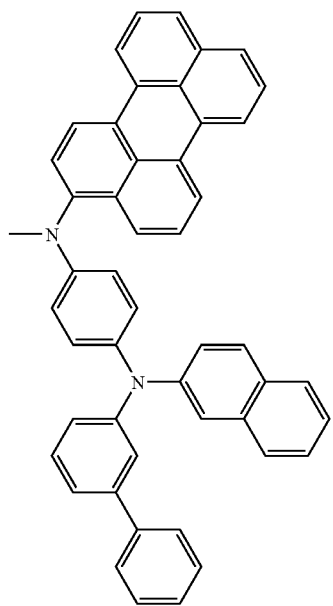
344
-continued
180
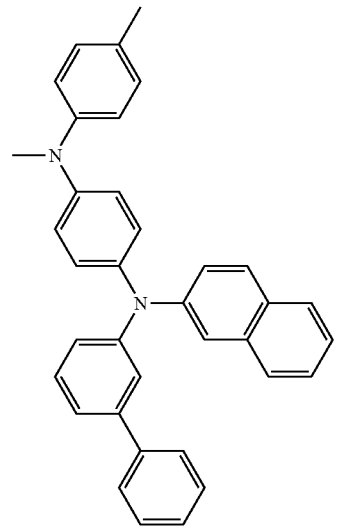
181
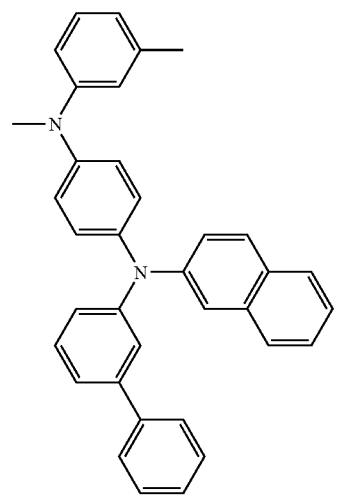
182
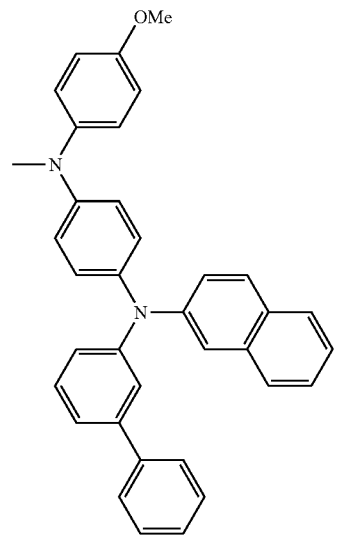

-continued
183
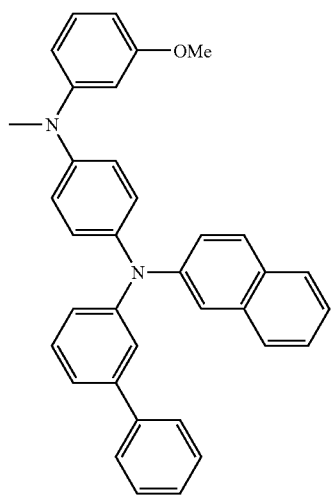
184
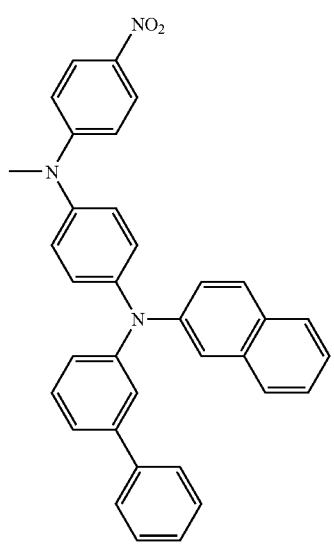
185
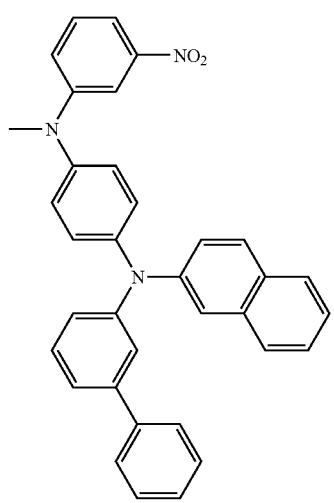
-continued
186
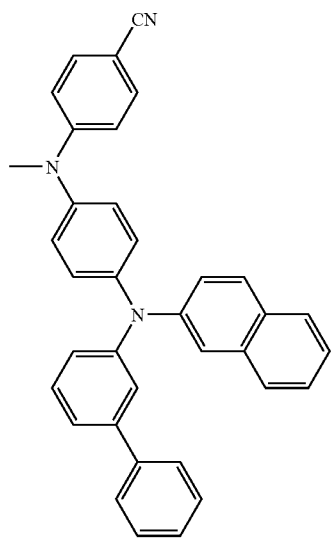
187
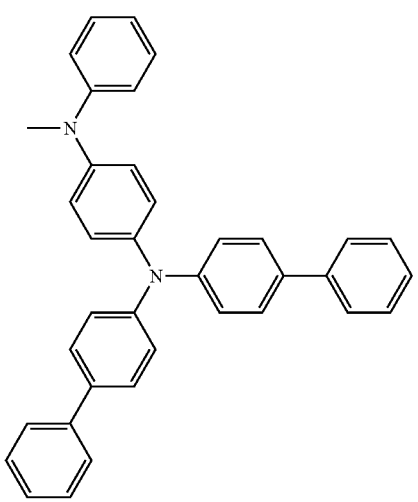
188

-continued
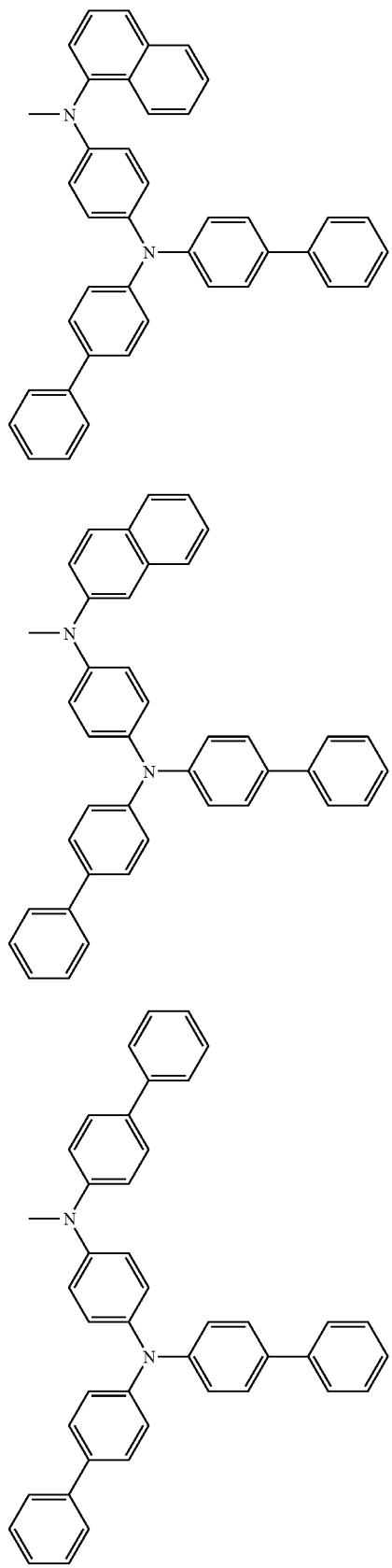
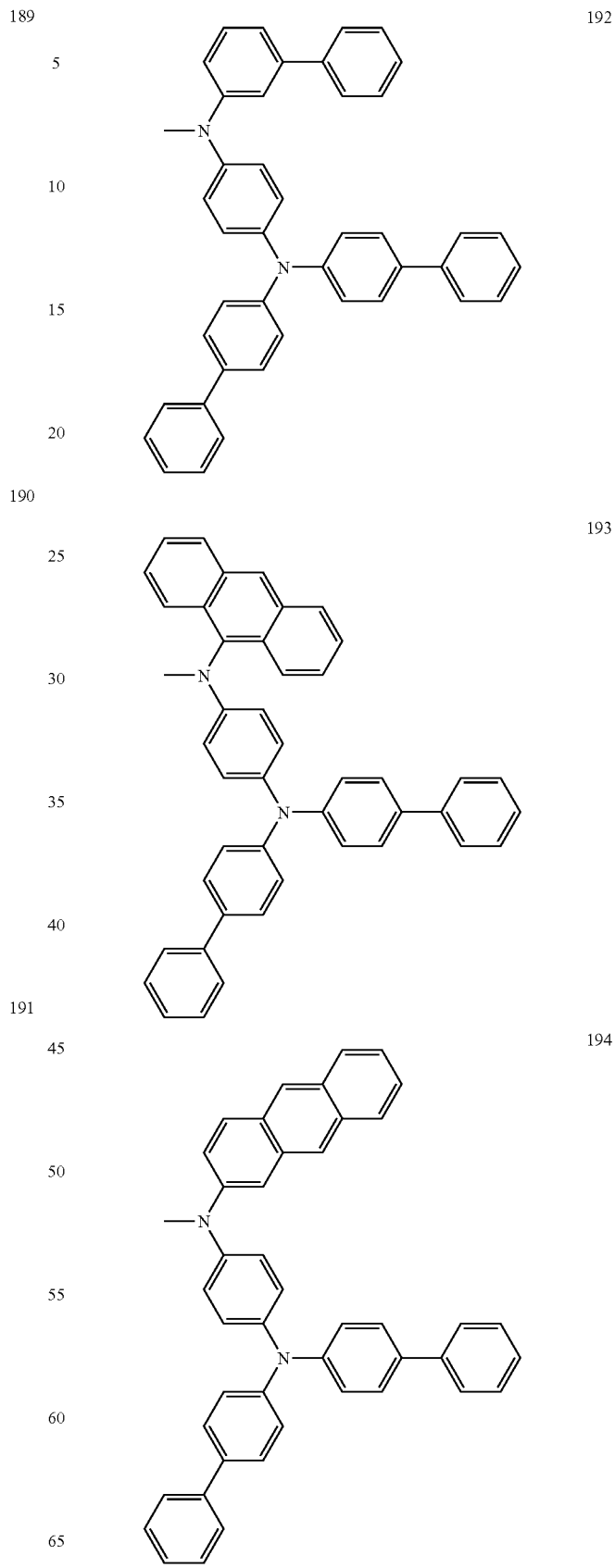

195
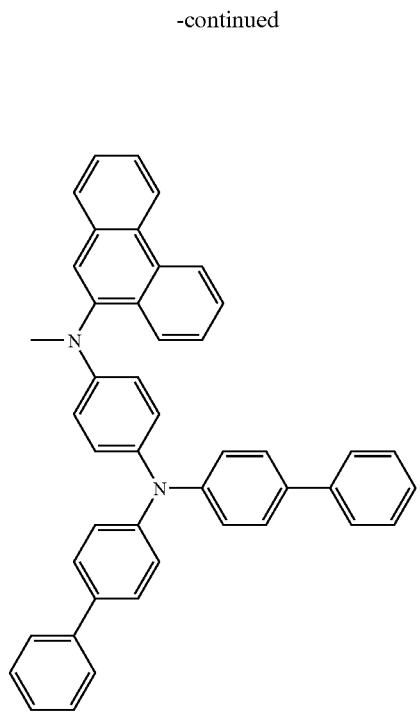
196
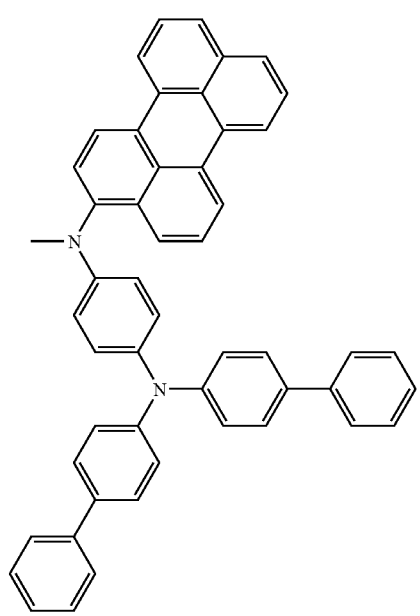
197
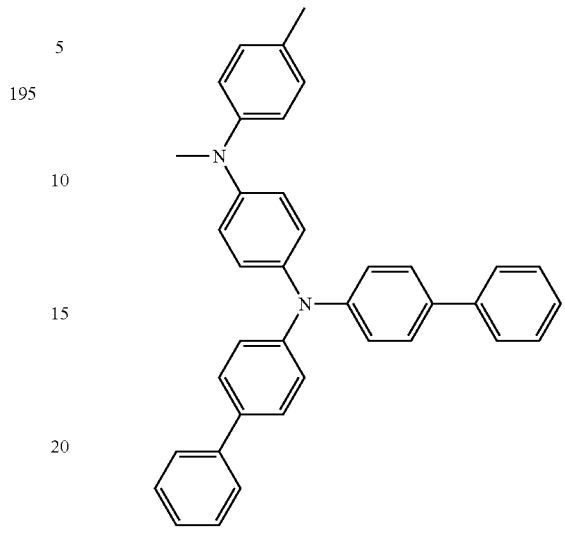
198
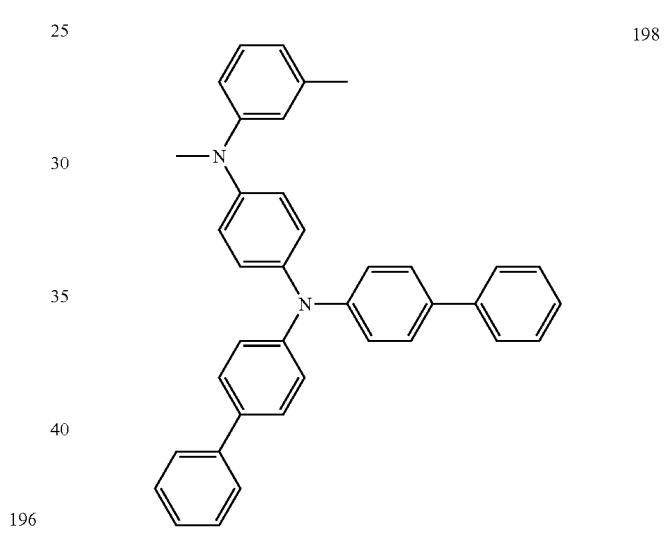
199
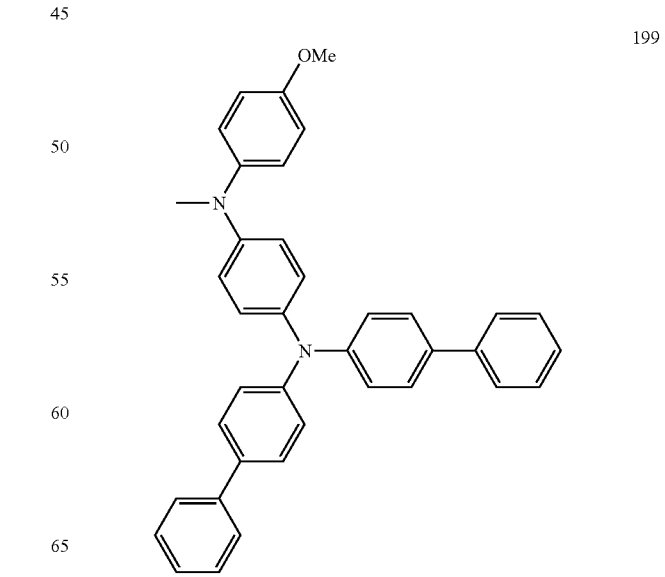

-continued
200
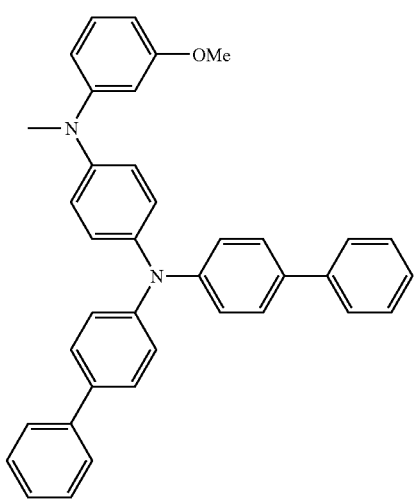
201
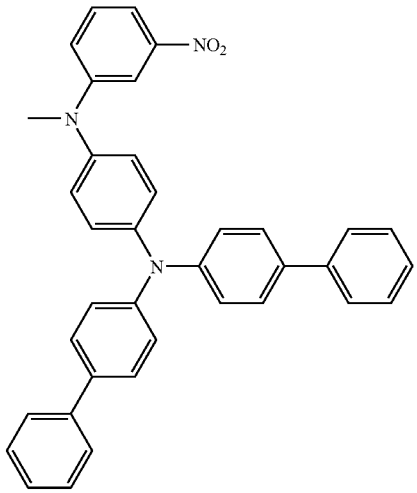
202
203
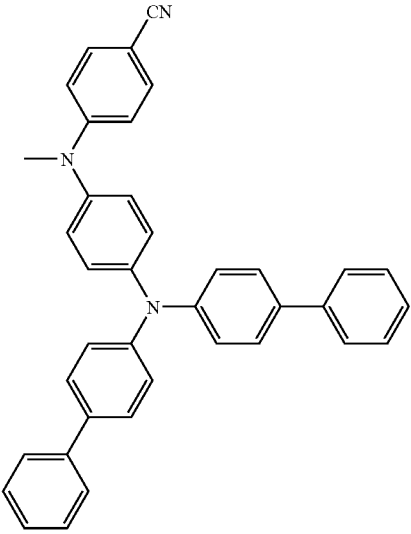
204
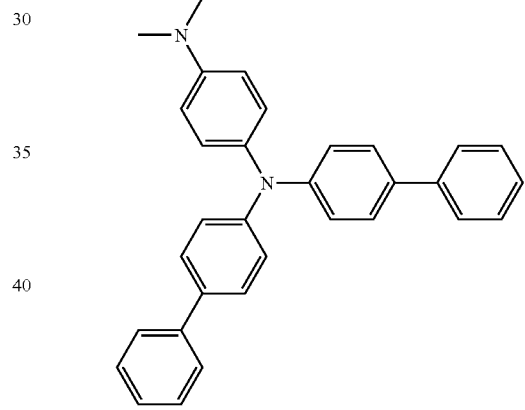
205
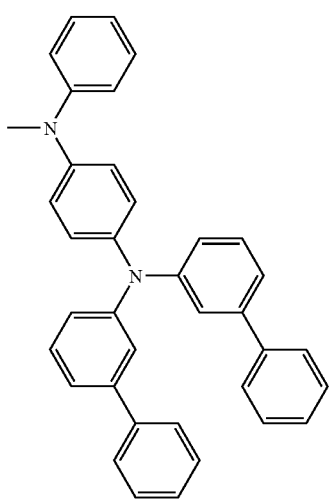

-continued
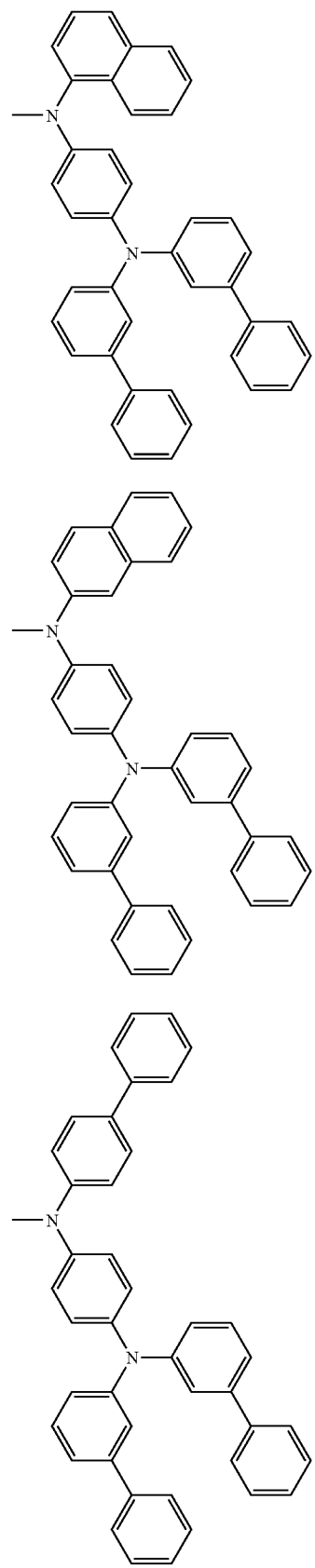
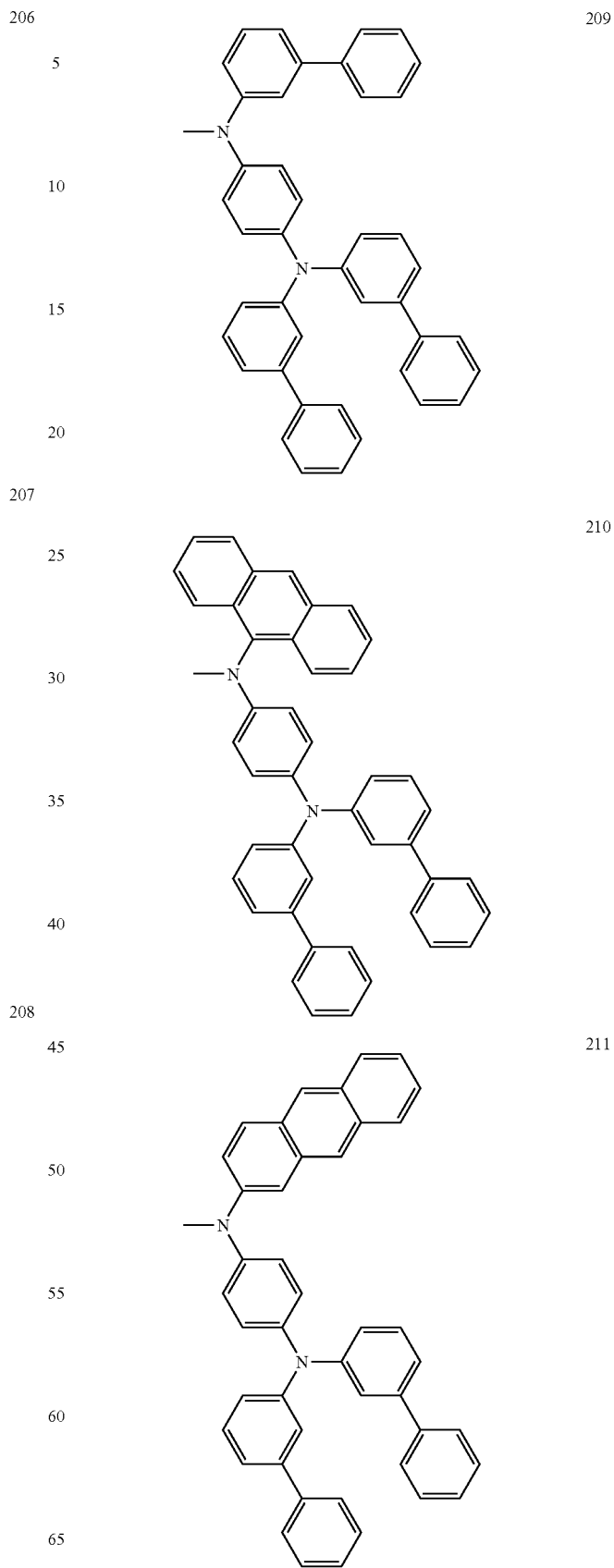

355
-continued
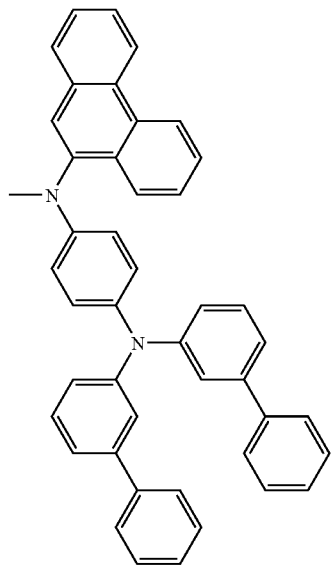
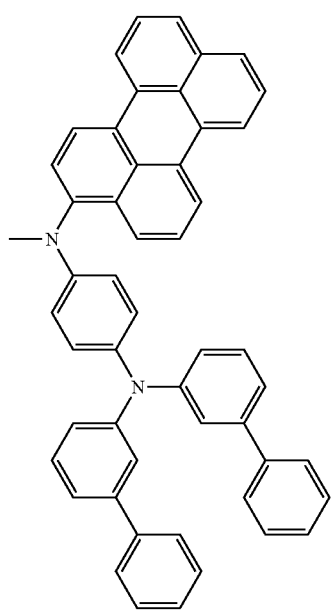
356
-continued
212
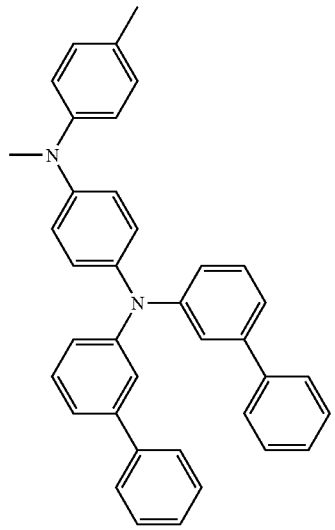
213
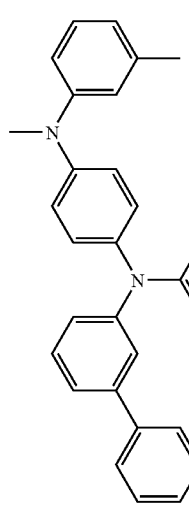
214
215
216
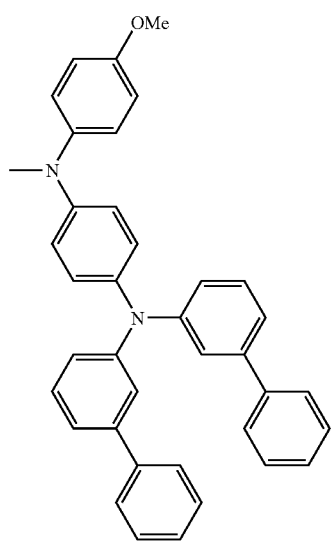

-continued
217
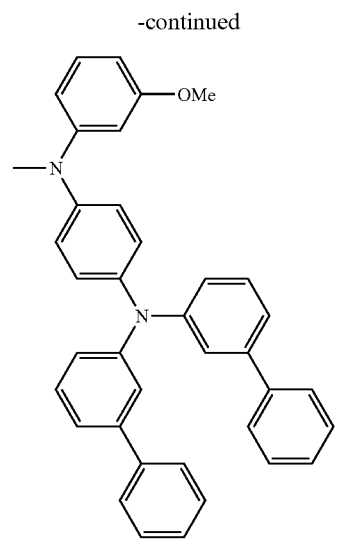
218
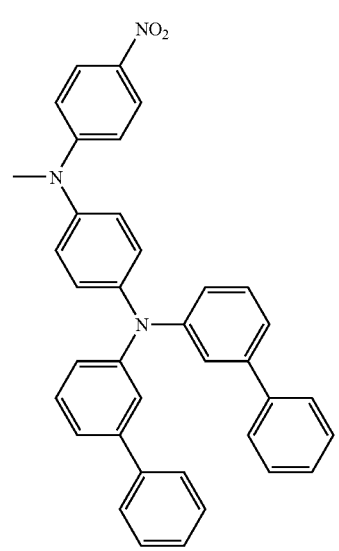
219
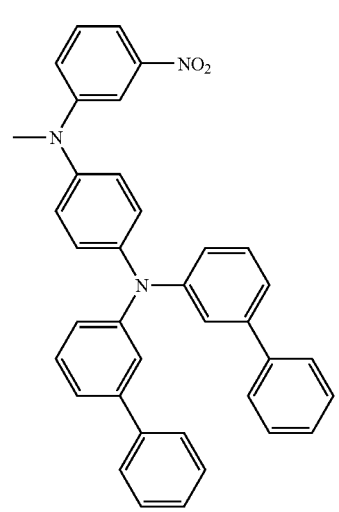
-continued
220
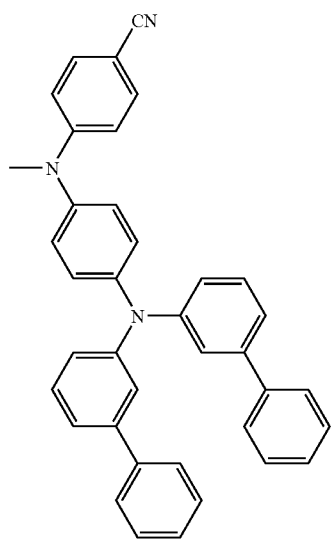
221
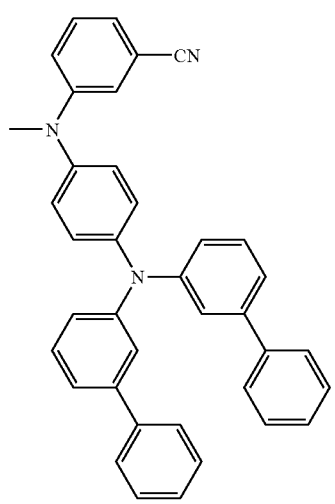
222
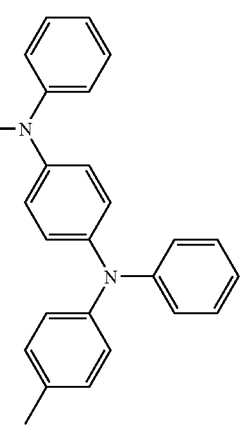

-continued
223
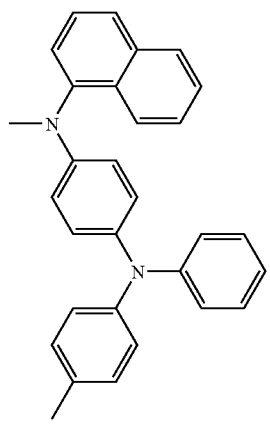
224
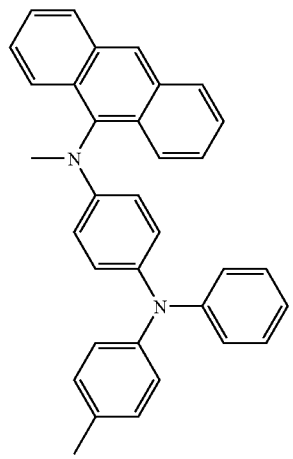
225
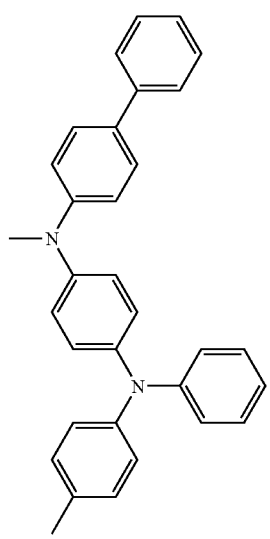
-continued
226
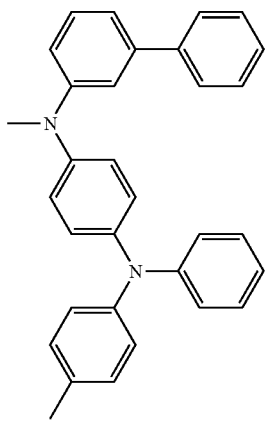
227
228

-continued
229
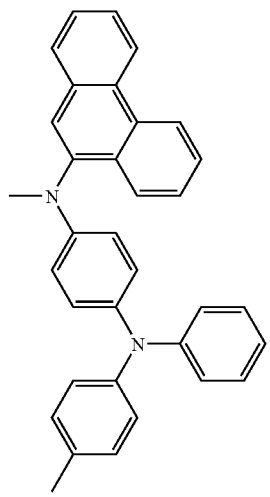
230
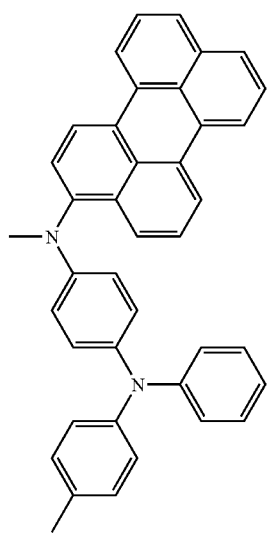
231
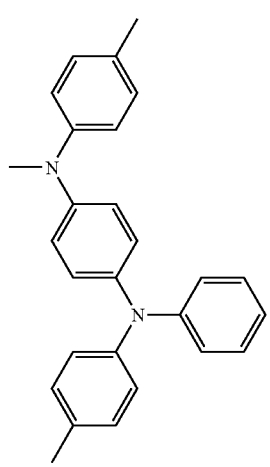
-continued
232
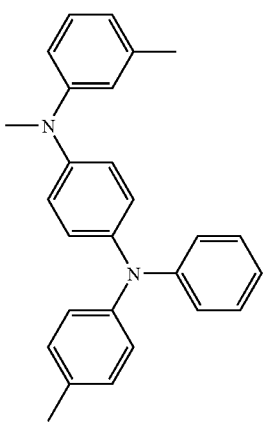
233
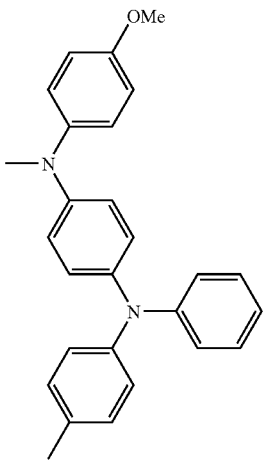
234
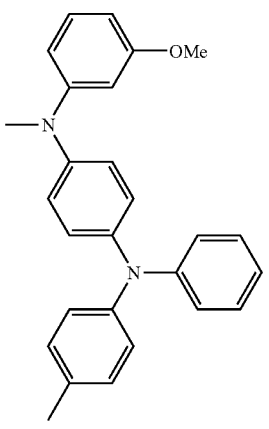

-continued
235
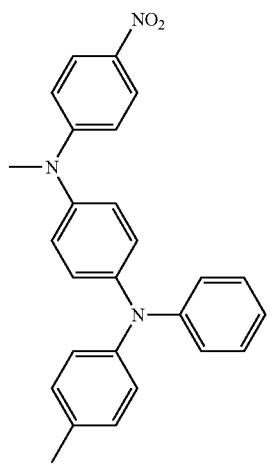
236
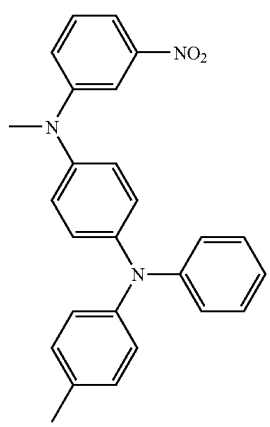
237
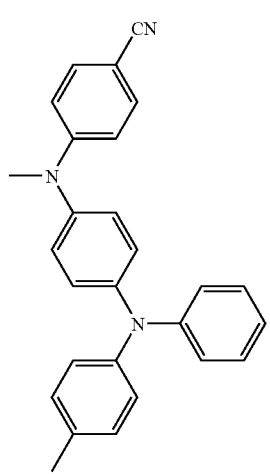
-continued
238
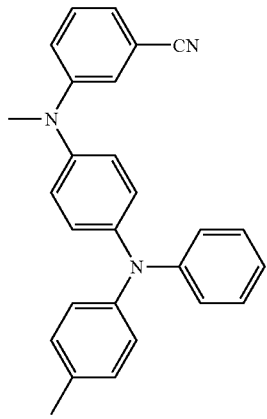
239
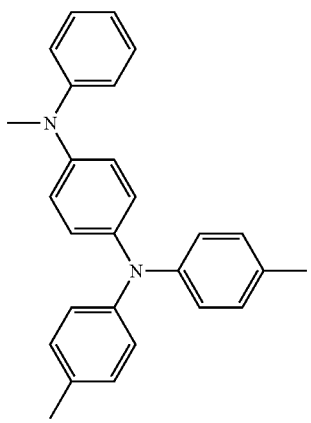
240
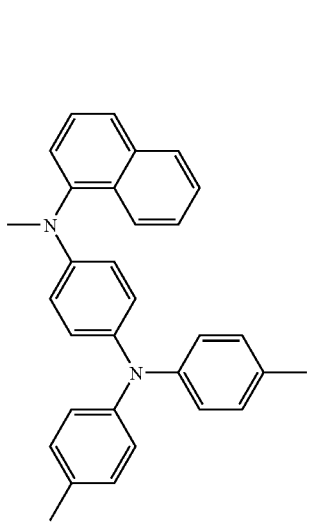

241
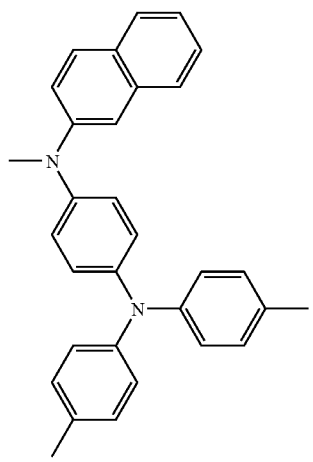
242
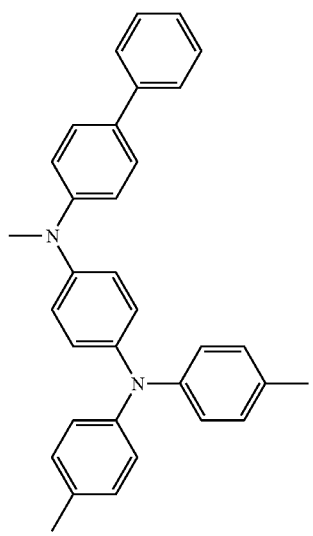
243
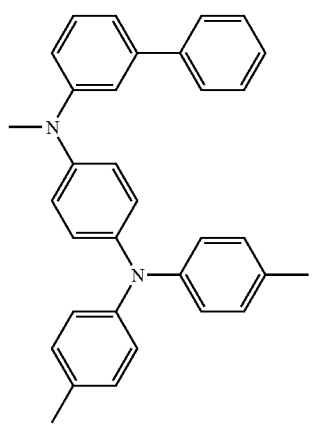
244
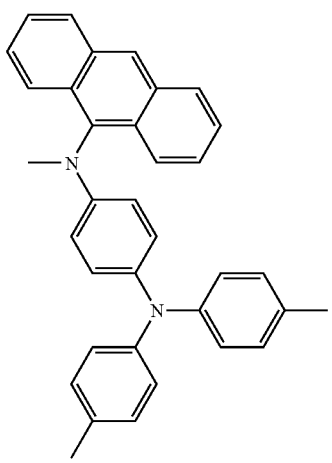
245
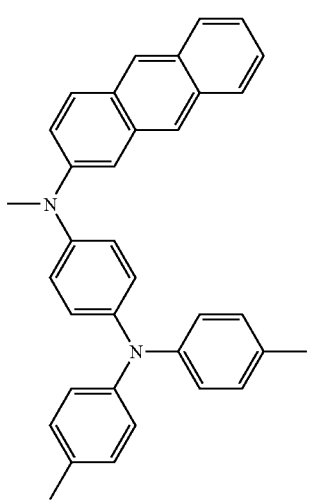
246
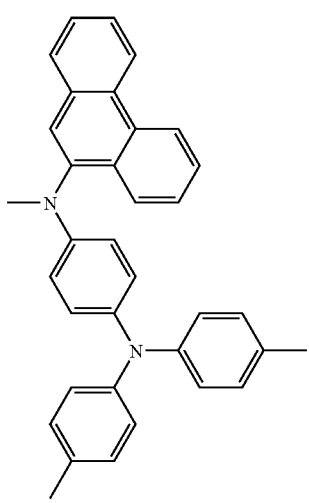

-continued
247 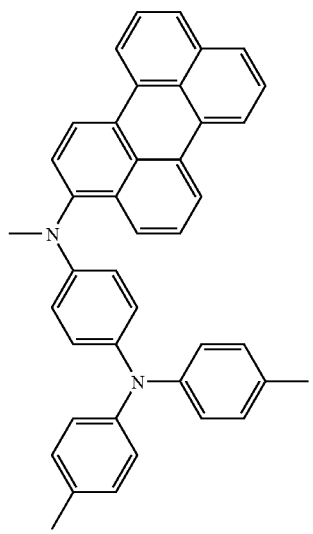
248 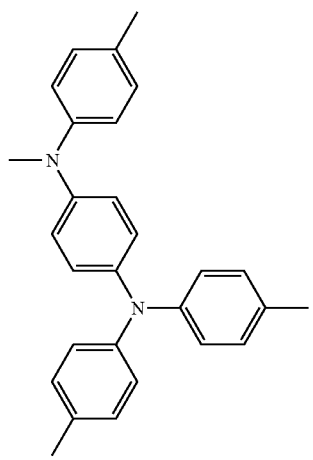
249 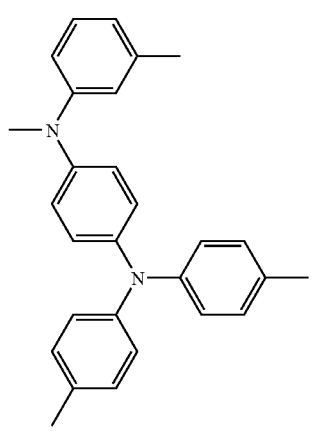
-continued
250 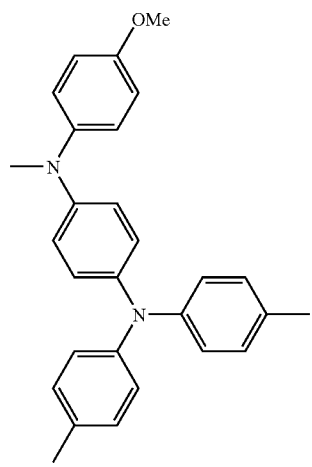
251 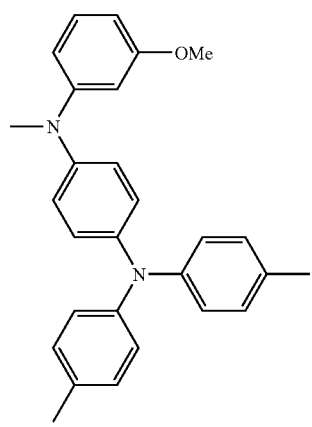
252 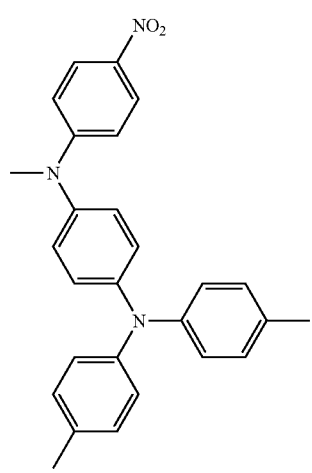

-continued
253
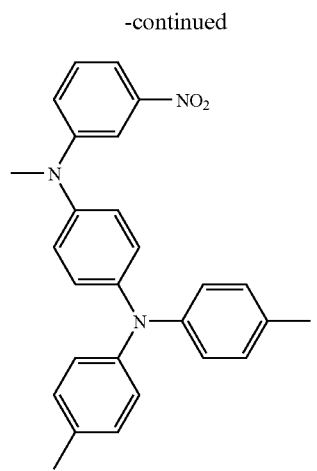
254
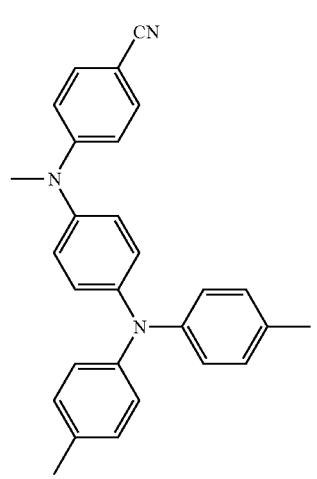
255
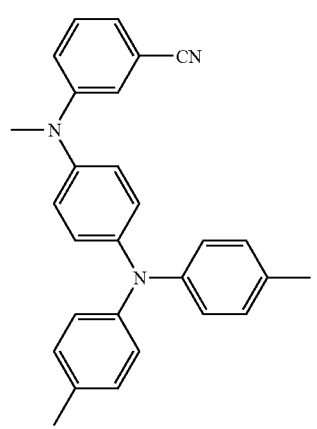
-continued
256
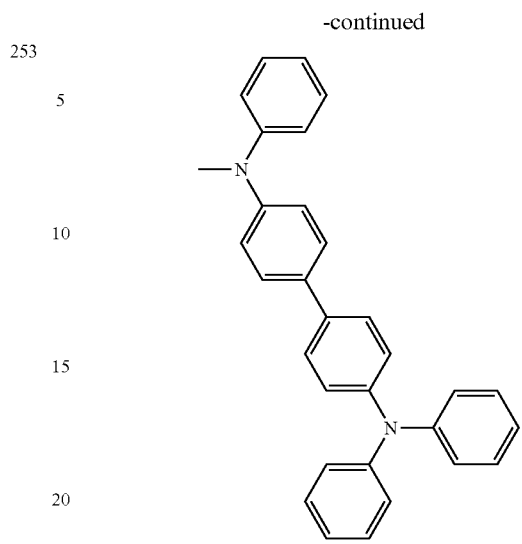
257
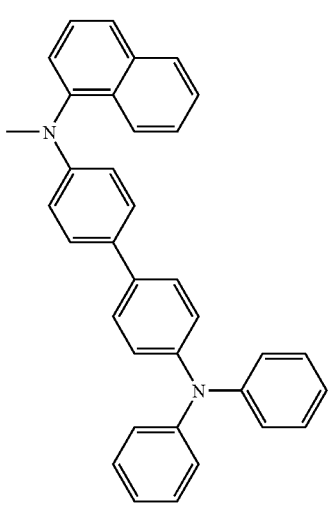
258
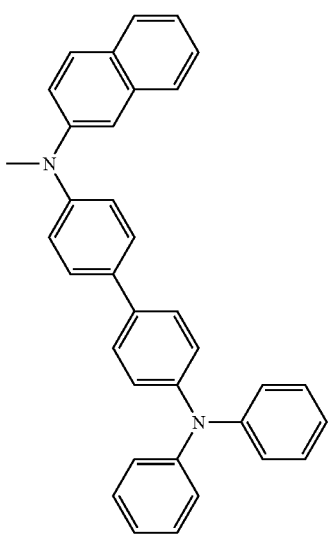

-continued
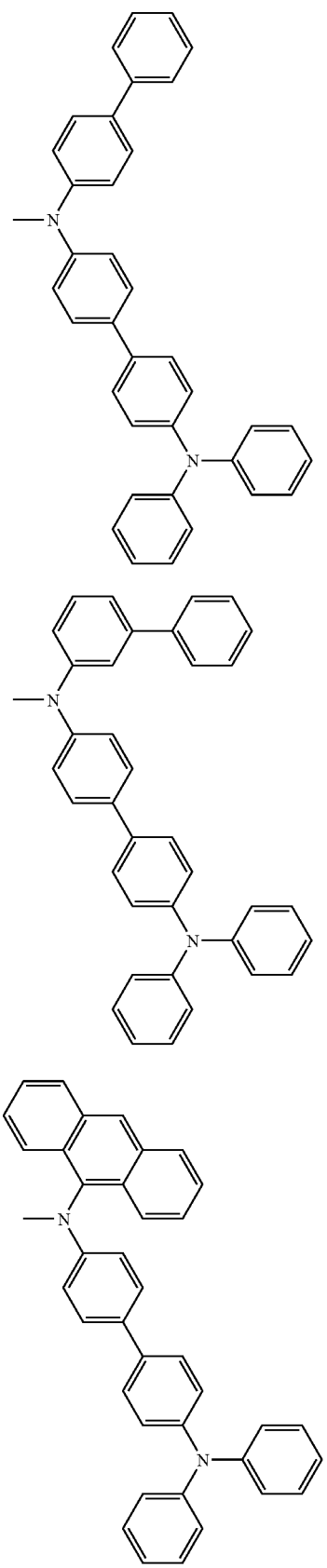
-continued

-continued
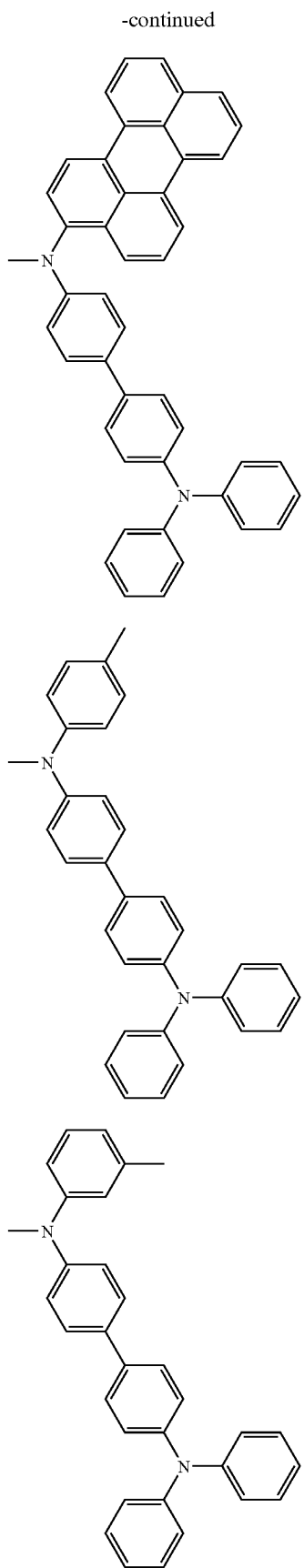
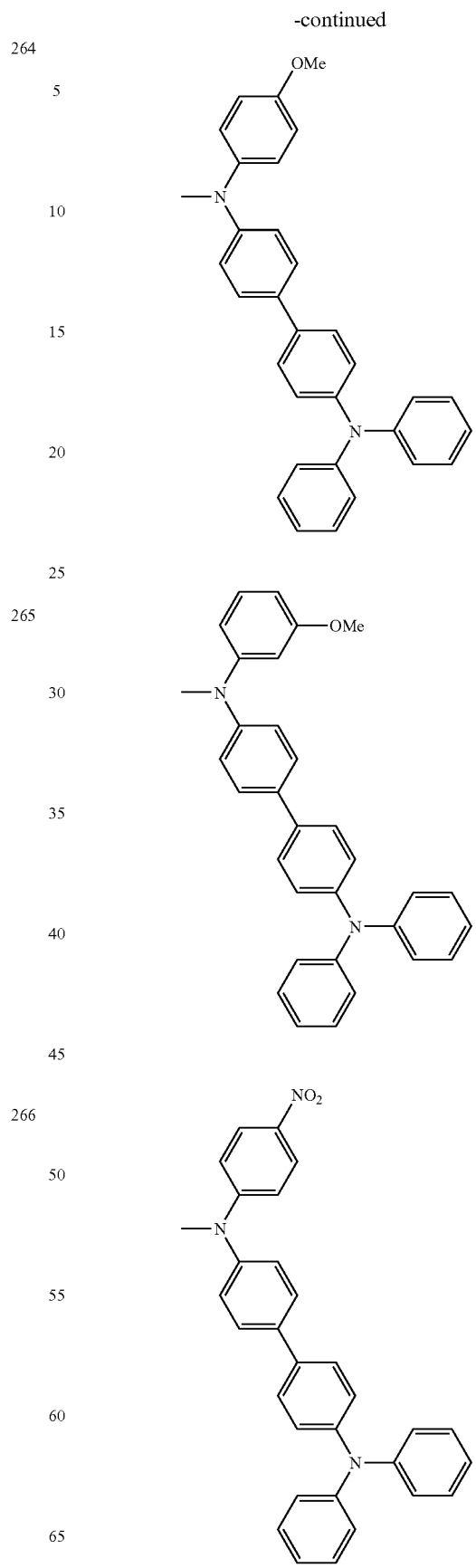

-continued
270
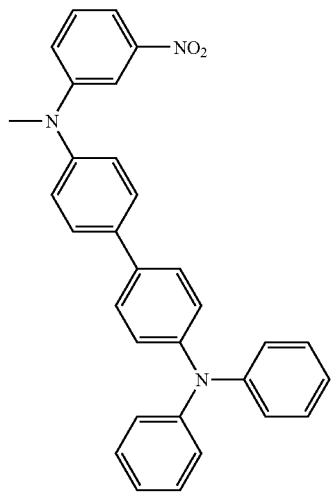
271
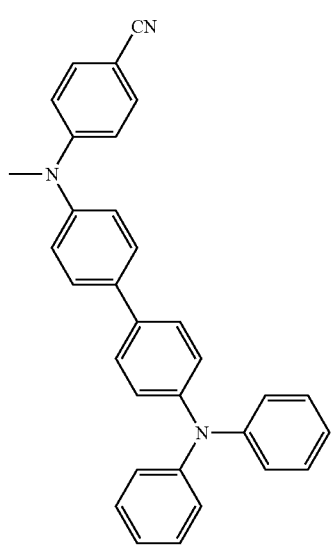
272
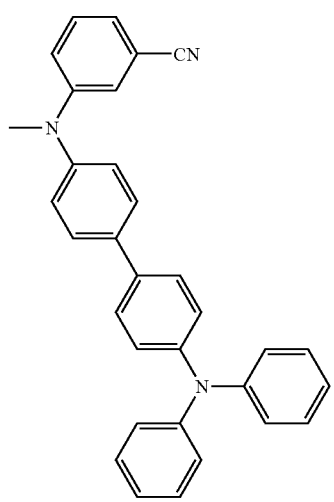
-continued
273
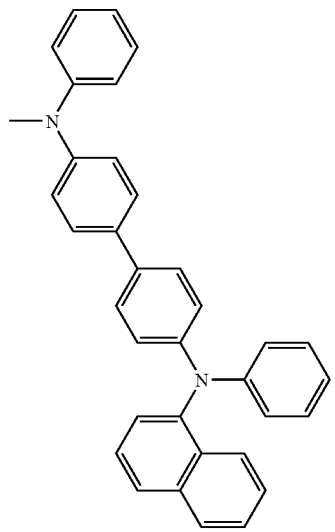
274
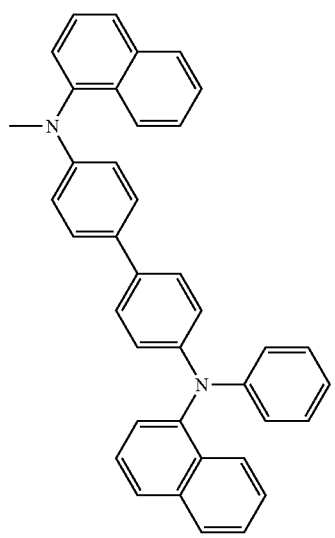
275
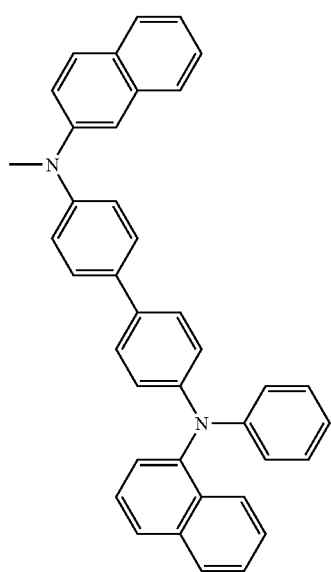

-continued
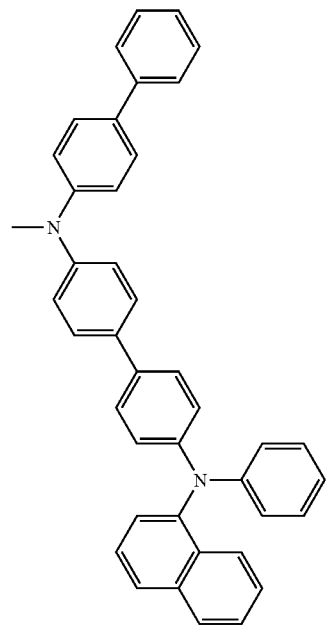
276
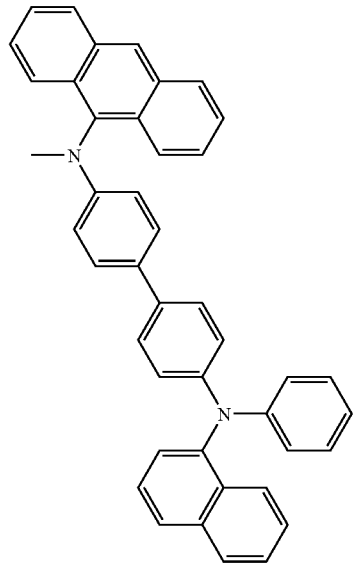
278
277
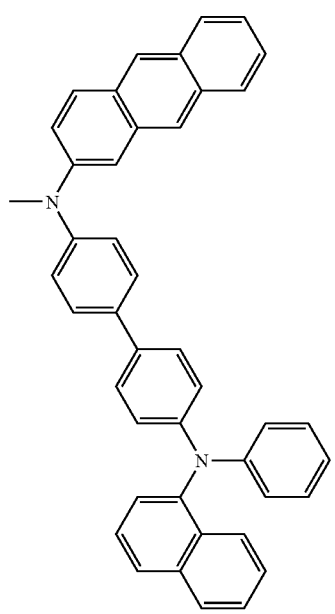
279

379
-continued
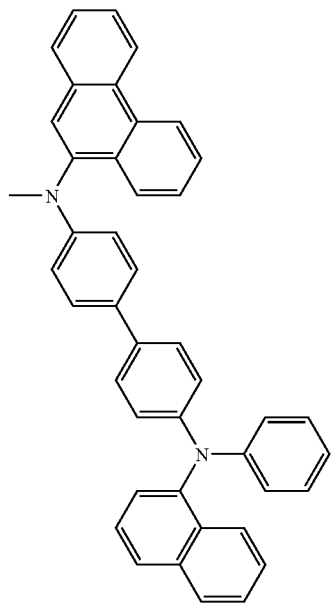
280
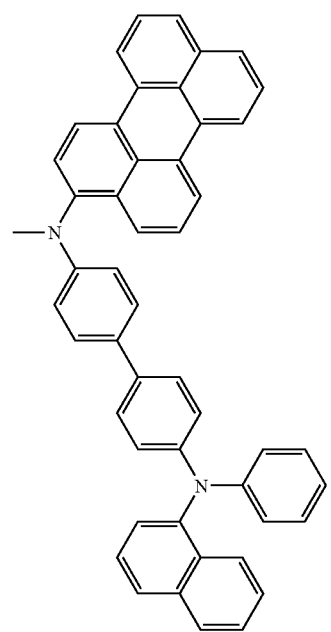
281
380
-continued
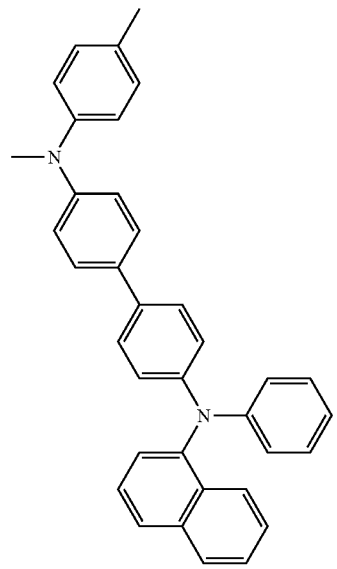
282
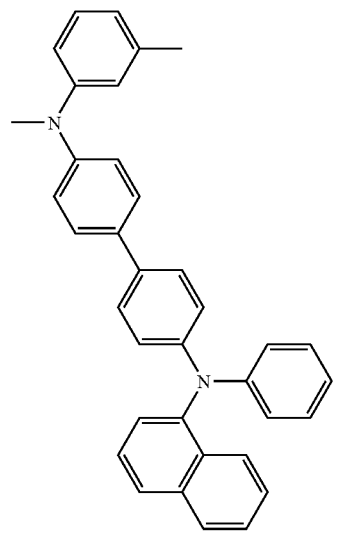
283

-continued
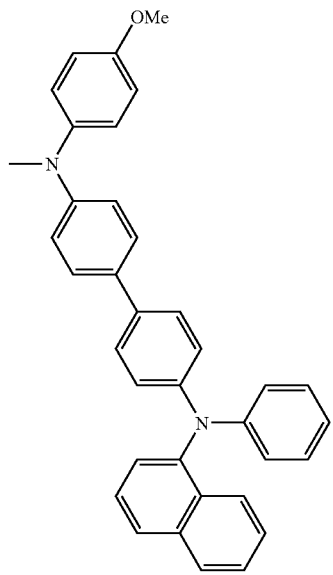
284
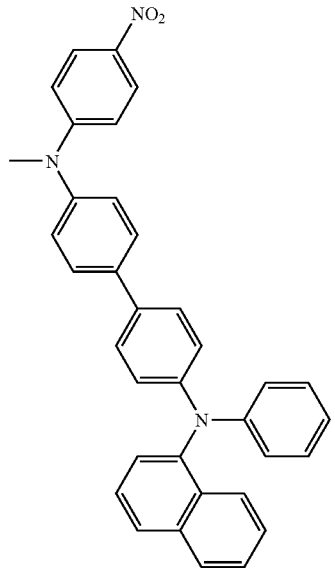
286
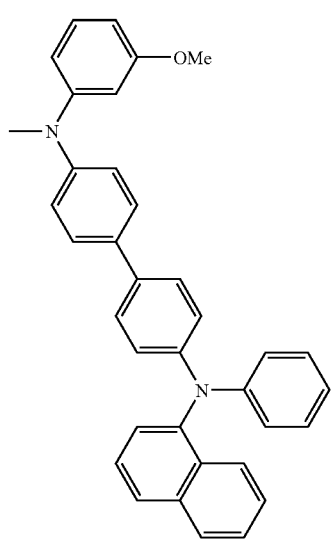
285
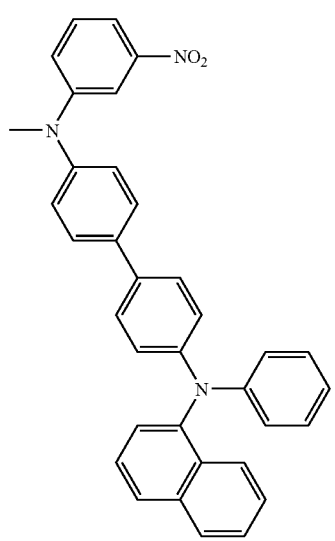
287

383
-continued
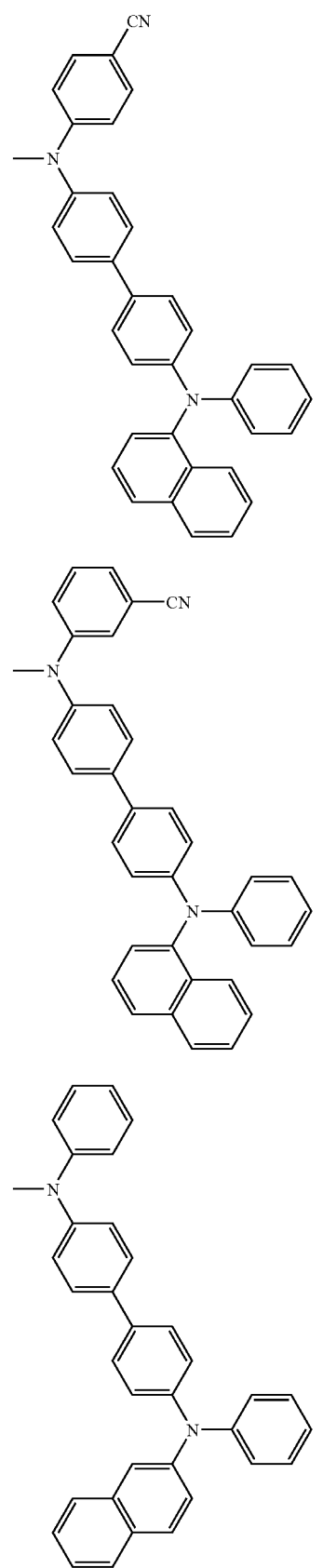
384
-continued

293
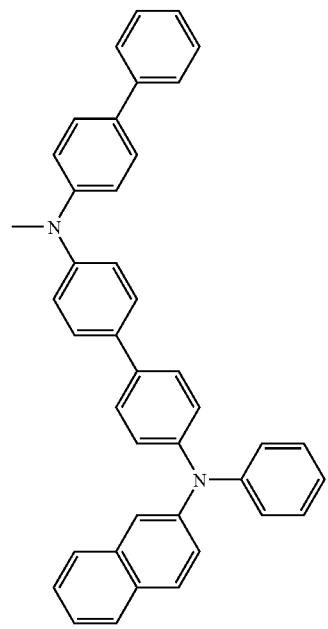
295
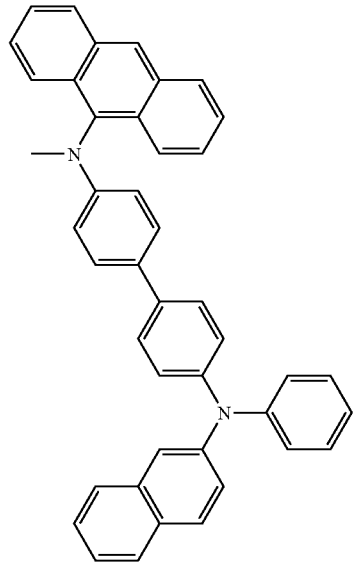
294
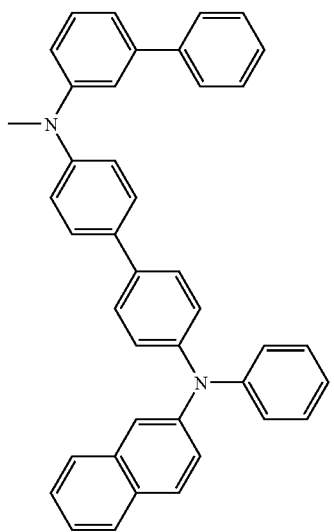
296
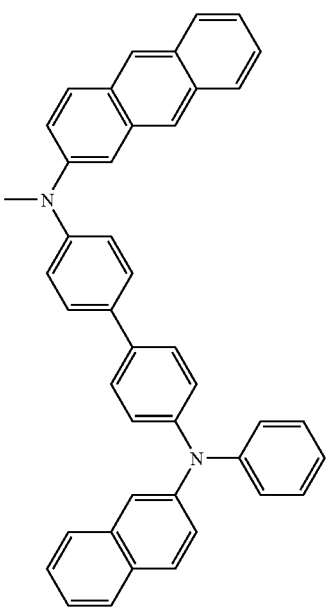

387
-continued
388
-continued
297
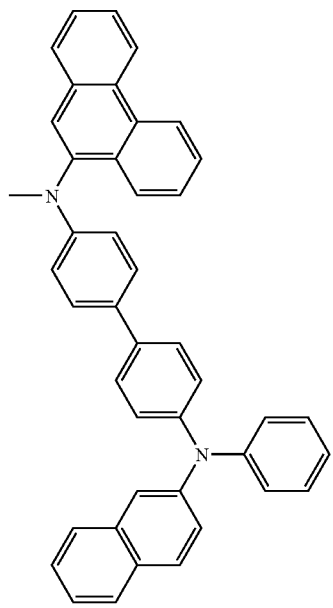
299
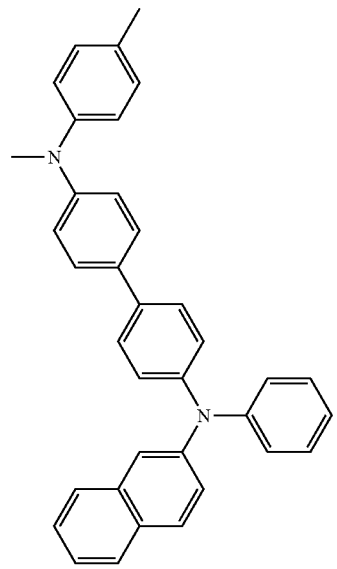
298
300
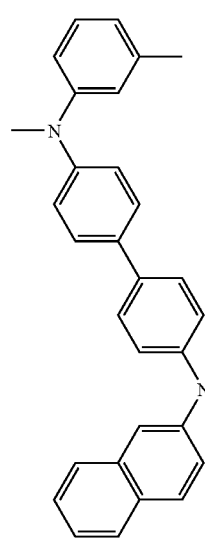

389
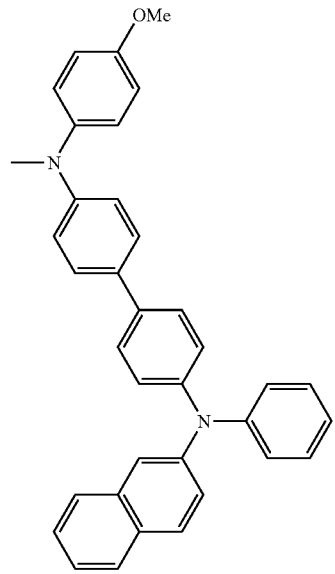
301
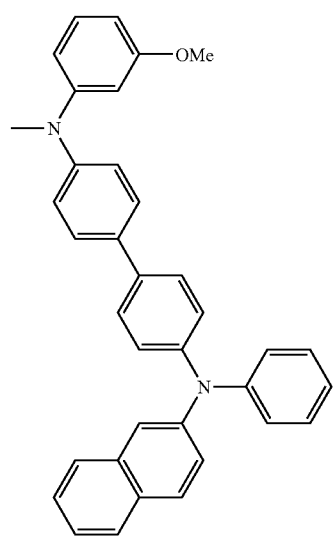
302
390
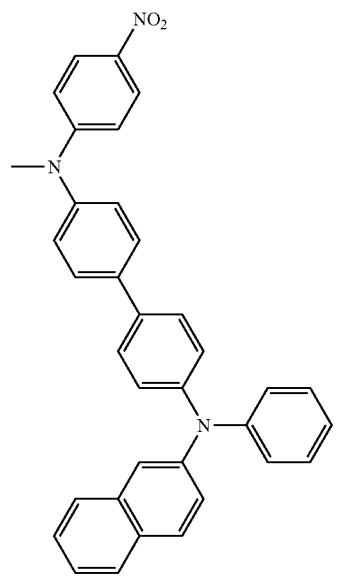
303
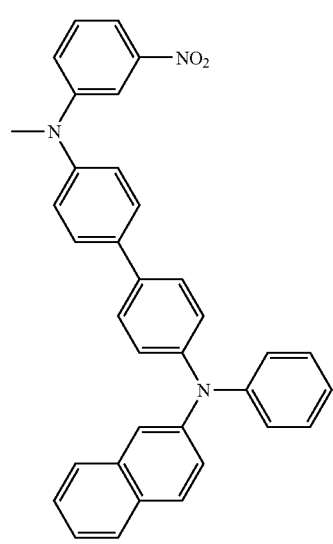
304

391
-continued
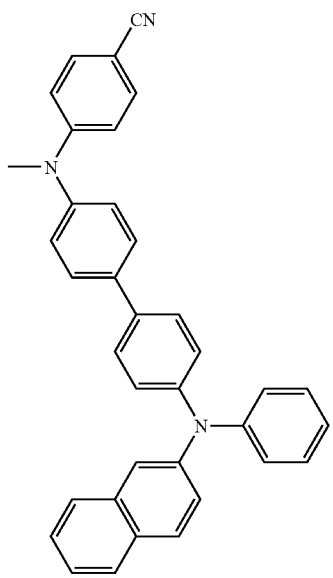
305
392
-continued
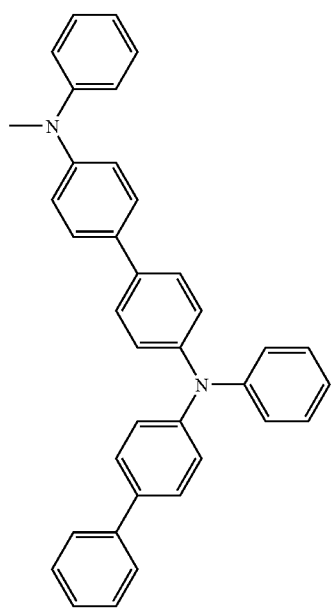
307
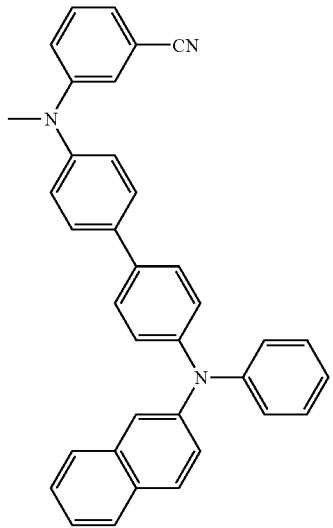
306
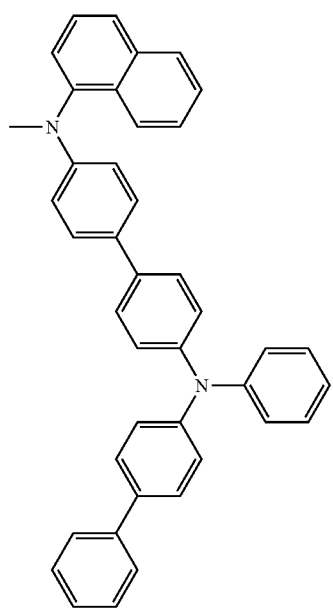
308

393
-continued
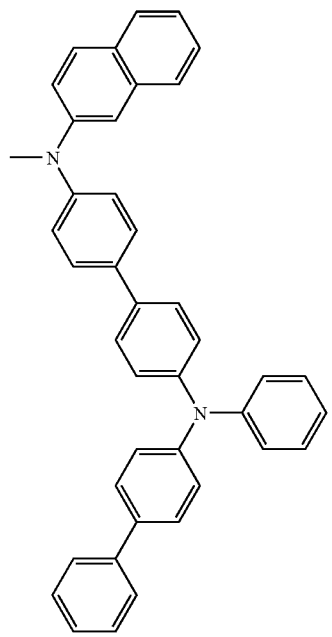
309
394
-continued
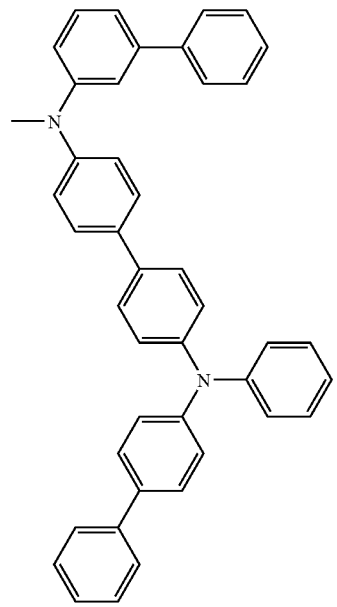
311
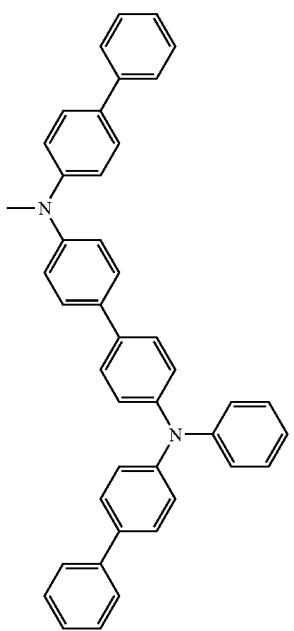
310
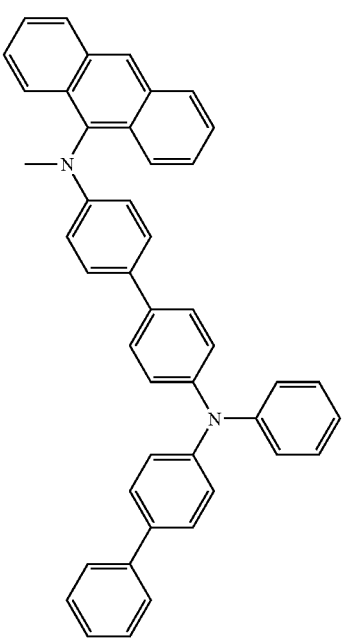
312

395
-continued
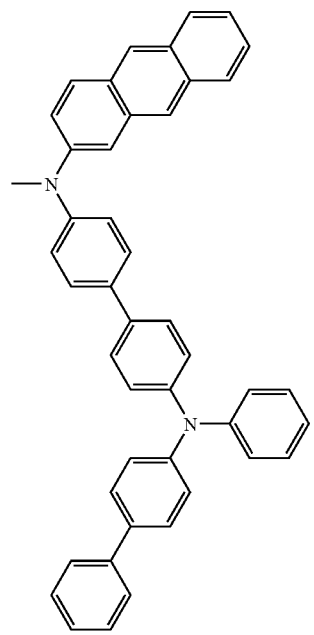
313
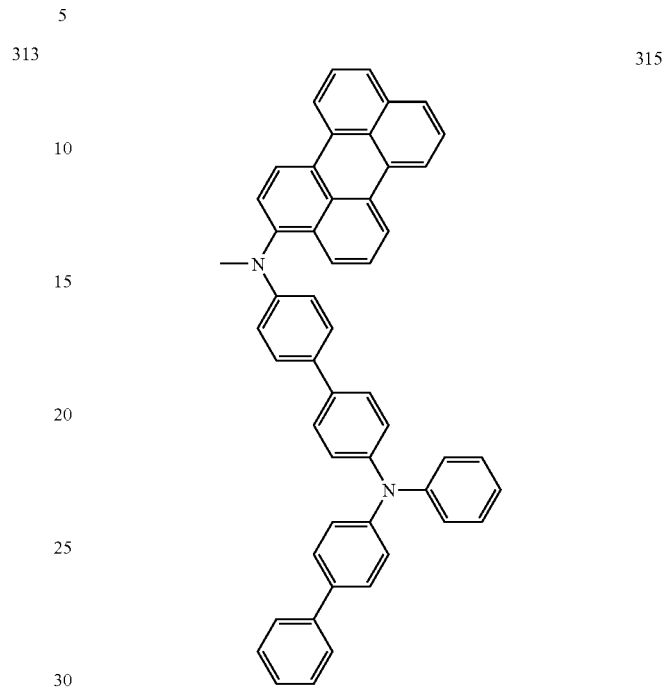
315
396
-continued
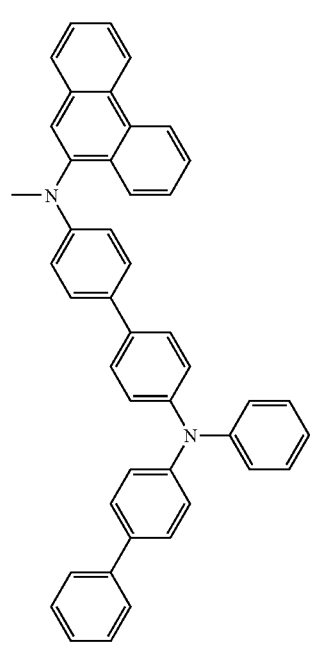
314
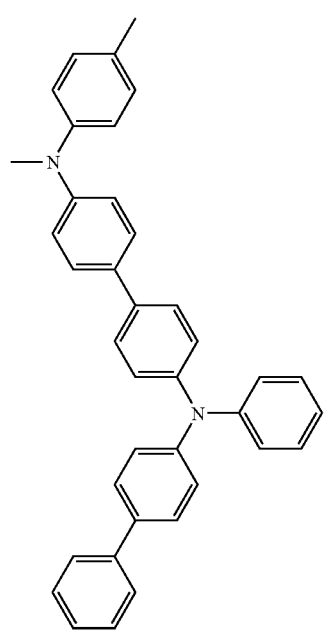
316

397
-continued
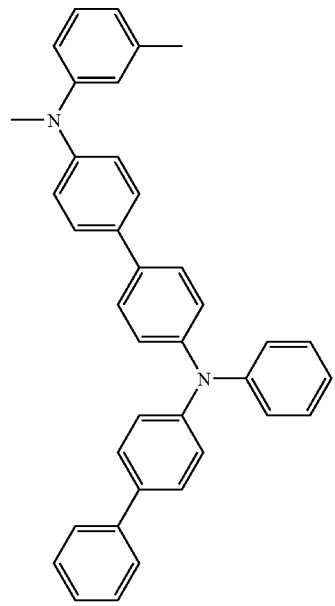
398
-continued
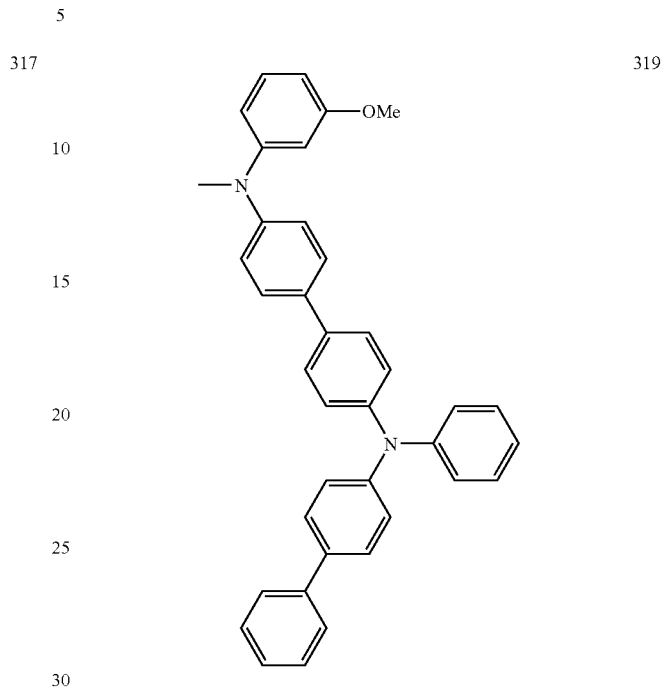
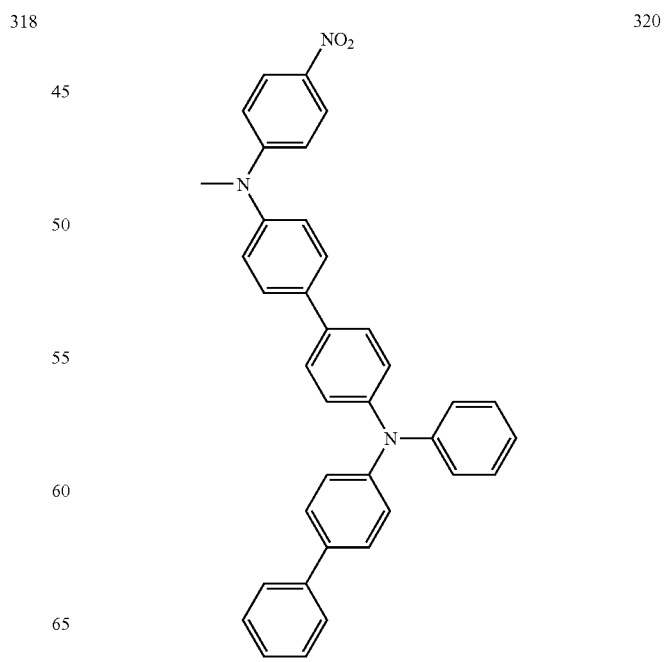

399
-continued
321
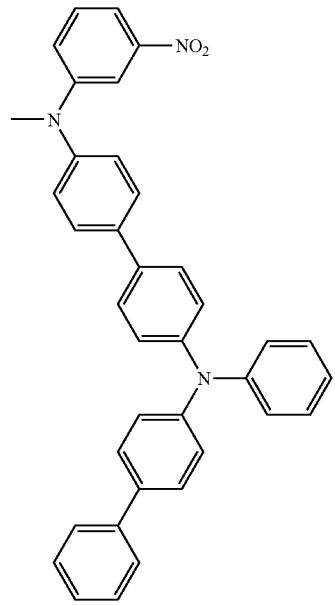
322
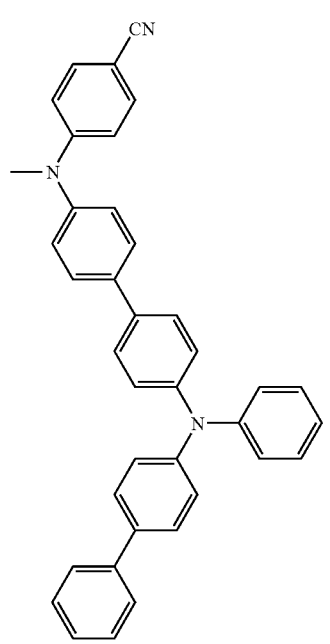
400
-continued
323
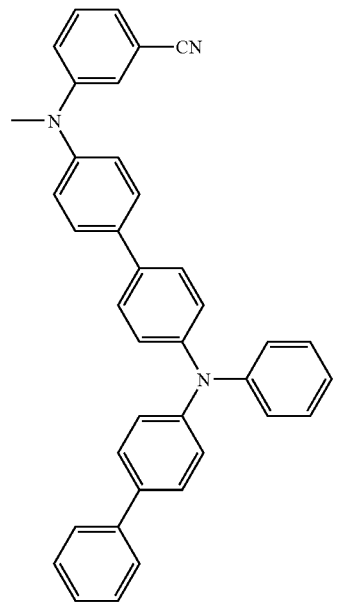
324
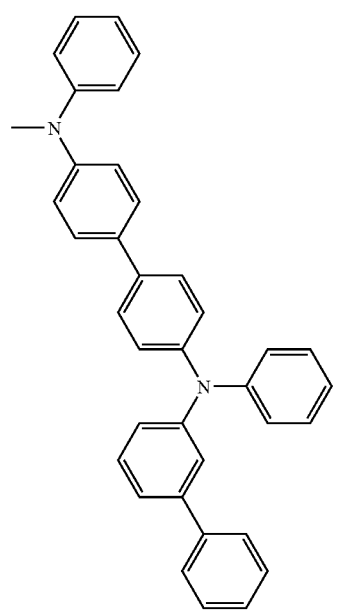

-continued
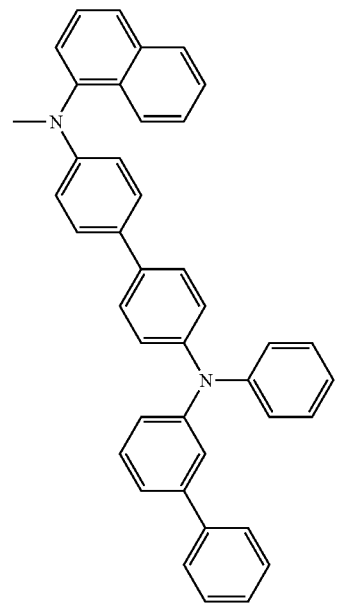
325
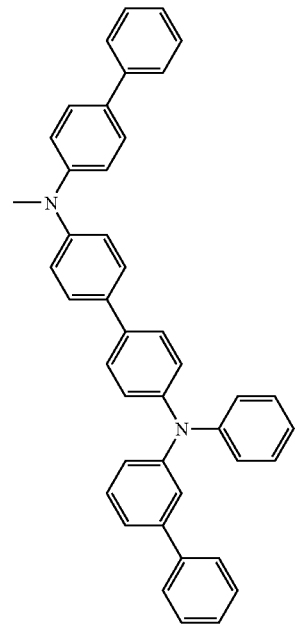
327
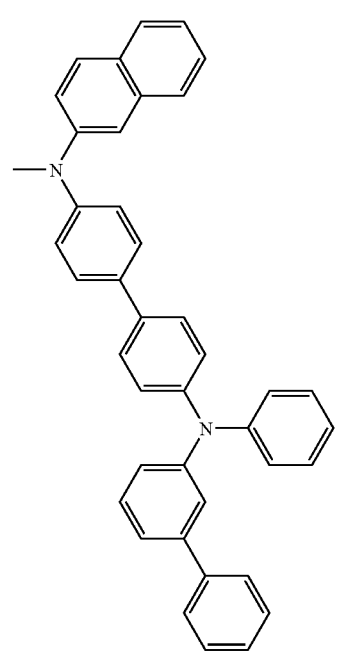
326
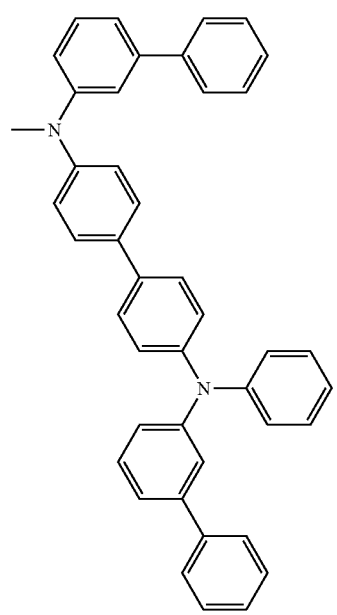
328

329
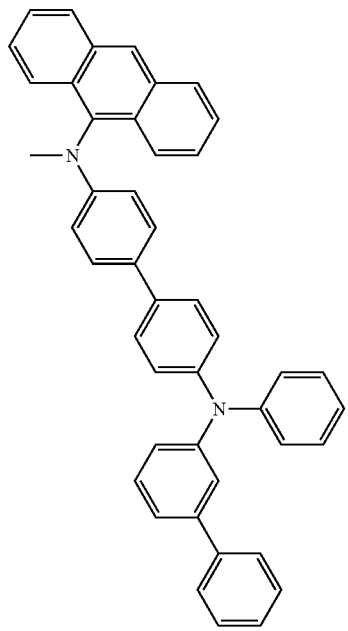
330
331
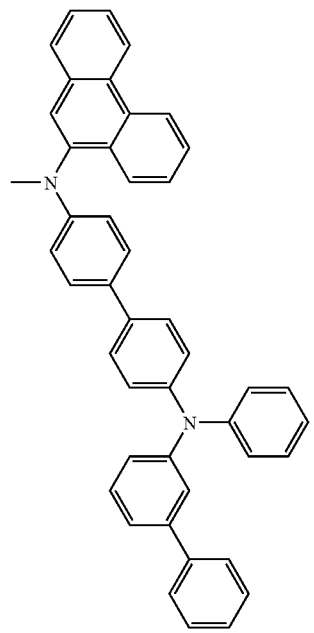
332
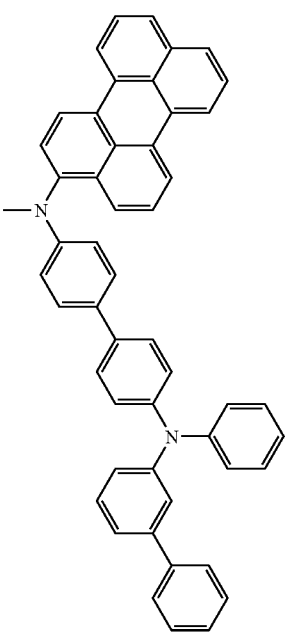

333
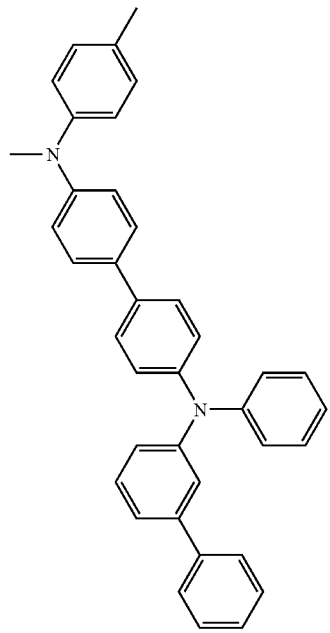
335
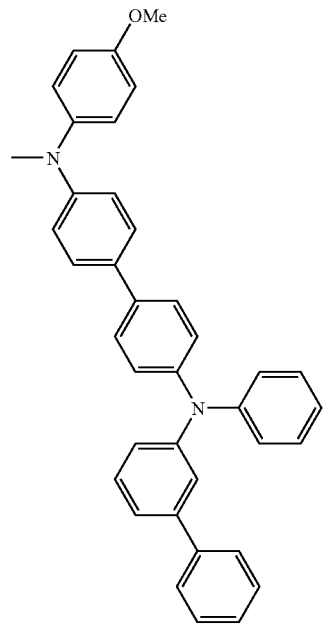
334
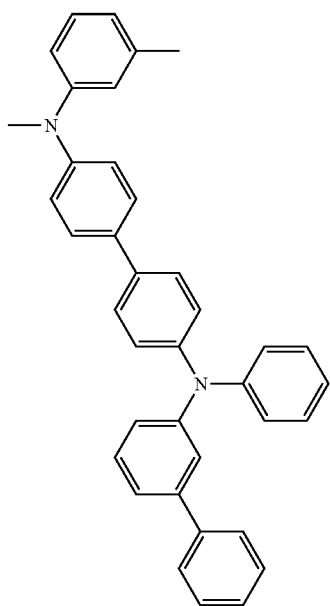
336
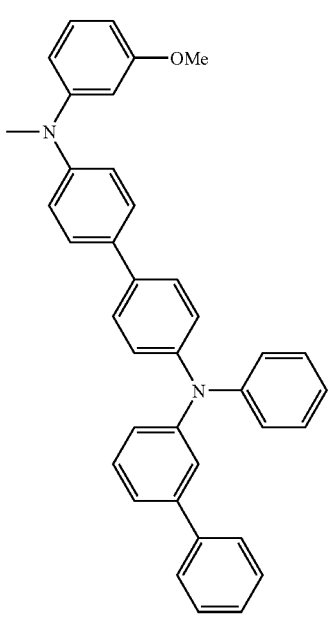

407
-continued
408
-continued
337
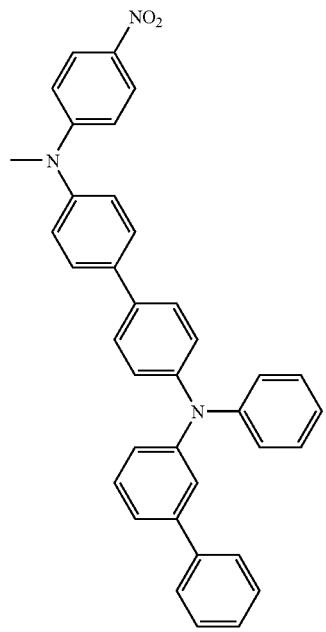
339
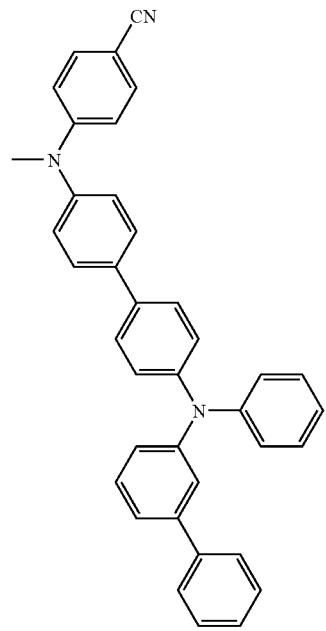
338
340

341
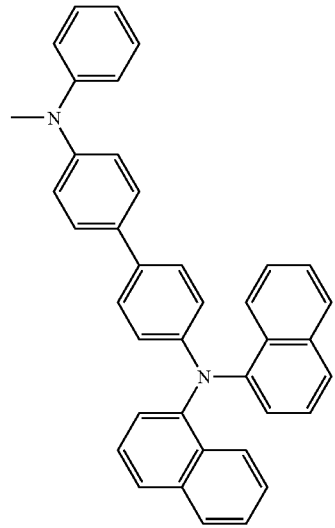
342
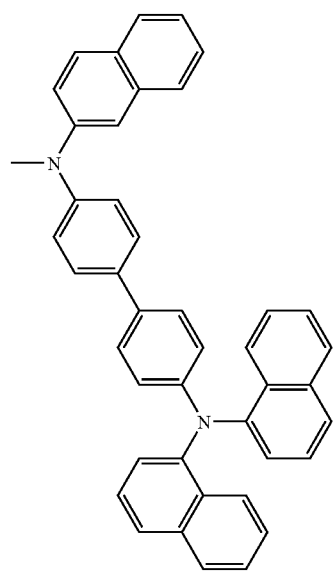
343
344
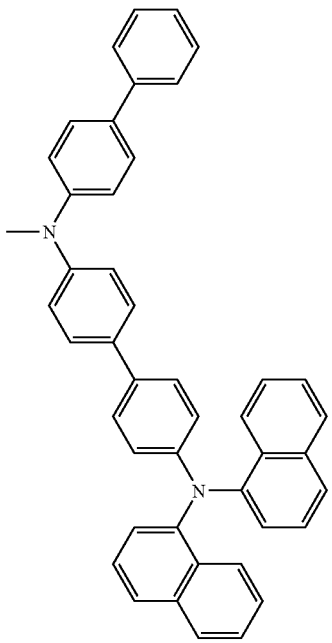
345
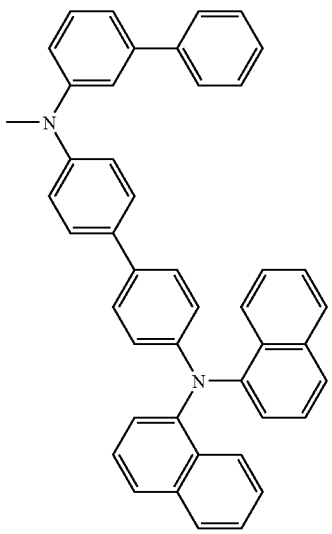

411
-continued
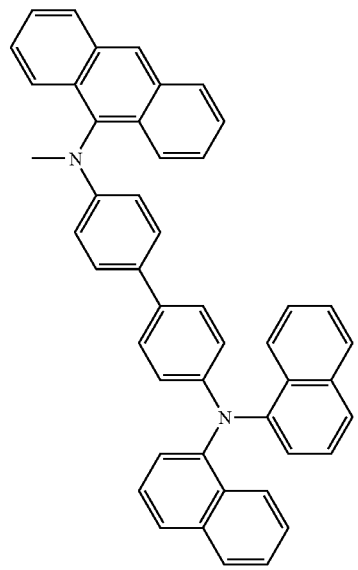
346
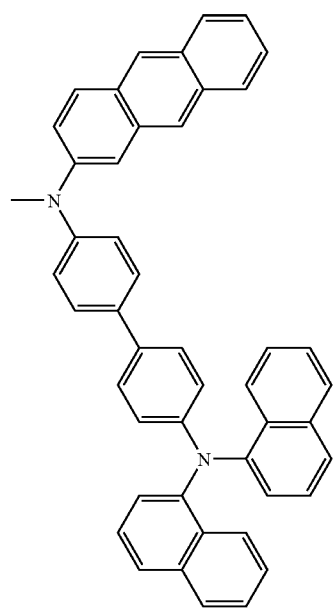
347
412
-continued
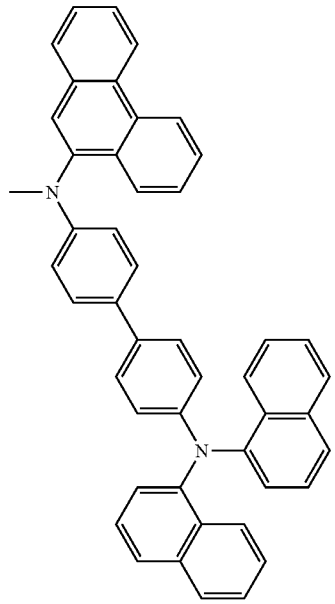
348
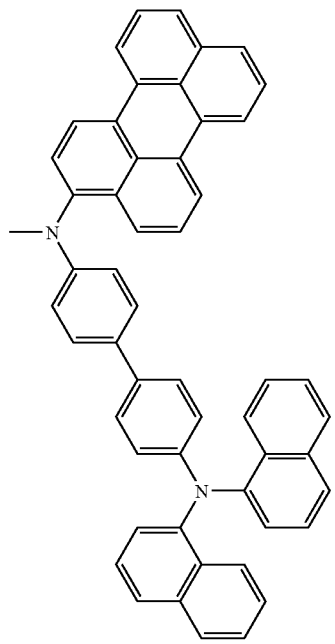
349

| 413 | 414 |
|---|---|
| -continued | -continued |
| 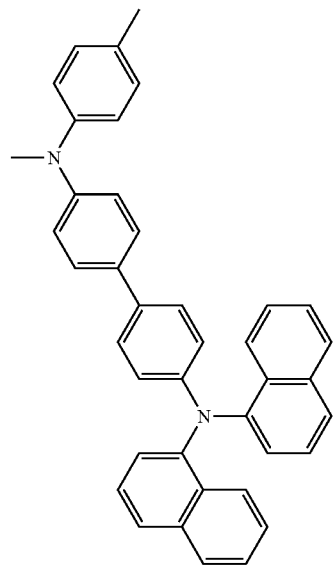 350 | 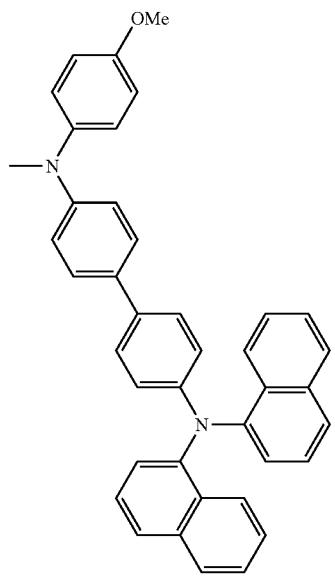 352 |
| 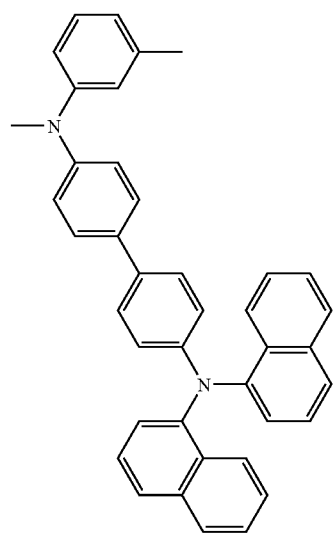 351 | 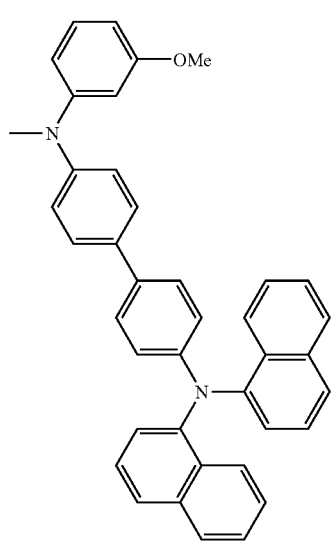 353 |

415
-continued
354
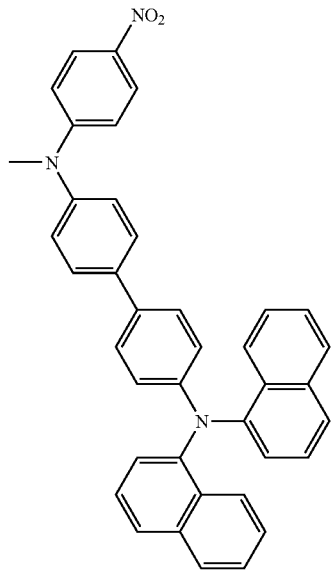
355
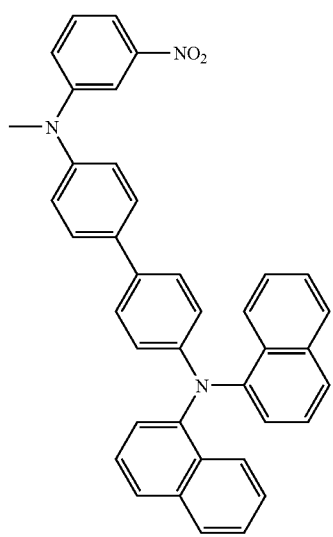
416
-continued
356
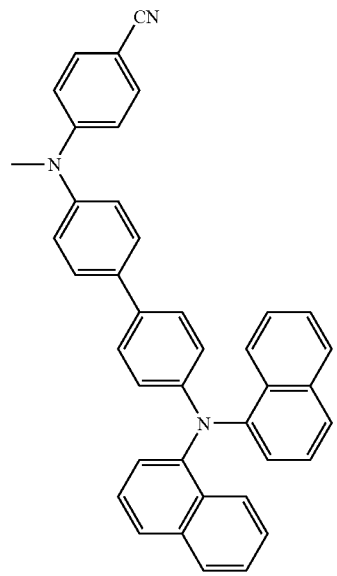
357
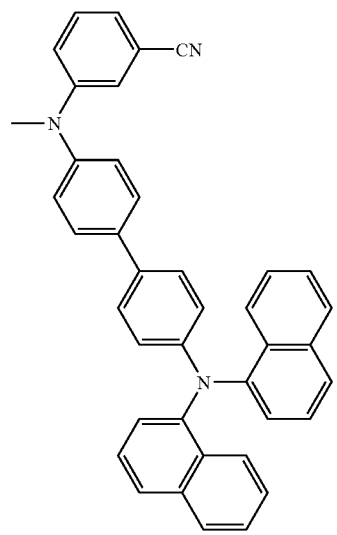
358
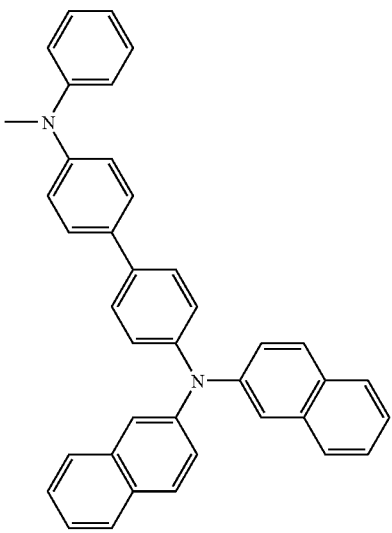

417
-continued
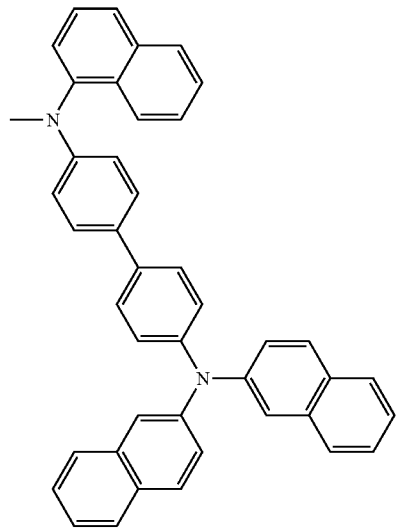
359
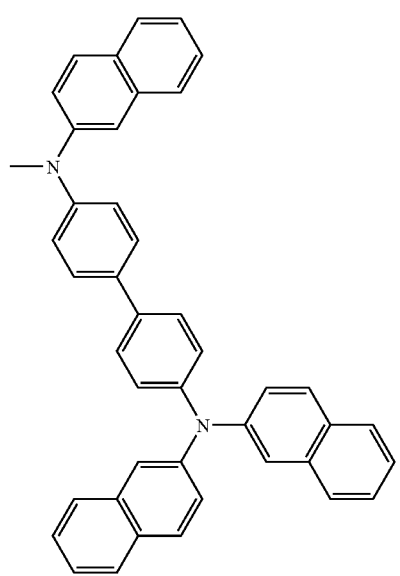
360
418
-continued
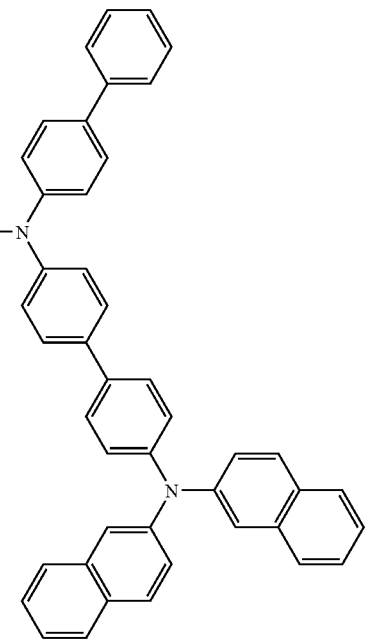
361
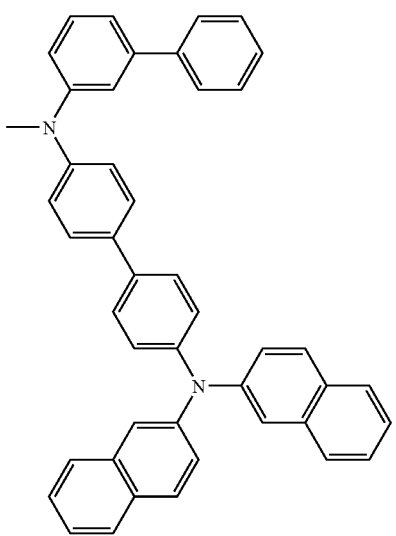
362

-continued
419
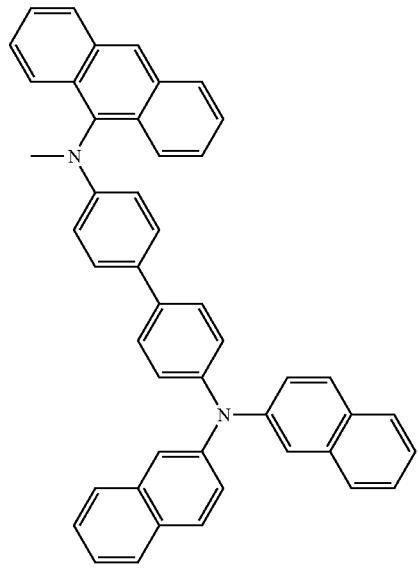
363
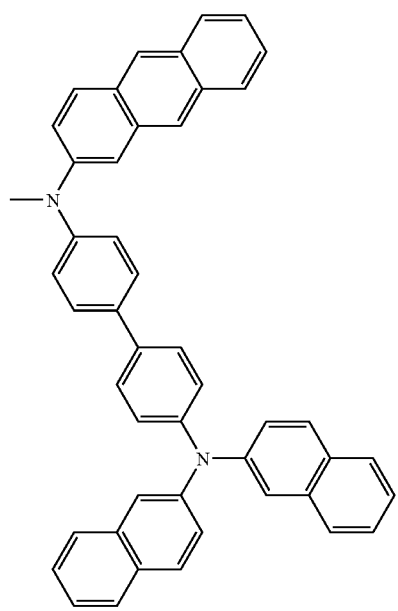
364
420
-continued
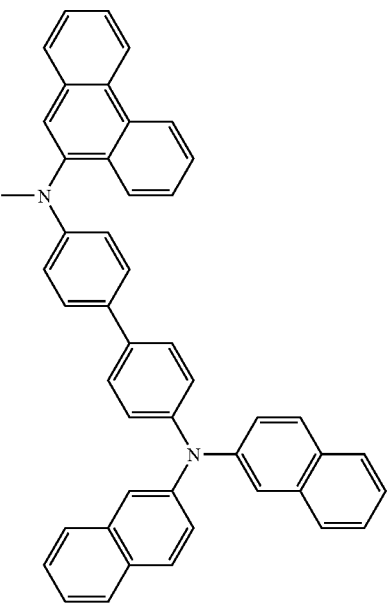
365
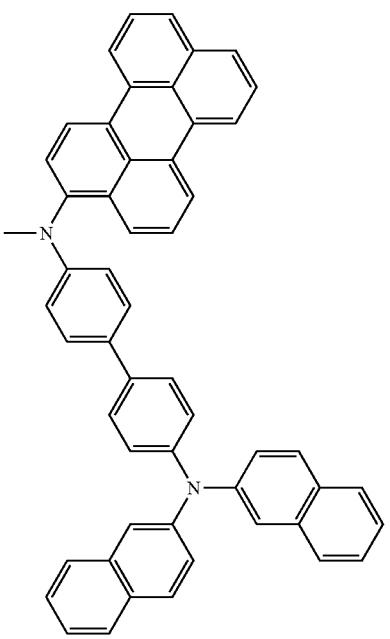
366

421
-continued
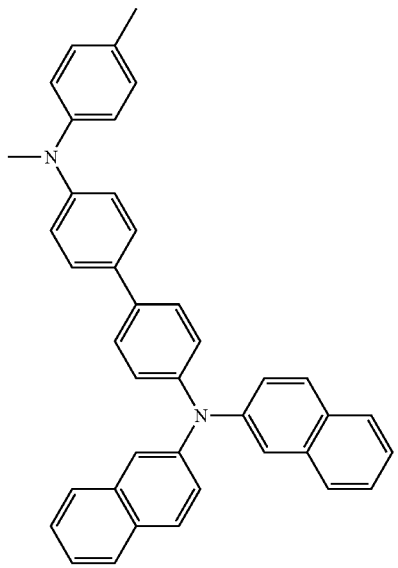
367
422
-continued
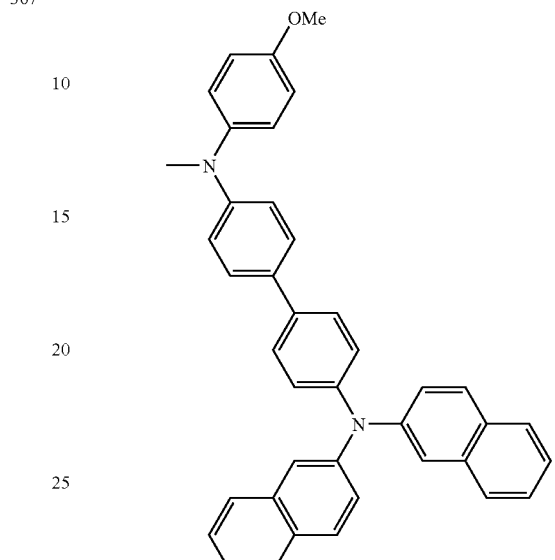
369
368
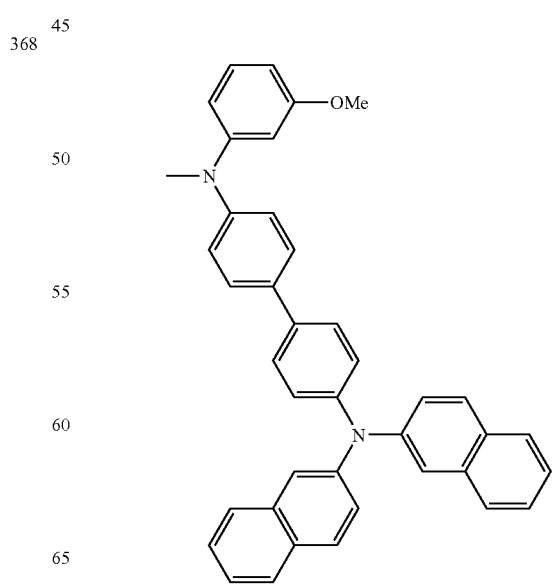
370

423
-continued
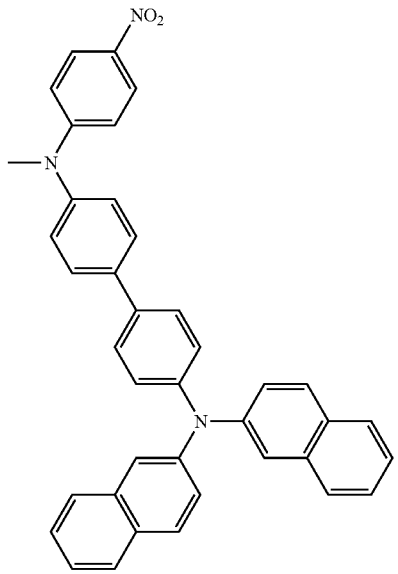
371
372
424
-continued
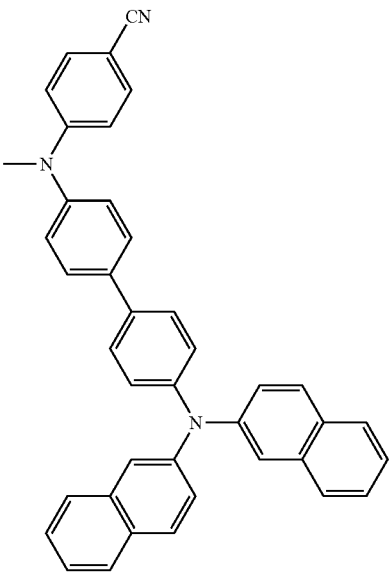
373
374

375
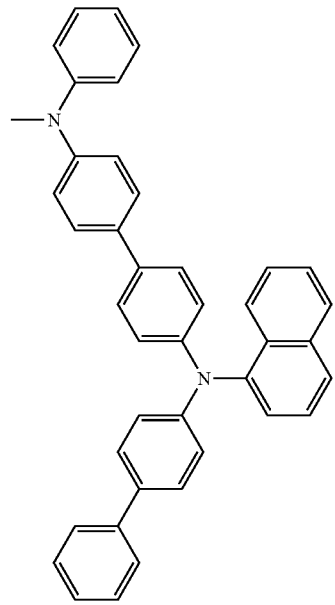
376
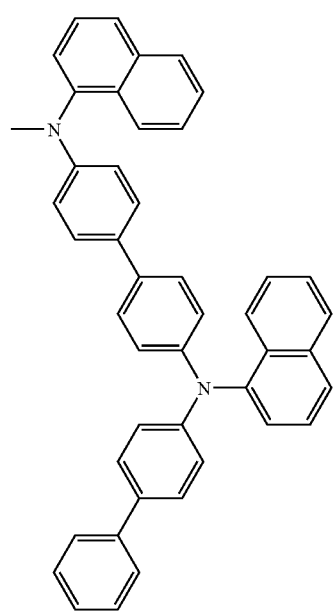
377
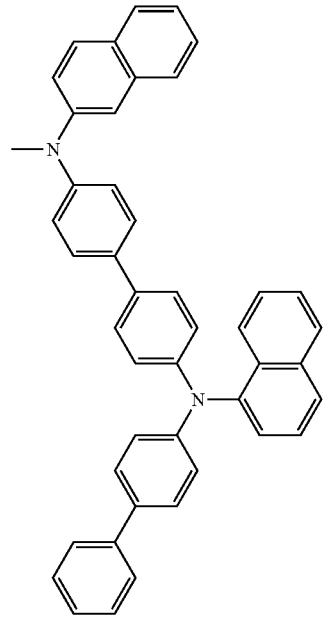
378
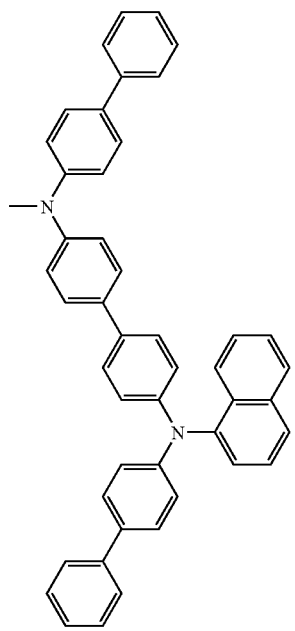

427
-continued
428
-continued
379
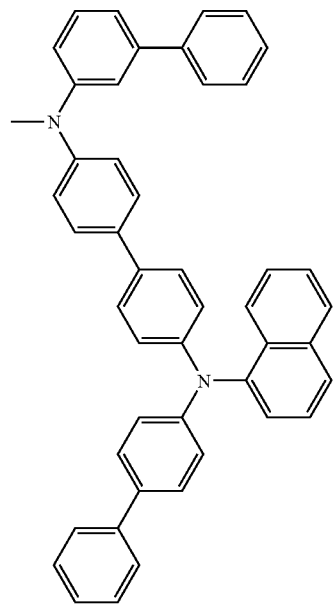
381
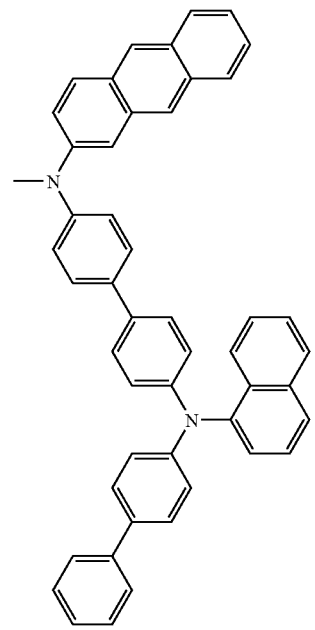
380
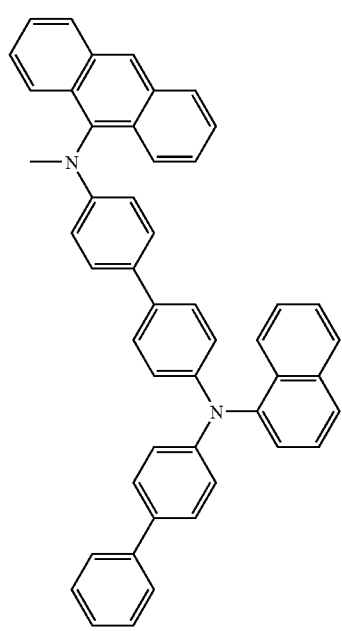
382
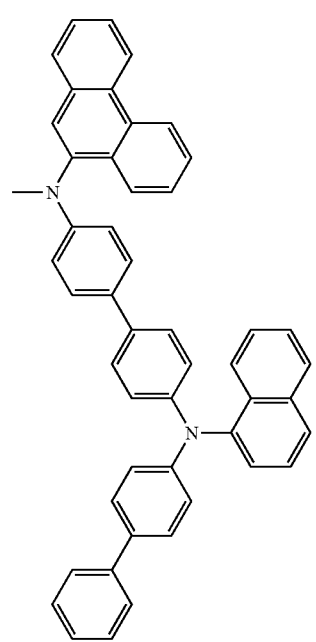

383
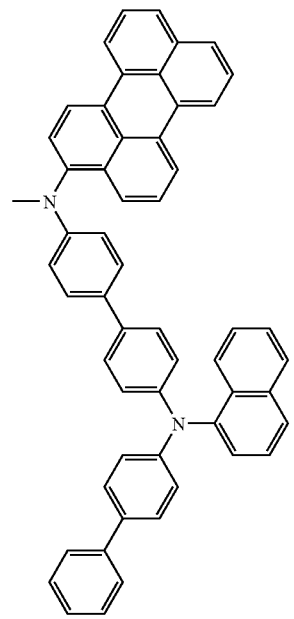
385
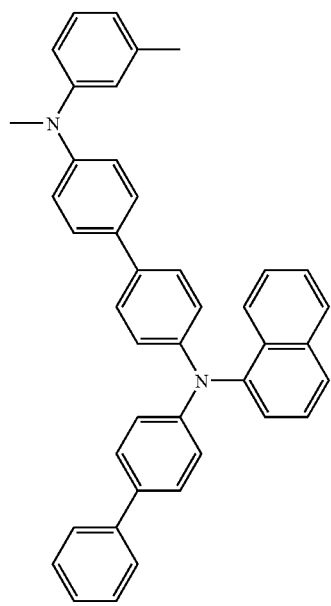
384
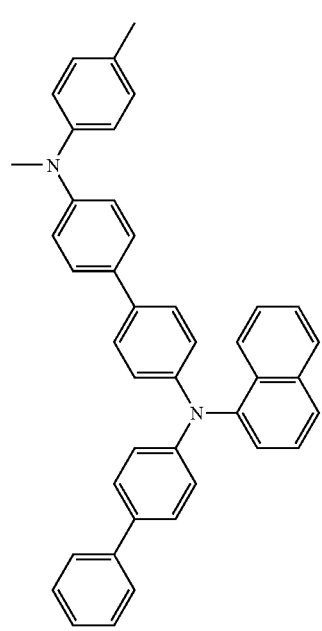
386
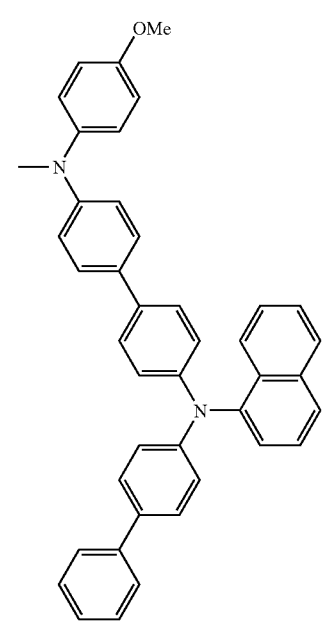

-continued
387
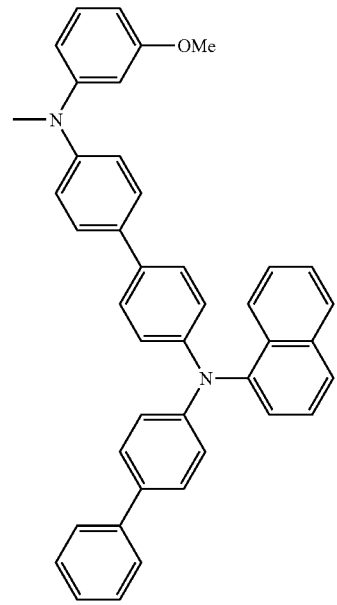
388
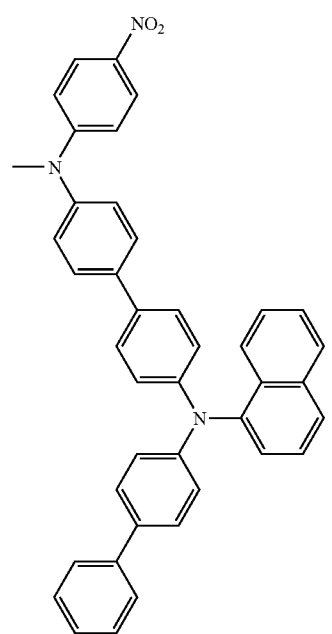
-continued
390
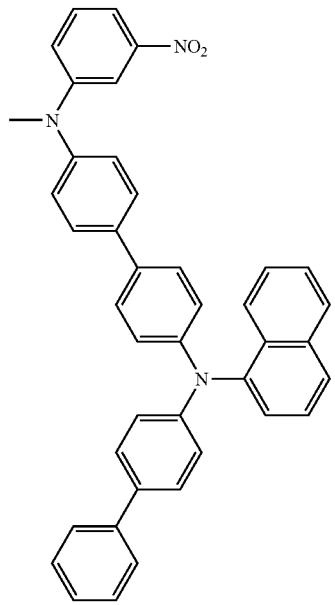
391
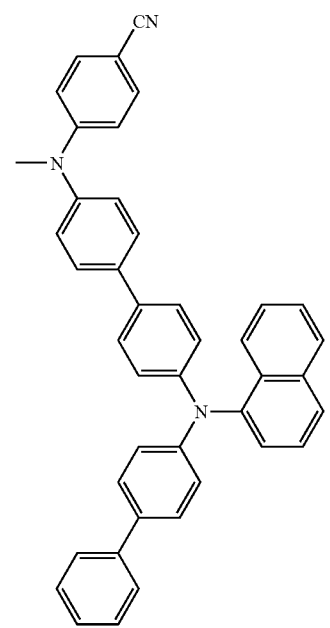

433
-continued
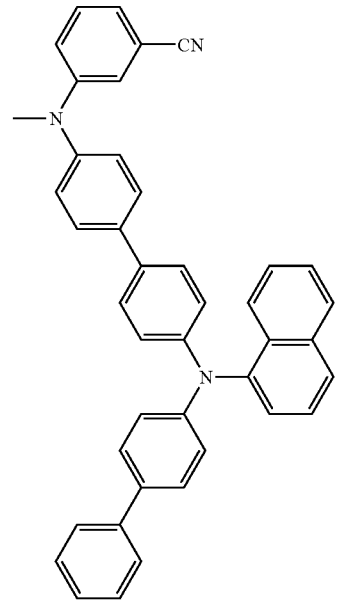
391
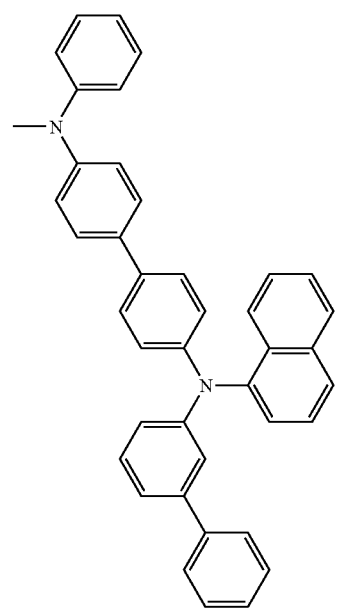
392
434
-continued
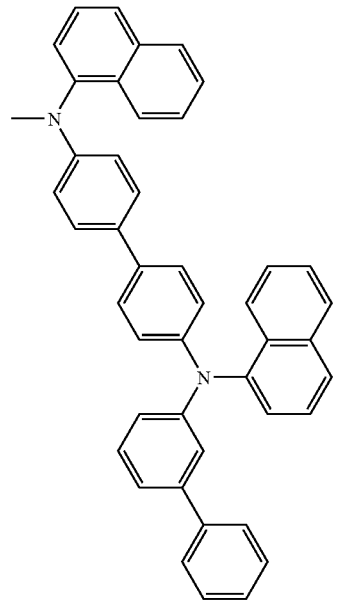
393
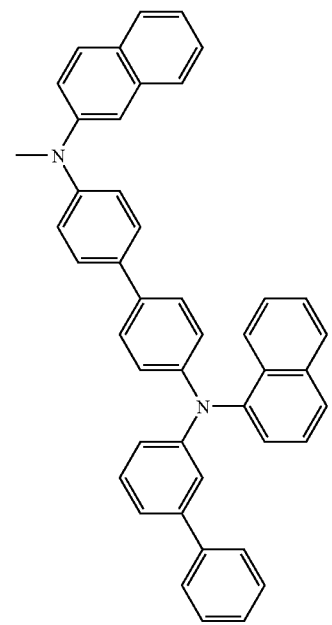
394

435
-continued
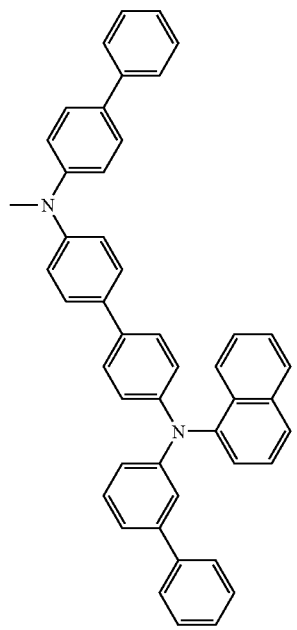
395
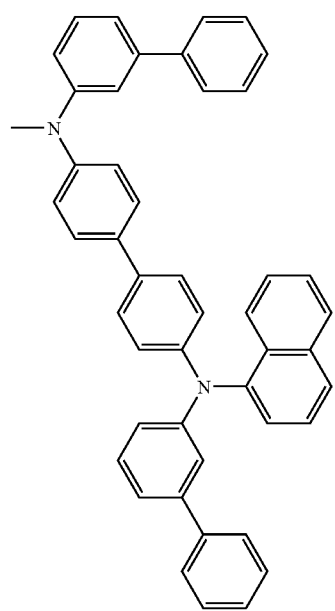
396
436
-continued
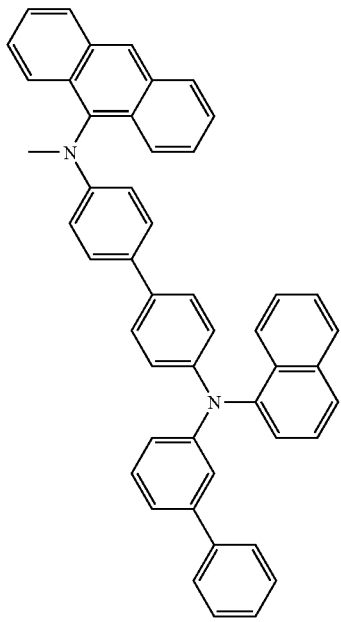
397
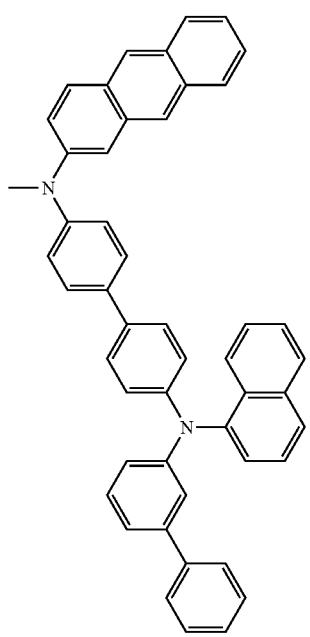
398

437
-continued
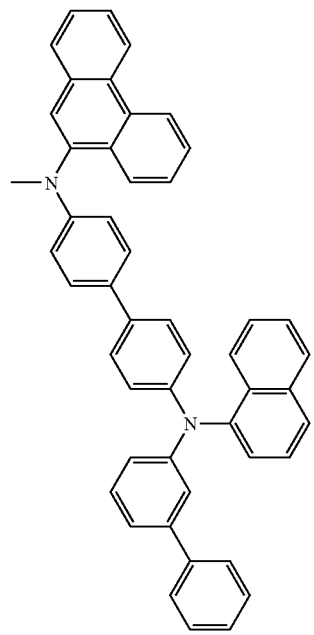
399
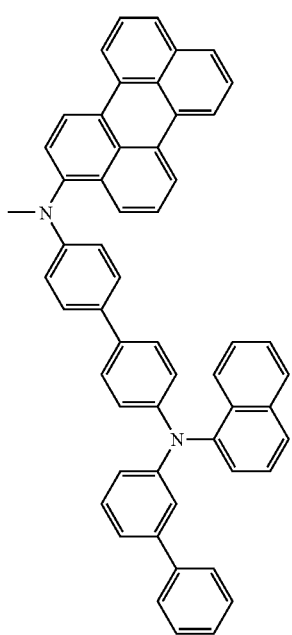
400
438
-continued
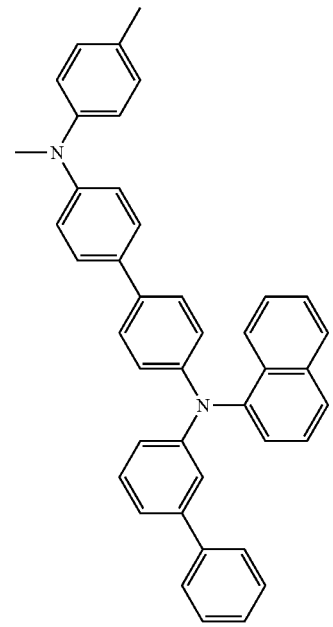
401
402

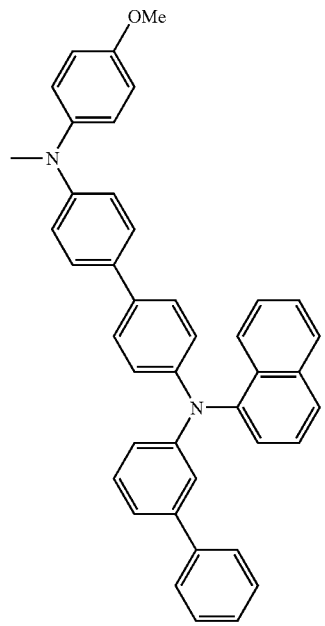
403
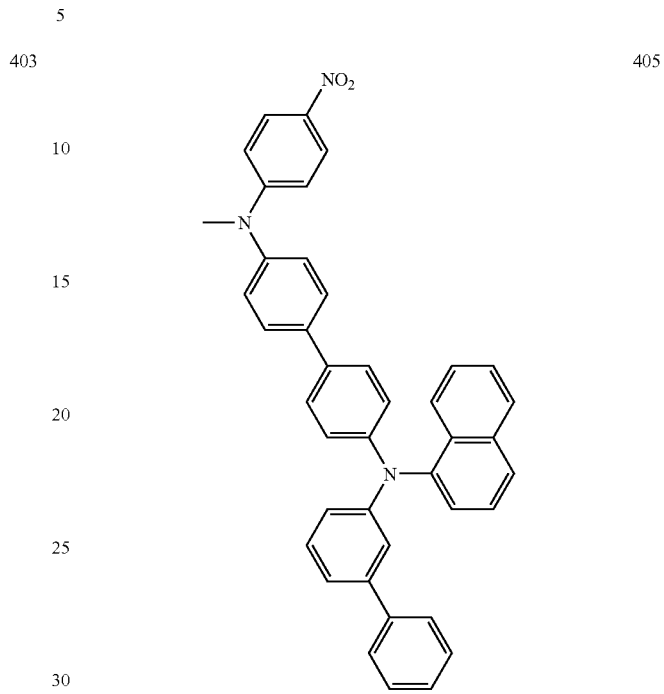
405
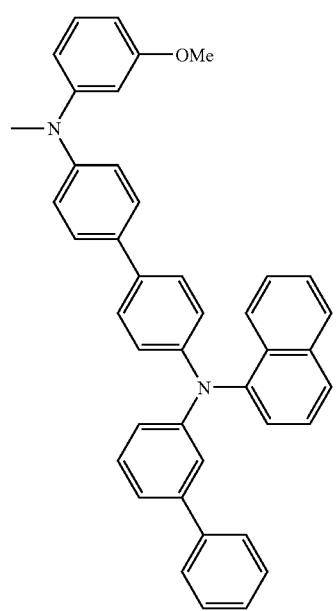
404
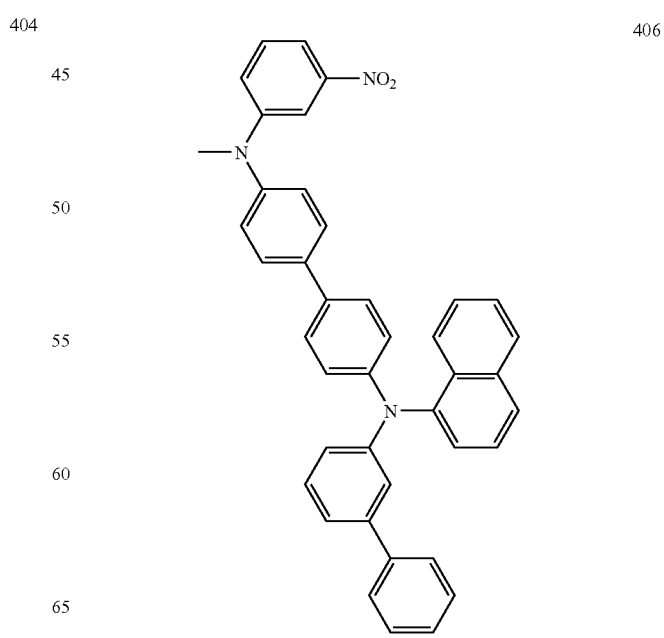
406

441
-continued
442
-continued
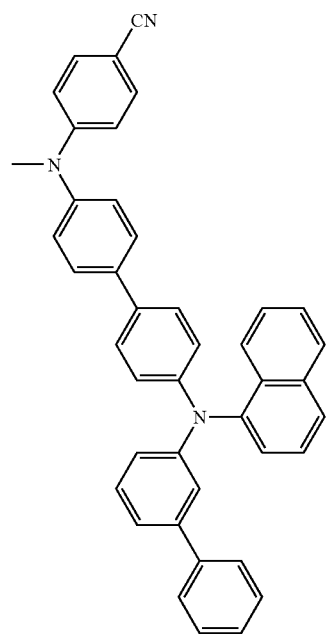
407
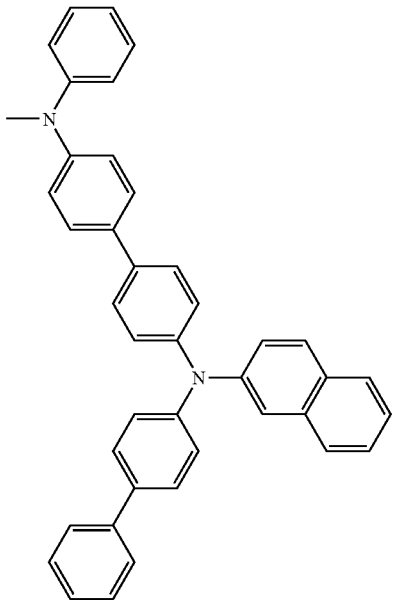
409
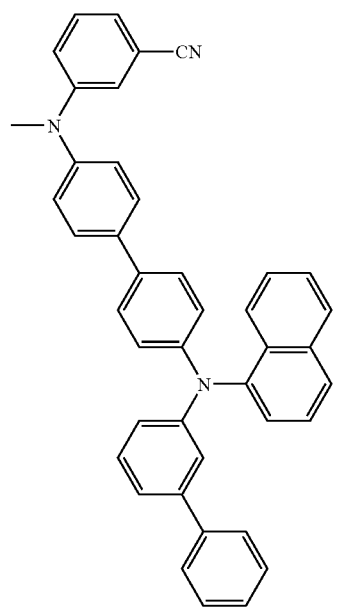
408
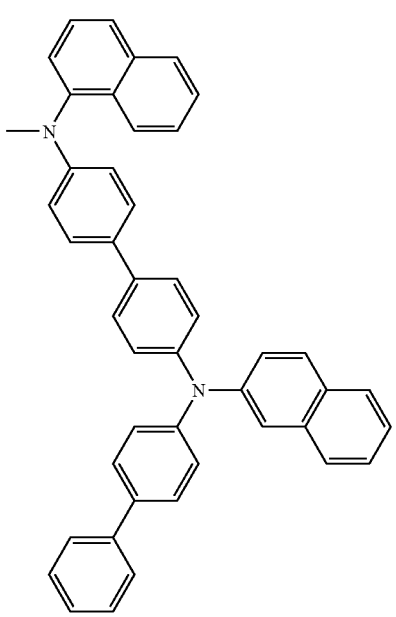
410

443
-continued
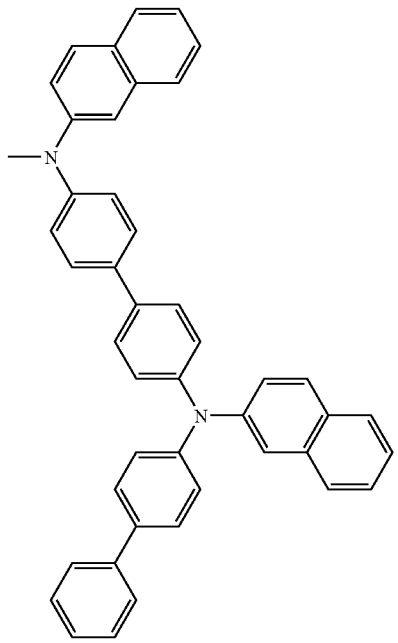
411
444
-continued
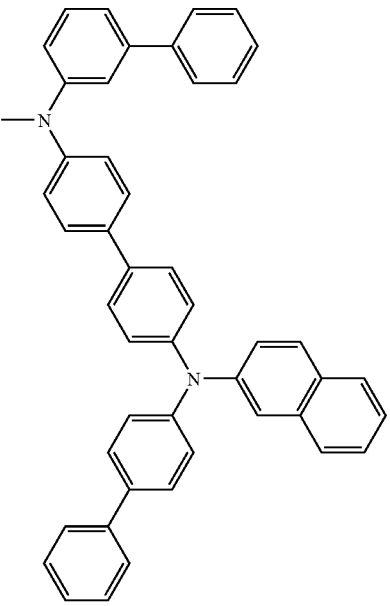
413
412
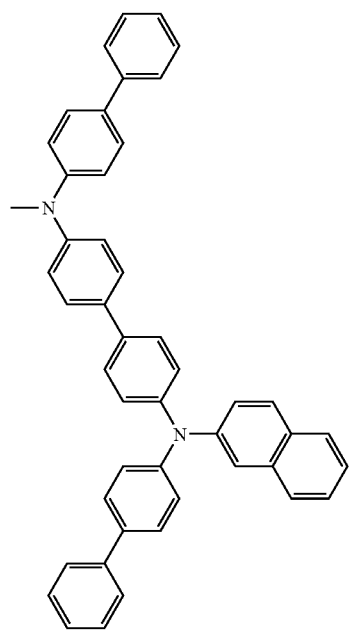
414
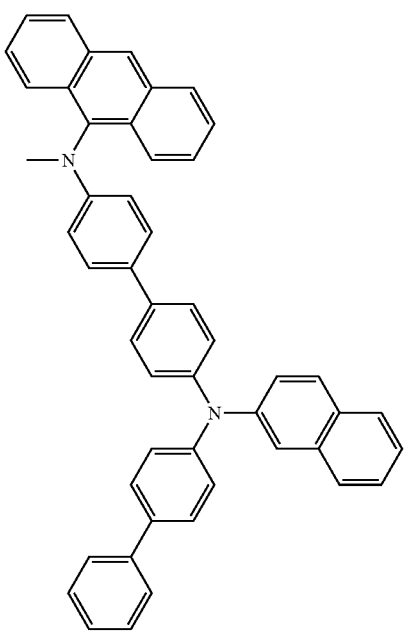

-continued
445
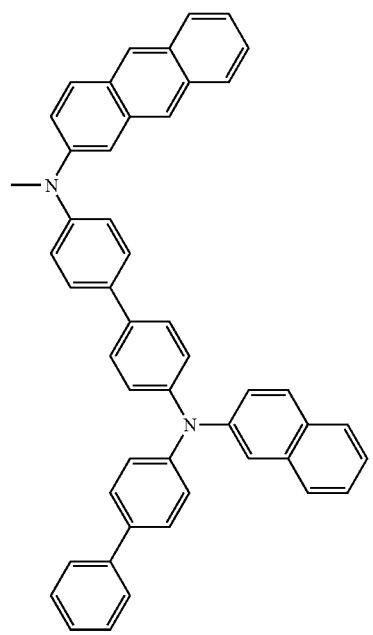
415
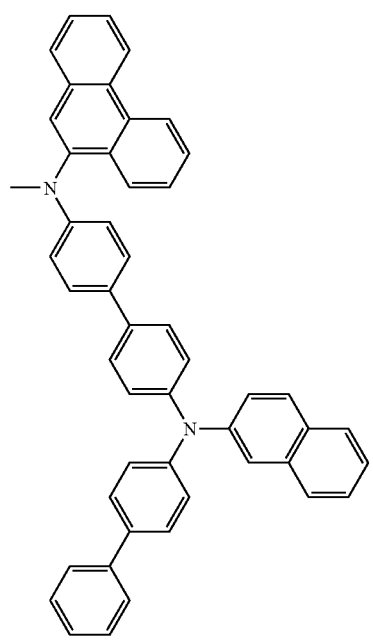
416
-continued
446
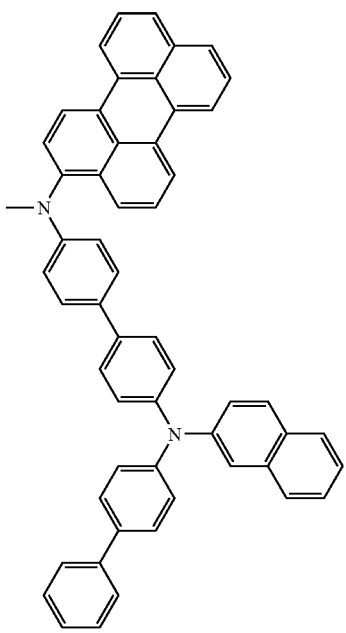
417
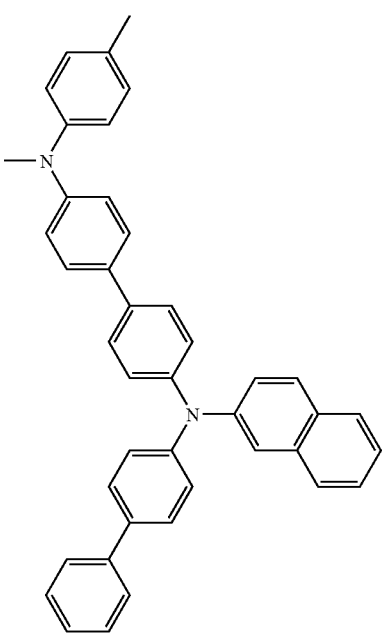
418

447
448
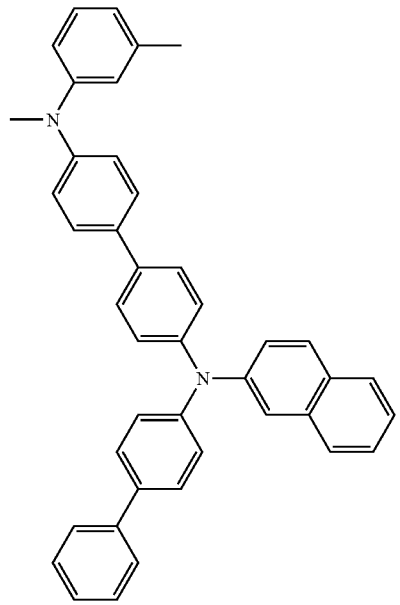
419
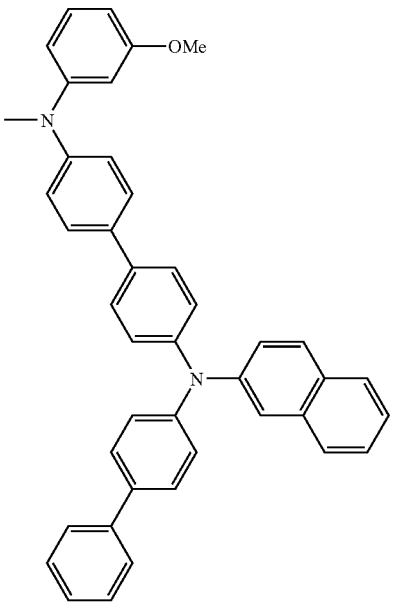
421
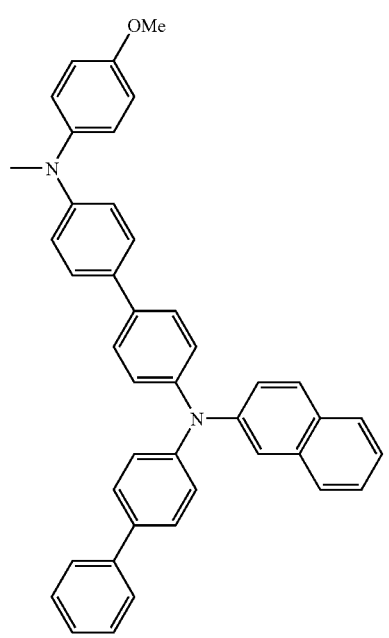
420
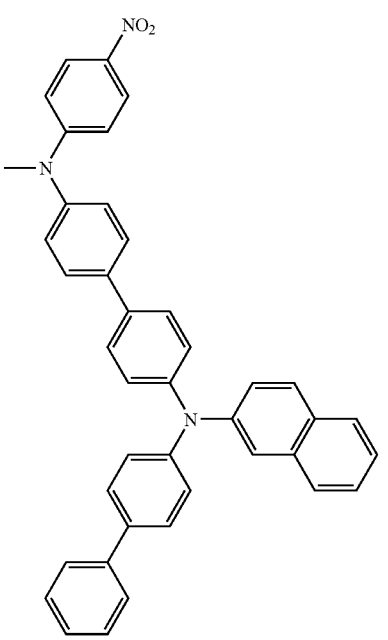
422

-continued
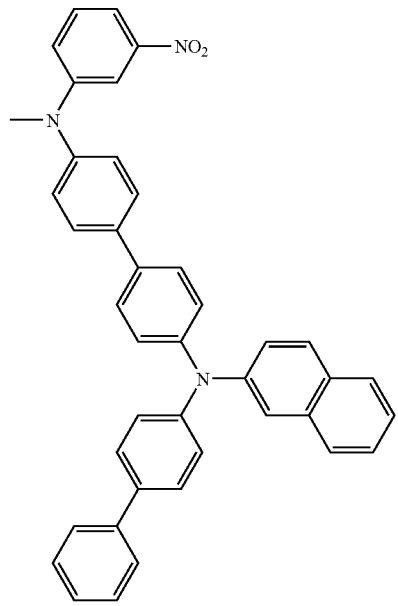
423
424
-continued
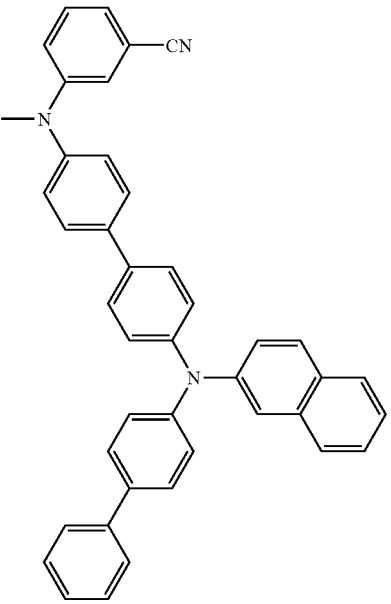
425
426

451 452
427
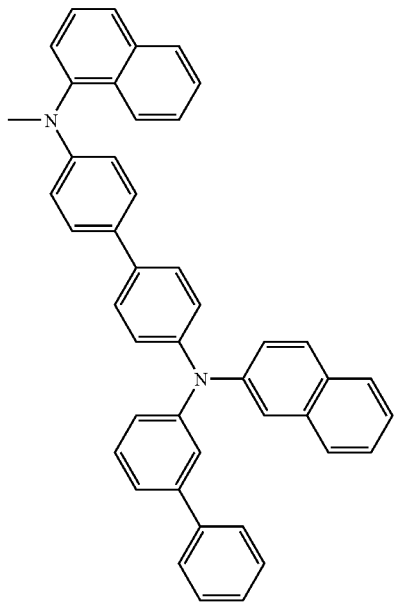
429
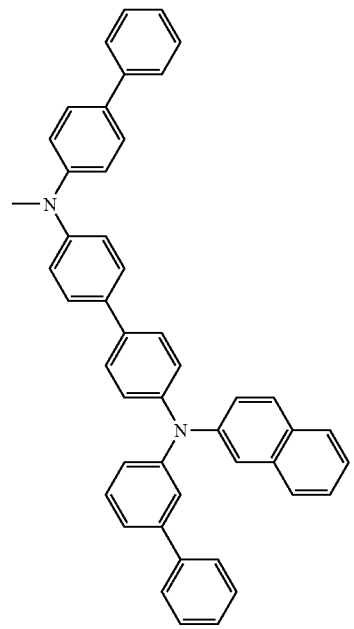
428
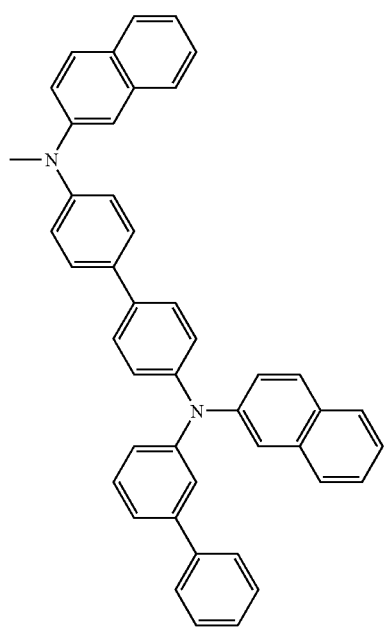
430
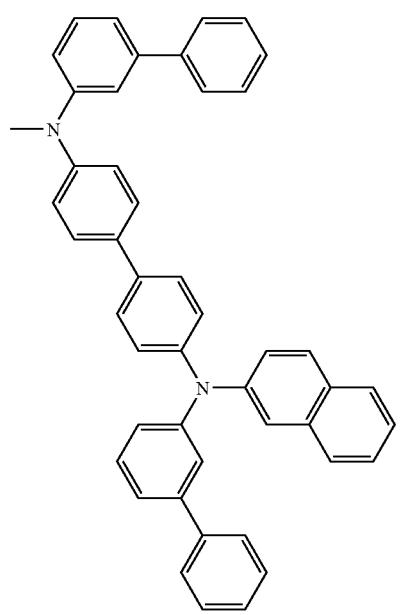

453
-continued
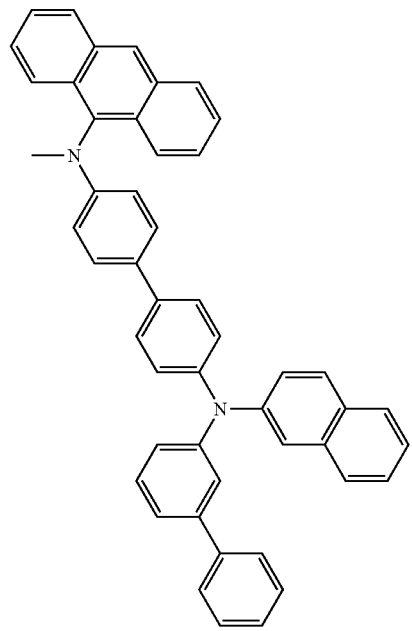
431
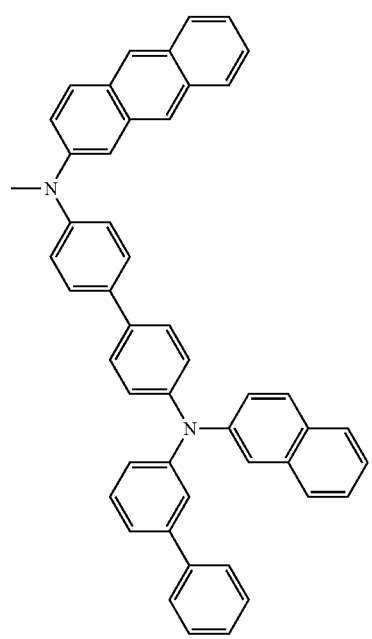
432
454
-continued
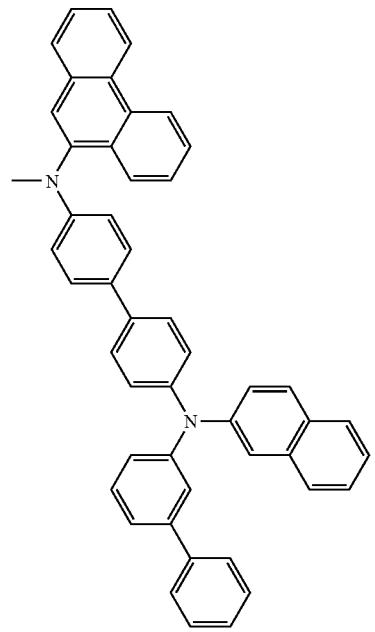
433
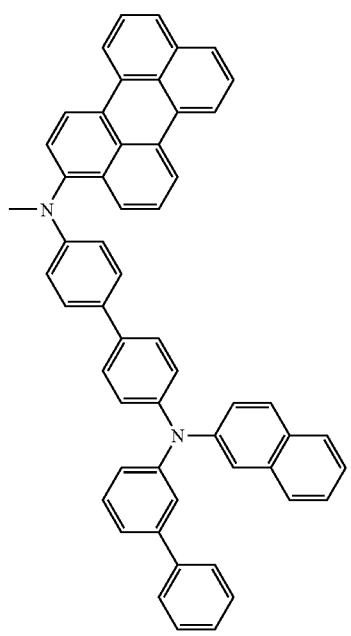
434

455
-continued
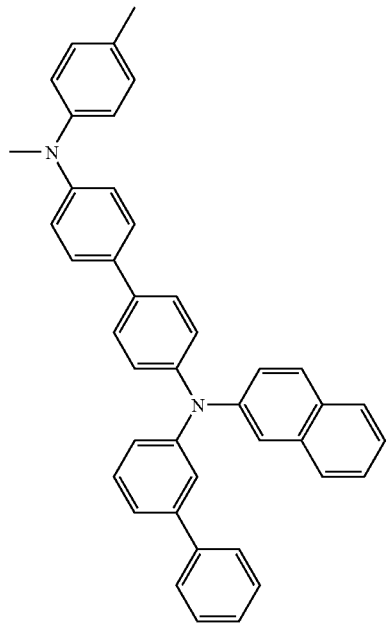
435
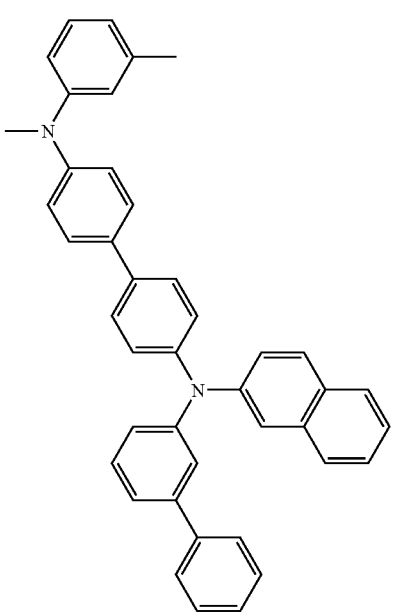
436
456
-continued
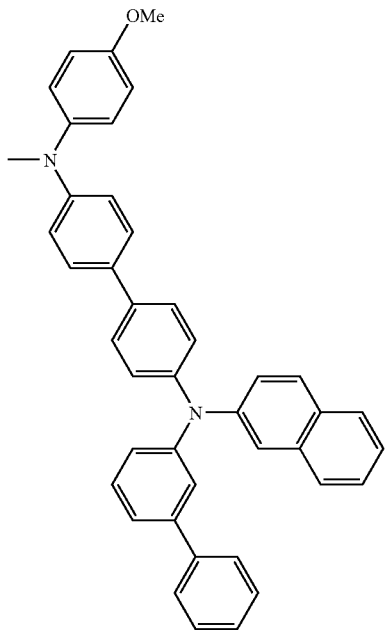
437
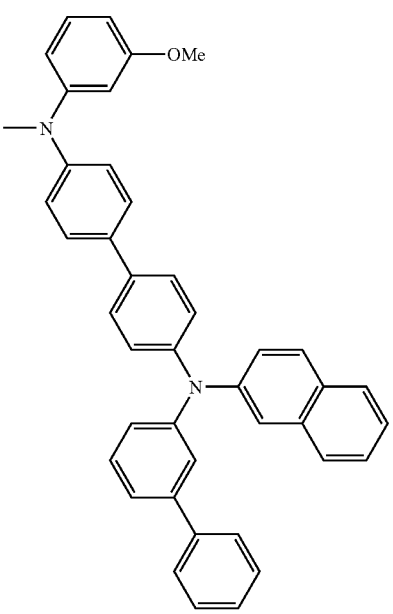
438

457
458
-continued
-continued
439
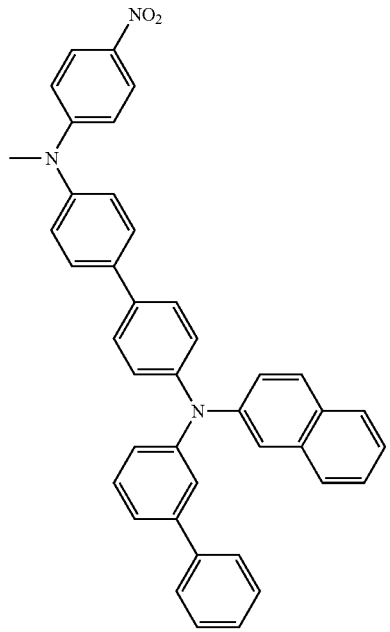
441
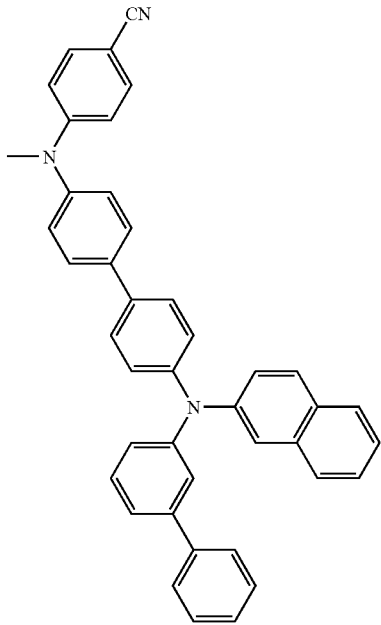
440
442

443
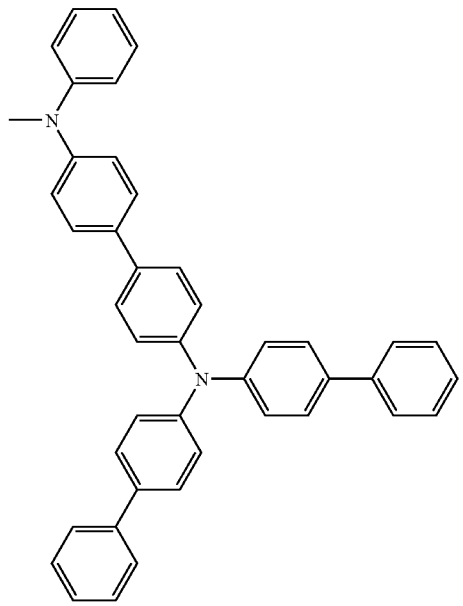
444
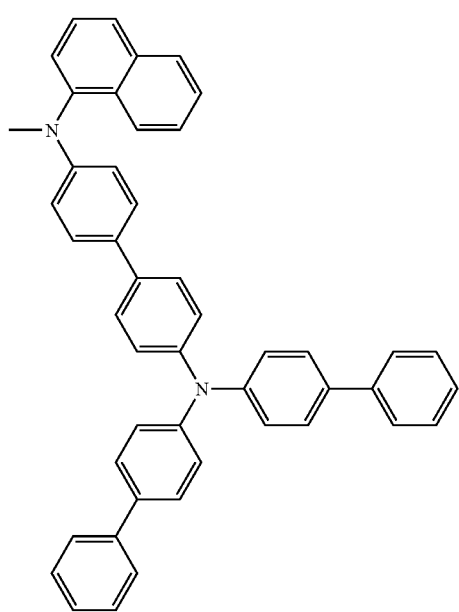
445
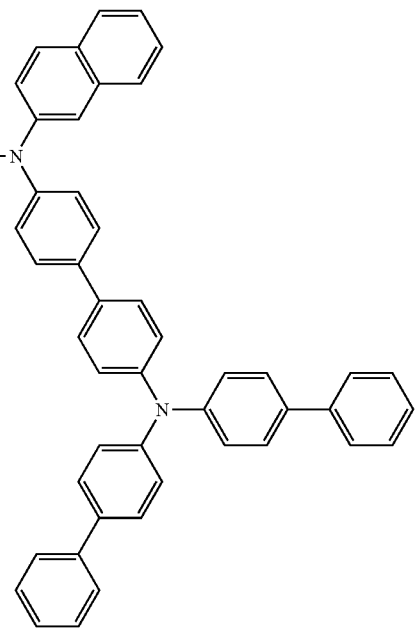
446
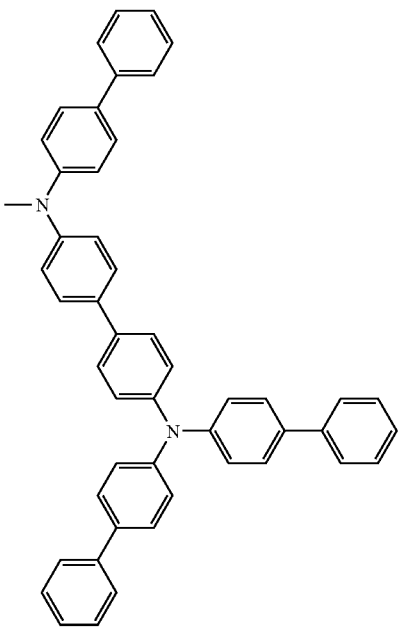

461
-continued
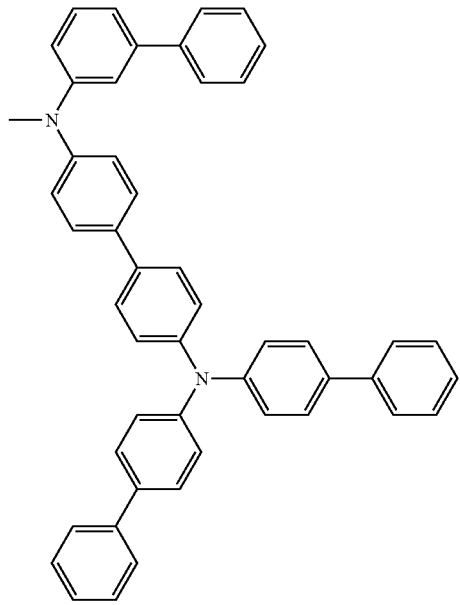
462
-continued
447
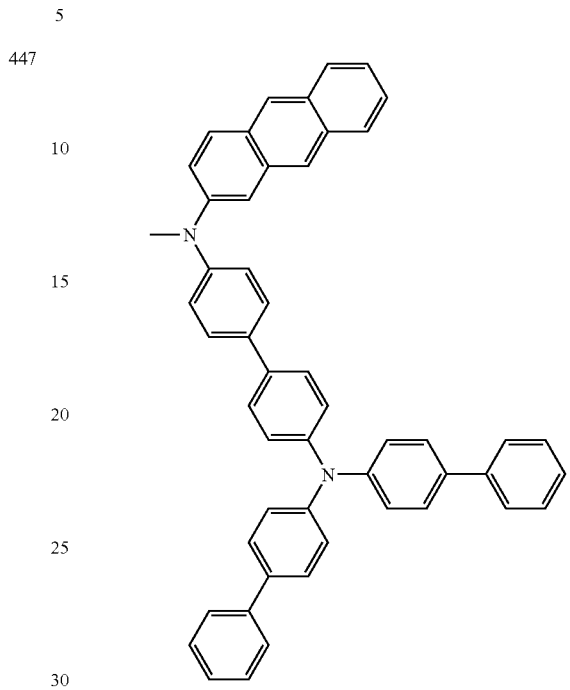
449
448
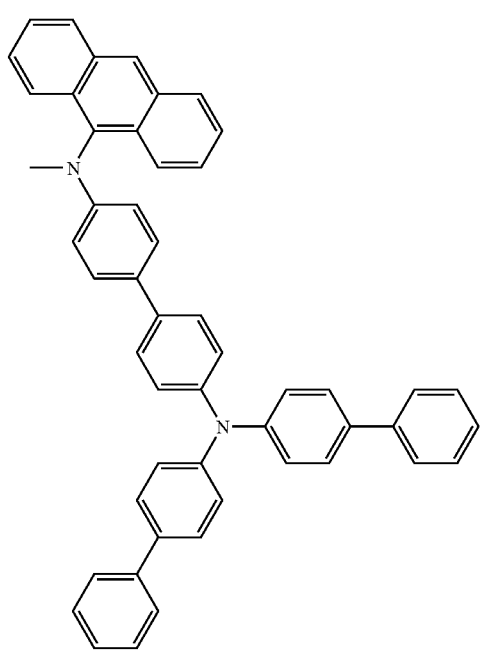
450
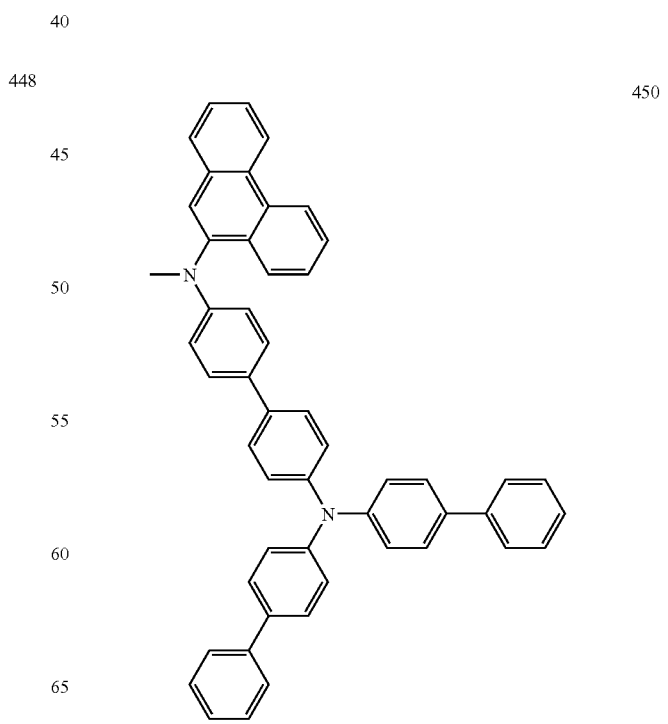

463
464
451 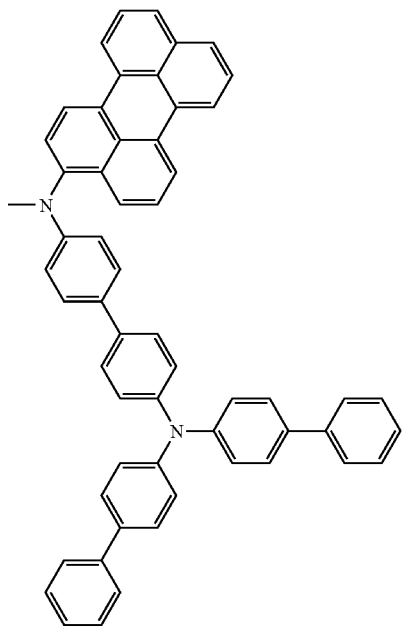
453 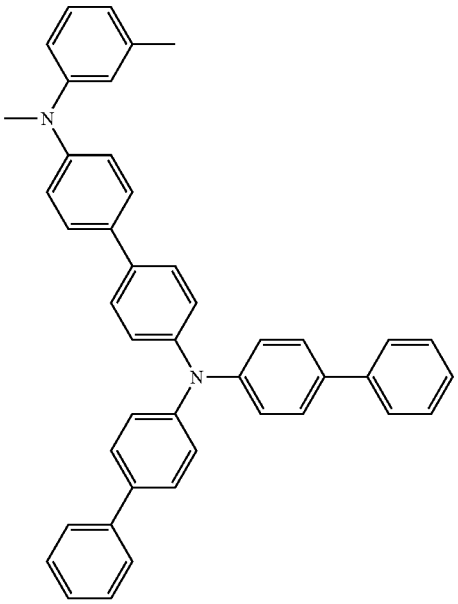
452 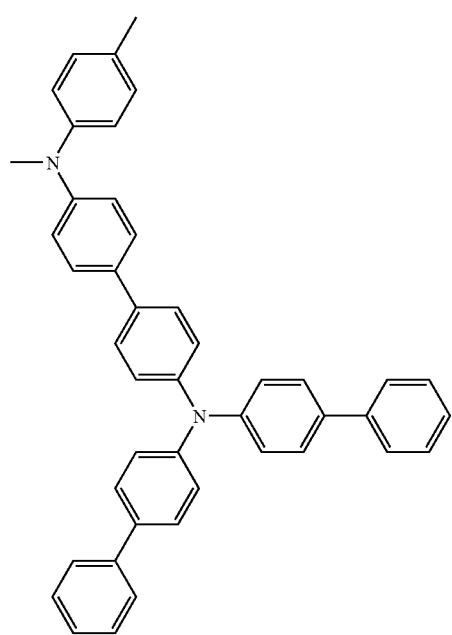
454 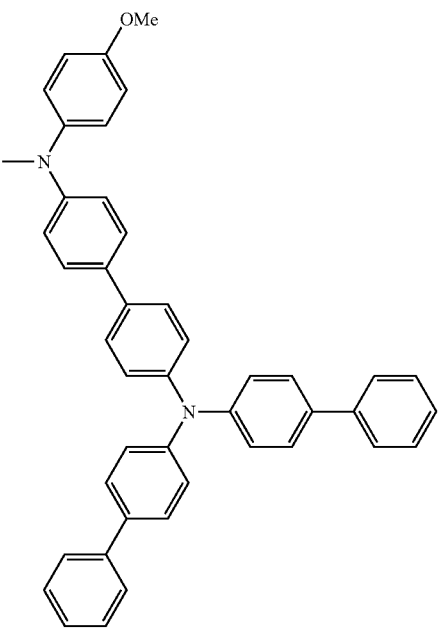

465
-continued
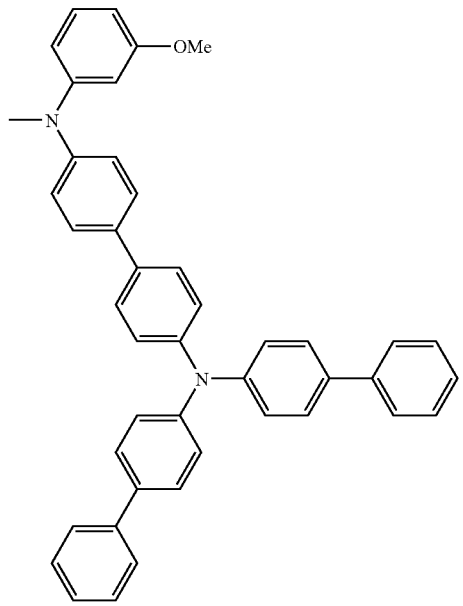
455
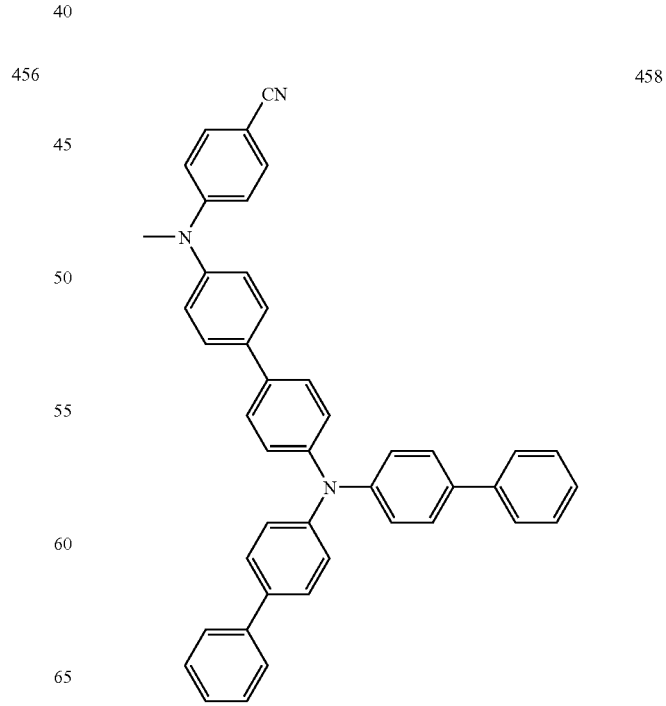
456
466
-continued
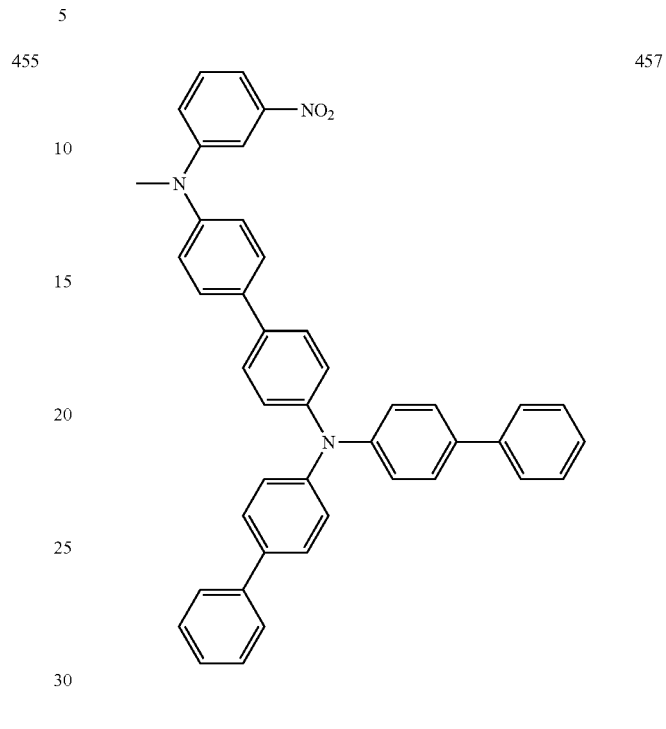
457
458

467
-continued
459
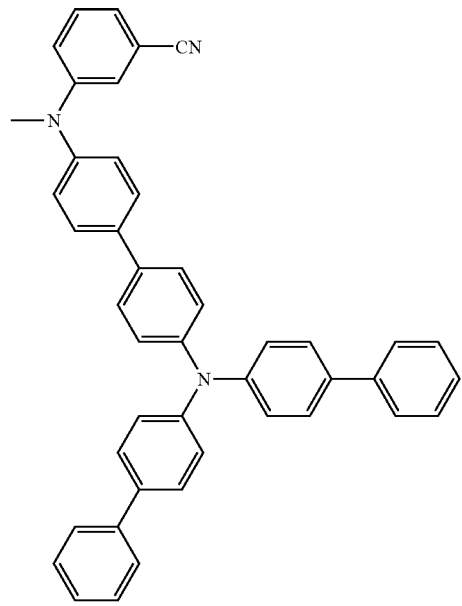
460
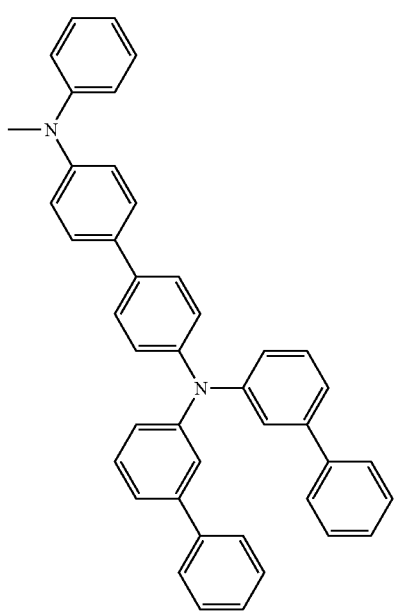
468
-continued
461
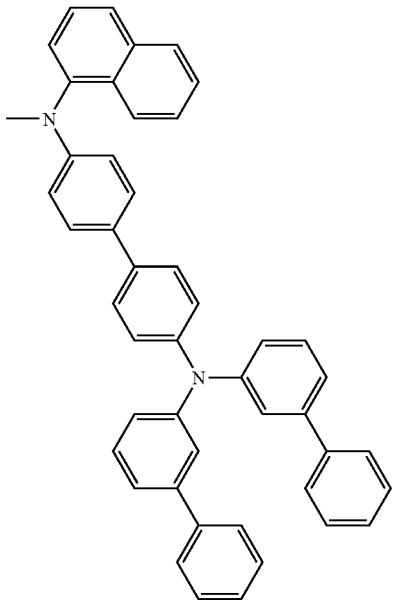
462
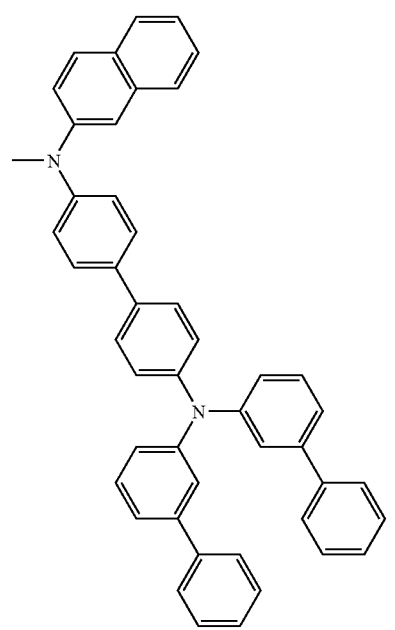

-continued
463
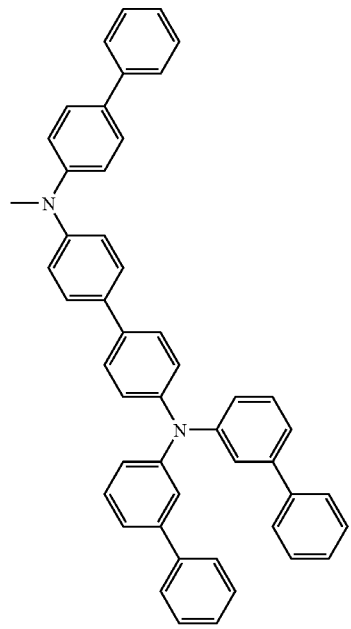
464
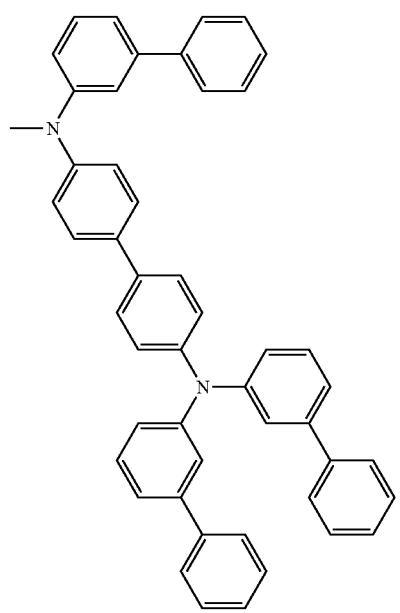
-continued
465
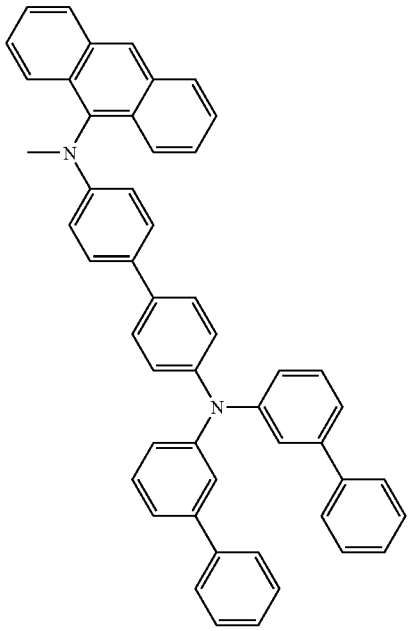
466
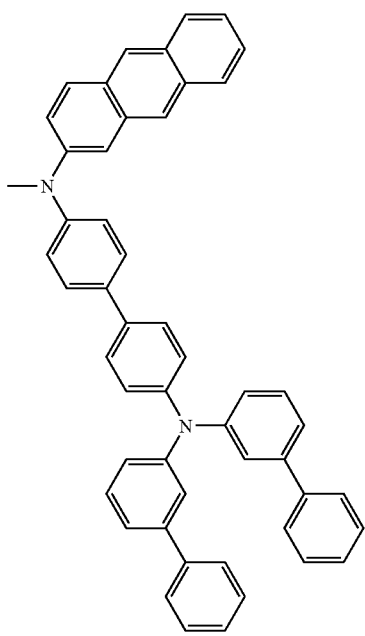

471
-continued
467
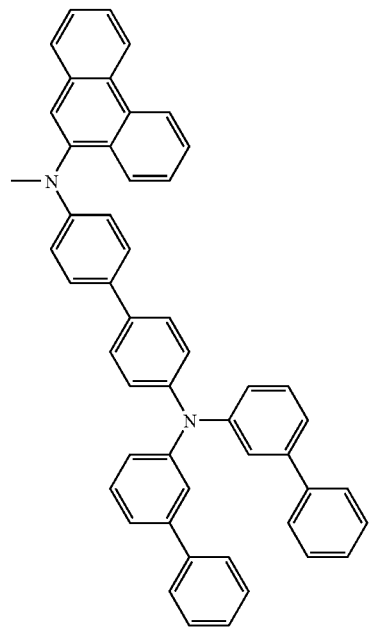
468
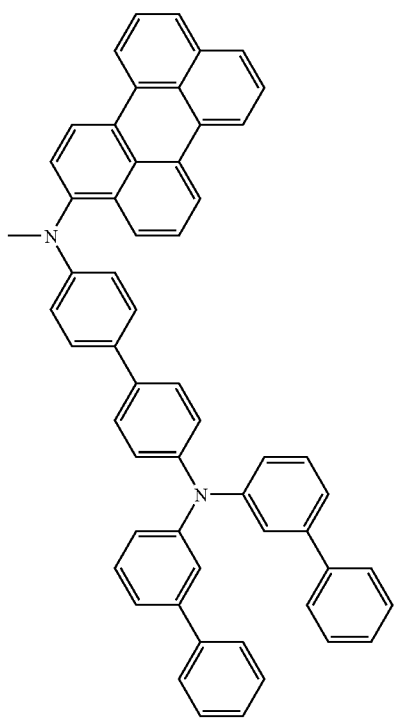
472
-continued
469
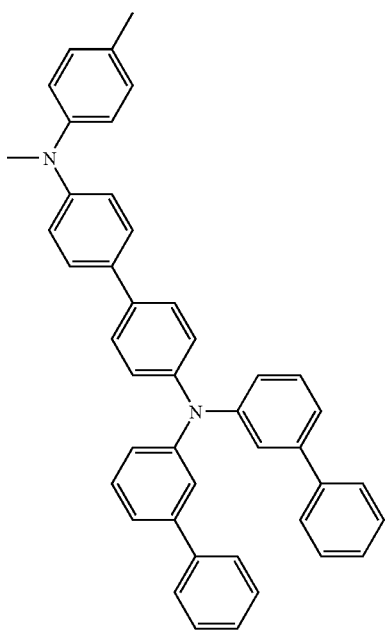
470
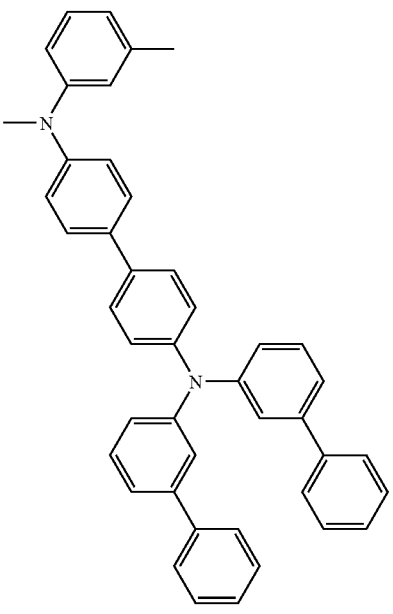

473
-continued
471
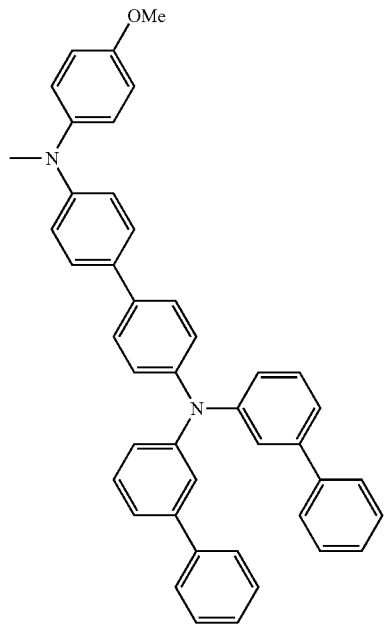
472
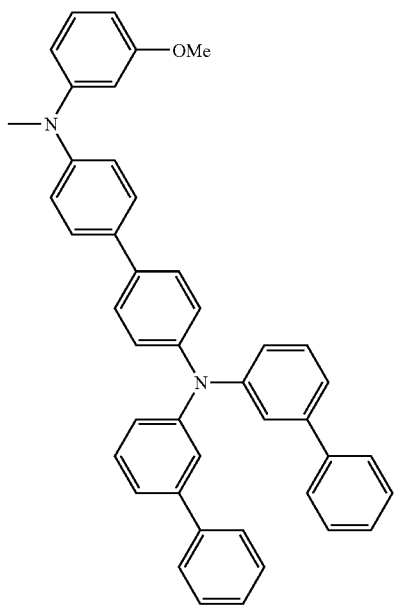
474
-continued
473
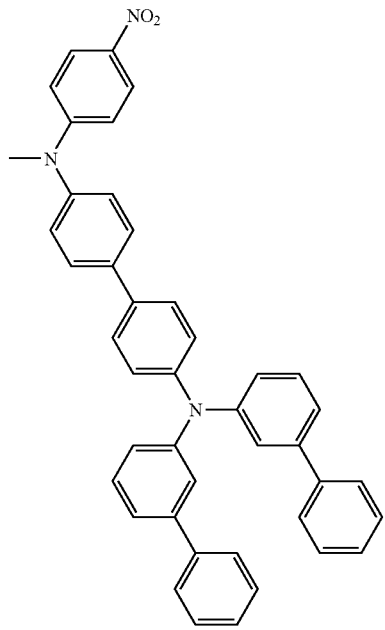
474
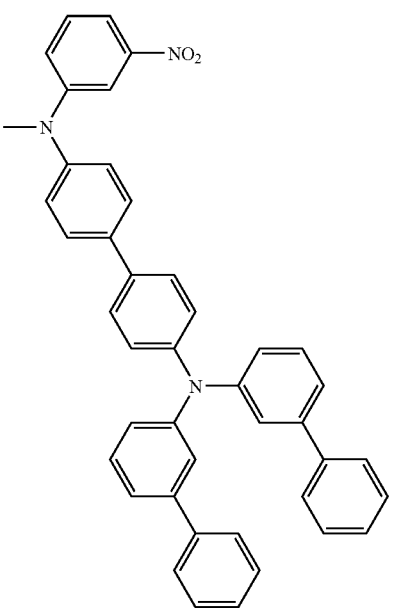

-continued

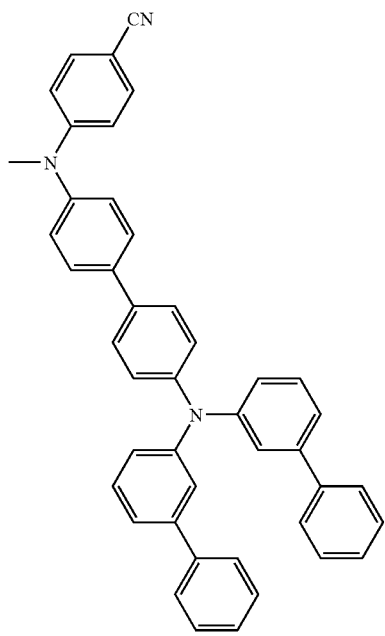

and

-continued

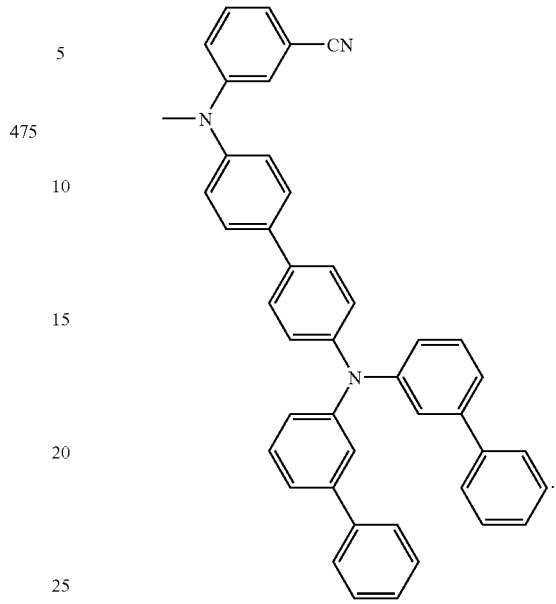

6. The organic light emitting device as set forth in claim 1, wherein the organic material layer(s) comprise a hole transport layer, and the hole transport layer includes the compound of Formula 1.

7. The organic light emitting device as set forth in claim 1, wherein the organic material layer(s) comprise a hole injection layer, and the hole injection layer includes the compound of Formula 1.

8. The organic light emitting device as set forth in claim 1, wherein the organic material layer(s) comprise a layer which both injects and transports holes and which includes the compound of Formula 1.

* * * * *